(12) United States Patent
Fridez et al.

(10) Patent No.: US 9,192,501 B2
(45) Date of Patent: Nov. 24, 2015

(54) REMOTELY POWERED REMOTELY ADJUSTABLE GASTRIC BAND SYSTEM

(71) Applicant: Apollo Endosurgery, Inc., Austin, TX (US)

(72) Inventors: Pierre Fridez, Froideville (CH); Alain Jordan, Denges (CH); Jean-Charles Montavon, Lausanne (CH); Tiago Bertolote, Geneva (CH); Laurent Mosimann, Commugry (CH); Xavier Raemy, Belmont-sur-Lausanne (CH); Razack Osseni, Lausanne (CH); Joel Bonny, Morges (CH)

(73) Assignee: Apollo Endosurgery, Inc., Austin, TX (US)

( * ) Notice: Subject to any disclaimer, the term of this patent is extended or adjusted under 35 U.S.C. 154(b) by 98 days.

(21) Appl. No.: 14/075,964

(22) Filed: Nov. 8, 2013

(65) Prior Publication Data

US 2014/0073848 A1  Mar. 13, 2014

Related U.S. Application Data

(63) Continuation of application No. 13/076,139, filed on Mar. 30, 2011, now abandoned.

(60) Provisional application No. 61/343,571, filed on Apr. 30, 2010.

(51) Int. Cl.
*A61F 5/00* (2006.01)
*H02J 5/00* (2006.01)
*H04B 5/00* (2006.01)

(52) U.S. Cl.
CPC ............. *A61F 5/0059* (2013.01); *H02J 5/005* (2013.01); *H04B 5/0031* (2013.01); *H04B 5/0037* (2013.01)

(58) Field of Classification Search
CPC ..... A61F 5/0003; A61F 5/0013; A61F 5/003; A61F 5/005; A61F 5/0053; A61F 5/0059; A61F 5/0066

USPC ............................................................ 600/37
See application file for complete search history.

(56) References Cited

U.S. PATENT DOCUMENTS 1,174,814 A   3/1916  Brennan
1,702,974 A   2/1929  MacDonald
(Continued)

FOREIGN PATENT DOCUMENTS

CA   949965     6/1974
CN   1250382 A  4/2000
(Continued)

OTHER PUBLICATIONS

'Innovative medical devices and implants'; LGSP medical futures, p. 5.
(Continued)

*Primary Examiner* — Charles A Marmor, II
*Assistant Examiner* — Thaddeus Cox
(74) *Attorney, Agent, or Firm* — Gordon & Jacobson, P.C.

(57) ABSTRACT

A remotely adjustable remotely power gastric band system may include a control device, an implant electronic device, and an implantable gastric band. The control device may telemetrically power and communicate with the implant electronic device, which may be used for adjusting the diameter of the implantable gastric band. The implant electronic device may store the gastric band adjustment history records of a patient and regulate the power received from the control device. To improve transmission efficiency, the implant electronic device may adopt a double modulation scheme for communicating with the control device. Furthermore, the implant electronic device may detect and resolve motor blockage issues related to the implantable gastric band.

7 Claims, 70 Drawing Sheets

(56) References Cited

U.S. PATENT DOCUMENTS

| | | |
|---|---|---|
| 1,830,947 A | 11/1931 | Klingel |
| 1,999,683 A | 4/1935 | Borresen |
| 2,163,048 A | 6/1939 | McKee |
| 2,339,138 A | 1/1944 | Black |
| 2,405,667 A | 8/1946 | Andrew |
| 2,438,231 A | 3/1948 | Schultz |
| 2,635,907 A | 4/1953 | Heimbuch |
| 2,714,469 A | 8/1955 | Carlson |
| 2,936,980 A | 5/1960 | Rapata |
| 3,059,645 A | 10/1962 | Hasbrouck |
| 3,189,961 A | 6/1965 | Heller |
| 3,569,660 A | 3/1971 | Houldcroft |
| 3,587,115 A | 6/1971 | Shiley |
| 3,596,660 A | 8/1971 | Melone |
| 3,667,081 A | 6/1972 | Burger |
| 3,688,764 A | 9/1972 | Reed |
| 3,719,973 A | 3/1973 | Bell |
| 3,731,352 A | 5/1973 | Okamoto |
| 3,840,018 A | 10/1974 | Heifetz |
| 3,919,724 A | 11/1975 | Sanders |
| 3,955,834 A | 5/1976 | Ahlrot |
| 3,958,562 A | 5/1976 | Hakim |
| 3,971,376 A | 7/1976 | Wichterle |
| 4,019,499 A | 4/1977 | Fitzgerald |
| 4,053,176 A | 10/1977 | Hilbush |
| 4,117,727 A | 10/1978 | Friswell |
| 4,118,805 A | 10/1978 | Reimels |
| 4,133,315 A | 1/1979 | Berman |
| 4,151,835 A | 5/1979 | Copeland |
| 4,157,713 A | 6/1979 | Clarey |
| 4,161,943 A | 7/1979 | Nogier |
| 4,164,943 A | 8/1979 | Hill |
| 4,176,412 A | 12/1979 | Peterson |
| 4,190,040 A | 2/1980 | Schulte |
| 4,233,992 A | 11/1980 | Bisping |
| 4,236,521 A | 12/1980 | Lauterjung |
| 4,265,252 A | 5/1981 | Chubbuck |
| 4,271,827 A | 6/1981 | Angelchik |
| 4,286,584 A | 9/1981 | Sampson |
| 4,299,012 A | 11/1981 | Oetiker |
| 4,370,982 A | 2/1983 | Reilly |
| 4,399,809 A | 8/1983 | Baro |
| 4,408,597 A | 10/1983 | Tenney |
| 4,413,985 A | 11/1983 | Wellner |
| 4,417,567 A | 11/1983 | Trick |
| 4,424,208 A | 1/1984 | Wallace |
| 4,430,392 A | 2/1984 | Kelley |
| 4,442,153 A | 4/1984 | Meltsch |
| 4,474,572 A | 10/1984 | McNaughton |
| 4,485,805 A | 12/1984 | Foster |
| 4,492,004 A | 1/1985 | Oetiker |
| 4,502,335 A | 3/1985 | Wamstad |
| 4,543,088 A | 9/1985 | Bootman |
| 4,545,367 A | 10/1985 | Tucci |
| 4,551,862 A | 11/1985 | Haber |
| 4,557,722 A | 12/1985 | Harris |
| 4,558,699 A | 12/1985 | Bashour |
| 4,559,699 A | 12/1985 | Owen |
| 4,569,675 A | 2/1986 | Prosl |
| 4,582,640 A | 4/1986 | Smestad |
| 4,582,865 A | 4/1986 | Balazs |
| 4,588,394 A | 5/1986 | Schulte |
| 4,592,339 A | 6/1986 | Kuzmak |
| 4,592,355 A | 6/1986 | Antebi |
| 4,598,699 A | 7/1986 | Garren |
| 4,601,713 A | 7/1986 | Fuqua |
| 4,603,699 A | 8/1986 | Himpens |
| 4,607,618 A | 8/1986 | Angelchik |
| 4,634,427 A | 1/1987 | Hannula |
| 4,636,213 A | 1/1987 | Pakiam |
| 4,655,765 A | 4/1987 | Swift |
| 4,671,351 A | 6/1987 | Rappe |
| 4,673,394 A | 6/1987 | Fenton |
| 4,692,146 A | 9/1987 | Hilger |
| 4,693,695 A | 9/1987 | Cheng |
| 4,694,827 A | 9/1987 | Weiner |
| 4,696,288 A | 9/1987 | Kuzmak |
| 4,704,103 A | 11/1987 | Stoeber |
| 4,708,140 A | 11/1987 | Baron |
| 4,710,174 A | 12/1987 | Moden |
| 4,716,154 A | 12/1987 | Maelson |
| 4,723,547 A | 2/1988 | Kullas |
| 4,738,657 A | 4/1988 | Hancock |
| 4,753,086 A | 6/1988 | Schmidt |
| 4,760,837 A | 8/1988 | Petit |
| 4,767,410 A | 8/1988 | Moden |
| 4,772,270 A | 9/1988 | Wiita |
| 4,778,452 A | 10/1988 | Moden |
| 4,781,680 A | 11/1988 | Redmond |
| 4,796,641 A | 1/1989 | Mills |
| 4,802,885 A | 2/1989 | Weeks |
| 4,803,075 A | 2/1989 | Wallace |
| 4,804,054 A | 2/1989 | Howson |
| 4,832,054 A | 5/1989 | Bark |
| 4,840,615 A | 6/1989 | Hancock |
| 4,850,227 A | 7/1989 | Luettgen |
| 4,858,619 A | 8/1989 | Toth |
| 4,858,623 A | 8/1989 | Bradshaw |
| 4,861,341 A | 8/1989 | Woodburn |
| 4,872,483 A | 10/1989 | Shah |
| 4,881,939 A | 11/1989 | Newman |
| 4,883,467 A | 11/1989 | Franetzki |
| 4,886,501 A | 12/1989 | Johnston |
| 4,886,787 A | 12/1989 | de Belder et al. |
| 4,896,787 A | 1/1990 | Delamour |
| 4,902,278 A | 2/1990 | Maget |
| 4,904,241 A | 2/1990 | Bark |
| 4,913,702 A | 4/1990 | Yum |
| 4,915,690 A | 4/1990 | Cone |
| 4,919,650 A | 4/1990 | Feingold |
| 4,925,446 A | 5/1990 | Garay |
| 4,929,230 A | 5/1990 | Pfleger |
| 4,929,236 A | 5/1990 | Sampson |
| 4,930,535 A | 6/1990 | Rinehold |
| 4,944,659 A | 7/1990 | Labbe |
| 4,958,791 A | 9/1990 | Nakamura |
| 4,966,588 A | 10/1990 | Rayman |
| 4,967,755 A | 11/1990 | Pohndorf |
| 4,969,899 A | 11/1990 | Cox |
| 4,978,338 A | 12/1990 | Melsky |
| 4,989,756 A | 2/1991 | Kagamihara |
| 4,994,019 A | 2/1991 | Fernandez |
| 5,006,115 A | 4/1991 | McDonald |
| 5,013,298 A | 5/1991 | Moden |
| 5,026,344 A | 6/1991 | Dijkstra |
| 5,041,098 A | 8/1991 | Loiterman |
| 5,045,060 A | 9/1991 | Melsky |
| 5,074,868 A | 12/1991 | Kuzmak |
| 5,084,061 A | 1/1992 | Gau |
| 5,089,019 A | 2/1992 | Grandjean |
| 5,090,954 A | 2/1992 | Geary |
| 5,091,171 A | 2/1992 | Yu |
| 5,092,897 A | 3/1992 | Forte |
| 5,094,244 A | 3/1992 | Callahan |
| 5,108,377 A | 4/1992 | Cone |
| 5,120,313 A | 6/1992 | Elftman |
| 5,125,408 A | 6/1992 | Basser |
| 5,133,753 A | 7/1992 | Bark |
| 5,137,529 A | 8/1992 | Watson |
| 5,143,724 A | 9/1992 | Leshchiner |
| 5,147,483 A | 9/1992 | Melsky |
| 5,152,747 A | 10/1992 | Olivier |
| 5,152,770 A | 10/1992 | Bengmark |
| 5,160,338 A | 11/1992 | Vincent |
| 5,167,638 A | 12/1992 | Felix |
| 5,171,228 A | 12/1992 | McDonald |
| 5,185,003 A | 2/1993 | Brethauer |
| 5,188,609 A | 2/1993 | Bayless |
| 5,207,644 A | 5/1993 | Strecker |
| 5,211,371 A | 5/1993 | Coffee |
| 5,213,574 A | 5/1993 | Tucker |
| 5,224,494 A | 7/1993 | Enhorning |
| 5,226,429 A | 7/1993 | Kuzmak |
| 5,226,894 A | 7/1993 | Haber |

(56) References Cited

U.S. PATENT DOCUMENTS

| | | |
|---|---|---|
| 5,246,456 A | 9/1993 | Wilkinson |
| 5,246,698 A | 9/1993 | Leshchiner |
| 5,250,026 A | 10/1993 | Ehrlich |
| 5,259,399 A | 11/1993 | Brown |
| 5,273,537 A | 12/1993 | Haskvitz |
| 5,277,333 A | 1/1994 | Shimano |
| 5,281,205 A | 1/1994 | McPherson |
| 5,284,479 A | 2/1994 | de Jong |
| 5,289,817 A | 3/1994 | Williams |
| 5,300,120 A | 4/1994 | Knapp |
| 5,318,533 A | 6/1994 | Adams |
| 5,318,545 A | 6/1994 | Tucker |
| 5,325,873 A | 7/1994 | Hirschi |
| 5,326,349 A | 7/1994 | Baraff |
| 5,336,194 A | 8/1994 | Polaschegg |
| 5,337,747 A | 8/1994 | Neftel |
| 5,356,883 A | 10/1994 | Kuo |
| 5,360,407 A | 11/1994 | Leonard |
| 5,360,445 A | 11/1994 | Goldowsky |
| 5,368,040 A | 11/1994 | Carney |
| 5,383,858 A | 1/1995 | Reilly |
| 5,387,192 A | 2/1995 | Glantz |
| 5,391,156 A | 2/1995 | Hildwein |
| 5,391,164 A | 2/1995 | Giampapa |
| 5,399,351 A | 3/1995 | Leshchiner |
| 5,425,716 A | 6/1995 | Kawasaki |
| 5,449,363 A | 9/1995 | Brust |
| 5,449,368 A | 9/1995 | Kuzmak |
| 5,458,568 A | 10/1995 | Racchini |
| 5,476,460 A | 12/1995 | Montalvo |
| 5,496,312 A | 3/1996 | Klicek |
| 5,496,313 A | 3/1996 | Gentelia |
| 5,509,888 A | 4/1996 | Miller |
| 5,514,174 A | 5/1996 | Heil |
| 5,527,340 A | 6/1996 | Vogel |
| 5,531,716 A | 7/1996 | Luzio |
| 5,535,752 A | 7/1996 | Halperin |
| 5,540,648 A | 7/1996 | Yoon |
| 5,554,113 A | 9/1996 | Novak |
| 5,556,388 A | 9/1996 | Johlin |
| 5,558,641 A | 9/1996 | Glantz |
| 5,562,617 A | 10/1996 | Finch |
| 5,562,714 A | 10/1996 | Grevious |
| 5,569,839 A | 10/1996 | Ajot |
| 5,571,104 A | 11/1996 | Li |
| 5,575,777 A | 11/1996 | Cover |
| 5,601,604 A | 2/1997 | Vincent |
| 5,607,418 A | 3/1997 | Arzbaecher |
| 5,633,001 A | 5/1997 | Ågerup |
| 5,637,102 A | 6/1997 | Tolkoff |
| 5,649,546 A | 7/1997 | Steinbeck |
| 5,653,718 A | 8/1997 | Yoon |
| 5,653,755 A | 8/1997 | Ledergerber |
| 5,658,298 A | 8/1997 | Vincent |
| 5,674,288 A | 10/1997 | Knapp |
| 5,674,397 A | 10/1997 | Pawlak |
| 5,676,162 A | 10/1997 | Larson |
| 5,681,284 A | 10/1997 | Herskowitz |
| 5,683,447 A | 11/1997 | Bush |
| 5,688,237 A | 11/1997 | Rozga |
| 5,693,014 A | 12/1997 | Abele |
| 5,695,490 A | 12/1997 | Flaherty |
| 5,695,504 A | 12/1997 | Gifford |
| 5,704,893 A | 1/1998 | Timm |
| 5,713,911 A | 2/1998 | Racenet |
| 5,716,342 A | 2/1998 | Dumbraveanu |
| 5,718,682 A | 2/1998 | Tucker |
| 5,722,957 A | 3/1998 | Steinbach |
| 5,725,507 A | 3/1998 | Petrick |
| 5,725,578 A | 3/1998 | Knapp |
| 5,733,257 A | 3/1998 | Sternby |
| 5,741,232 A | 4/1998 | Reilly |
| 5,748,200 A | 5/1998 | Funahashi |
| 5,758,667 A | 6/1998 | Slettenmark |
| 5,759,015 A | 6/1998 | Van Lintel et al. |
| 5,766,232 A | 6/1998 | Grevious |
| 5,769,877 A | 6/1998 | Barreras |
| 5,785,295 A | 7/1998 | Tsai |
| 5,795,333 A | 8/1998 | Reilly |
| 5,808,203 A | 9/1998 | Nolan |
| 5,810,735 A | 9/1998 | Halperin |
| 5,814,019 A | 9/1998 | Steinbach |
| 5,817,113 A | 10/1998 | Gifford |
| 5,819,749 A | 10/1998 | Lee |
| 5,827,529 A | 10/1998 | Ono |
| 5,833,603 A | 11/1998 | Kovacs |
| 5,833,654 A | 11/1998 | Powers |
| 5,833,698 A | 11/1998 | Hinchliffe |
| 5,843,033 A | 12/1998 | Ropiak |
| 5,855,609 A | 1/1999 | Knapp |
| 5,861,014 A | 1/1999 | Familoni |
| RE36,176 E | 3/1999 | Kuzmak |
| 5,883,654 A | 3/1999 | Katsuyama |
| 5,886,042 A | 3/1999 | Yu |
| 5,891,089 A | 4/1999 | Katz |
| 5,902,598 A | 5/1999 | Chen |
| 5,904,697 A | 5/1999 | Gifford |
| 5,906,596 A | 5/1999 | Tallarida |
| 5,910,149 A | 6/1999 | Kuzmak |
| 5,911,704 A | 6/1999 | Humes |
| 5,923,001 A | 7/1999 | Morris |
| 5,928,195 A | 7/1999 | Malamud |
| 5,931,829 A | 8/1999 | Burbank |
| 5,932,460 A | 8/1999 | Mills |
| 5,935,083 A | 8/1999 | Williams |
| 5,938,669 A | 8/1999 | Klaiber |
| 5,944,696 A | 8/1999 | Bayless |
| 5,944,751 A | 8/1999 | Laub |
| 5,951,512 A | 9/1999 | Dalton |
| 5,977,431 A | 11/1999 | Knapp |
| 5,993,473 A | 11/1999 | Chan |
| 5,997,502 A | 12/1999 | Reilly |
| 6,010,511 A | 1/2000 | Murphy |
| 6,013,679 A | 1/2000 | Kuo |
| 6,024,340 A | 2/2000 | Lazarus |
| 6,024,704 A | 2/2000 | Meador |
| 6,030,369 A | 2/2000 | Engelson |
| 6,039,712 A | 3/2000 | Fogarty |
| 6,042,345 A | 3/2000 | Bishop |
| 6,048,309 A | 4/2000 | Flom |
| 6,067,991 A | 5/2000 | Forsell |
| 6,074,341 A | 6/2000 | Anderson |
| 6,074,378 A | 6/2000 | Mouri |
| 6,083,249 A | 7/2000 | Familoni |
| 6,090,064 A | 7/2000 | Reilly |
| 6,090,066 A | 7/2000 | Schnell |
| 6,090,131 A | 7/2000 | Daley |
| 6,098,405 A | 8/2000 | Miyata |
| 6,102,678 A | 8/2000 | Peclat |
| 6,102,897 A | 8/2000 | Lang |
| 6,102,922 A | 8/2000 | Jakobsson |
| 6,117,086 A | 9/2000 | Shulze |
| 6,123,700 A | 9/2000 | Mills |
| 6,129,668 A | 10/2000 | Haynor |
| 6,152,885 A | 11/2000 | Taepke |
| 6,152,922 A | 11/2000 | Ouchi |
| 6,164,933 A | 12/2000 | Tani |
| 6,171,252 B1 | 1/2001 | Roberts |
| 6,171,321 B1 | 1/2001 | Gifford |
| 6,179,569 B1 | 1/2001 | Kojima |
| 6,183,449 B1 | 2/2001 | Sibbitt |
| 6,193,734 B1 | 2/2001 | Bolduc |
| 6,203,523 B1 | 3/2001 | Haller |
| 6,210,345 B1 | 4/2001 | Van Brunt |
| 6,210,347 B1 | 4/2001 | Forsell |
| 6,213,973 B1 | 4/2001 | Eliasen |
| 6,221,024 B1 | 4/2001 | Miesel |
| 6,224,857 B1 | 5/2001 | Romeo |
| 6,234,973 B1 | 5/2001 | Meador |
| 6,258,079 B1 | 7/2001 | Burbank |
| 6,264,676 B1 | 7/2001 | Gellman |
| 6,270,475 B1 | 8/2001 | Bestetti |
| 6,283,949 B1 | 9/2001 | Roorda |
| 6,290,575 B1 | 9/2001 | Shipp |

(56) References Cited

U.S. PATENT DOCUMENTS

| | | |
|---|---|---|
| 6,305,381 B1 | 10/2001 | Weijand |
| 6,306,088 B1 | 10/2001 | Krausman |
| 6,306,116 B1 | 10/2001 | Hancock |
| 6,321,124 B1 | 11/2001 | Cigaina |
| 6,327,503 B1 | 12/2001 | Familoni |
| 6,349,740 B1 | 2/2002 | Cho |
| 6,371,942 B1 | 4/2002 | Schwartz |
| 6,371,965 B2 | 4/2002 | Gifford |
| 6,387,105 B1 | 5/2002 | Gifford |
| 6,402,717 B1 | 6/2002 | Reilly |
| 6,402,718 B1 | 6/2002 | Reilly |
| 6,417,750 B1 | 7/2002 | Sohn |
| 6,419,696 B1 | 7/2002 | Ortiz |
| 6,432,040 B1 | 8/2002 | Meah |
| 6,439,539 B1 | 8/2002 | Powell |
| 6,443,957 B1 | 9/2002 | Addis |
| 6,443,965 B1 | 9/2002 | Gifford |
| 6,450,173 B1 | 9/2002 | Forsell |
| 6,450,946 B1 | 9/2002 | Forsell |
| 6,451,034 B1 | 9/2002 | Gifford |
| 6,453,907 B1 | 9/2002 | Forsell |
| 6,454,699 B1 | 9/2002 | Forsell |
| 6,454,700 B1 | 9/2002 | Forsell |
| 6,454,701 B1 | 9/2002 | Forsell |
| 6,454,785 B2 | 9/2002 | De Hoyos Garza |
| 6,457,801 B1 | 10/2002 | Fish |
| 6,459,917 B1 | 10/2002 | Gowda |
| 6,460,543 B1 | 10/2002 | Forsell |
| 6,461,293 B1 | 10/2002 | Forsell |
| 6,463,935 B1 | 10/2002 | Forsell |
| 6,464,628 B1 | 10/2002 | Forsell |
| 6,470,213 B1 | 10/2002 | Alley |
| 6,470,892 B1 | 10/2002 | Forsell |
| 6,474,584 B2 | 11/2002 | Ekich |
| 6,475,136 B1 | 11/2002 | Forsell |
| 6,475,192 B1 | 11/2002 | Reilly |
| 6,478,783 B1 | 11/2002 | Moorehead |
| 6,485,496 B1 | 11/2002 | Suyker |
| 6,491,704 B2 | 12/2002 | Gifford |
| 6,491,705 B2 | 12/2002 | Gifford |
| 6,503,264 B1 | 1/2003 | Birk |
| 6,511,490 B2 | 1/2003 | Robert |
| 6,517,556 B1 | 2/2003 | Monassevitch |
| 6,527,701 B1 | 3/2003 | Sayet |
| 6,547,801 B1 | 4/2003 | Dargent |
| 6,562,008 B1 | 5/2003 | Reilly |
| 6,565,582 B2 | 5/2003 | Gifford |
| 6,572,587 B2 | 6/2003 | Lerman |
| 6,579,301 B1 | 6/2003 | Bales |
| 6,589,184 B2 | 7/2003 | Noren |
| 6,601,604 B1 | 8/2003 | Cooper |
| 6,615,084 B1 | 9/2003 | Cigaina |
| 6,622,043 B1 | 9/2003 | Kraus |
| 6,629,776 B2 | 10/2003 | Bell |
| 6,632,239 B2 | 10/2003 | Snyder |
| 6,635,014 B2 | 10/2003 | Starkweather |
| 6,635,020 B2 | 10/2003 | Tripp |
| 6,636,769 B2 | 10/2003 | Govari |
| 6,638,231 B2 | 10/2003 | Govari |
| 6,638,258 B2 | 10/2003 | Schwartz |
| 6,646,628 B2 | 11/2003 | Shirochi |
| 6,647,298 B2 | 11/2003 | Abrahamson |
| 6,647,299 B2 | 11/2003 | Bourget |
| 6,648,823 B2 | 11/2003 | Thompson |
| 6,648,849 B2 | 11/2003 | Tenhuisen |
| 6,658,300 B2 | 12/2003 | Govari |
| 6,664,897 B2 | 12/2003 | Pape |
| 6,665,558 B2 | 12/2003 | Kalgren |
| 6,666,821 B2 | 12/2003 | Keimel |
| 6,666,845 B2 | 12/2003 | Hooper |
| 6,667,725 B1 | 12/2003 | Simons |
| 6,671,550 B2 | 12/2003 | Iaizzo |
| 6,675,049 B2 | 1/2004 | Thompson |
| 6,676,674 B1 | 1/2004 | Dudai |
| 6,681,135 B1 | 1/2004 | Davis |
| 6,685,668 B1 | 2/2004 | Cho |
| 6,689,100 B2 | 2/2004 | Connelly |
| 6,691,047 B1 | 2/2004 | Fredericks |
| 6,704,602 B2 | 3/2004 | Berg |
| 6,715,731 B1 | 4/2004 | Post |
| 6,723,053 B2 | 4/2004 | Ackerman |
| 6,725,726 B1 | 4/2004 | Adolfs |
| 6,729,600 B2 | 5/2004 | Mattes |
| 6,733,478 B2 | 5/2004 | Reilly |
| 6,733,512 B2 | 5/2004 | McGhan |
| 6,733,513 B2 | 5/2004 | Boyle |
| 6,733,519 B2 | 5/2004 | Lashinski |
| 6,746,460 B2 | 6/2004 | Gannoe |
| 6,754,527 B2 | 6/2004 | Stroebel |
| 6,778,927 B2 | 8/2004 | Cha |
| 6,792,309 B1 | 9/2004 | Noren |
| 6,799,698 B2 | 10/2004 | Ono |
| 6,808,513 B2 | 10/2004 | Reilly |
| 6,810,880 B1 | 11/2004 | Jennings |
| 6,811,136 B2 | 11/2004 | Eberhardt |
| 6,813,964 B1 | 11/2004 | Clark |
| 6,820,651 B2 | 11/2004 | Seuret |
| 6,834,201 B2 | 12/2004 | Gillies |
| 6,860,857 B2 | 3/2005 | Noren |
| 6,871,090 B1 | 3/2005 | He |
| 6,889,086 B2 | 5/2005 | Mass |
| 6,915,162 B2 | 7/2005 | Noren |
| 6,916,326 B2 | 7/2005 | Benchetrit |
| 6,921,267 B2 | 7/2005 | van Oostrom et al. |
| 6,929,631 B1 | 8/2005 | Brugger |
| 6,939,299 B1 | 9/2005 | Petersen |
| 6,940,467 B2 | 9/2005 | Fischer |
| 6,953,444 B2 | 10/2005 | Rosenberg |
| 6,964,204 B2 | 11/2005 | Clark |
| 6,966,875 B1 | 11/2005 | Longobardi |
| 6,994,095 B2 | 2/2006 | Burnett |
| 6,997,914 B2 | 2/2006 | Smith |
| 7,017,583 B2 | 3/2006 | Forsell |
| 7,017,883 B2 | 3/2006 | Bayer |
| 7,020,531 B1 | 3/2006 | Colliou |
| 7,021,147 B1 | 4/2006 | Subramanian |
| 7,027,935 B2 | 4/2006 | Shimase |
| 7,037,344 B2 | 5/2006 | Kagan |
| 7,040,349 B2 | 5/2006 | Moler |
| 7,044,933 B2 | 5/2006 | VanDiver |
| 7,048,519 B2 | 5/2006 | Fong |
| 7,054,690 B2 | 5/2006 | Imran |
| 7,056,286 B2 | 6/2006 | Ravenscroft |
| 7,056,305 B2 | 6/2006 | Garza |
| 7,058,434 B2 | 6/2006 | Wang |
| 7,060,080 B2 | 6/2006 | Bachmann |
| 7,063,669 B2 | 6/2006 | Brawner |
| 7,066,486 B2 | 6/2006 | Lee |
| 7,073,387 B2 | 7/2006 | Zdeblick |
| 7,082,843 B2 | 8/2006 | Clark |
| 7,118,526 B2 | 10/2006 | Egle |
| 7,119,062 B1 | 10/2006 | Alvis |
| 7,128,750 B1 | 10/2006 | Stergiopulos |
| 7,131,945 B2 | 11/2006 | Fink |
| 7,144,400 B2 | 12/2006 | Byrum |
| 7,149,587 B2 | 12/2006 | Wardle |
| 7,172,607 B2 | 2/2007 | Hoefle |
| 7,177,693 B2 | 2/2007 | Starkebaum |
| 7,191,007 B2 | 3/2007 | Desai |
| 7,191,011 B2 | 3/2007 | Cantlon |
| 7,195,610 B1 | 3/2007 | Flachbart |
| 7,195,774 B2 | 3/2007 | Carvalho |
| 7,198,250 B2 | 4/2007 | East |
| 7,204,821 B1 | 4/2007 | Clare et al. |
| 7,206,637 B2 | 4/2007 | Salo |
| 7,214,233 B2 | 5/2007 | Gannoe |
| 7,223,239 B2 | 5/2007 | Schulze |
| 7,226,419 B2 | 6/2007 | Lane |
| 7,238,191 B2 | 7/2007 | Bachmann |
| 7,240,607 B2 | 7/2007 | Fish |
| 7,255,675 B2 | 8/2007 | Gertner |
| 7,261,003 B2 | 8/2007 | McDonald |
| 7,263,405 B2 | 8/2007 | Boveja |
| 7,267,645 B2 | 9/2007 | Anderson |

(56) References Cited

U.S. PATENT DOCUMENTS

| | | |
|---|---|---|
| 7,282,023 B2 | 10/2007 | Frering |
| 7,284,966 B2 | 10/2007 | Xu |
| 7,288,064 B2 | 10/2007 | Boustani |
| 7,297,103 B2 | 11/2007 | Jarsaillon |
| 7,299,082 B2 | 11/2007 | Feldman |
| 7,310,557 B2 | 12/2007 | Maschino |
| 7,311,503 B2 | 12/2007 | Van Lintel et al. |
| 7,311,716 B2 | 12/2007 | Byrum |
| 7,311,717 B2 | 12/2007 | Egle |
| 7,314,443 B2 | 1/2008 | Jordan |
| 7,314,598 B2 | 1/2008 | Nishino |
| 7,314,636 B2 | 1/2008 | Caseres |
| 7,338,433 B2 | 3/2008 | Coe |
| 7,340,306 B2 | 3/2008 | Barrett |
| 7,351,198 B2 | 4/2008 | Byrum |
| 7,351,226 B1 | 4/2008 | Herskowitz |
| 7,351,240 B2 | 4/2008 | Hassler |
| 7,353,747 B2 | 4/2008 | Swayze |
| 7,364,542 B2 | 4/2008 | Jambor |
| 7,366,571 B2 | 4/2008 | Armstrong |
| 7,367,340 B2 | 5/2008 | Nelson |
| 7,367,937 B2 | 5/2008 | Jambor |
| 7,374,557 B2 | 5/2008 | Conlon |
| 7,374,565 B2 | 5/2008 | Hassler |
| 7,390,294 B2 | 6/2008 | Hassler |
| 7,396,353 B2 | 7/2008 | Lorenzen |
| 7,413,547 B1 | 8/2008 | Lichtscheidl |
| 7,416,528 B2 | 8/2008 | Crawford |
| 7,437,951 B2 | 10/2008 | McDonald |
| 7,438,718 B2 | 10/2008 | Milliman |
| 7,445,614 B2 | 11/2008 | Bunodiere |
| 7,457,668 B2 | 11/2008 | Cancel |
| 7,468,038 B2 | 12/2008 | Ye |
| 7,481,763 B2 | 1/2009 | Hassler |
| 7,500,944 B2 | 3/2009 | Byrum |
| 7,502,649 B2 | 3/2009 | Ben-Haim |
| 7,507,221 B2 | 3/2009 | Neer |
| 7,510,530 B2 | 3/2009 | Hashimoto |
| 7,530,943 B2 | 5/2009 | Lechner |
| 7,553,298 B2 | 6/2009 | Hunt |
| 7,561,916 B2 | 7/2009 | Hunt |
| 7,580,746 B2 | 8/2009 | Gilkerson |
| 7,585,280 B2 | 9/2009 | Wilson |
| 7,591,185 B1 | 9/2009 | Mothilal |
| 7,593,777 B2 | 9/2009 | Gerber |
| 7,594,885 B2 | 9/2009 | Byrum |
| 7,599,743 B2 | 10/2009 | Hassler |
| 7,599,744 B2 | 10/2009 | Giordano |
| 7,601,162 B2 | 10/2009 | Hassler |
| 7,615,001 B2 | 11/2009 | Jambor |
| 7,618,365 B2 | 11/2009 | Jambor |
| 7,634,319 B2 | 12/2009 | Schneider |
| 7,651,483 B2 | 1/2010 | Byrum |
| 7,658,196 B2 | 2/2010 | Ferreri |
| 7,670,279 B2 | 3/2010 | Gertner |
| 7,699,770 B2 | 4/2010 | Hassler |
| 7,708,722 B2 | 5/2010 | Glenn |
| 7,712,470 B2 | 5/2010 | Gertner |
| 7,727,141 B2 | 6/2010 | Hassler |
| 7,727,143 B2 | 6/2010 | Birk |
| 7,741,476 B2 | 6/2010 | Lebreton |
| 7,758,493 B2 | 7/2010 | Gingras |
| 7,762,998 B2 | 7/2010 | Birk |
| 7,762,999 B2 | 7/2010 | Byrum |
| 7,763,039 B2 | 7/2010 | Ortiz |
| 7,766,815 B2 | 8/2010 | Ortiz |
| 7,771,439 B2 | 8/2010 | Griffiths |
| 7,775,215 B2 | 8/2010 | Hassler |
| 7,775,966 B2 | 8/2010 | Dlugos |
| 7,775,967 B2 | 8/2010 | Gertner |
| 7,780,590 B2 | 8/2010 | Birk |
| 7,794,386 B2 | 9/2010 | Brooks |
| 7,811,275 B2 | 10/2010 | Birk |
| 7,811,298 B2 | 10/2010 | Birk |
| 7,828,813 B2 | 11/2010 | Mouton |
| 7,832,407 B2 | 11/2010 | Gertner |
| 7,841,978 B2 | 11/2010 | Gertner |
| 7,844,342 B2 | 11/2010 | Dlugos |
| 7,850,660 B2 | 12/2010 | Uth |
| 7,862,502 B2 | 1/2011 | Pool |
| 7,862,546 B2 | 1/2011 | Conlon |
| 7,879,068 B2 | 2/2011 | Dlugos |
| 7,909,754 B2 | 3/2011 | Hassler |
| 7,909,804 B2 | 3/2011 | Stats |
| 7,927,270 B2 | 4/2011 | Dlugos |
| 7,951,067 B2 | 5/2011 | Byrum |
| 8,007,474 B2 | 8/2011 | Uth |
| 2001/0011543 A1 | 8/2001 | Forsell |
| 2002/0013545 A1 | 1/2002 | Soltanpour |
| 2002/0032435 A1 | 3/2002 | Levin |
| 2002/0038105 A1 | 3/2002 | Schwartz |
| 2002/0058969 A1 | 5/2002 | Noren |
| 2002/0072780 A1 | 6/2002 | Foley |
| 2002/0087147 A1 | 7/2002 | Hooper |
| 2002/0091395 A1 | 7/2002 | Gabbay |
| 2002/0095181 A1 | 7/2002 | Beyar |
| 2002/0098097 A1 | 7/2002 | Singh |
| 2002/0123716 A1 | 9/2002 | VanDiver |
| 2002/0133081 A1 | 9/2002 | Ackerman |
| 2002/0139208 A1 | 10/2002 | Yatskov |
| 2002/0152816 A1 | 10/2002 | Kim |
| 2002/0177811 A1 | 11/2002 | Reilly |
| 2002/0183765 A1 | 12/2002 | Adams |
| 2002/0198548 A1 | 12/2002 | Robert |
| 2003/0009123 A1 | 1/2003 | Brugger |
| 2003/0014003 A1 | 1/2003 | Gertner |
| 2003/0019498 A1 | 1/2003 | Forsell |
| 2003/0045775 A1 | 3/2003 | Forsell |
| 2003/0045800 A1 | 3/2003 | Noren |
| 2003/0045902 A1 | 3/2003 | Weadock |
| 2003/0045910 A1 | 3/2003 | Sorensen |
| 2003/0055311 A1 | 3/2003 | Neukermans |
| 2003/0060754 A1 | 3/2003 | Reilly |
| 2003/0060873 A1 | 3/2003 | Gertner |
| 2003/0066536 A1 | 4/2003 | Forsell |
| 2003/0073880 A1 | 4/2003 | Polsky |
| 2003/0078506 A1 | 4/2003 | Noren |
| 2003/0093157 A1 | 5/2003 | Casares |
| 2003/0100910 A1 | 5/2003 | Gifford |
| 2003/0106761 A1 | 6/2003 | Taylor |
| 2003/0120288 A1 | 6/2003 | Benchetrit |
| 2003/0139690 A1 | 7/2003 | Aebli |
| 2003/0148995 A1 | 8/2003 | Piron |
| 2003/0158564 A1 | 8/2003 | Benchetrit |
| 2003/0158569 A1 | 8/2003 | Wazne |
| 2003/0167022 A1 | 9/2003 | Dijkman |
| 2003/0171887 A1 | 9/2003 | Cha |
| 2003/0181890 A1 | 9/2003 | Schulze |
| 2003/0181917 A1 | 9/2003 | Gertner |
| 2003/0191433 A1 | 10/2003 | Prentiss |
| 2003/0208212 A1 | 11/2003 | Cigaina |
| 2003/0213285 A1 | 11/2003 | Wheeler |
| 2004/0000843 A1 | 1/2004 | East |
| 2004/0034479 A1 | 2/2004 | Shimase |
| 2004/0044332 A1 | 3/2004 | Stergiopulos |
| 2004/0049209 A1 | 3/2004 | Benchetrit |
| 2004/0059393 A1 | 3/2004 | Policker |
| 2004/0064110 A1 | 4/2004 | Forsell |
| 2004/0065615 A1 | 4/2004 | Hooper |
| 2004/0068233 A1 | 4/2004 | DiMatteo |
| 2004/0068847 A1 | 4/2004 | Belisle |
| 2004/0069714 A1 | 4/2004 | Ferguson |
| 2004/0082908 A1 | 4/2004 | Whitehurst |
| 2004/0111050 A1 | 6/2004 | Smedley |
| 2004/0133219 A1 | 7/2004 | Forsell |
| 2004/0147816 A1 | 7/2004 | Policker |
| 2004/0148034 A1 | 7/2004 | Kagan |
| 2004/0153106 A1 | 8/2004 | Dudai |
| 2004/0162595 A1 | 8/2004 | Foley |
| 2004/0171942 A1 | 9/2004 | Ackerman |
| 2004/0204692 A1 | 10/2004 | Eliasen |
| 2004/0215159 A1 | 10/2004 | Forsell |
| 2004/0230137 A1 | 11/2004 | Mouton |
| 2004/0235025 A1 | 11/2004 | Mori |

(56) References Cited

U.S. PATENT DOCUMENTS

| | | |
|---|---|---|
| 2004/0243057 A1 | 12/2004 | Vinten-Johansen |
| 2004/0250819 A1 | 12/2004 | Blair |
| 2004/0254533 A1 | 12/2004 | Schriver |
| 2004/0254536 A1 | 12/2004 | Conlon |
| 2004/0254537 A1 | 12/2004 | Conlon |
| 2004/0260229 A1 | 12/2004 | Meir |
| 2004/0260319 A1 | 12/2004 | Egle |
| 2004/0267288 A1 | 12/2004 | Byrum |
| 2004/0267291 A1 | 12/2004 | Byrum |
| 2004/0267292 A1 | 12/2004 | Byrum |
| 2004/0267293 A1 | 12/2004 | Byrum |
| 2004/0267377 A1 | 12/2004 | Egle |
| 2005/0002984 A1 | 1/2005 | Byrum |
| 2005/0010177 A1 | 1/2005 | Tsai |
| 2005/0038484 A1 | 2/2005 | Knudson |
| 2005/0038498 A1 | 2/2005 | Dubrow |
| 2005/0049578 A1 | 3/2005 | Tu |
| 2005/0055039 A1 | 3/2005 | Burnett |
| 2005/0070875 A1 | 3/2005 | Kulessa |
| 2005/0070934 A1 | 3/2005 | Tanaka |
| 2005/0070937 A1 | 3/2005 | Jambor |
| 2005/0085778 A1 | 4/2005 | Parks |
| 2005/0092093 A1 | 5/2005 | Kang |
| 2005/0100779 A1 | 5/2005 | Gertner |
| 2005/0104457 A1 | 5/2005 | Jordan |
| 2005/0119672 A1 | 6/2005 | Benchetrit |
| 2005/0119674 A1 | 6/2005 | Gingras |
| 2005/0131325 A1 | 6/2005 | Chen |
| 2005/0131352 A1 | 6/2005 | Conlon |
| 2005/0131383 A1 | 6/2005 | Chen |
| 2005/0131485 A1 | 6/2005 | Knudson |
| 2005/0136122 A1 | 6/2005 | Sadozai |
| 2005/0142152 A1 | 6/2005 | Leshchiner |
| 2005/0143765 A1 | 6/2005 | Bachmann |
| 2005/0143766 A1* | 6/2005 | Bachmann et al. ........... 606/158 |
| 2005/0148956 A1 | 7/2005 | Conlon |
| 2005/0149143 A1 | 7/2005 | Libbus |
| 2005/0154274 A1 | 7/2005 | Jarsaillon |
| 2005/0171568 A1 | 8/2005 | Duffy |
| 2005/0177111 A1 | 8/2005 | Ozeri |
| 2005/0183730 A1 | 8/2005 | Byrum |
| 2005/0190070 A1 | 9/2005 | Rudduck |
| 2005/0192531 A1 | 9/2005 | Birk |
| 2005/0192601 A1 | 9/2005 | Demarais |
| 2005/0192615 A1 | 9/2005 | Torre |
| 2005/0192629 A1 | 9/2005 | Saadat |
| 2005/0209573 A1 | 9/2005 | Brugger |
| 2005/0216042 A1 | 9/2005 | Gertner |
| 2005/0226936 A1 | 10/2005 | Agerup |
| 2005/0228415 A1 | 10/2005 | Gertner |
| 2005/0228504 A1 | 10/2005 | Demarais |
| 2005/0240155 A1 | 10/2005 | Conlon |
| 2005/0240156 A1 | 10/2005 | Conlon |
| 2005/0240279 A1 | 10/2005 | Kagan |
| 2005/0244288 A1 | 11/2005 | ONeill |
| 2005/0250979 A1 | 11/2005 | Coe |
| 2005/0251181 A1 | 11/2005 | Bachmann |
| 2005/0251182 A1 | 11/2005 | Bachmann |
| 2005/0261711 A1 | 11/2005 | Okada |
| 2005/0267406 A1 | 12/2005 | Hassler |
| 2005/0267500 A1 | 12/2005 | Hassler |
| 2005/0267533 A1 | 12/2005 | Gertner |
| 2005/0267595 A1 | 12/2005 | Chen |
| 2005/0267596 A1 | 12/2005 | Chen |
| 2005/0271729 A1 | 12/2005 | Wang |
| 2005/0277899 A1 | 12/2005 | Conlon |
| 2005/0283041 A1 | 12/2005 | Egle |
| 2005/0283118 A1 | 12/2005 | Uth |
| 2005/0283119 A1 | 12/2005 | Uth |
| 2005/0288739 A1* | 12/2005 | Hassler et al. ................. 607/61 |
| 2005/0288740 A1 | 12/2005 | Hassler |
| 2006/0009697 A1 | 1/2006 | Banet |
| 2006/0015138 A1 | 1/2006 | Gertner |
| 2006/0020278 A1 | 1/2006 | Burnett |
| 2006/0020298 A1 | 1/2006 | Camilleri |
| 2006/0025799 A1 | 2/2006 | Basu |
| 2006/0041183 A1 | 2/2006 | Massen |
| 2006/0069403 A1 | 3/2006 | Shalon |
| 2006/0074439 A1 | 4/2006 | Garner |
| 2006/0074473 A1 | 4/2006 | Gertner |
| 2006/0079766 A1 | 4/2006 | Neer |
| 2006/0079767 A1 | 4/2006 | Gibbs |
| 2006/0089571 A1 | 4/2006 | Gertner |
| 2006/0122147 A1 | 6/2006 | Wohlrab |
| 2006/0122578 A1 | 6/2006 | Lord |
| 2006/0142700 A1 | 6/2006 | Sobelman |
| 2006/0142790 A1 | 6/2006 | Gertner |
| 2006/0149161 A1 | 7/2006 | Wilson |
| 2006/0161186 A1 | 7/2006 | Hassler |
| 2006/0167531 A1 | 7/2006 | Gertner |
| 2006/0173238 A1 | 8/2006 | Starkebaum |
| 2006/0173423 A1 | 8/2006 | Conlon |
| 2006/0173424 A1 | 8/2006 | Conlon |
| 2006/0178555 A1 | 8/2006 | Bortolotti |
| 2006/0178647 A1 | 8/2006 | Stats |
| 2006/0178648 A1 | 8/2006 | Barron |
| 2006/0183967 A1 | 8/2006 | Lechner |
| 2006/0184141 A1 | 8/2006 | Smith |
| 2006/0189887 A1 | 8/2006 | Hassler |
| 2006/0189888 A1 | 8/2006 | Hassler |
| 2006/0189889 A1 | 8/2006 | Gertner |
| 2006/0190039 A1 | 8/2006 | Birk |
| 2006/0194758 A1 | 8/2006 | Lebreton |
| 2006/0195139 A1 | 8/2006 | Gertner |
| 2006/0197412 A1 | 9/2006 | Rasmussen |
| 2006/0199997 A1 | 9/2006 | Hassler |
| 2006/0211912 A1 | 9/2006 | Dlugos |
| 2006/0211913 A1 | 9/2006 | Dlugos |
| 2006/0211914 A1 | 9/2006 | Hassler |
| 2006/0212051 A1 | 9/2006 | Snyder |
| 2006/0212053 A1 | 9/2006 | Gertner |
| 2006/0217668 A1 | 9/2006 | Schulze |
| 2006/0217673 A1 | 9/2006 | Schulze |
| 2006/0229702 A1 | 10/2006 | Agnew |
| 2006/0235445 A1 | 10/2006 | Birk |
| 2006/0235448 A1 | 10/2006 | Roslin |
| 2006/0246137 A1 | 11/2006 | Hermitte |
| 2006/0247539 A1 | 11/2006 | Schugt |
| 2006/0247721 A1 | 11/2006 | Maschino |
| 2006/0247722 A1 | 11/2006 | Maschino |
| 2006/0252982 A1 | 11/2006 | Hassler |
| 2006/0252983 A1 | 11/2006 | Lembo |
| 2006/0257488 A1 | 11/2006 | Hubbard |
| 2006/0264699 A1 | 11/2006 | Gertner |
| 2006/0264762 A1 | 11/2006 | Starr |
| 2006/0266128 A1 | 11/2006 | Clark |
| 2006/0276812 A1 | 12/2006 | Hill |
| 2006/0293625 A1 | 12/2006 | Hunt |
| 2006/0293626 A1 | 12/2006 | Byrum |
| 2006/0293627 A1 | 12/2006 | Byrum |
| 2006/0293628 A1 | 12/2006 | Hunt |
| 2007/0001447 A1 | 1/2007 | Fennington |
| 2007/0010790 A1 | 1/2007 | Byrum |
| 2007/0015954 A1 | 1/2007 | Dlugos |
| 2007/0015955 A1 | 1/2007 | Tsonton |
| 2007/0015956 A1 | 1/2007 | Crawford |
| 2007/0016231 A1 | 1/2007 | Jambor |
| 2007/0016262 A1 | 1/2007 | Gross |
| 2007/0027356 A1 | 2/2007 | Ortiz |
| 2007/0027358 A1 | 2/2007 | Gertner |
| 2007/0038255 A1 | 2/2007 | Kieval |
| 2007/0044655 A1 | 3/2007 | Fish |
| 2007/0060959 A1 | 3/2007 | Salo |
| 2007/0073250 A1 | 3/2007 | Schneiter |
| 2007/0077292 A1 | 4/2007 | Pinsky |
| 2007/0078391 A1 | 4/2007 | Wortley |
| 2007/0078476 A1 | 4/2007 | Hull |
| 2007/0083224 A1 | 4/2007 | Hively |
| 2007/0088336 A1 | 4/2007 | Dalton |
| 2007/0088391 A1 | 4/2007 | McAlexander |
| 2007/0106153 A1 | 5/2007 | Neer |
| 2007/0125826 A1 | 6/2007 | Shelton |
| 2007/0129765 A1 | 6/2007 | Gilkerson |
| 2007/0135758 A1 | 6/2007 | Childers |

(56) References Cited

U.S. PATENT DOCUMENTS

| | | |
|---|---|---|
| 2007/0135829 A1 | 6/2007 | Paganon |
| 2007/0147170 A1 | 6/2007 | Hood |
| 2007/0149947 A1 | 6/2007 | Byrum |
| 2007/0156013 A1 | 7/2007 | Birk |
| 2007/0156248 A1 | 7/2007 | Marco |
| 2007/0158769 A1 | 7/2007 | You |
| 2007/0161958 A1 | 7/2007 | Glenn |
| 2007/0167672 A1 | 7/2007 | Dlugos |
| 2007/0167982 A1 | 7/2007 | Gertner |
| 2007/0173685 A1 | 7/2007 | Jambor |
| 2007/0173881 A1 | 7/2007 | Birk |
| 2007/0173888 A1 | 7/2007 | Gertner |
| 2007/0179335 A1 | 8/2007 | Gertner |
| 2007/0185373 A1 | 8/2007 | Tsonton |
| 2007/0185462 A1 | 8/2007 | Byrum |
| 2007/0191717 A1 | 8/2007 | Rosen |
| 2007/0205384 A1 | 9/2007 | Kurosawa |
| 2007/0208313 A1 | 9/2007 | Conlon |
| 2007/0213836 A1 | 9/2007 | Paganon |
| 2007/0213837 A1 | 9/2007 | Ferreri |
| 2007/0218083 A1 | 9/2007 | Brooks |
| 2007/0219510 A1 | 9/2007 | Zinn |
| 2007/0232848 A1 | 10/2007 | Forsell |
| 2007/0232849 A1 | 10/2007 | Gertner |
| 2007/0233170 A1 | 10/2007 | Gertner |
| 2007/0235083 A1 | 10/2007 | Dlugos |
| 2007/0243227 A1 | 10/2007 | Gertner |
| 2007/0250085 A1 | 10/2007 | Bachmann |
| 2007/0250086 A1 | 10/2007 | Wiley |
| 2007/0255165 A1 | 11/2007 | Uesugi |
| 2007/0255234 A1 | 11/2007 | Haase |
| 2007/0255335 A1 | 11/2007 | Herbert |
| 2007/0255336 A1 | 11/2007 | Herbert |
| 2007/0265598 A1 | 11/2007 | Karasik |
| 2007/0265645 A1 | 11/2007 | Birk |
| 2007/0265646 A1 | 11/2007 | McCoy |
| 2007/0265666 A1 | 11/2007 | Roberts |
| 2007/0282196 A1 | 12/2007 | Birk |
| 2007/0288033 A1 | 12/2007 | Murature |
| 2007/0293829 A1 | 12/2007 | Conlon |
| 2007/0298005 A1 | 12/2007 | Thibault |
| 2008/0004642 A1 | 1/2008 | Birk |
| 2008/0009680 A1 | 1/2008 | Hassler |
| 2008/0015406 A1 | 1/2008 | Dlugos |
| 2008/0015501 A1 | 1/2008 | Gertner |
| 2008/0027269 A1 | 1/2008 | Gertner |
| 2008/0027469 A1 | 1/2008 | Bachmann |
| 2008/0039772 A1 | 2/2008 | Chantriaux |
| 2008/0051722 A1 | 2/2008 | Ellsmere |
| 2008/0058632 A1 | 3/2008 | Tai |
| 2008/0071306 A1 | 3/2008 | Gertner |
| 2008/0097496 A1 | 4/2008 | Chang |
| 2008/0108862 A1 | 5/2008 | Jordan |
| 2008/0108896 A1 | 5/2008 | Gibbs |
| 2008/0108941 A1 | 5/2008 | Neer |
| 2008/0108943 A1 | 5/2008 | Wagner |
| 2008/0114302 A1 | 5/2008 | Neer |
| 2008/0114308 A1 | 5/2008 | di Palma et al. |
| 2008/0119798 A1 | 5/2008 | Chantriaux |
| 2008/0147002 A1 | 6/2008 | Gertner |
| 2008/0161717 A1 | 7/2008 | Gertner |
| 2008/0161875 A1 | 7/2008 | Stone |
| 2008/0166028 A1 | 7/2008 | Turek |
| 2008/0167647 A1 | 7/2008 | Gertner |
| 2008/0167648 A1 | 7/2008 | Gertner |
| 2008/0172072 A1 | 7/2008 | Pool |
| 2008/0172079 A1 | 7/2008 | Birk |
| 2008/0188766 A1 | 8/2008 | Gertner |
| 2008/0195092 A1 | 8/2008 | Kim |
| 2008/0208240 A1 | 8/2008 | Paz |
| 2008/0221598 A1 | 9/2008 | Dlugos |
| 2008/0243071 A1 | 10/2008 | Quijano |
| 2008/0243093 A1 | 10/2008 | Kalpin |
| 2008/0249806 A1 | 10/2008 | Dlugos |
| 2008/0250340 A1 | 10/2008 | Dlugos |
| 2008/0250341 A1 | 10/2008 | Dlugos |
| 2008/0255403 A1 | 10/2008 | Voegele |
| 2008/0255414 A1 | 10/2008 | Voegele |
| 2008/0255425 A1 | 10/2008 | Voegele |
| 2008/0255459 A1 | 10/2008 | Voegele |
| 2008/0255537 A1 | 10/2008 | Voegele |
| 2008/0255601 A1 | 10/2008 | Birk |
| 2008/0275294 A1 | 11/2008 | Gertner |
| 2008/0275295 A1 | 11/2008 | Gertner |
| 2008/0275484 A1 | 11/2008 | Gertner |
| 2008/0281347 A1 | 11/2008 | Gertner |
| 2008/0281412 A1 | 11/2008 | Smith |
| 2008/0287969 A1 | 11/2008 | Tsonton |
| 2008/0287974 A1 | 11/2008 | Widenhouse |
| 2008/0287976 A1 | 11/2008 | Weaner |
| 2008/0294097 A1 | 11/2008 | Kim |
| 2008/0300618 A1 | 12/2008 | Gertner |
| 2008/0306443 A1 | 12/2008 | Neer |
| 2008/0312553 A1 | 12/2008 | Timmons |
| 2008/0319435 A1 | 12/2008 | Rioux |
| 2009/0018608 A1 | 1/2009 | Schwartz |
| 2009/0048524 A1 | 2/2009 | Wildau |
| 2009/0054914 A1 | 2/2009 | Lechner |
| 2009/0062825 A1 | 3/2009 | Pool |
| 2009/0062826 A1 | 3/2009 | Steffen |
| 2009/0071258 A1 | 3/2009 | Kouda |
| 2009/0076466 A1 | 3/2009 | Quebbemann |
| 2009/0082757 A1 | 3/2009 | Rogers |
| 2009/0082793 A1 | 3/2009 | Birk |
| 2009/0093768 A1 | 4/2009 | Conlon |
| 2009/0099538 A1 | 4/2009 | Paganon |
| 2009/0105735 A1 | 4/2009 | Stam |
| 2009/0112308 A1 | 4/2009 | Kassem |
| 2009/0118572 A1 | 5/2009 | Lechner |
| 2009/0131968 A1 | 5/2009 | Birk |
| 2009/0149874 A1 | 6/2009 | Ortiz |
| 2009/0157106 A1 | 6/2009 | Marcotte |
| 2009/0157107 A1 | 6/2009 | Kierath |
| 2009/0157113 A1 | 6/2009 | Marcotte |
| 2009/0163803 A1 | 6/2009 | Neer |
| 2009/0171375 A1 | 7/2009 | Coe |
| 2009/0171378 A1 | 7/2009 | Coe |
| 2009/0171379 A1 | 7/2009 | Coe |
| 2009/0187202 A1 | 7/2009 | Ortiz |
| 2009/0188494 A1 | 7/2009 | Imai |
| 2009/0192404 A1 | 7/2009 | Ortiz |
| 2009/0192415 A1 | 7/2009 | Ortiz |
| 2009/0192533 A1 | 7/2009 | Dlugos |
| 2009/0192534 A1 | 7/2009 | Ortiz |
| 2009/0192541 A1 | 7/2009 | Ortiz |
| 2009/0198261 A1 | 8/2009 | Schweikert |
| 2009/0202387 A1 | 8/2009 | Dlugos |
| 2009/0204131 A1 | 8/2009 | Ortiz |
| 2009/0204132 A1 | 8/2009 | Ortiz |
| 2009/0204141 A1 | 8/2009 | Dlugos |
| 2009/0204179 A1 | 8/2009 | Dlugos |
| 2009/0209995 A1 | 8/2009 | Byrum |
| 2009/0216193 A1 | 8/2009 | Schriver |
| 2009/0216255 A1 | 8/2009 | Coe |
| 2009/0220176 A1 | 9/2009 | Fusco |
| 2009/0221974 A1 | 9/2009 | Paganon |
| 2009/0222028 A1 | 9/2009 | Dlugos |
| 2009/0222031 A1 | 9/2009 | Axelsson |
| 2009/0222065 A1 | 9/2009 | Dlugos |
| 2009/0227862 A1 | 9/2009 | Smith |
| 2009/0228028 A1 | 9/2009 | Coe |
| 2009/0228063 A1 | 9/2009 | Dlugos |
| 2009/0228072 A1 | 9/2009 | Coe |
| 2009/0241677 A1 | 10/2009 | Klees |
| 2009/0248125 A1 | 10/2009 | Brostrom |
| 2009/0248126 A1 | 10/2009 | Nippoldt |
| 2009/0254052 A1 | 10/2009 | Birk |
| 2009/0259190 A1 | 10/2009 | Birk |
| 2009/0259191 A1 | 10/2009 | Birk |
| 2009/0259246 A1 | 10/2009 | Eskaros |
| 2009/0264901 A1 | 10/2009 | Franklin |
| 2009/0270759 A1 | 10/2009 | Wilson |
| 2009/0270904 A1 | 10/2009 | Birk |
| 2009/0299216 A1 | 12/2009 | Chen |

(56) References Cited

U.S. PATENT DOCUMENTS

| | | |
|---|---|---|
| 2009/0299672 A1 | 12/2009 | Zhang |
| 2009/0306462 A1 | 12/2009 | Lechner |
| 2009/0308169 A1 | 12/2009 | Mothilal |
| 2009/0312635 A1 | 12/2009 | Shimchuk |
| 2009/0312785 A1 | 12/2009 | Stone |
| 2010/0010291 A1 | 1/2010 | Birk |
| 2010/0087843 A1 | 4/2010 | Bertolote |
| 2010/0099945 A1 | 4/2010 | Birk |
| 2010/0100079 A1 | 4/2010 | Berkcan |
| 2010/0114149 A1 | 5/2010 | Albrecht |
| 2010/0130941 A1 | 5/2010 | Conlon |
| 2010/0145378 A1 | 6/2010 | Gertner |
| 2010/0152532 A1 | 6/2010 | Marcotte |
| 2010/0168508 A1 | 7/2010 | Gertner |
| 2010/0168783 A1 | 7/2010 | Murature |
| 2010/0174307 A1 | 7/2010 | Birk |
| 2010/0185049 A1 | 7/2010 | Birk |
| 2010/0191265 A1 | 7/2010 | Lau |
| 2010/0191271 A1 | 7/2010 | Lau |
| 2010/0204647 A1 | 8/2010 | Gertner |
| 2010/0204723 A1 | 8/2010 | Gertner |
| 2010/0211085 A1 | 8/2010 | Uth |
| 2010/0217198 A1 | 8/2010 | Franklin |
| 2010/0217199 A1 | 8/2010 | Uth |
| 2010/0217200 A1 | 8/2010 | Uth |
| 2010/0226988 A1 | 9/2010 | Lebreton |
| 2010/0228080 A1 | 9/2010 | Tavori |
| 2010/0234682 A1 | 9/2010 | Gertner |
| 2010/0234808 A1 | 9/2010 | Uth |
| 2010/0249803 A1 | 9/2010 | Griffiths |
| 2010/0274194 A1 | 10/2010 | Sobelman |
| 2010/0280310 A1 | 11/2010 | Raven |
| 2010/0305397 A1 | 12/2010 | Birk |
| 2010/0312147 A1 | 12/2010 | Gertner |
| 2010/0324358 A1 | 12/2010 | Birk |
| 2010/0324359 A1 | 12/2010 | Birk |
| 2011/0082426 A1 | 4/2011 | Conlon |
| 2011/0130626 A1 | 6/2011 | Hassler |
| 2011/0201874 A1 | 8/2011 | Birk |

FOREIGN PATENT DOCUMENTS

| | | |
|---|---|---|
| CN | 1367670 A | 9/2002 |
| DE | 8804765 U1 | 5/1989 |
| DE | 3927001 | 2/1991 |
| DE | 4211045 | 10/1993 |
| DE | 4225524 | 2/1994 |
| DE | 19745654 | 4/1999 |
| DE | 19751791 | 5/1999 |
| DE | 19802615 A1 | 8/1999 |
| DE | 10020688 | 12/2000 |
| DE | 102007025312 A1 | 11/2008 |
| EP | 0119596 | 9/1984 |
| EP | 0230747 | 8/1987 |
| EP | 0343910 A2 | 11/1989 |
| EP | 0416250 | 3/1991 |
| EP | 0611561 | 8/1994 |
| EP | 0695558 | 2/1996 |
| EP | 0858814 | 8/1998 |
| EP | 0867197 | 9/1998 |
| EP | 0867808 | 11/1998 |
| EP | 1036545 A2 | 9/2000 |
| EP | 1057457 | 12/2000 |
| EP | 1072282 | 1/2001 |
| EP | 1105073 | 6/2001 |
| EP | 1346753 | 9/2003 |
| EP | 1396242 A1 | 3/2004 |
| EP | 1396243 A1 | 3/2004 |
| EP | 1488824 A1 | 12/2004 |
| EP | 1491167 | 12/2004 |
| EP | 1491168 | 12/2004 |
| EP | 1529502 | 5/2005 |
| EP | 1543861 A1 | 6/2005 |
| EP | 1547549 A2 | 6/2005 |
| EP | 1547643 | 6/2005 |
| EP | 1574189 | 9/2005 |
| EP | 1591140 A1 | 11/2005 |
| EP | 1600183 A1 | 11/2005 |
| EP | 1602346 A1 | 12/2005 |
| EP | 1704833 A2 | 9/2006 |
| EP | 1719480 A2 | 11/2006 |
| EP | 1754890 | 11/2006 |
| EP | 1736123 A1 | 12/2006 |
| EP | 1736194 A1 | 12/2006 |
| EP | 1736195 | 12/2006 |
| EP | 1736196 | 12/2006 |
| EP | 1736197 | 12/2006 |
| EP | 1736198 | 12/2006 |
| EP | 1736199 | 12/2006 |
| EP | 1736202 | 12/2006 |
| EP | 1743605 A1 | 1/2007 |
| EP | 1774929 A2 | 4/2007 |
| EP | 1829504 | 9/2007 |
| EP | 1829505 | 9/2007 |
| EP | 1829506 | 9/2007 |
| EP | 1870126 | 12/2007 |
| EP | 1949875 | 7/2008 |
| EP | 1967168 A2 | 9/2008 |
| EP | 1985263 | 10/2008 |
| EP | 1992315 | 11/2008 |
| EP | 1992316 A2 | 11/2008 |
| EP | 2070494 A1 | 6/2009 |
| EP | 2074970 A1 | 7/2009 |
| EP | 2074971 A1 | 7/2009 |
| EP | 2087862 A1 | 8/2009 |
| EP | 2095796 A1 | 9/2009 |
| EP | 2095797 A2 | 9/2009 |
| EP | 2095798 | 9/2009 |
| FR | 1566202 | 5/1969 |
| FR | 2688693 | 9/1993 |
| FR | 2740977 | 5/1997 |
| FR | 2769491 | 4/1999 |
| FR | 2783153 | 3/2000 |
| FR | 2797181 A1 | 2/2001 |
| FR | 2799118 | 4/2001 |
| FR | 2823663 A1 | 10/2002 |
| FR | 2851168 | 8/2004 |
| FR | 2852821 A1 | 10/2004 |
| FR | 2855744 A1 | 12/2004 |
| FR | 2916980 | 12/2008 |
| FR | 2921822 A1 | 4/2009 |
| FR | 2941617 A1 | 8/2010 |
| GB | 1174814 A | 12/1969 |
| GB | 2086792 A | 5/1982 |
| GB | 2090747 | 7/1982 |
| JP | 57171676 | 10/1982 |
| JP | S63279854 A | 11/1988 |
| JP | 1049572 A | 2/1989 |
| JP | 167309 | 4/1989 |
| JP | 2019147 | 1/1990 |
| JP | 2119877 | 5/1990 |
| JP | 2132104 | 11/1990 |
| JP | 3105702 | 11/1991 |
| JP | 8107934 | 4/1996 |
| JP | 63264078 | 10/1998 |
| JP | 11244395 | 9/1999 |
| JP | 2003526410 | 9/2003 |
| JP | 2005131380 | 5/2005 |
| JP | 2005334658 | 12/2005 |
| SE | 8503144 | 12/1986 |
| SU | 1823791 | 6/1991 |
| WO | 8600079 | 1/1986 |
| WO | 8600912 | 2/1986 |
| WO | 8911701 | 11/1989 |
| WO | 9000369 | 1/1990 |
| WO | 9220349 | 11/1992 |
| WO | 9402517 | 2/1994 |
| WO | 9422520 | 10/1994 |
| WO | 9633751 | 1/1996 |
| WO | 9640357 | 12/1996 |
| WO | 9701370 | 1/1997 |
| WO | 9835639 | 8/1998 |
| WO | 9835640 | 8/1998 |

(56) References Cited

FOREIGN PATENT DOCUMENTS

| | | |
|---|---|---|
| WO | 9920338 | 4/1999 |
| WO | 9926543 | 6/1999 |
| WO | 9934859 | 7/1999 |
| WO | 0000108 A1 | 1/2000 |
| WO | 0001428 | 1/2000 |
| WO | 0009047 A1 | 2/2000 |
| WO | 0009048 A1 | 2/2000 |
| WO | 0015158 A1 | 3/2000 |
| WO | 0033901 | 6/2000 |
| WO | 0066196 | 11/2000 |
| WO | 0110359 A1 | 2/2001 |
| WO | 0112078 A1 | 2/2001 |
| WO | 0141671 | 6/2001 |
| WO | 0147435 | 7/2001 |
| WO | 0147575 A2 | 7/2001 |
| WO | 0149245 A2 | 7/2001 |
| WO | 0152777 | 7/2001 |
| WO | 0166166 A2 | 9/2001 |
| WO | 0168007 | 9/2001 |
| WO | 0170131 | 9/2001 |
| WO | 0180926 | 11/2001 |
| WO | 0185071 | 11/2001 |
| WO | 0195813 A1 | 12/2001 |
| WO | 0205753 | 1/2002 |
| WO | 0209792 | 2/2002 |
| WO | 0219953 | 3/2002 |
| WO | 0226317 | 4/2002 |
| WO | 0235980 A2 | 5/2002 |
| WO | 02053093 | 7/2002 |
| WO | 02065948 | 8/2002 |
| WO | 02074381 | 9/2002 |
| WO | 02096326 | 12/2002 |
| WO | 03007782 | 1/2003 |
| WO | 03055419 | 7/2003 |
| WO | 03055420 | 7/2003 |
| WO | 03057092 | 7/2003 |
| WO | 03059215 | 7/2003 |
| WO | 03077191 | 9/2003 |
| WO | 03101352 A1 | 12/2003 |
| WO | 03105732 A1 | 12/2003 |
| WO | 2004014245 | 2/2004 |
| WO | 2004016971 | 2/2004 |
| WO | 2004019671 | 3/2004 |
| WO | 2004030536 | 4/2004 |
| WO | 2004108025 | 12/2004 |
| WO | 2004112563 A2 | 12/2004 |
| WO | 2005007231 | 1/2005 |
| WO | 2005007232 | 1/2005 |
| WO | 2005009305 | 2/2005 |
| WO | 2005037055 | 4/2005 |
| WO | 2005067994 | 7/2005 |
| WO | 2005072195 | 8/2005 |
| WO | 2005072627 | 8/2005 |
| WO | 2005087147 | 9/2005 |
| WO | 2005094447 | 10/2005 |
| WO | 2005112888 | 12/2005 |
| WO | 2006021695 | 3/2006 |
| WO | 2006049725 | 5/2006 |
| WO | 2006020370 | 6/2006 |
| WO | 2006063593 | 6/2006 |
| WO | 2006083885 | 8/2006 |
| WO | 2006090018 | 8/2006 |
| WO | 2006096686 | 9/2006 |
| WO | 2006108203 A2 | 10/2006 |
| WO | 2006118744 A1 | 11/2006 |
| WO | 2007067206 | 6/2007 |
| WO | 2007081304 A2 | 7/2007 |
| WO | 2007106727 A2 | 9/2007 |
| WO | 2007011086 | 10/2007 |
| WO | 2007114905 | 10/2007 |
| WO | 2007145638 | 12/2007 |
| WO | 2008063673 | 5/2008 |
| WO | 2008109300 A2 | 9/2008 |
| WO | 2008134755 | 11/2008 |
| WO | 2009007526 | 1/2009 |
| WO | 2009023247 | 2/2009 |
| WO | 2009050709 | 4/2009 |
| WO | 2009129474 A1 | 10/2009 |
| WO | 2009132127 A1 | 10/2009 |
| WO | 2009136126 A2 | 11/2009 |
| WO | 2010042062 A1 | 4/2010 |
| WO | 2010042493 | 4/2010 |

OTHER PUBLICATIONS

Acuna-Goycolea et al.; 'Mechanism of Neuropeptide Y, Peptide YY, and Pancreatic Polypeptide Inhibition of Identified Green Fluorescent Protein-Expressing GABA Neurons in the Hypothalamic Neuroendocrine Acruate Nucleus'; The Journal of Neuroscience; V. 25(32); pp. 7406-7419; Aug. 10, 2005.

Adrian et al.; 'Mechanism of Pancreatic Polypeptide Release in Man.' The Lancet; pp. 161-163; Jan. 22, 1977.

Anson; 'Shape Memory Alloys—Medical Applications,' Source: Materials World, vol. 7, No. 12, pp. 745-747, Dec. 1999.

Asakawa et al; 'Antagonism of Ghrelin Receptor Reduces Food Intake and Body Weight Gain in Mice'; Gut.; V.52; pp. 947-952; 2003.

Baggio et al. 'Biology of Integrins: GLP-1 and GIP'; Gastroenrology; V. 132; pp. 2131-2157; 2007.

Ballantyne; 'Peptide YY(1-36) and Peptide YY(3-36): Part I. Distribution, Release, and Actions'; Obesity Surgery; V.16; pp. 651-658; 2006.

Ballantyne; "Peptide YY(1-36) and Peptide YY(3-36): Part II. Changes after Gastrointestinal Surgery and Bariatric Surgery"; Obesity Surgery; V.16; pp. 795-803; 2006.

Berne et al; 'Physiology'; V. 5; pp. 55-57, 210, 428, 540, 554, 579, 584, 591; 2004.

BioEnterics Corporation, an Inamed Company, BioEnterics Intragastric Balloon; Directions for Use Published Document, P/N. 94200 Rev: B, pp. 1-56.

Bio Enterics Lap-Band Adjustable Gastric Banding System, Inamed Health, pub. Aug. 28, 2003, pp. 1-115.

Boulant et al.; 'Cholecystokinin in Transient Lower Oesophageal Sphincter Relation Due to Gastric Distension in Humans'; Gut; V. 40; pp. 575-581; 1997.

Bradjewin et al; 'Dose Ranging Study of the Effects of Cholecystokinin in Healthy Volunteers'; J. Psychiatr. Neurosci.; V. 16 (2); pp. 91-95; 1991.

Burdyga et al.; 'Cholecystokinin Regulates Expression of Y2 Receptors in Vagal Afferent Neurons Serving the Stomach'; The Journal of Neuroscience; V. 28; No. 45; pp. 11583-11592; Nov. 5, 2008.

Chaptini et al.; "Neuroendocrine Regulation of Food Intake"; Current Opinion in Gastroenterology; V. 24; pp. 223-229; 2008.

Chaudhri; 'Can Gut Hormones Control Appetite and Prevent Obesity?' Diabetes Care; V. 31; Supp 2; pp. S284-S289; Feb. 2008.

Cohen et al.; 'Oxyntomodulin Suppresses Appetite and Reduces Food in Humans'; J. Clin. Endocrinol. Metab.; V. 88; pp. 4696-4701; 2003.

Corno et al.; 'A new implantable device for telemetric control of pulmonary blood flow'; New ideas; received in revised form Jul. 12, 2002; 10 pages.

Corno et al.; 'FlowWatchTM in clipped and inclipped position'; Interact Cardio Vase Thorac Surg 2002; 1:46-49; Copyright © 2002 The European Asociation for Cardio-thoracic Surgery; 1 page.

Cummings et al.; 'Plasma Ghrelin Levels After Diet-Induced Weight Loss or Gastric Bypass Surgery'; N. Engl J. Med; V. 346, No. 21; pp. 1623-1630; May 23, 2002.

Cummings; 'Gastrointestinal Regulation of Foot Intake'; The Food Journal of Clinical Investigation; V. 117, N. 1; pp. 13-23; Jan. 2007.

Dakin et al.; 'Oxyntomodulin Inhibits Food Intake in the Rat'; Endocrinology; V. 142; pp. 4244-4250; 2001.

Dakin et al.; 'Peripheral Oxyntomodulin Reduces Food Intake and Body Weight gain in Rats'; Endocrinology; V. 145; No. 6; pp. 2687-2695; Jun. 2004.

Davison; 'Activation of Vagal-Gastric Mechanoreceptors by Cholecystokinin'; Proc. West. Pharmocol. Soc; V. 29; pp. 363-366; 1986.

(56) References Cited

OTHER PUBLICATIONS

De Waele et al.; "Endoscopic Volume Adjustment of Intragastric Balloons for Intolerance"; Obesity Surgery; V. 11; pp. 223-224; 2001.
De Waele et al.; "Intragastric Balloons for Preoperative Weight Reduction"; Obesity Surgery; V. 58; pp. 58-60; 2001.
Desai et al.; 'Molecular Weight of Heparin Using 13C Nuclear Magnetic Resonance Spectroscopy' Journal of Pharmaceutical Science, V. 84,12; 1995, Abstract only.
Doldi et al.; 'Intragastric Balloon: Another Option for Treatment of Obesity and Morbid Obesity'; Hepato-Gastroenterology; V. 51, N. 55; pp. 294-307; Jan.-Feb. 2004.
Doldi et al.; 'Treatment of Morbid Obesity with Intragastric Balloon in Association with Diet'; Obesity Surgery; V. 10, pp. 583-587; 2000.
Ekblad et al.; 'Distribution of Pancreatic Peptide and Peptide-YY'; Peptides; V. 23; pp. 251-261 ;2002.
El Khoury et al.; "Variation in Postprandial Ghrelin Status Following Ingestion of High-Carbohydrate, High Fat, and High Protein Meals in Males"; Ann Nutr Metab; V. 50; pp. 260-269; 2006.
Galloro et al; "Preliminary Endoscopic Technical Report of an New Silicone Intragastric Balloon in the Treatment of Morbid Obesity"; Obesity Surgery; V. 9, pp. 68-71; 1999.
GinShiCel MH Hydroxy Propyl Methyl Cellulose, Web Page http://www.ginshicel.cn/MHPC.html, Nov. 12, 2008.
Girard; 'The Incretins: From the concept to their use in the treatment of type 2 diabetes. Part A: IncretinsIncretinsIncretinsIncretinsIncretins: Concept and physiological functions'; Diabetes and Metabolism; V. 34; pp. 550-559; 2008.
Greenough et al.; 'Untangling the Effects of Hunger, Anxiety and Nausea on Energy Intake During Intravenous Cholecystokinin Octapeptide (CCK-8) Infusion' Physiology and Behavior; V. 65 (2); pp. 303-310; 1998.
Grise et al.; "Peptide YY Inhibits Growth of Human Breast Cancer in Vitro and in Vivo"; Journal of Surgical Research; V. 82; pp. 151-155; 1999.
Grundy; "Signaling the State of the Digestive Tract"; Autonomic Neuroscience: Basic and Clinical; V. 125; pp. 76-80; 2006.
Grundy; "Vagal Control of Gastrointestinal Function"; Bailliere's Clinical Gastroenterology; V. 2; No. 1; pp. 23-43; 1988.
Hallden et al. "Evidence for a Role of the Gut Hormone PYY in the Regulation of Intestinal Fatty Acid Binding Protein Transcripts in Differentiated Subpopulations of Intestinal Epithelial Cell Hybrids"; Journal of Biological Chemistry; V. 272 (19); pp. 125916-126000; 1997.
Hameed et al., 'Gut Hormones and Appetite Control', Oral Diseases, 2009, 15:18-26.
Hassan et al.; 'Effects of Adjuvants to Local Anesthetics on Their Duration III Experimental Studies of Hyaluronic Acid' Abstract Pub Med [Acta Anesthesiol Scand.; 29 (4): 384-8], 1 page; May 1985.
Hodson et al.; 'Management of Obesity with the New Intragastric Balloon'; Obesity Surgery; V. 11, pp. 327-329,2001.
Holzer; "Gastrointestinal Afferents as Targets of Novel Drugs for the Treatment of Functional Bowel Disorders and Visceral Pain"; European Journal of Pharmacology; V. 429; pp. 177-193; 2001.
Houpt; 'Gastrointestinal Factors in Hunger and Satiety'; Neurosci. and Behav. Rev.; V. 6; pp. 145-164; 1982.
Iverson et al.; 'Recent Advances in Microscale Pumping Technologies: A Review and Evaluation'; Microfluid Nanofluid; vol. 5; pp. 145-174; Feb. 19, 2008.
Jones; "Molecular, pharmacological, and clinical aspects of liraglutide, a oncedaily human GLP-1 analogue"; Molecular and Cellular Endocrinology; V. 297; pp. 137-140; 2009.
Kerem et al.; 'Exogenous Ghrelin Enhances Endocrine and Exocrine Regeneration in Pancreatectomized Rats'; J. Gastrointest Surg.; V. 13; pp. 775-783, 2009.
Kesty et al., 'Hormone-based Therapies in the Regulation of Fuel Metabolism and Body Weight', Expert Opin. Biol. Ther., 2008, 8(11): 1733-1747.
Kissileff et al.; 'Peptides that Regulate Food Intake: Cholecystokinin and Stomach Distension Combine to Reduce Food Intake in Humans'; Am. J. Physiol. Regul. lntegr. Comp. Physiol.; V. 285; pp. 992-998; 2003.
Kojima et al., 'A Role for Pancreatic Polypeptide in Feeding and Body Weight Regulation', Peptides, 2007, 28:459-463.
Kulicke et al. "Visco-Elastic Propeerties of Sodium Hyaluronate Solutions," American Institute of Physics; pp. 585-587; 2008.
Lap-Band AP System Adjustable Gastric Banding System With OmniformTM Design: Directions for Use (DFU); Allergan, 16 pages; 2009.
Le Roux et al.; 'Gut Hormone Profiles Following Bariatric Surgery Favor an Anorectic State, Facilitate Weight Loss, and Improve Metabolic Parameters'; Ann. Surg; V. 243; No. 1; pp. 108-114; Jan. 2006.
Liu et al.; 'Adjuvant Hormonal Treatment With Peptide YY or Its Analog Decreases Human Pancreatic Carcinoma Growth'; The American Journal of Surgery; V. 171; pp. 192-196; Jan. 1996.
Mathus-Vliegen et al. 'Intragastric Balloons for Morbid Obesity: Results, Patient Tolerance and Balloon Life Span'; Br. J. Surg.; V. 77, No. 7, pp. 76-79; Jan. 1990.
Mathus-Vliegen et al. "Treating Morbid and Supermorbid Obesity" International Journal of Gastroenterology; V. 5, No. 1, pp. 9-12; 2000.
Medeiros et al.; 'Processing and metabolism of Peptide-YY: Pivotal roles of Dipeptidase-IV, Aminopeptidase-P, and Endopeptidase-24. 11'; Endocrinology; V. 134, No. 5; pp. 2088-2094;1994.
Naslund et al.; 'Prandial Subcutaneous Injection of Glucagon-Like Peptide'; Br. J. Nutr.; V. 91; pp. 439-446; 2004.
Potier et al.; "Protein, amino acids, and the control of food intake"; Current Opinion in Clinical Nutrition and Metabolic Care; V. 12; pp. 54-58; 2009.
Qjan et al.; 'Pulmonary delivery of a GLP-1 receptor agonist, BMS-686117'; International Journal of Pharmaceutics; V. 366; pp. 218-220; 2008.
Rang et al.; 'Pharmacology'; V. 5; pp. 203, 397,402, 524; 2004.
Raybould et al.; "Integration of Postprandial Gastrointestinal Tract: Role of CCK and Sensory Pathways"; Annals of New York Academy of Science; pp. 143-156; 1994.
Renshaw et al. 'Peptide YY: A Potential Therapy for Obesity'; Current Drug Targets; V. 6; pp. 171-179; 2005.
Sannino et al., 'Crosslinking of Cellulose Derivatives and Hyaluronic Acid with Water-Soluble Carbodiimide,' Polymer 46(2005)pp. 11206-11212.
Shechter et al.; "Reversible PEGylation of peptide YY3-36 prolongs its inhibition of food intake in mice"; FEBS Letters; V. 579; pp. 2439-2444; 2005.
Silver et al.; 'Physical Properties of Hyaluronic Acid and Hydroxypropylmethylcellulose in Solution: Evaluation of Coating Ability' Journal of Applied Biomaterials, V. 5; pp. 89-98, 1994.
Small et al.; 'Gut hormones and the control of appetite'; Trends in Endocrinology and Metabolism; V. 15; No. 6; pp. 259-263; Aug. 2004.
Stanley et al.; 'Gastrointestinal Satiety Signals III. Glucagon-like Peptide 1, oxyntomodulin, peptide YY, and pancreatic polypeptide'; Am. J. Physiol Gastrointest Liver Physiol; V. 286; pp. 693-697; 2004.
Tezel, 'The Science of Hyaluronic Acid Dermal Fillers,' Journal of Cosmetic and Laser Therapy (2008) 10: pp. 35-42.
Tolhurst et al.; 'Nutritional regulation of glucagon-like peptidel secretion'; J. Physiol.; V. 587, No. I;pp. 27-32; 2009.
Totte et al.; "Weight Reduction by Means of Intragastric Device: Experience with the Bioenterics Intragastric Balloon"; Obesity Surgery; V. 11, pp. 519-523; 2001.
Tough et al.; 'Y4 Receptors Mediate the Inhibitory Responses of Pancreatic Polypeptide in Human and Mouse Colon Mucosa'; The Journal of Pharmacology and Experimental Therapeutics; V. 319, No. 1; pp. 20-30; 2006.
Tseng et al; "Peptide YY and cancer: Current findings and potential clinical applications"; Peptides; V. 23; pp. 389-395; 2002.
Valassi et al.; "Neuroendocrine control of food intake"; Nut. Metab. & Cariovasc. Disease; V. 18; pp. 158-168; 2008.
Van Der Lely et al.; "Biological, Physiological, Pathophysiological Aspects of Ghrelin"; Endocrine Reviews; V. 25, No. 3; pp. 426-457; 2004.

(56) References Cited

OTHER PUBLICATIONS

Verdich et al. 'A Meta-Analysis of the Effect of Glucagon-Like-Peptide-1 (7-36) Amide on ad Libitum Energy Intake in Humans'; J. Clin. Endocrinal. Metab. V. 86; pp. 4382-4389; Sep. 2001.

Wahlen et al.; 'The BioEnterics Intragastric Balloon (BIB): How to Use It'; Obesity Surgery; V. 11; pp. 524-527; 2001.

Wang et al.; "Plasma Ghrelin Modulation in Gastric Band Operation and Sleeve Gastrectomy"; Obes. Surg.; pp. 357-362; 2008.

Weiner et al.; 'Preparation of Extremely Obese Patients for Laparoscopic Gastric Banding by Gastric Balloon Therapy'; Obesity Surgery; V. 9, pp. 261-264, 1999.

Wynne et al.; 'Subcutaneous Oxyntomodulin Reduces Body Weight in Overweight and Obese Subjects: A Double-Blind Randomized, Controlled Trial': Diabetes; V. 54; pp. 2390-2395; 2005.

Yamagami, Takuji; 'Technical Developments; Use of Targeting Guide Wire in Left Subclavian Puncture During Percutaneous Implantation of Port-Catheter Systems Using the Catheter Tip Fixation Method' European Radiology; vol. 13; pp. 863-866; 2003.

Yurdumakan B., et al.; 'Synthetic Gecko Foot-Hairs from Multiwalled Carbon Nanotubes'; The Royal Society of Chemistry; p. 3799-3801; 2005.

Yuzuriha et al.; "Gastrointestinal Hormones (anorexigenic peptide YY and orexigenic ghrelin) influence neural tube development"; FASEB J.; V. 21; pp. 2108-2112; 2007.

'Living With the Bib/BioEnterics Intragastric Balloon Program,' Inamed Health; 1-10 Patient Information Brochure; pp.; May 1, 2005.

BIB Bioenterics Intragastric Balloon Program, 'Take Control of Your Weight and Your Life/The Solution for You,' Inamed Health, pp. 1-2; Jan. 19, 2004.

BIB Bioenterics Intragastric Balloon Program, 'Taking the Next Step/Take Control of Your Weight and Your Life,' Inamed Health, pp. 1-9; Apr. 29, 2004.

BIB Data Sheet Directions for Use, 'BioEnterics Intragastric Balloon System,' Inamed Health, 1-12 pp.

Brown et al; 'Symmetrical Pouch Dilation After Laparoscopic Adjustable Gastric Banding: Incidence and Management'; Obesity Surgery; V. 18, pp. 1104-1108; 2008.

Ceelen et al.; 'Surgical Treatment of Severe Obesity With a Low-Pressure Adjustable Gastric Band: Experimental Data and Clinical Results in 625 Patients'; Annals of Surgery; V. 237, No. I;pp. 10-16; 2003.

Dixon et al.; 'Pregnancy After Lap-Band Surgery: Management of the Band to Achieve Healthy Weight Outcomes'; Obesity Surgery; V. 11, pp. 59-65; 2001.

Helioscopie Product Insert for Heliogast, pp. 1-11 (undated).

Neary et al.; 'Peptide YY(3-36) and Glucagon-Like Peptide-1.sub. (7-36) Inhibit Food Intake Additively'; Endocrinology; V.146; pp. 5120-5127; 2005.

Padidela et al.; 'Elevated basal and post-feed glucagon-like petide 1 (GLP-1) concentrations in the neonatel period'; European Journal of Endocrinology; v. 160; pp. 53-58; 2009.

Patient Management After Lap-Band Placement; http://www.core.monash.org/patient-care.pdf.

Shi et al; 'Sexually Dimorphic Responses to Fat Loss After Caloric Restriction or Surgical Lipectomy'; Am. J. Physiol. Endocrinol. Metab.; V. 293; E316-E326; 2007.

The Lap-Band Device & How it Works; http://lapband.com/en/learn_about-lapband/device_how_it_works/.

Xanthakos et al.; 'Bariatric Surgery for Extreme Adolescent Obesity: Indications, Outcomes, and Physiologic Effects on the Gut-Brain Axis'; Pathophysiology; V. 15; pp. 135-146; 2008.

\* cited by examiner

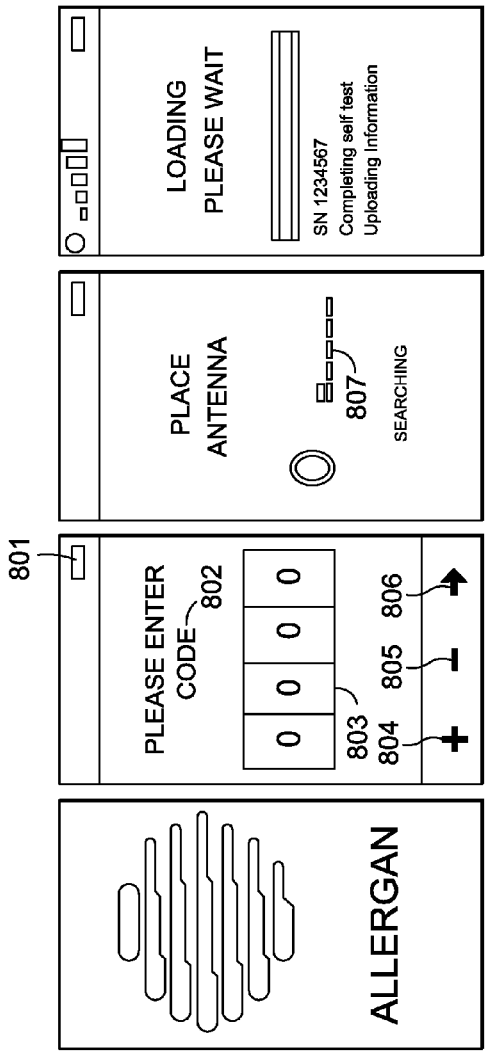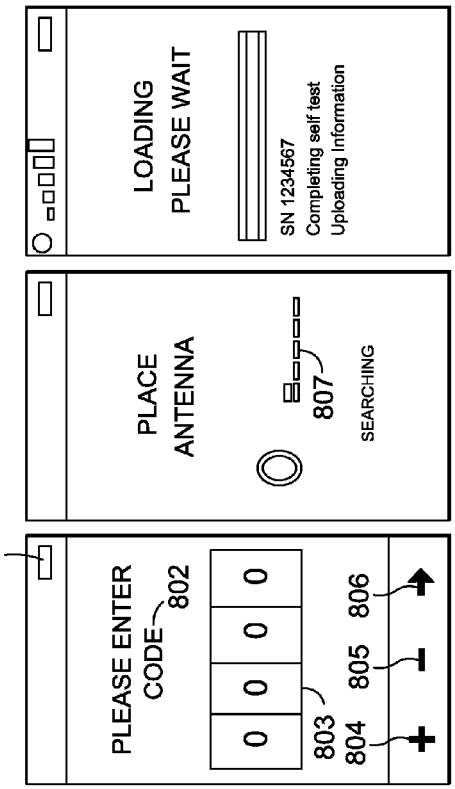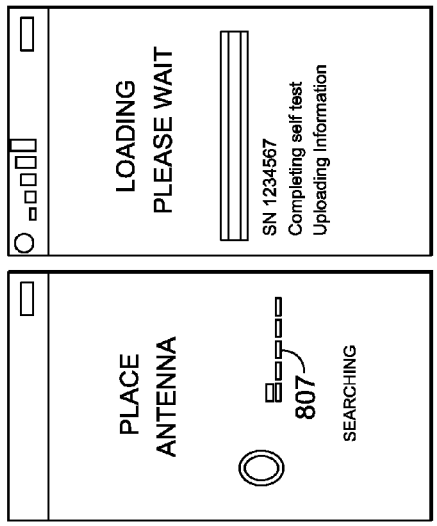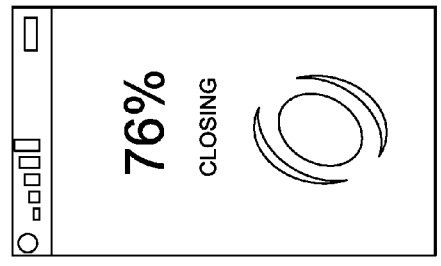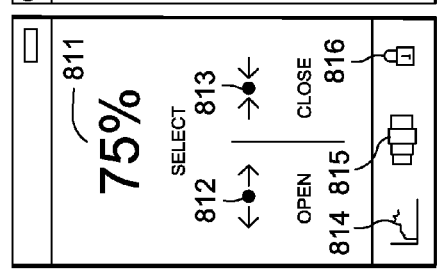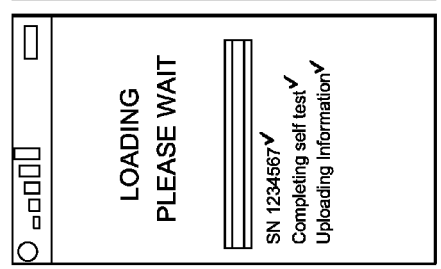

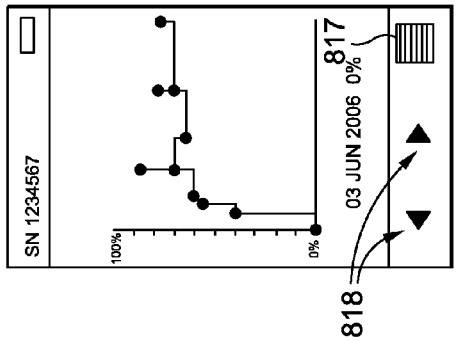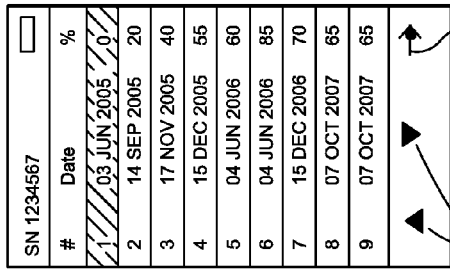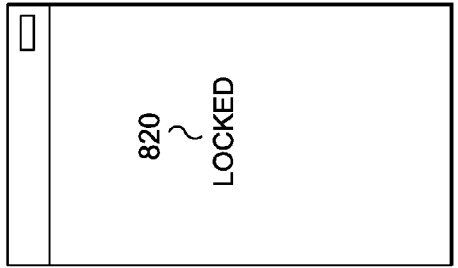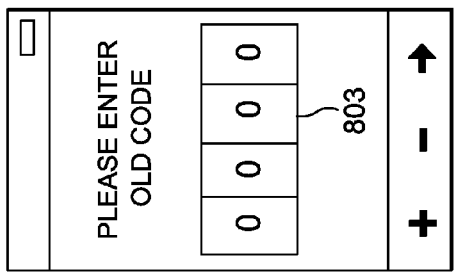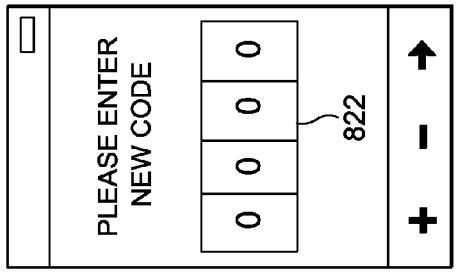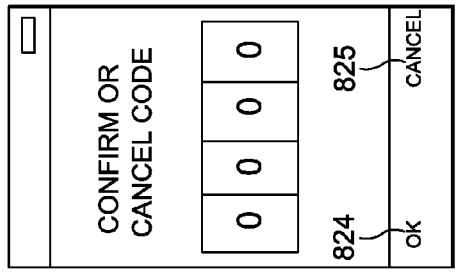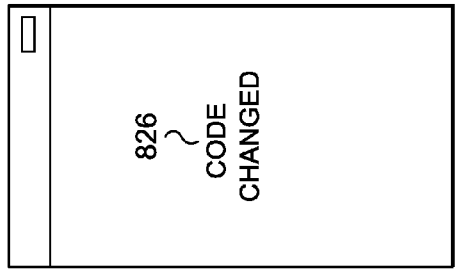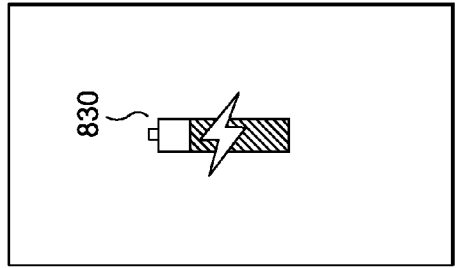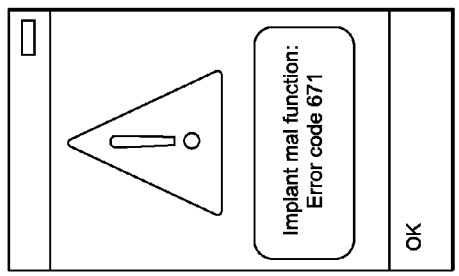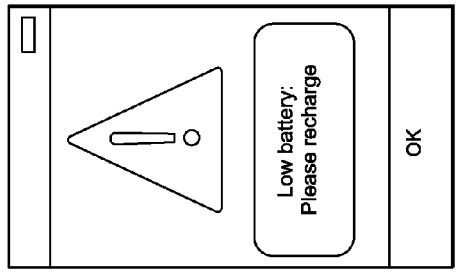

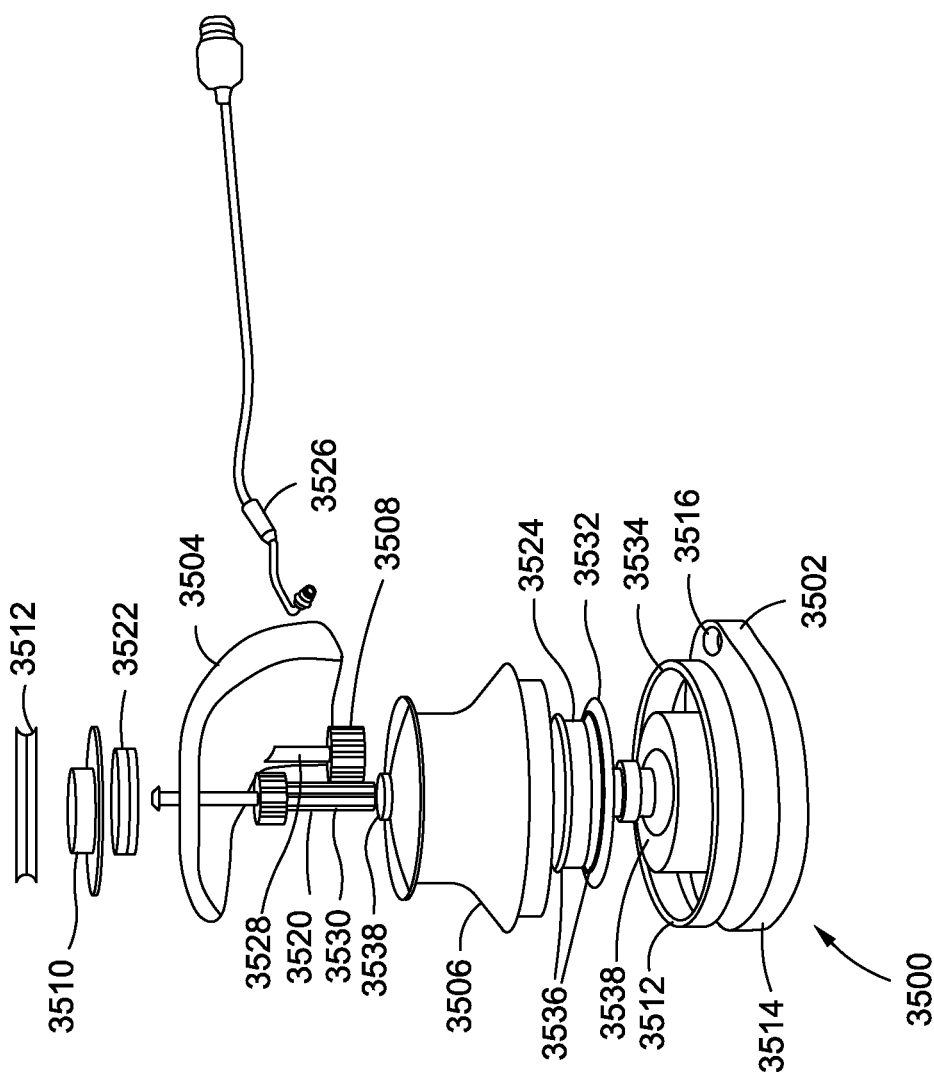
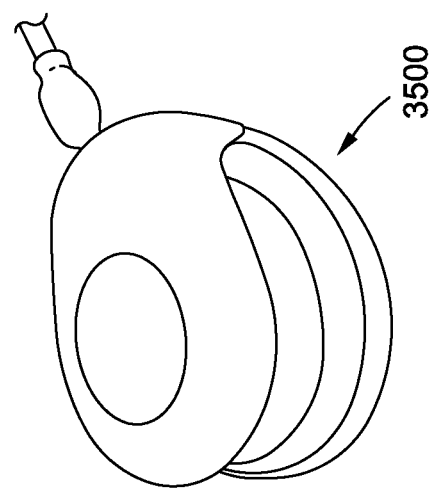
FIG. 35B
FIG. 35A

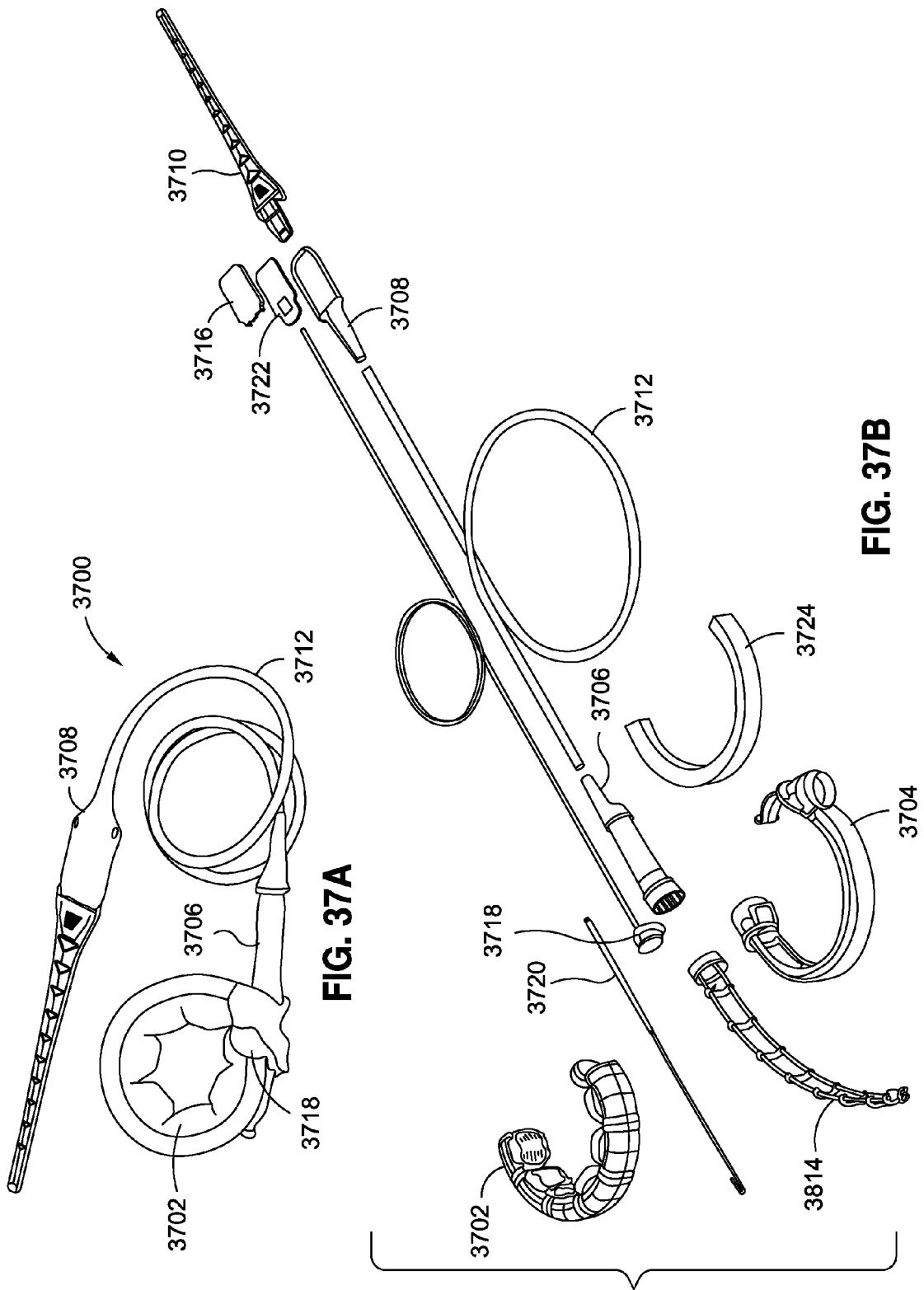

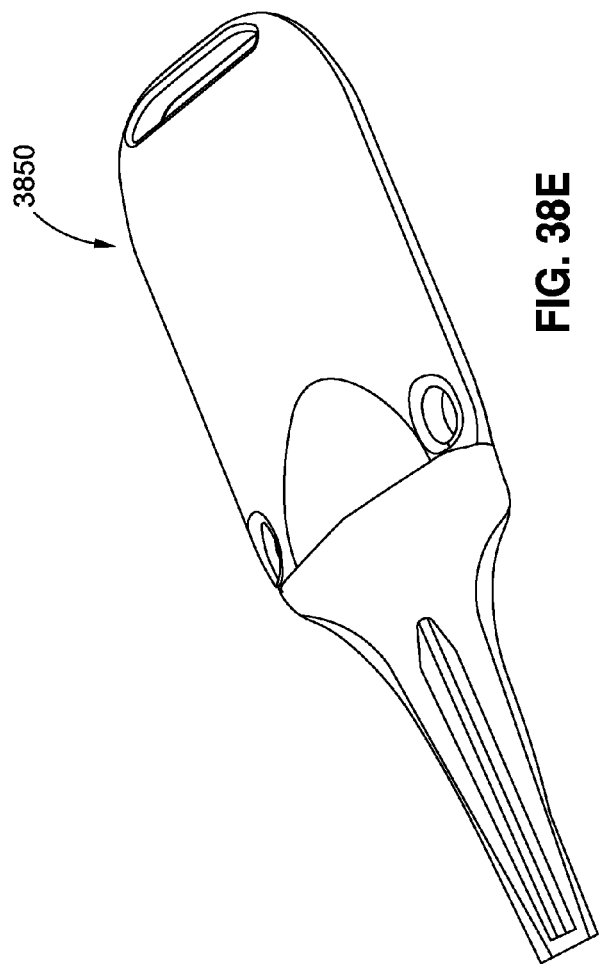
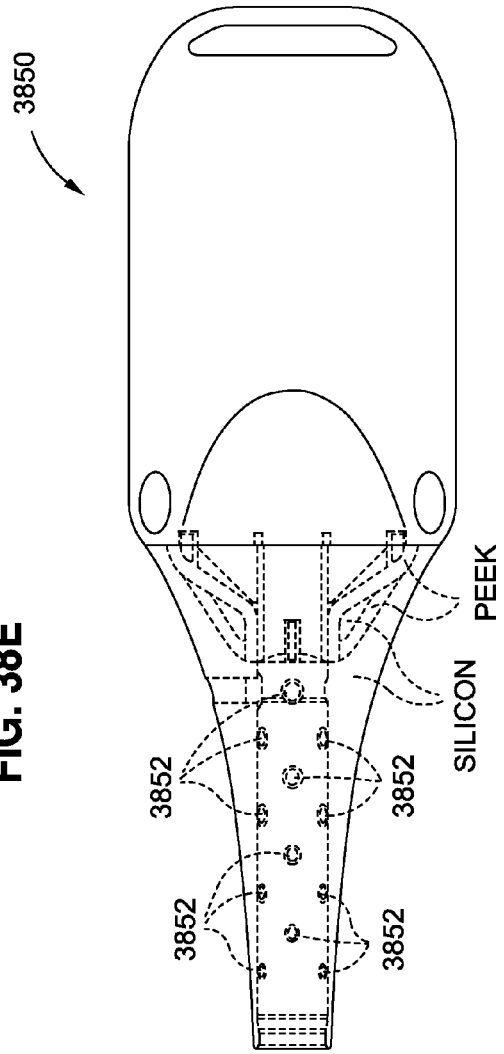
FIG. 38E
FIG. 38F

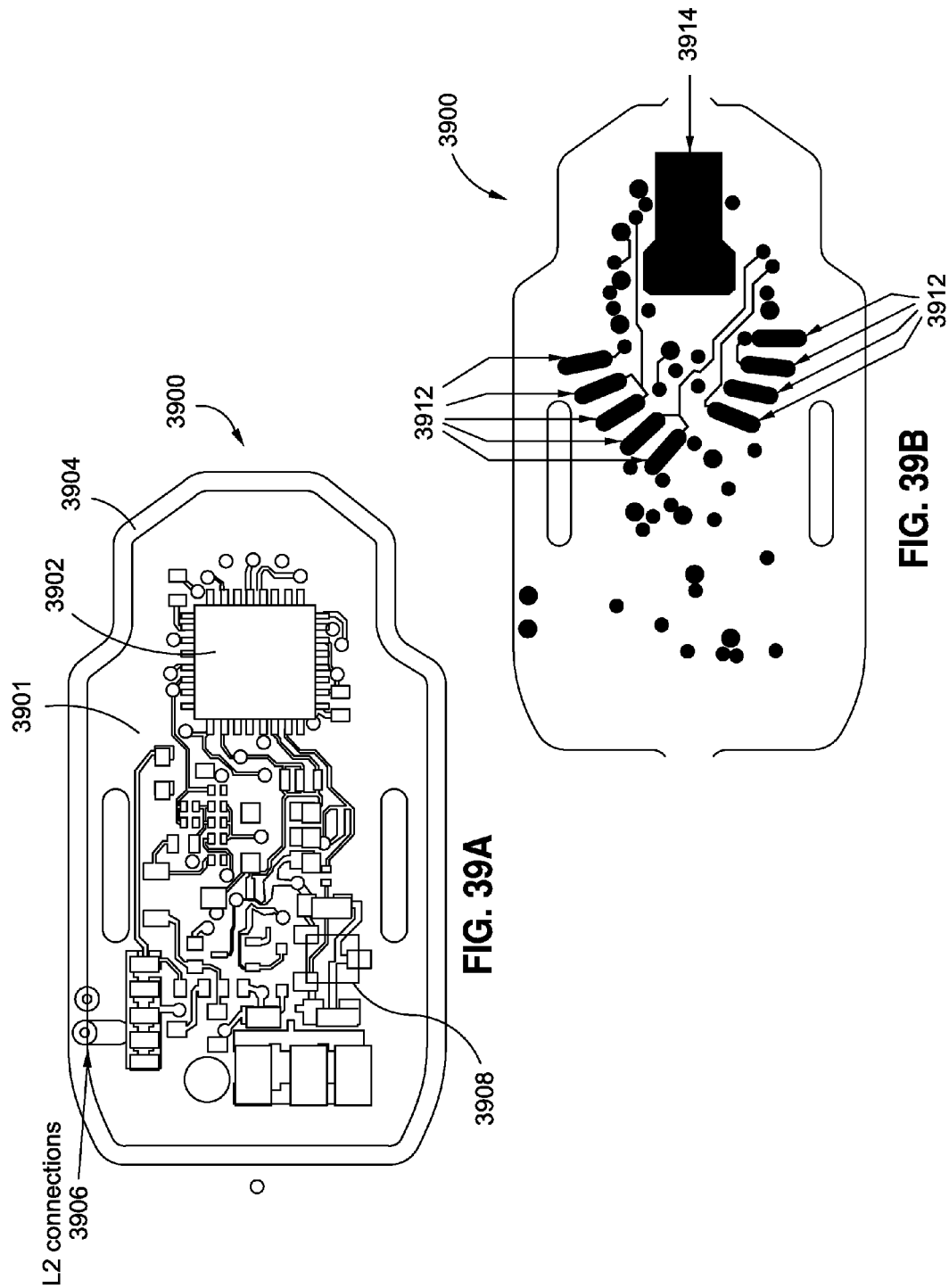

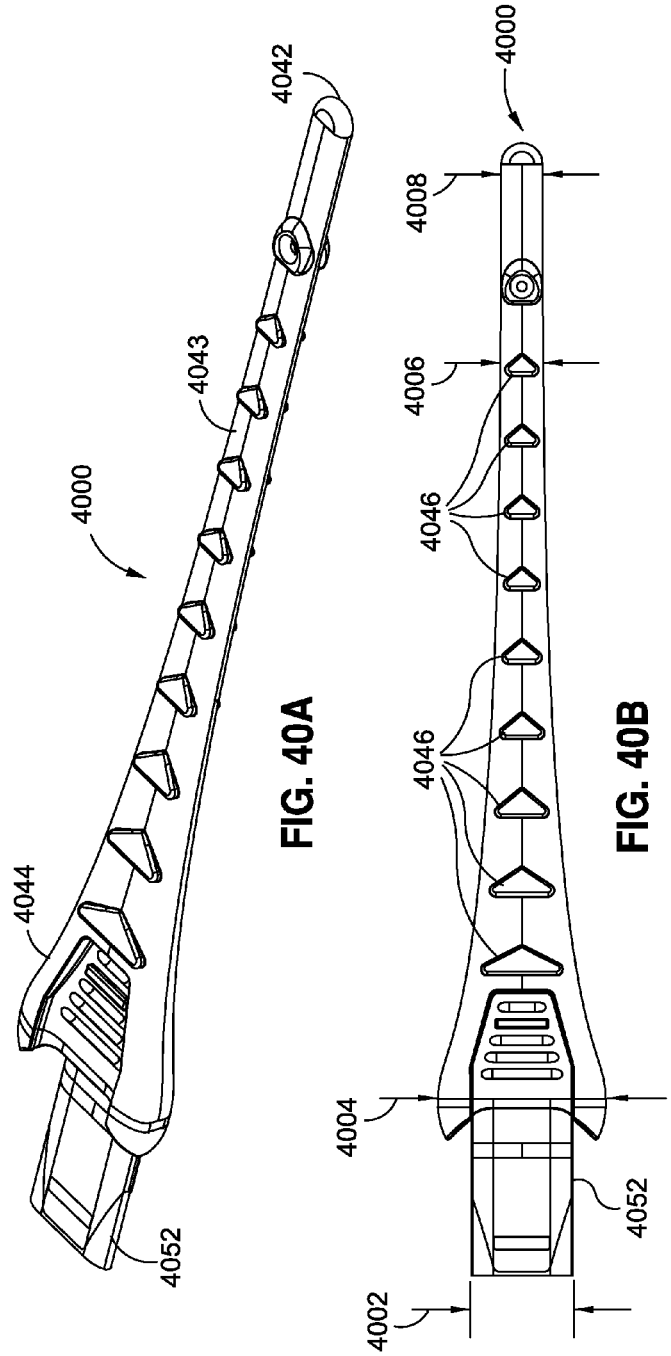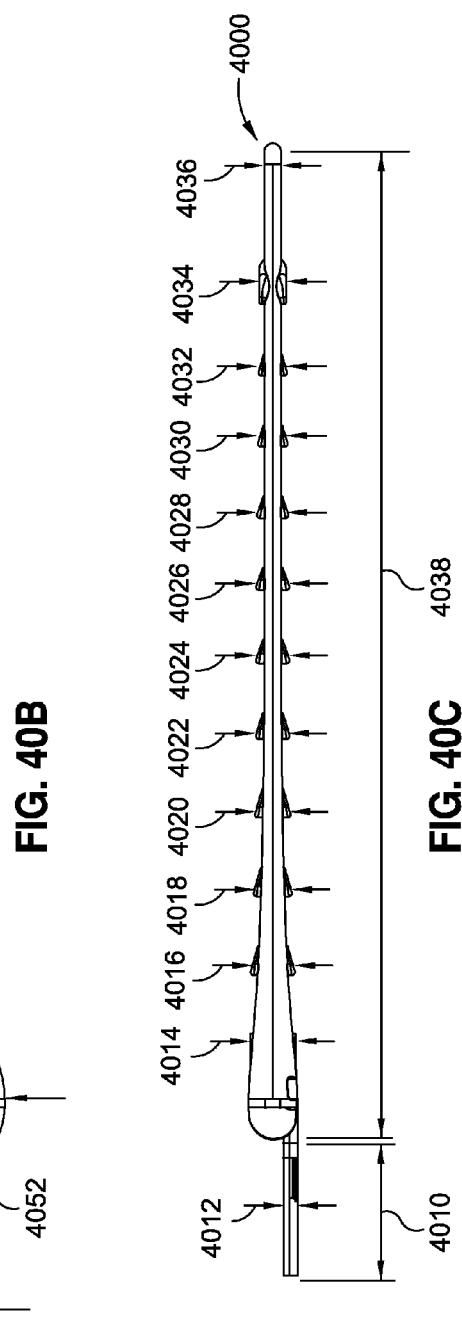
FIG. 40A
FIG. 40B
FIG. 40C

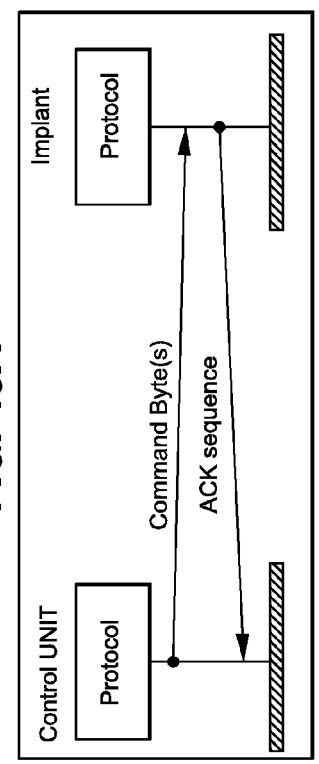
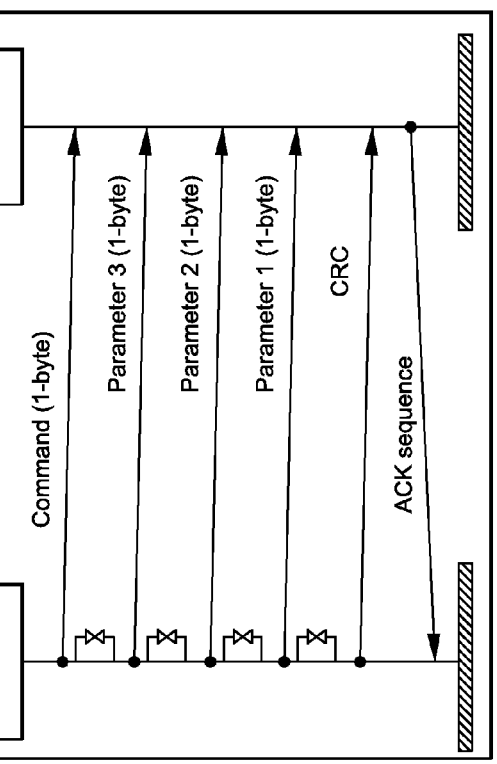
FIG. 43A
FIG. 43B
FIG. 44A
FIG. 44B

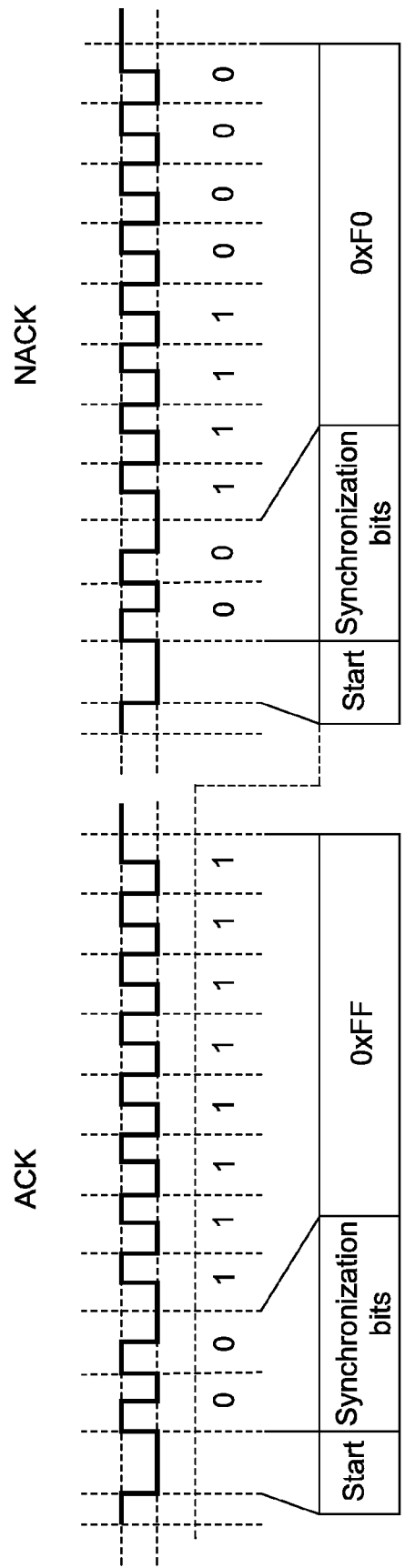

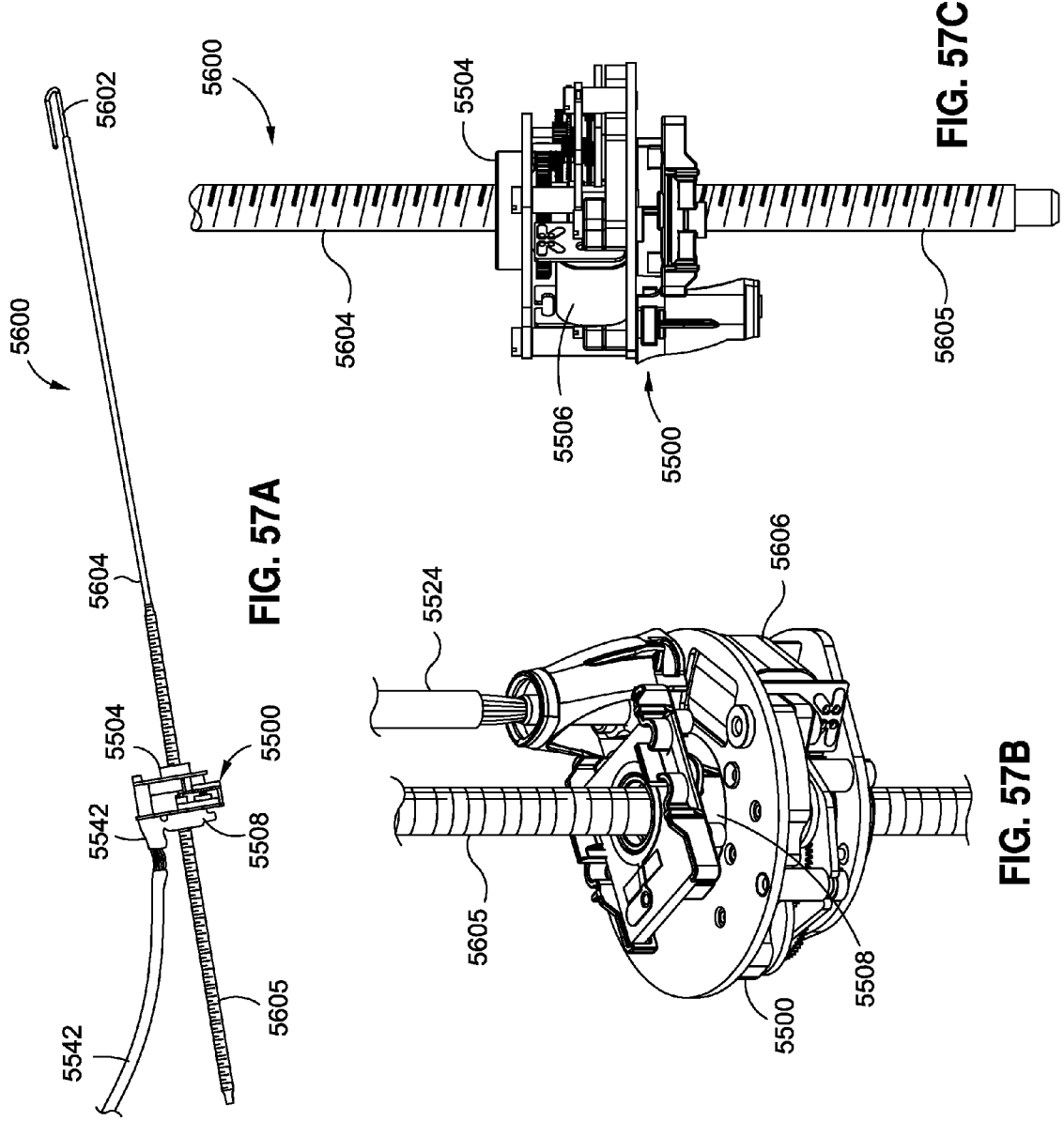

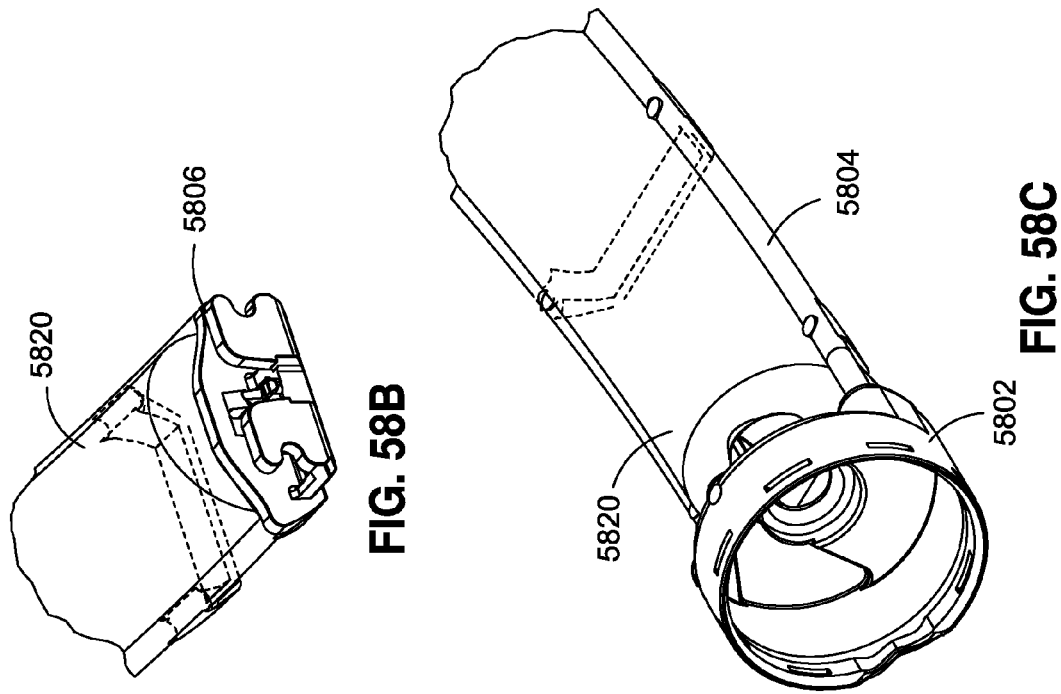
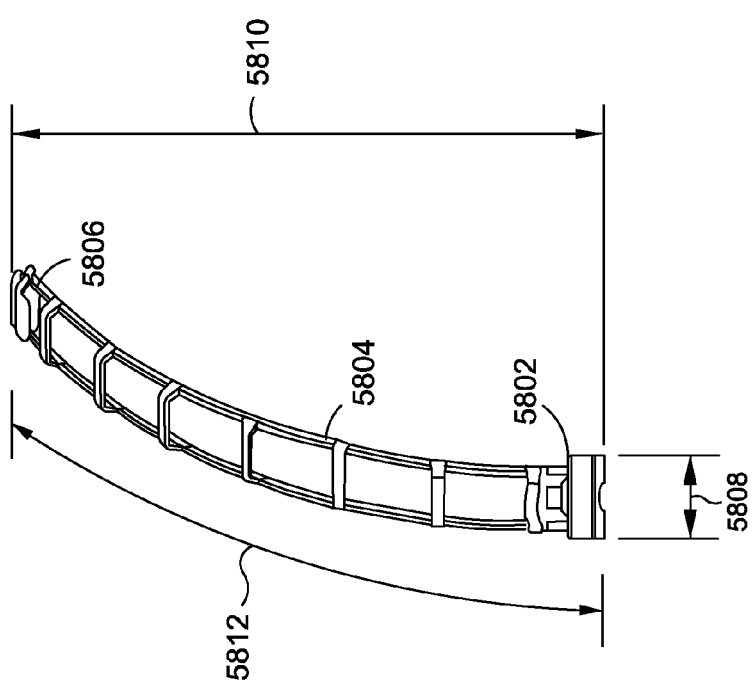

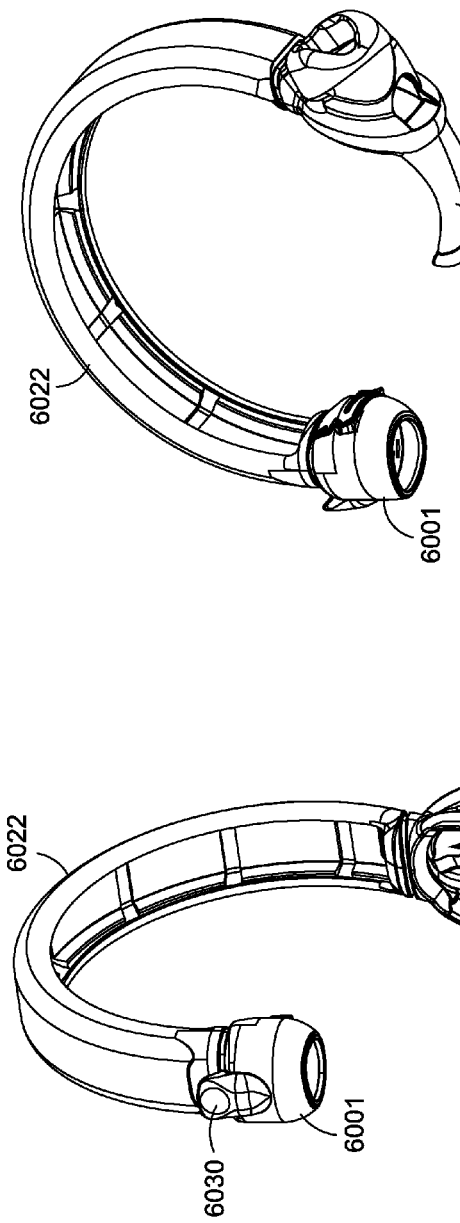
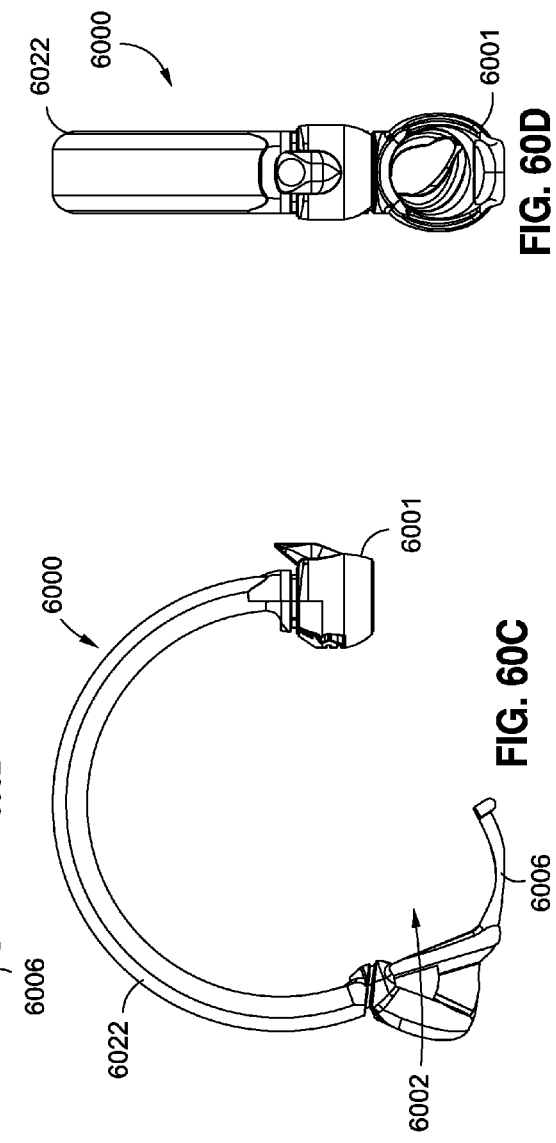
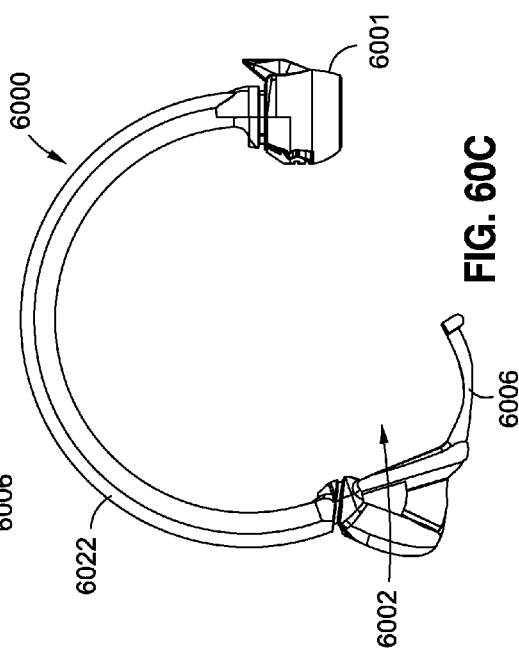
FIG. 60A
FIG. 60B
FIG. 60C
FIG. 60D

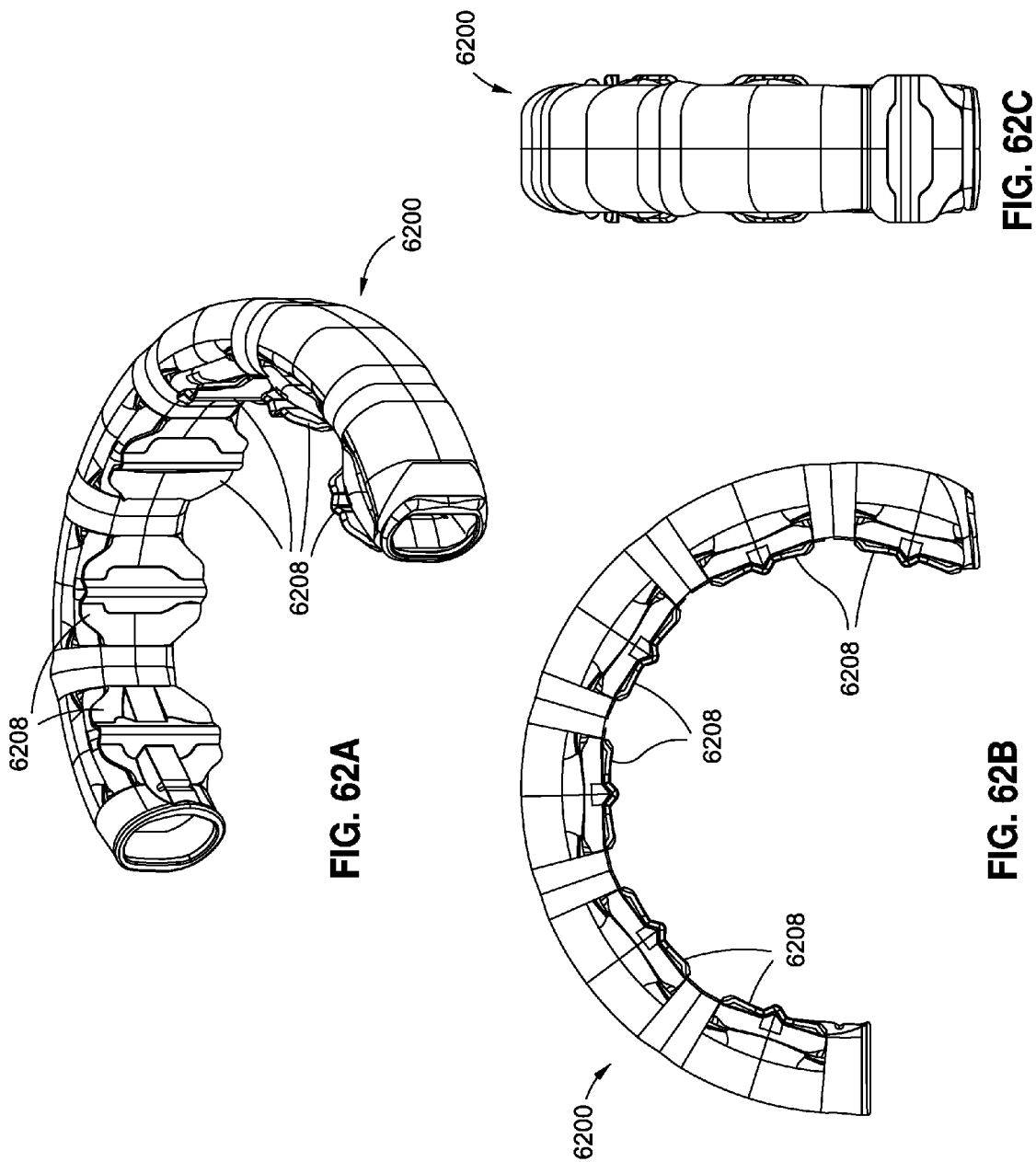

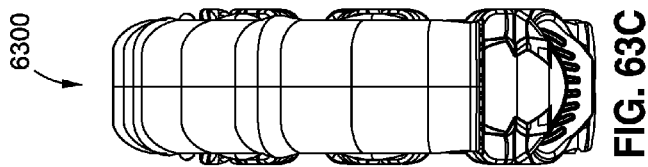
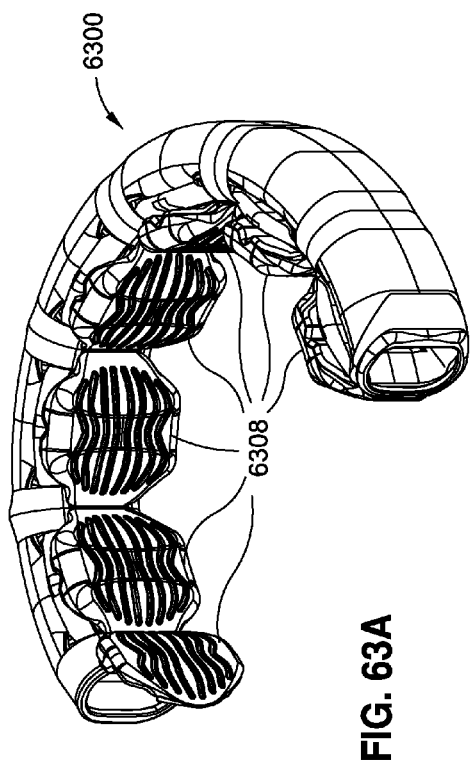
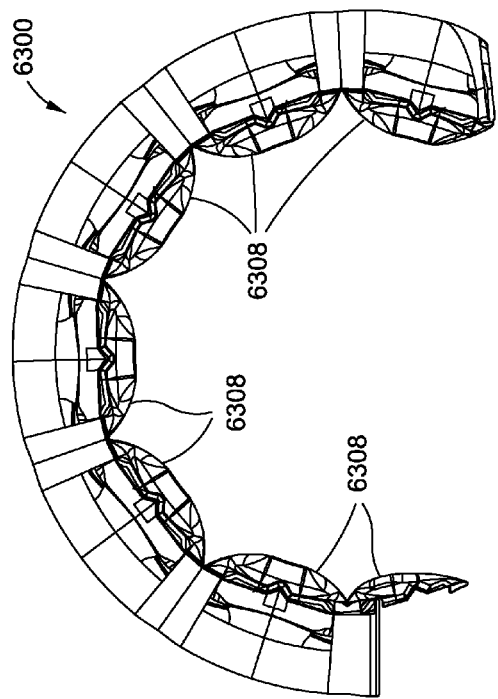

REMOTELY POWERED REMOTELY ADJUSTABLE GASTRIC BAND SYSTEM

CROSS REFERENCE TO RELATED APPLICATIONS

This application is a continuation of U.S. patent application Ser. No. 13/076,139, filed Mar. 30, 2011, which claims priority to and the benefit of U.S. Provisional Application No. 61/343,571, filed on Apr. 30, 2010, which is assigned to the assignee hereof and hereby expressly incorporated by reference herein.

FIELD

The present invention generally relates to medical systems and apparatus and uses thereof for treating obesity and/or obesity-related diseases, and more specifically, related to gastric band systems that are remotely adjustable and remotely powered by a wireless control device.

BACKGROUND

Adjustable gastric banding apparatus have provided an effective and substantially less invasive alternative to gastric bypass surgery and other conventional surgical weight loss procedures. Despite the positive outcomes of invasive weight loss procedures, such as gastric bypass surgery, it has been recognized that sustained weight loss can be achieved through a laparoscopically-placed gastric band, for example, the LAP-BAND® (Allergan, Inc., Irvine, Calif.) gastric band or the LAP-BAND AP® (Allergan, Inc., Irvine, Calif.) gastric band. Generally, gastric bands are placed about the cardia, or upper portion, of a patient's stomach forming a stoma that restricts the passage of food into a lower portion of the stomach. When the stoma is of an appropriate size that is restricted by a gastric band, food held in the upper portion of the stomach provides a feeling of satiety or fullness that discourages overeating. Unlike gastric bypass procedures, the gastric band apparatus are reversible and require no permanent modification to the gastrointestinal tract.

Over time, a stoma created by a gastric band may need adjustment in order to maintain an appropriate size, which is neither too restrictive nor too passive. Some non-invasive procedures for adjustment of gastric bands without the use of a hypodermic needle have been proposed. For example, a remotely adjustable gastric band is a medical device which allows a healthcare worker to adjust a gastric band without requiring hypodermic needles to connect to an implanted, subcutaneous access port. A handheld controller can be used to send radio frequency waves for powering and communicating with the implanted device. The implanted device can tighten or relax the gastric band as requested by the healthcare worker via the handheld controller.

Birk, et al., U.S. Patent Pub. No. 2010-0010291, and Birk, et al., U.S. Ser. No. 12/705,245, which are commonly-assigned and co-pending with the present application, are incorporated herein in their entirety by this specific reference. Both of these applications disclose certain approaches to implantable systems that may be relevant.

Some mechanically adjustable implantable devices have a disadvantage of becoming inoperable if the adjustment mechanism fails. Furthermore, because the motor and the driving mechanisms are located near the restricting band itself, they are more subject to strain and damage from the implantation process. Therefore, it is desirable to develop a remotely adjustable gastric band where the motor is separated from the restricting band to reduce the strain from the implantation process such that the risk of damage during implantation is decreased.

Thus, there continues to remain a need for more effective implantable motor systems for use with adjustable gastric bands, particularly such implantable motor systems with increased and more efficient motoring capability.

SUMMARY

Generally described herein are remotely adjustable and remotely powered gastric band systems, and methods of use thereof. The apparatus, systems and methods described herein aid in facilitating obesity control and/or treating obesity related diseases while being non-invasive once implanted.

In one embodiment, the present may provide a power system for use in conjunction with a gastric band coupled with an implantable antenna for receiving a telemetric signal from a remote control device. The power system may include a rectifying device coupled to the implantable antenna, and configured to rectify the received telemetric signal to form a DC input voltage at a DC input node, a power sensing device configured to receive the DC input voltage and generate a regulation signal when the DC input voltage exceeds a predetermined threshold, a regulation device coupled to the power sensing device, and configured to generate a regulation voltage based on the regulation signal, and a switching device coupled to the regulation device, and configured to generate a feedback signal having a frequency based on the regulation voltage.

In another embodiment, the present invention may provide a communication system for use in conjunction with a gastric band coupled with an implantable antenna for receiving a telemetric signal from a remote control device. The communication system may include a regulation device configured to generate a regulation voltage at a first node, the regulation voltage based on a margin between a DC input voltage and a predetermined threshold, a data path arranged in parallel with the regulation device, and configured to adjust the regulation voltage to a set voltage at a second node, the set voltage based partially on an output data sequence, and a frequency modulation device coupled to the second node, and configured to generate a frequency modulation signal having a modulated frequency corresponding to the set voltage.

In another embodiment, the present invention may provide a remotely powered and remotely adjustable gastric band system, which may include a remote control device configured to transmit a telemetric signal having an amplitude and a carrier frequency, an implantable power device telemetrically coupled to the remote control device, and configured to extract power from the telemetric signal and generate a feedback signal having a message frequency based on the extracted power, and a gastric band for forming a ventral ring surface around a stomach of a patient, the gastric band coupled to the implantable power device, and configured to receive the extracted power from the implantable power device and adjust the ventral ring surface in response to the telemetric signal.

In another embodiment, the present invention may provide a method for detecting motor blockage of a motor for use in conjunction with an implantable gastric band. The motor may include a motor coil for conducting a motor coil current and a plurality of gears for adjusting an inner ring surface of the implantable gastric band in response to the motor coil current. The method may include the steps of applying a voltage pulse across the motor coil, measuring a plurality of transient motor coil currents, measuring a maximum motor coil current, and detecting the motor blockage based on the plurality of transient motor coil currents and the maximum motor coil current.

In another embodiment, the present invention may provide a tangible computer medium for storing instructions, upon being executed by a processor, that cause the processor to perform a method, which may comprise the steps of receiving measurements of a plurality of transient motor coil currents conducted by a motor coil of a motor for use in conjunction with an implantable gastric band, receiving a measurement of a maximum motor coil current conducted by the motor coil, and detecting a blockage of the motor based on the measurements of the plurality of transient motor coil currents and the measurement of the maximum motor coil current.

In another embodiment, the present invention may provide a motorized gastric band system, which may include an implantable gastric band for forming a loop having a ventral surface for contacting a stomach of a patient, a motor coupled to the implantable gastric band, and including a motor coil for conducting a motor coil current, and a gear responsive to the motor coil current, and for adjusting the ventral surface of the implantable gastric band, and a processor coupled to the motor, and configured to receive measurements of a plurality of transient motor coil currents conducted by the motor coil, receive a measurement of a maximum motor coil current conducted by the motor coil, and detect a blockage of the motor based on the measurements of the plurality of transient motor coil currents and the measurement of the maximum motor coil current.

In another embodiment, the present invention may include a retractable antenna device for a remotely adjustable and remotely powered an implantable gastric band. The retractable antenna device may include a housing having a top wall and a bottom wall, a winding drum disposed within the housing and along the axle, the winding drum having a neck and a base, the winding drum is configured to rotate about an axis between a first position and a second position, an antenna disposed between the base of the winding drum and the bottom wall of the housing, a cable configured to coil around the neck of the winding drum when the winding drum is at the first position, and configured to uncoil and substantially extend outside of the housing when the winding drum is at the second position, and a locking device configured to lock the winding drum when the winding drum rotates from the first position to reach the second position, so that the winding drum remains stationary at the second position.

In another embodiment, the present invention may provide a remote control device for use in conjunction with a remotely adjustable and remotely powered implantable gastric band. The remote control device may include a handle, a display screen having a proximal side and a distal side, the proximal side positioned between the handle and the distal side, a sensing device configured to determine an orientation of the remote control device by sensing the relative position of the distal side and the proximal side of the display screen, and a processing device coupled to the sensing device, configured to transmit a display signal to the display screen for displaying an image on the display screen with a first image orientation or a second image orientation depending on the orientation of the remote control device, and configured to adjust the implantable gastric band.

In another embodiment, the present invention may provide a system for rapidly charging a remote control device for remotely adjusting and powering an implantable gastric band via a telemetric coupling. The system may include a battery for providing power to the remote control device, and having a battery voltage, and a charging station for charging the battery, the charging station configured to monitor the battery voltage of the battery, deliver a constant charging current to the battery until the battery voltage reaches a predefined threshold, and deliver a constant charging voltage to the remote control device thereafter to maintain the battery voltage.

In another embodiment, the present invention may provide a system for remotely adjusting and powering an implantable gastric band configured to be installed around a stomach of a patient. The system may include an implantable memory configured to be disposed inside the patient and to store a patient record relatable to the patient and an adjustment record relatable to an adjustment history of the implantable gastric band, and a processor coupled to the memory, and configured to retrieve the adjustment history upon receiving a telemetric data retrieval signal from a remote control device, generate a signal for adjusting the implantable gastric band upon receiving a telemetric band adjustment signal from the remote control device, and update the adjustment record based on the telemetric band adjustment signal.

In yet another embodiment, the present invention may provide an implantable gastric band, which may include a tubular member having a first end and a second end, the second end defining an opening, the first end having a flange configured to engage the second end of the tubular member, thereby forming a tubular ring having an adjustable ventral ring surface and a substantially rigid dorsal ring surface, a skeleton disposed between the adjustable ventral ring surface and the substantially rigid dorsal ring surface of the tubular ring, the skeleton having a distal end pushing against the first end of the tubular member and a proximal end pushing against the second end of the tubular member, the skeleton configured to support the substantially rigid dorsal ring surface of the tubular ring, a flexible screw slid between the skeleton and the adjustable ventral ring surface, the flexible screw having a hook anchoring the distal end of the skeleton and a crimped end extending beyond the opening of the tubular member, the flexible screw having an outer portion disposed outside of the tubular ring and an inner portion disposed inside of the tubular ring, the inner portion of the flexible screw defining a circumference of the adjustable ventral ring surface, a motor anchoring the proximal end of the skeleton and engaging the flexible screw, and configured to increase or decrease the inner portion of the flexible screw, thereby adjusting the circumference of the adjustable ventral ring surface, a processor for receiving an telemetric signal and for controlling the motor, and a cable having a processor end coupled to the processor and a motor end coupled to the motor.

BRIEF DESCRIPTION OF THE DRAWINGS

The features, objects, and advantages of the invention will become more apparent from the detailed description set forth below when taken in conjunction with the drawings, wherein:

FIGS. 8A-8R show the sample screen shots of the control device according to an embodiment of the present invention;

FIGS. 35A-35B show a perspective view and an exploded view of an external antenna with a retractable cable according to an embodiment of the present invention;

FIGS. 37A-37B show a perspective view and an exploded view of the implant according to an embodiment of the present invention;

FIGS. 38A-38F show the perspective views of various implant electronic device protection case components according to an embodiment of the present invention;

FIGS. 39A-39B show a top view and a bottom view of an implant electronic system board according to an embodiment of the present invention;

FIGS. 40A-40C show various views of a manipulation handle according to an embodiment of the present invention;

FIGS. 43A-43B show the command only protocol and a data structure of the command according to an embodiment of the present invention;

FIGS. 44A-44B show the command-parameter protocol and a data structure of the command-parameter according to an embodiment of the present invention;

FIGS. 45A-45B show the data structures of an ACK message and a NACK message according to an embodiment of the present invention;

FIGS. 57A-57H show various views of the motor engaging the flexible screw according to an embodiment of the present invention;

FIGS. 58A-58C show various views of a bendable skeleton embedded with a stabilizing tube according to an embodiment of the present invention;

FIGS. 60A-60D show various views of a dorsal element according to an embodiment of the present invention;

FIGS. 62A-62C show various views of a membrane shell according to an embodiment of the present invention; and FIGS. 63A-63C show various views of a cushioned membrane shell according to an embodiment of the present invention.

DETAILED DESCRIPTION

Figure 1:
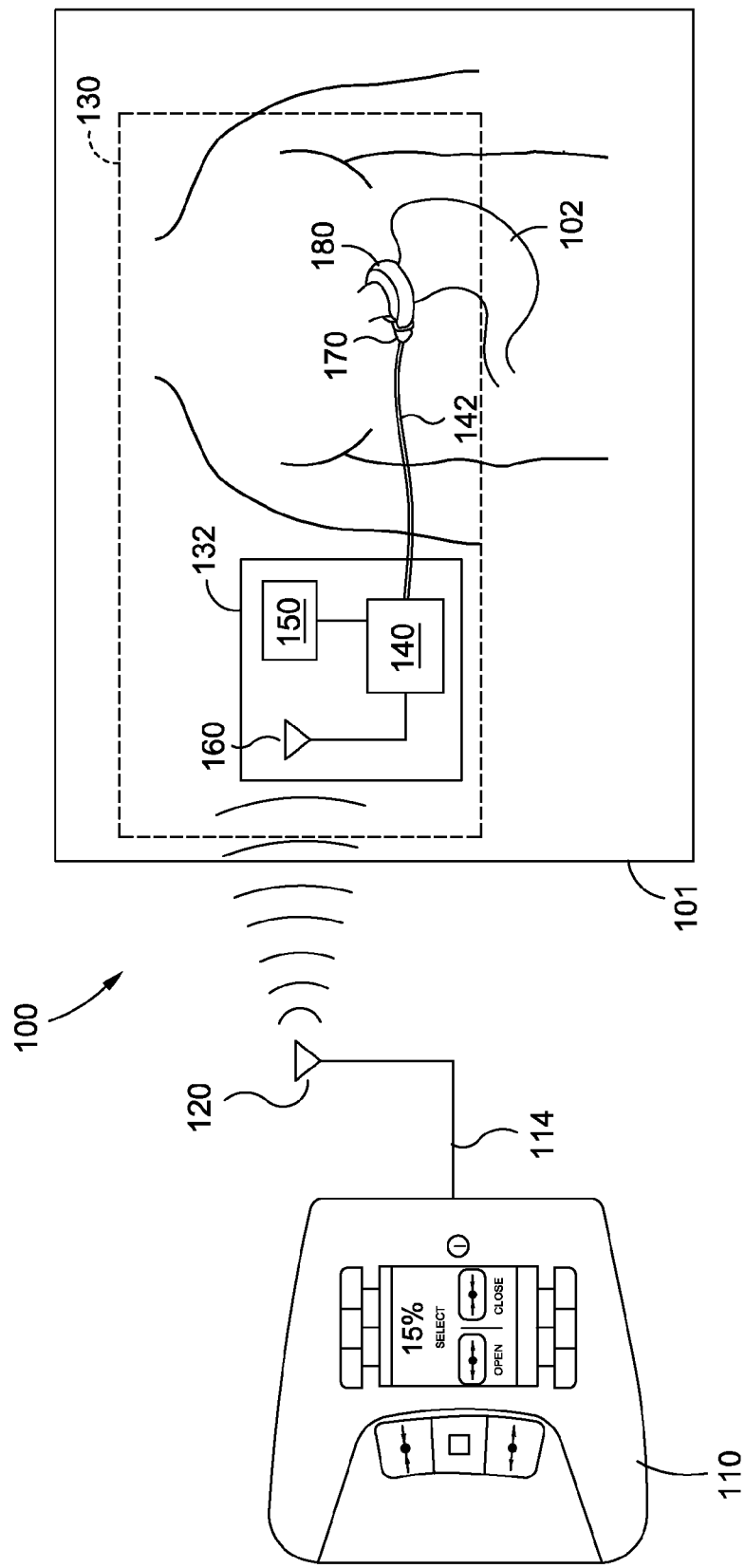
FIG. 1 shows a perspective view of a remotely adjustable remotely powered (RARP) gastric band system according to an embodiment of the present invention.

In FIG. 1, a remotely adjustable and remotely powered (RARP) gastric band system 100 is shown according to an embodiment of the present invention. Generally, the RARP gastric band system 100 may include an external subsystem and an implant (internal) subsystem. The external subsystem may include a control device (a.k.a. control unit) 110, an external antenna 120, and a retractable antenna cable 114, which may be used for coupling the external antenna 120 to the control device 110.

From a high level standpoint, the control device 110 may serve various functions. In one embodiment, for example, the control device 110 may be used as an interface for a user, such as a physician or a care taker. In another embodiment, for example, the control device 110 may be used for transmitting telemetric signal 122 to the implant 130 for inducing power therein. In yet another embodiment, for example, the control device 110 may be used for remotely controlling various functionalities of the implant 130, such as adjusting the size of a gastric band 180, retrieving information from the implant memory device 150, and/or regulating power inside the implant 130.

The implant subsystem (a.k.a. the implant) 130 may be implanted inside a patient's body 101, and it may include an implant electronic device 132, a gastric band 180, a motor 170, and a motor cable 142. The gastric band 180 may be used for forming a stoma around the patient's stomach 102, and the motor 170 may be used for controlling the gastric band 180, which may in turn, adjust the size of the stoma. Moreover, the implant electronic device 132 may include an implant (internal) antenna 160, a microprocessor (a.k.a. microcontroller) 140, and a memory device 150.

From a high level standpoint, the microprocessor 140 may serve various functions. In one embodiment, for example, the microprocessor 140 may coordinate the reception, rectification, and regulation of power received via the implant antenna 160. Generally, the implant antenna 160 may receive the signal transmitted from the external antenna 120 when they are separated by a distance of about 3 cm or less. In another embodiment, for example, the microprocessor 140 may retrieve past gastric band adjustment information from the memory device 150 or store current gastric band adjustment information to the memory device 150. In yet another embodiment, for example, the microprocessor 140 may control the motor 170 for adjusting the gastric band 180, and for detecting and preventing motor blockage.

Figure 2:
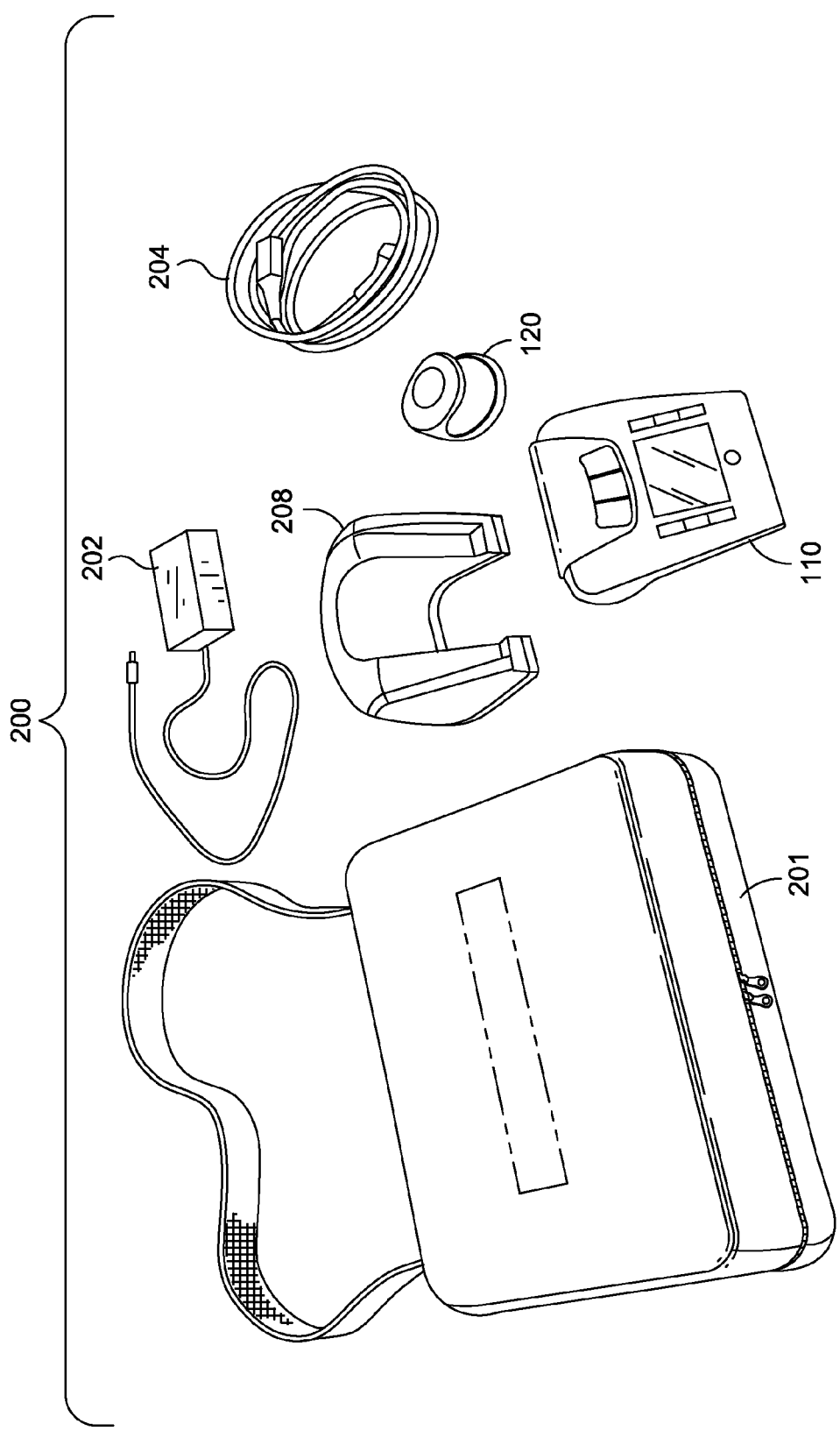
FIG. 2 shows a perspective view of various external components of the RARP gastric band system according to an embodiment of the present invention.

In FIG. 2, a perspective view of various external subsystem components of the RARP gastric band system 100 are shown according to various embodiments of the present invention. In addition to the control device 110 and the external antenna 120, the external subsystem 200 may include a carrying case 201, a power adaptor 202, a power cord 204, and a docking station 208.

The power adaptor 202 may connect a power source (not shown) to the docking station 208, such that the docking station 208 may receive electricity for charging the control device 110. The external antenna 120 may be connected to the control device 110 (interchangeably "control unit") during gastric band adjustment. The external antenna 120 may be stored at the back of the control device 110 when it is not in use. In between gastric adjustments, the control device 110 may be docked at the docking station 208 for recharging. The connection between the control device 110 and the docking station 208 may be established by contacting several spring loaded connectors located on the docking station 208 with several matching metallic surfaces located on the control device 110. The spring loaded connectors and the matching metallic surfaces may provide additional physical stability when the control device 206 is docked at the docking station 208.

Figure 3:
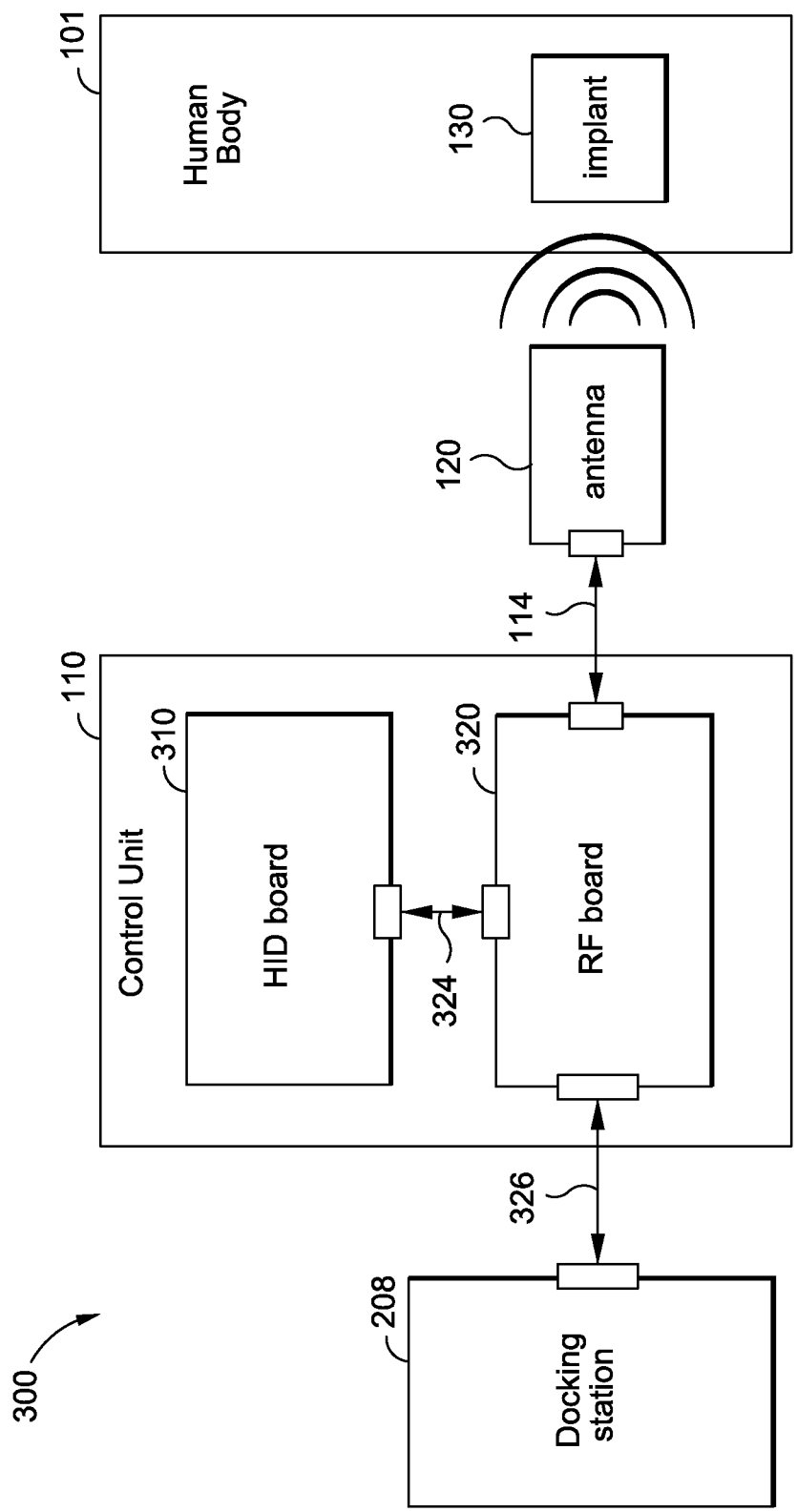
FIG. 3 shows a block diagram of the RARP gastric band system according to an embodiment of the present invention.

FIG. 3 shows a block diagram of a RARP gastric band system 300 according to an embodiment of the present invention. Generally, the RARP gastric band system 300 may include the control device 110, the docking station 208, the external antenna 120, and the implant 130. Particularly, the control device 110 may include a Human Interface Device (HID) board 310 and a Radio Frequency (RF) board 320.

The HID board 310 may be used for implementing an HID subsystem. The HID subsystem may receive input from a user and generate output for the user during or in between gastric band adjustments. As such, a physician and/or a care taker may use the HID subsystem to adjust the size of the gastric band and to retrieve information regarding the gastric band adjustment history of a particular patient. The size of the gastric band can be understood as diameter of a ventral (inner) ring surface of the gastric band.

The RF board 320 may be used for implementing an RF subsystem. The RF subsystem may execute various tasks as instructed by the HID subsystem. Generally, the HID subsystem and the RF subsystem may setup a master-slave configuration 324, in which the HID subsystem may command the RF subsystem to perform a recharging task, a power transmission task, a band adjustment task, and/or an information retrieval task.

To perform the recharging task, the RF subsystem may establish a power connection 326 with the docking station 208. The power connection 326 may be used for transmitting power from the docking station 208 to the RF board 320. Moreover, the power connection 326 may conduct signals that may be used for monitoring and controlling the recharge process.

To perform the power transmission task, the RF subsystem may drive the external antenna 120 with an RF signal that induces power in the implant 130. Generally, the RF signal may be amplitude modulated and have a carrier frequency within the radio frequency range. In one embodiment, for example, the carrier frequency may range from about 30 kHz to about 300 GHz. In another embodiment, for example, the carrier frequency may range from about 10 MHz to about 50 MHz. In yet another embodiment, for example, the carrier frequency may approximately be about 27 MHz.

To perform the band adjustment task, the RF subsystem may momentarily transmit adjustment instruction via the external antenna 120 to the implant 130. The transmission of the adjustment instruction may include a series of handshake protocols, which may ensure that the adjustment instruction is being received and executed properly by the implant 130.

To perform the information retrieval task, the RF subsystem may sense and demodulate a feedback signal from the implant 130. Generally, the feedback signal may be a double modulation signal, which may include a frequency modulation component and an amplitude modulation component. In one embodiment, for example, the frequency modulation component may be used for embedding gastric band adjustment data and power regulation signal while the amplitude modulation component may be used as a carrier. In another embodiment, for example, the amplitude modulation component may be used for embedding gastric band adjustment data and power regulation signal while the amplitude modulation component may be used as the carrier.

Figure 4:
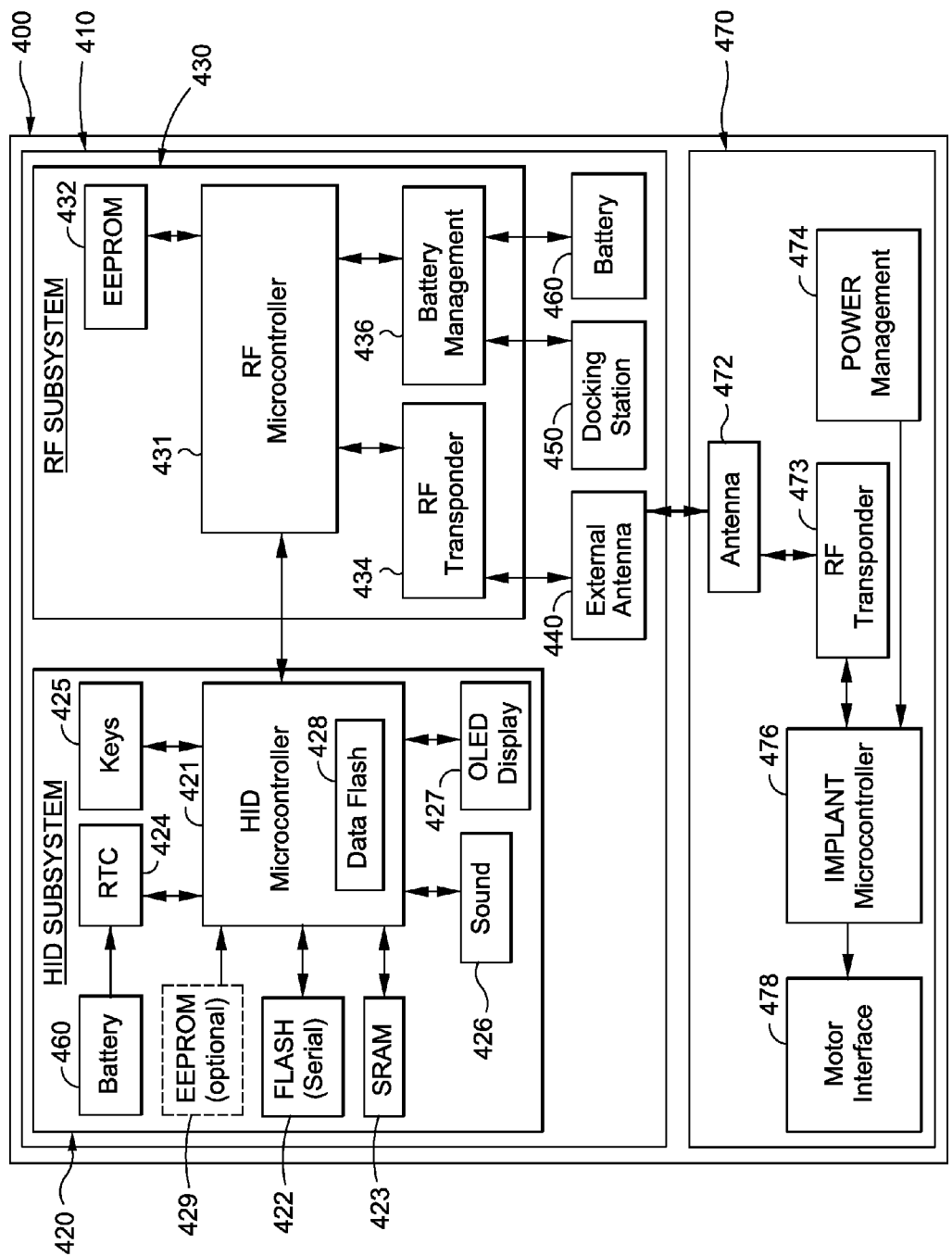
FIG. 4 shows a system architecture block diagram of the RARP gastric band system according to an embodiment of the present invention.

FIG. 4 shows a system architecture block diagram of a RARP gastric band system 400 according to an embodiment of the present invention. Generally, the RARP gastric band system 400 may include an external system 410 and an implant (internal) system 470. The external system 410 may include an HID subsystem 420, an RF subsystem 430, an external antenna 440, a docking station 450, and a rechargeable battery 460. The implant system 470 may include an implant antenna 472, an RF transponder subsystem 473, a power management subsystem 474, an implant microcontroller (microprocessor) 476, and a motor interface device 478. The RF transponder subsystem 473 may include various electronic components connecting the antenna 472 and the microcontroller 476. For example, the RF transponder subsystem 473 may include rectifying circuits and a LTC6900 chip.

The HID subsystem 420 may include: several input keys (buttons) 425 for receiving input from a user, a video device (OLED Display) 427 for outputting visual information to the user, an audio device 426 for outputting audio information to the user, a real-time control (RTC) device 424 for monitoring the charge level of the rechargeable battery 460, an HID microcontroller (microprocessor) 421 for processing information received from the keys 425 and the RTC device 424. In order to store and retrieve various data, the HID subsystem 420 may include several memory devices, such as a data flash device 428, a serial flash device 422, a SRAM device 423, and an optional EEPROM device 429.

The RF subsystem 430 may include: an EEPROM device 432 for storing various data, an RF microcontroller (microprocessor) 431 for performing various tasks requested by the HID microcontroller 421, an RF transponder 434 for driving and receiving information from the external antenna 440, and a battery management device 436 for interfacing with the docking station 450 and for controlling the recharging of the battery 460.

Figure 5B:
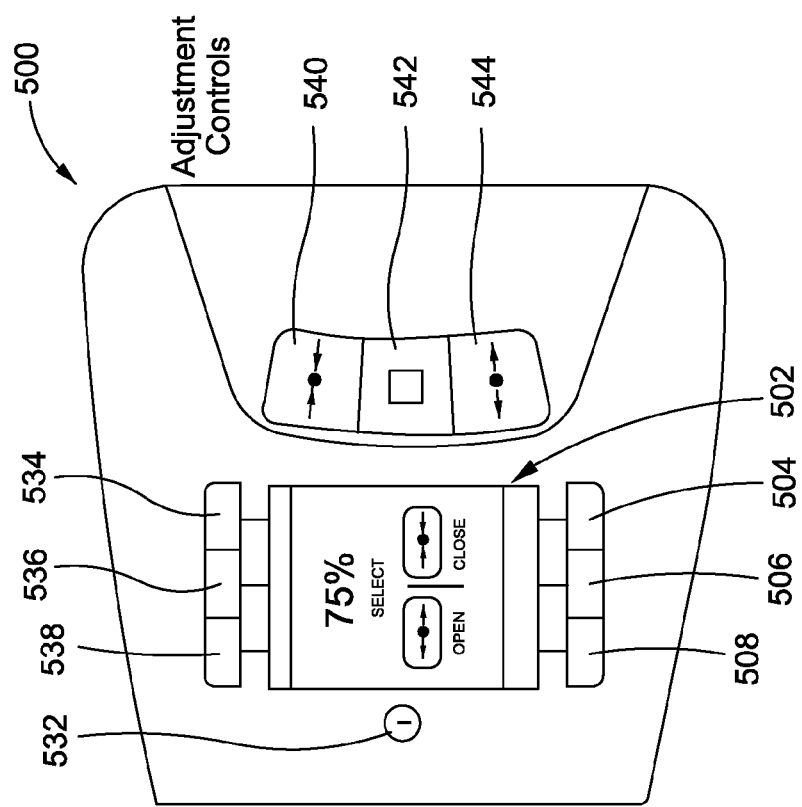
FIGS. 5A-5B show the button configuration and display screen orientation of a control device according to an embodiment of the present invention.
Figure 5A:
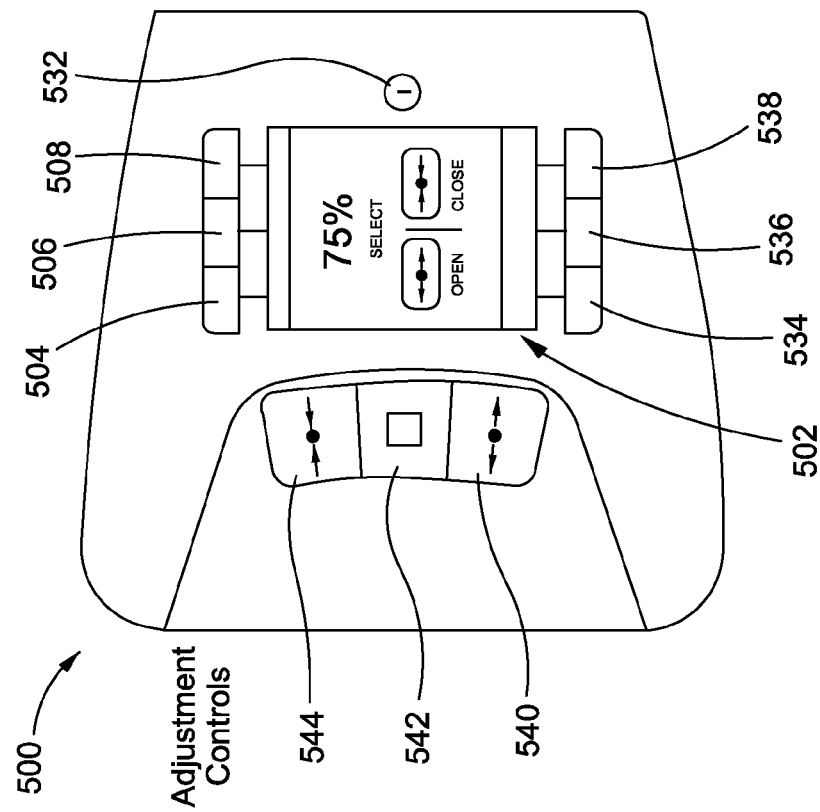

FIGS. 5A-5B show the button configuration and display screen orientation of a control device 500 according to an embodiment of the present invention. Generally, the front surface of the control device 500 may include a display screen 502, a power button (sensor) 532, a first set of auxiliary buttons (sensors) 504, 506, and 508, a second set of auxiliary buttons (sensors) 534, 536, and 538, and a set of adjustment control buttons (sensors), such as a band open button (sensor) 540, a stop adjustment button (sensor) 542, and a band close button (sensor) 544.

The first and second set of auxiliary buttons 504, 506, 508, 534, 536, and 538 may be configured to adapt to both left-handed and right-handed users. In one embodiment, for example, the button configuration and the display screen orientation as shown in FIG. 5A may be used by a left-handed user. Particularly, in the left-handed configuration (orientation), the first set of auxiliary buttons 504, 506, and 508 may be inactivated or disabled, whereas the second set of auxiliary buttons 534, 536, and 538 may serve as the left, center, and right buttons, respectively.

In another embodiment, for example, the button configuration and the display screen orientation as shown in FIG. 5B may be used by a right-handed user. Particularly, in the right-handed configuration, the second set of auxiliary buttons 534, 536, and 538 may be inactivated or disabled, whereas the first set of auxiliary buttons 504, 506, and 508 serve as the right, center, and left buttons, respectively.

As the first and second set of auxiliary buttons 504, 506, 508, 534, 536, and 538 are being reconfigured, the display screen 502 may be reoriented as well. When the second set of auxiliary buttons 534, 536, and 538 are activated, the display screen 502 may have a first (left-handed) orientation as shown in FIG. 5A. When the first set of auxiliary buttons 504, 506, and 508 are activated, the display screen 502 may have a second (right-handed) orientation as shown in FIG. 5B. Generally, the control device 500 may have a gyroscopic device (not shown) for sensing its orientation. Particularly, the control device 500 may use the sensed orientation to generate one or more signals for reconfiguring the first and second set of auxiliary buttons 504, 506, 508, 534, 536, and 538, and for reorienting the display screen 502.

Figure 6:
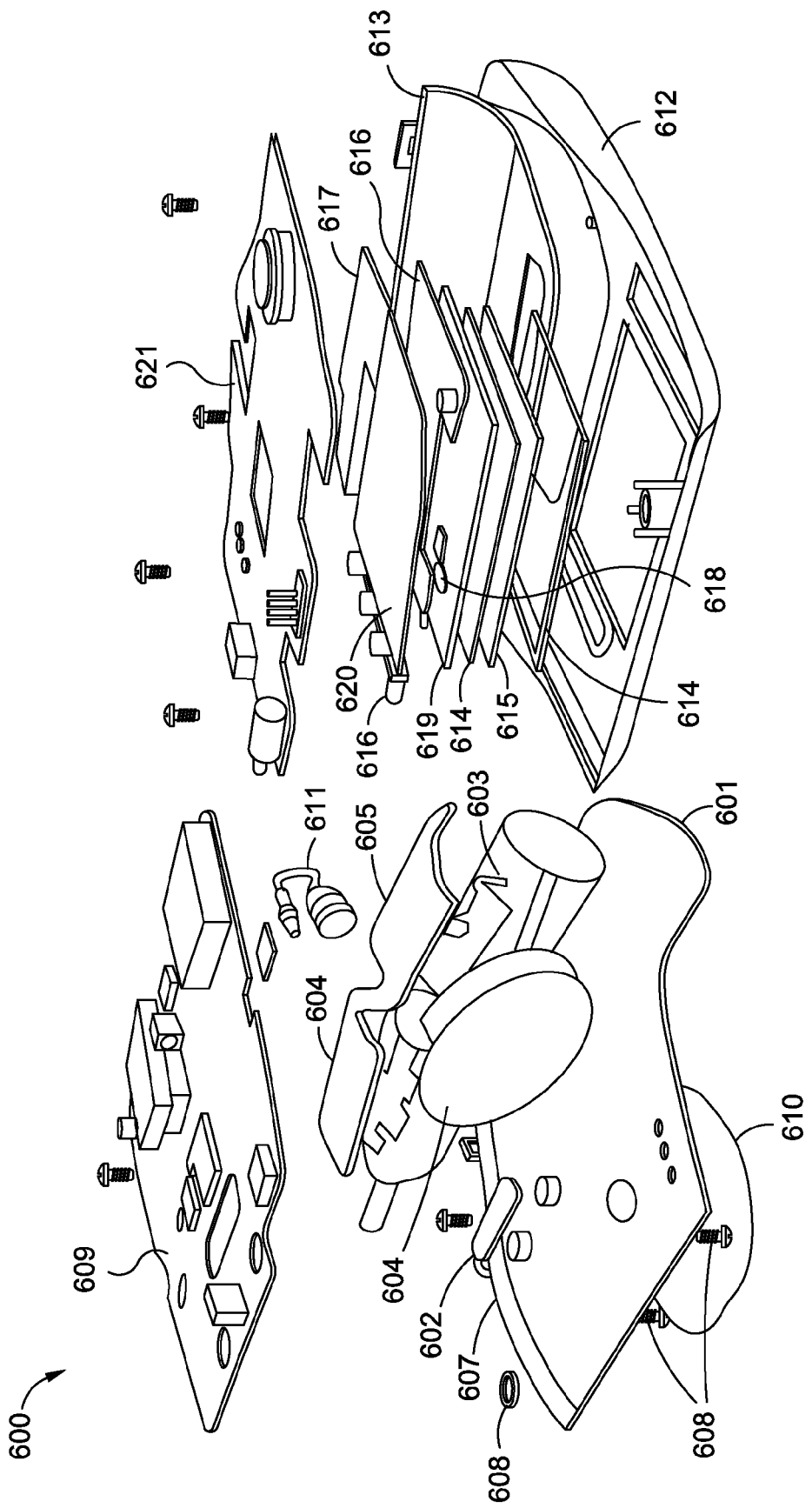
FIG. 6 shows an exploded view of a control device according to an embodiment of the present invention.
Figure 7:
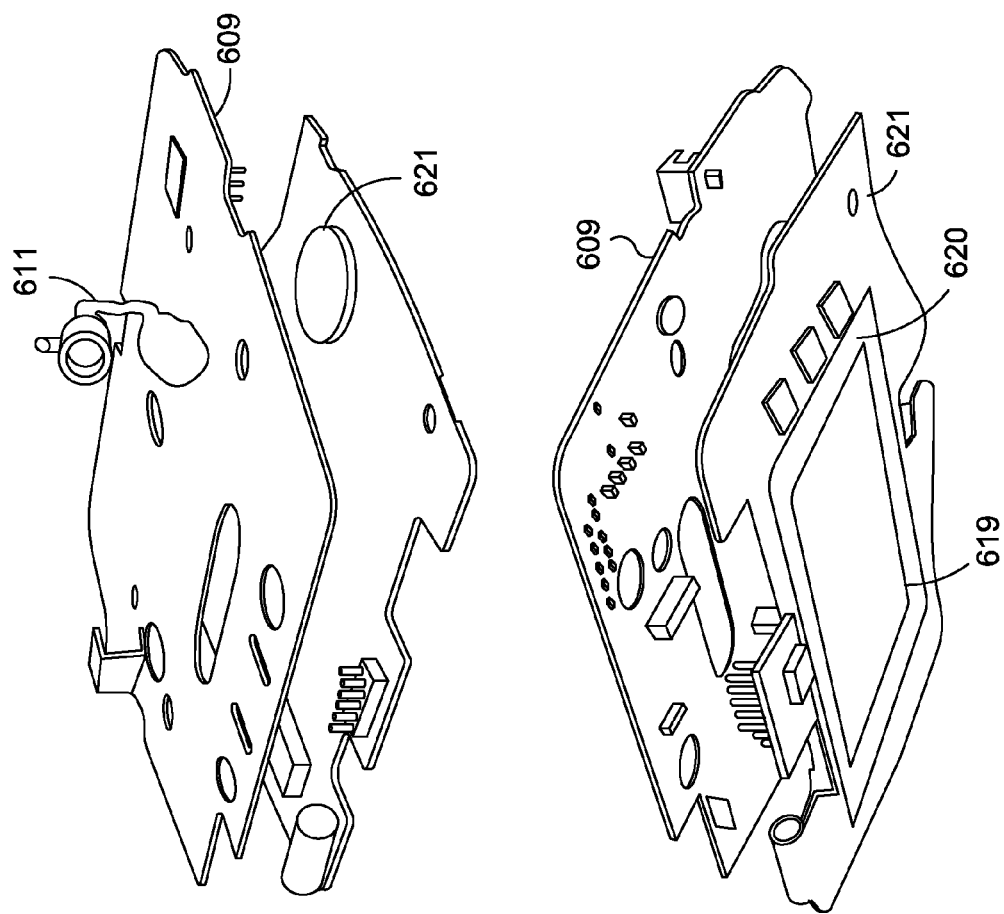
FIG. 7 shows the perspective bottom and top views of a Human Interface Device (HID) Printed Circuit Board (PCB) being coupled to a Radio Frequency (RF) Printed Circuit Board (PCB) according to an embodiment of the present invention.

FIG. 6 shows an exploded view of a control device 600 according to an embodiment of the present invention. The control device 600 may include a bottom shell 601, a bottom shell lid 602, a battery pack 603, a left battery holder 604, a right battery holder 605, a metal plate 606, a magnet 607, a metal pad 608, an RF PCB 609, a regulatory sticker 610, an RF cable 611, a top shell 612, a bottom shell 613, an adhesive display glass 614, a display glass 615, an auxiliary buttons group 616, an adjustment control buttons group 617, a power button 618, a display OLED 619, a Gasket display 620, and an HID PCB 621. As shown in FIG. 6, the components of the control device can be grouped as the top shell assembly (right) and the bottom shell assembly (left). The two assemblies can be snapped or screen fastened together after the HID PCB 621 and the RF PCB 609 are properly coupled as shown in FIG. 7.

FIGS. 8A-8R show the sample screen shots of the control device according to an embodiment of the present invention. In FIG. 8A, the control device may be powered up and it may display a "Welcome" screen, which include a logo and/or a slogan. In FIG. 8B, the control device may display the "Code Entering" screen for receiving authentication information. In the "Code Entering" screen, a battery strength symbol 801 and a user code request message 802 may be displayed. Accordingly, a user may enter a four-digit access code 803. Particularly, the user may use the left auxiliary button, which may be associated with the plus sign 804, to increase the value of a digit, the center auxiliary button, which may be associated with the minus sign 805, to decrease the digit value, and the right auxiliary button, which may be associated with the arrow sign 806, to go to the next digit and eventually to accept the entry.

In FIG. 8C, the control device may display the "Antenna Search" screen, in which the user may be instructed to place the external antenna near the implant antenna. A number of reception bars 807 may be shown in the "Antenna Search" screen once the control device detects a nearby implant antenna. The number of reception bars 807 may indicate the strength of the connection between the external antenna and the implant antenna. For example, a signal strength represented by two or less reception bars 807 may be considered insufficient, whereas a signal strength represented by three or more reception bars 807 may be considered sufficient.

In FIGS. 8D and 8E, the control device may display the "Loading" screens once the control device detects a signal strength represented by two or more reception bars 807. The "Loading" screens may show the progress of downloading the patient's information from the implant.

Once the downloading is complete, the control device may display the "Adjustment" screen (a.k.a. "Default" screen) as shown in FIG. 8F. In the "Adjustment" screen, the user may adjust the implanted gastric band. In adjusting the implanted gastric band, the user may use the band open button, which may be associated with the band open symbol 812, and the band close button, which may be associated with the band close symbol 813. Moreover, the user may choose to perform other functions. In one embodiment, for example, the user may use the left auxiliary button, which may be associated with the chart symbol 814, to review the past adjustment history of a patient. In another embodiment, for example, the user may use the center auxiliary button, which may be associated with the code change symbol 815, to change the password (or pass code) of the control device. In yet another embodiment, for example, the user may use the right auxiliary button, which may be associated with the lock symbol 816, to lock the control device.

When the user presses or selects the open band button, the control device may display the "Opening" screen as shown in FIG. 8G. In the "Opening" screen, the user may increase the size of the patient's stoma by loosening the implanted gastric band. Alternatively, when the user presses or selects the close band button, the control device may display the "Closing" screen as shown in FIG. 8H. In the "Closing" screen, the user may decrease the size of the patient's stoma by tightening the implanted gastric band. The user may press the stop button to stop the loosening process or the tightening process to terminate the adjustment process, after which the "Adjustment" screen may be reloaded.

When the user selects the chart function, the control device may display the "Adjustment History Plot" screen as shown in FIG. 8I. In the "Adjustment History Plot" screen, the user may use the left or center auxiliary button, which may be associated with the left and right arrow signs 818, to view previous and/or current records. Alternatively, the user may use the right auxiliary button, which may be associated with the list symbol 817, to view the adjustment history list.

When the user selects the adjustment history list, the control device may display the "Adjustment History List" screen as shown in FIG. 8J. In the "Adjustment History List" screen, the user may use the left or center auxiliary button, which may be associated with the up and down arrow signs 818, to view previous and/or current records. Alternatively, the user may use the right auxiliary button, which may be associated with the forward symbol 819, to return to the "Adjustment History Plot" screen.

Referring again to FIG. 8F, the user may lock the control device 110 by selecting the lock symbol 816. When the control device 110 is locked, the control device may display the "Locked" screen as shown in FIG. 8K. To exit the "Locked" screen, the user may press any button except for the power button. Then, the control device may display the "Code Entering" screen as shown in FIG. 8B. In the "code entering" screen, the user may be instructed to enter the pass code again.

Referring again to FIG. 8F, the user may change the old pass code by selecting the code change symbol 815. As shown in FIG. 8L, the control device may display the "Old Code Entering" screen, in which the user may enter the old pass code. After receiving and verifying the validity of the old pass code, the control device may display the "New Code Entering" screen as shown in FIG. 8M. After receiving the new code 822, the control device may display the "Confirm or Cancel Code" screen as shown in FIG. 8N. At this point, the user may select the left auxiliary button, which may be associated with the OK symbol 804, to accept the new code 822, or select the right auxiliary button, which may be associated with the CANCEL symbol 825, to cancel the new code 822. Upon receiving the confirmation, the control device may display the "Code Changed" screen as shown in FIG. 8O.

As shown in FIG. 8P, the "Battery Recharge" screen may be displayed when the control device is being recharged. The "Adjustment" screen may return once the control device is disconnected from the docking station. FIGS. 8Q and 8K show the "Error Message" screens, which may notify the user with warning messages. For example, the "Error Message" screen may notify the user when the implant is malfunction or when the battery level is low.

Table 1 below may provide a summary of screen shot with respect to the button functionality.

TABLE 1

Button assignments for the different screen shots.

| Screen shot | Activated Auxiliary Buttons | | |
| --- | --- | --- | --- |
| | Left | Center | Right |
| Welcome | N/A | N/A | N/A |
| Code Entering | Increase value | Decrease value | Next digit |
| Antenna Search | N/A | N/A | N/A |
| Loading | N/A | N/A | N/A |

TABLE 1-continued

Button assignments for the different screen shots.

| | Activated Auxiliary Buttons | | |
|---|---|---|---|
| Screen shot | Left | Center | Right |
| Adjustment | History plot | Code Change | Lock |
| Opening | N/A | N/A | N/A |
| Closing | N/A | N/A | N/A |
| History Plot | Previous point | Next point | List |
| History List | Scroll up | Scroll down | Adjustment |
| Locked | Code entering | Code entering | Code entering |
| Old Code | Increase value | Decrease value | Next digit |
| New Code | Increase value | Decrease value | Next digit |
| Confirm Code | Confirm | N/A | Cancel |
| Code Changed | N/A | N/A | Adjustment |
| Battery Recharge | N/A | N/A | N/A |
| Error Message | Adjustment | N/A | N/A |
| Warning | N/A | Adjustment | N/A |

Figure 9:
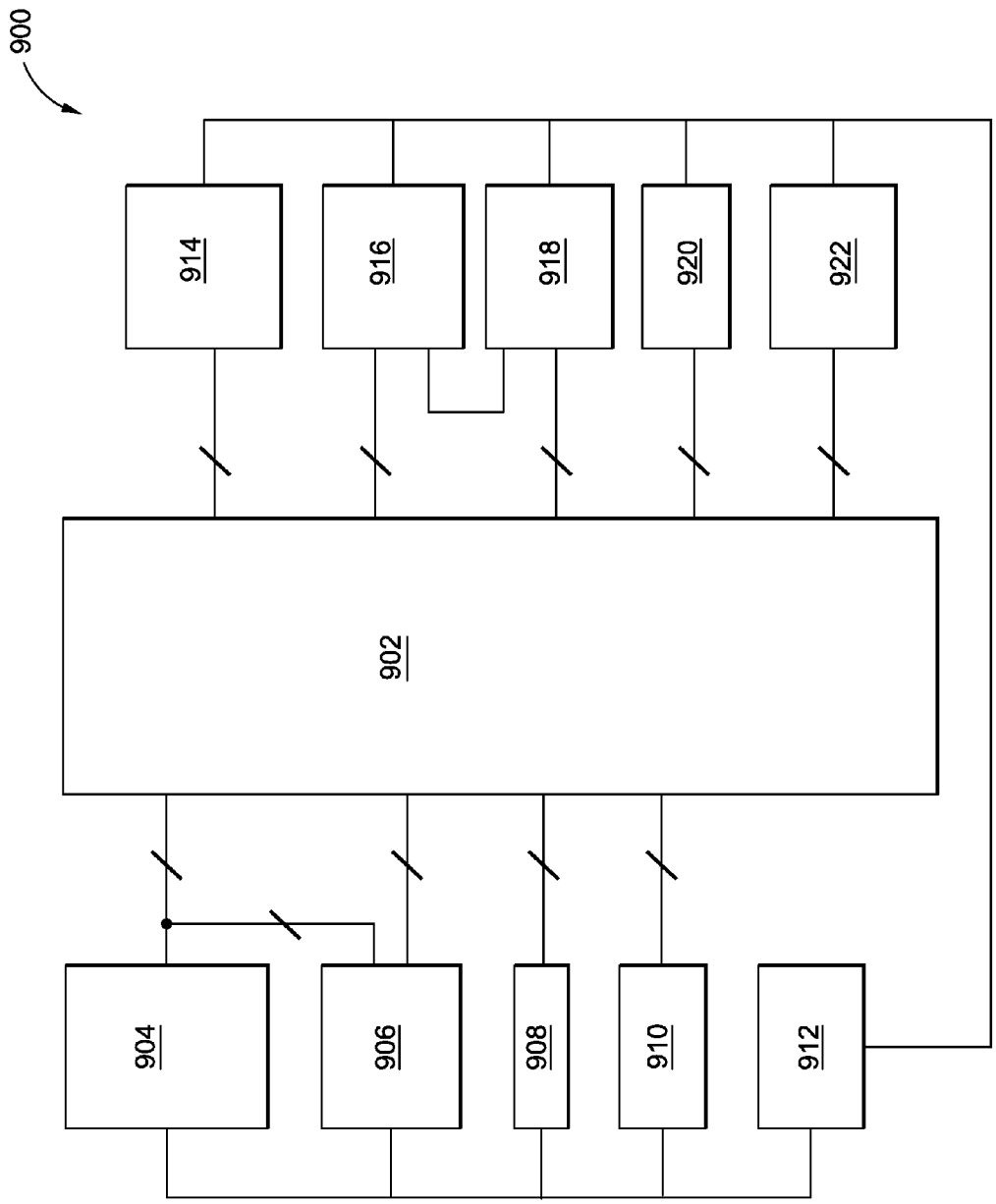
FIG. 9 shows a schematic view of the HID subsystem according to an embodiment of the present invention.

Referring to FIG. 9, a schematic view of the HID subsystem 900 is shown according to an embodiment of the present invention. Generally, the HID subsystem 900 may include eleven device blocks, such as a microcontroller block 902, a memory block 904, a display screen block 906, a buzzer and vibrator block 908, a sound interface block 910, an accelerometer and RTC block 914, an interface block 918, a USB block 920, an input button block 916, a JTAG/TRACE connector block 922, and a power supply block 912.

Figure 10:
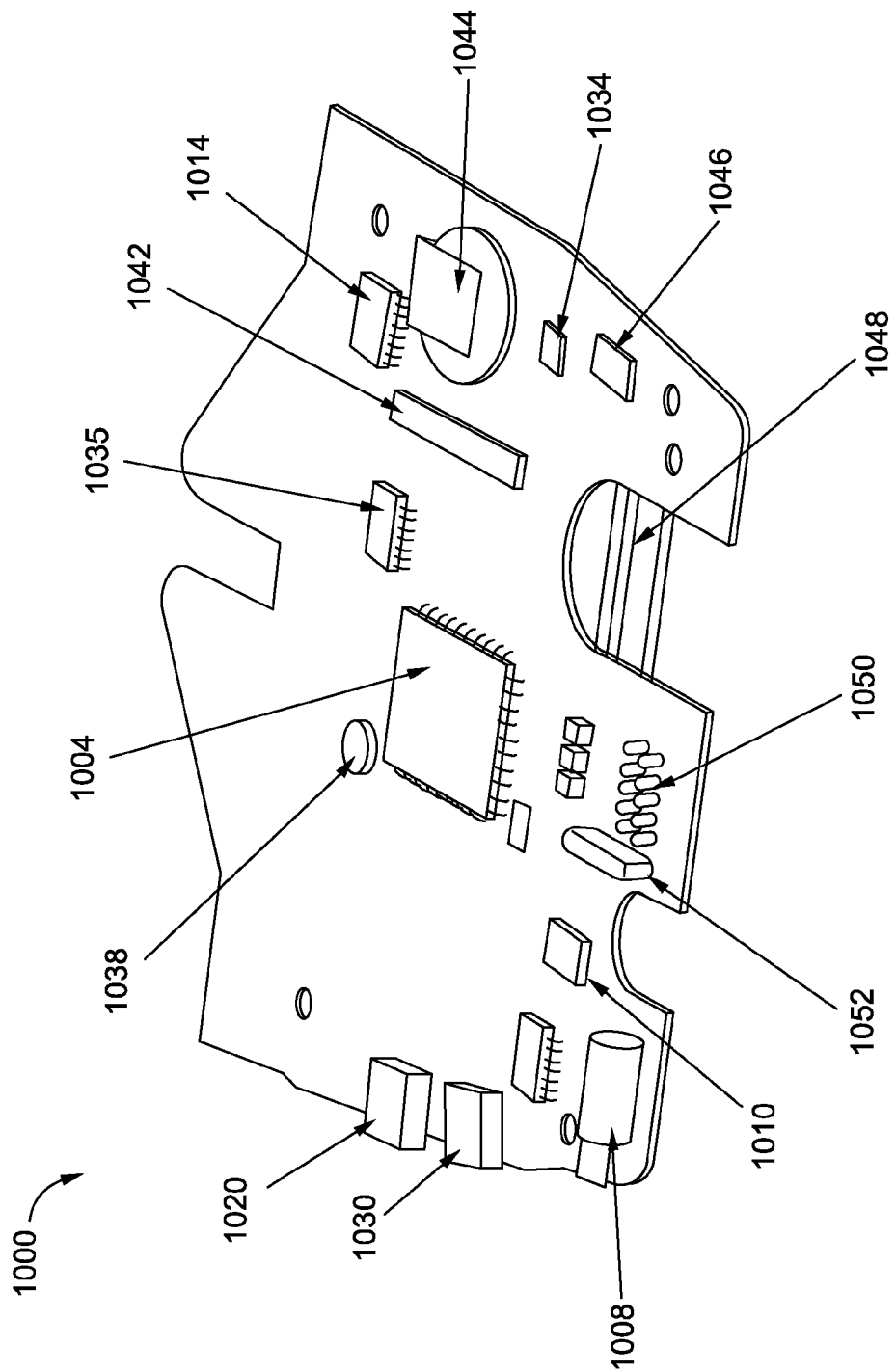
FIG. 10 shows a perspective view of the HID PCB components and connectors according to an embodiment of the present invention.

Referring to FIG. 10, a perspective view of the HID PCB 1000 is shown according to an embodiment of the present invention. Generally, each of the components on the HID PCB 1000 may be included in, associated with, or controlled by one of the eleven device blocks of the HID subsystem 900.

The microcontroller block 902 may include the microcontroller device (microprocessor) 1004, which may be configured as the master of the control device and may control all the user interface components, such as the display screen, the buttons, the sound interface, and the memory. The microcontroller block 902 may also include a crystal oscillator, two pull-down resistors and a pull-up resistor. The memory block 904 may include a 128-Mb flash memory 1034 and a 1-Mb EEPROM 1046, along with five pull-up resistors and four regulating capacitors.

The display screen block 906 may include an OLED display, an OLED display flat connector 1048 and a display driver supply (not shown). The buzzer and vibrator block 908 may include various components for driving a buzzer 1038 and a vibrator 1008. The sound interface block 910 may include an audio power amplifier 1010, which may be connected to the speaker (not shown). The accelerometer and RTC block 914 may include an RTC chip 1041 and a PC30 accelerometer chip 1035 as well as a lithium ion battery 1044 for back-up power.

The input button block 916 may include a power button (not shown) for sending power up signals to the HID PCB and the RF PCB. The input button block 916 may also include two set of triplet buttons (auxiliary buttons) selectable by three output keys. The interface block 918 may include two connectors 1050 and 1052 for connecting cards together and for connecting between RF PCB. The USB block 920 may include two mini USB connectors 1020 and 1030, an ESD input protection chip (not shown), and an RS232 translator chip FT232RL (not shown). The JTAG block 922 may include two connectors (not shown). Finally, the power block 912 may comprise a 3.3V voltage regulator (not shown) and several 3.3V power connections.

Figure 11:
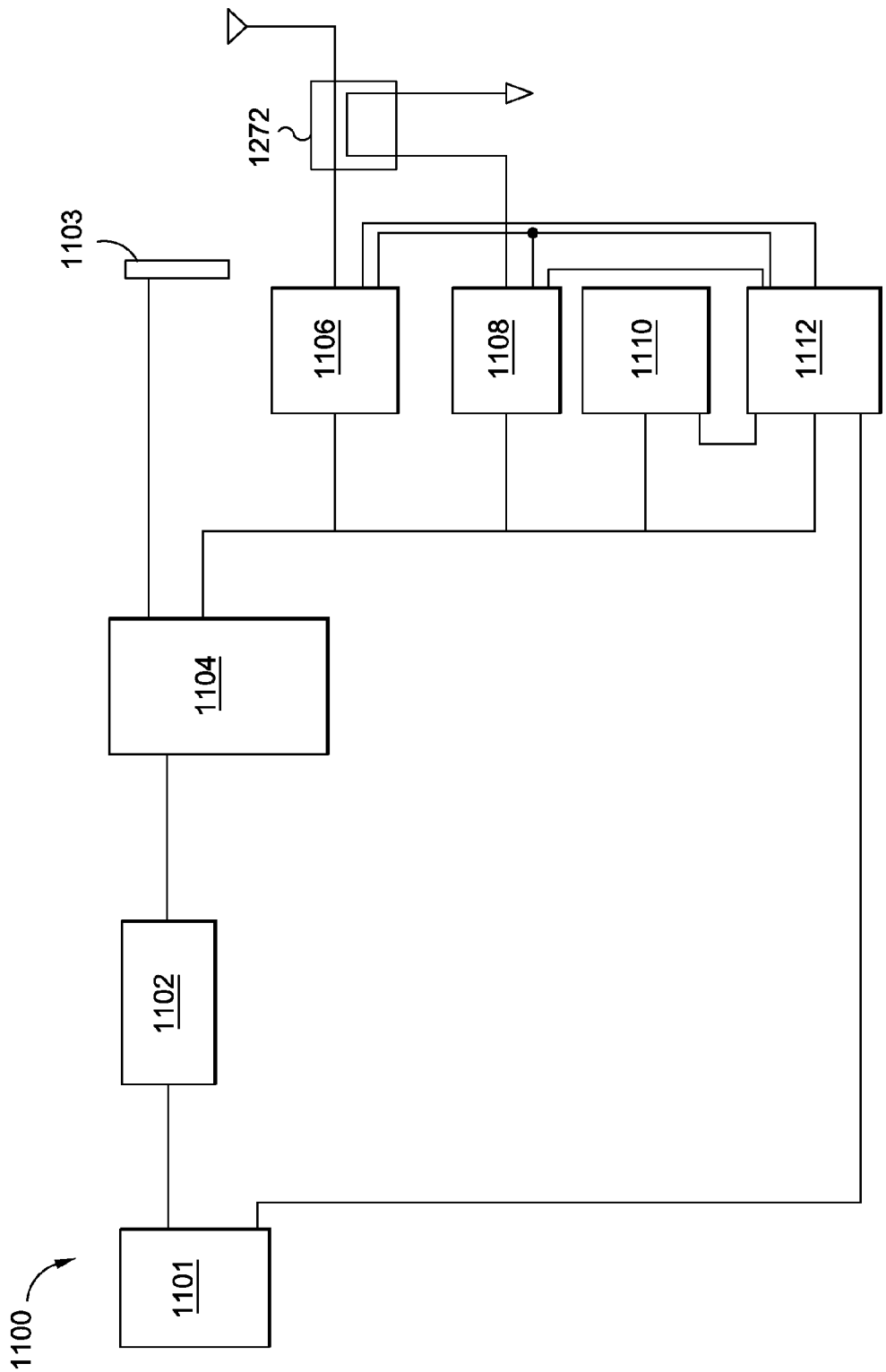
FIG. 11 shows a schematic view of the RF subsystem according to an embodiment of the present invention.

Referring to FIG. 11, a schematic view of the RF subsystem 1100 is shown according to an embodiment of the present invention. Generally, the RF subsystem 1100 may include seven device blocks, such as a main controller block 1104, a modulation block 1106, a demodulation block 1108, an auxiliary controller block 1110, an RF power supplies block 1112, a system power block 1101, and a battery block 1102.

Figure 12:
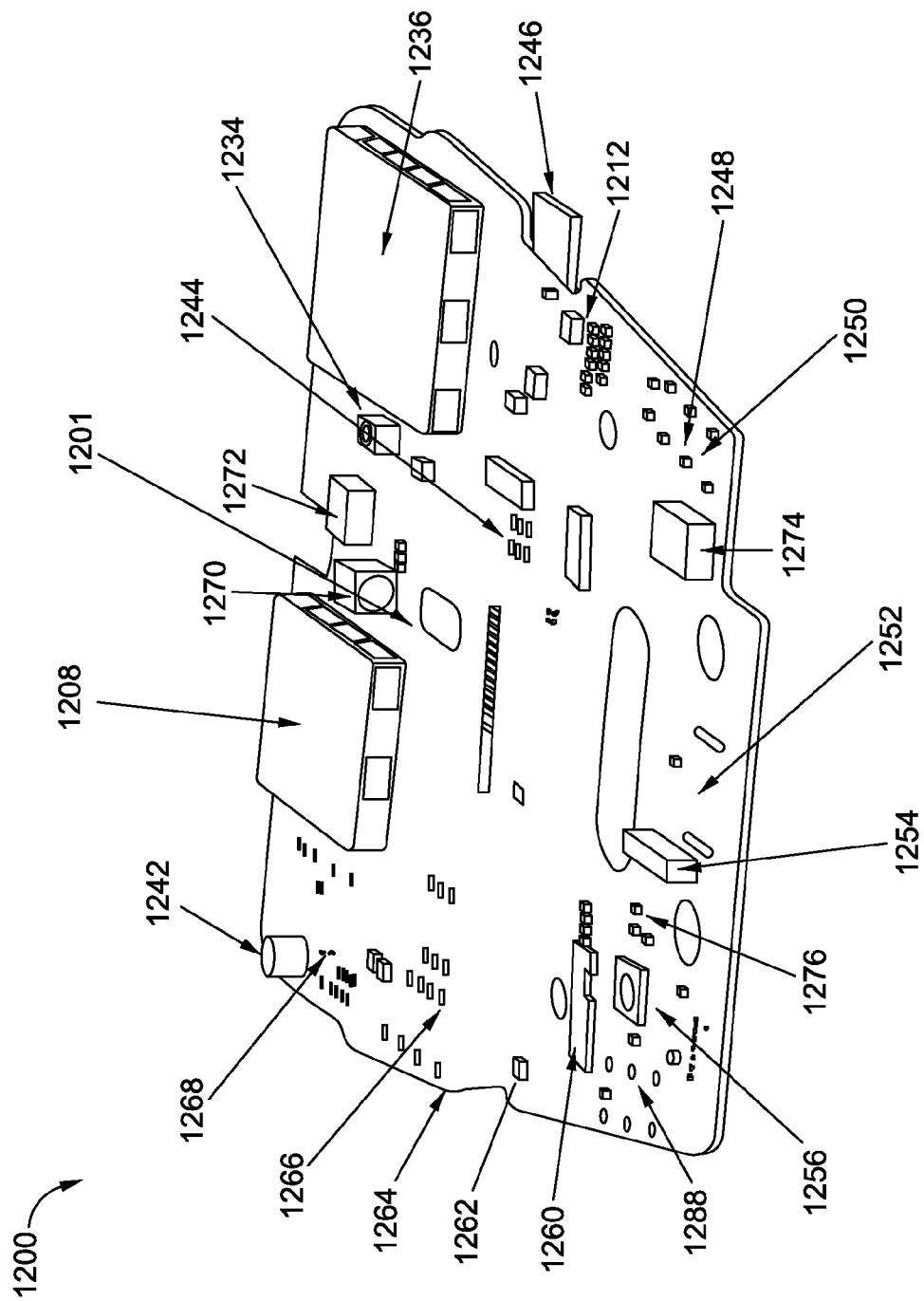
FIG. 12 shows a perspective view of the RF PCB components and connectors according to an embodiment of the present invention.

Referring to FIG. 12, a perspective view of the RF PCB 1200 is shown according to an embodiment of the present invention. Generally, each of the components on the HID PCB 1200 may be included in, associated with, or controlled by one of the seven device blocks of the RF subsystem 1100.

The RF main controller block 1104 may include a microcontroller (processing device) 1201, which may perform as a slave to the HID microcontroller block 902. The RF microcontroller 1201 may control the power induction in the implant, the charging circuitry in the docking station, the communication to and from the implant, and the communication with the HID microcontroller block 902. The RF microcontroller 1201 may further receive multiple monitoring inputs and the reset command from the HID microcontroller block 902. The USB connection may be established through a mini USB connector 1274 with the USB protocol translated into a UART serial interface through an RS232 translator chip (not shown).

The modulation block 1106 may include a class E amplifier 1234 for generating an amplitude modulation signal with carrier frequency at about 27 MHz. Particularly, the modulation block 1106 may be involved in generating a 27 MHz carrier frequency with an amplitude that equals the RF supply voltage VSUP, while the data signal may contain the digital command being sent to the implant via the external antenna.

The demodulation block 1108 may include a FM demodulator chip 1208 to demodulate the signals received from the implant and extracted from the external antenna via a directional coupler 1272. As such, the FM demodulator chip 1208 may be used for retrieving useful information, such as the received signal strength RSSI and the feedback message from the implant. The RF demodulator chip 1208 may also generate regulating signals, including REG_LEVEL, VSUP_CTRL, VSUP, and FORCE_RF_LEVEL.

The power supplies block may comprise a LT1961 voltage regulator (not shown), the amplitude of which may be controlled by either the VSUP_CTRL input indirectly from the implant or the DAC_IN input from the RF controller. The VSUP_CTRL input helps implement the control loop between the implant and the control device which adjusts the power induced in the implant. The RF microcontroller 1201 may also shutdown VSUP through the VSUP_ON/OFF input. Moreover, VSUP_INHIBIT1 may shutdown VSUP whenever the control device is powered from an external source to avoid any danger to the patient from power line surges. BSUP_INHIBIT2 may provide another shutdown path from the auxiliary controller block.

The auxiliary controller block 1110 may include an auxiliary controller 1244 and the associating connectors. The auxiliary controller 1244 may allow the overall system to implement a software oriented version of the implant power induction control.

The system power block 1101 may comprise the LM22672M voltage regulator 1256 for regulating the power supplies at 3.6V, the LP2985-33 voltage regulator U18 1276 for regulating the power supplies at 3.3V, and several monitoring signals indicating the power being turned on (KON), the presence of external power (EXTPWR_PRESENT) and the current load to the battery (ILOAD). The battery block 1102 may include a battery management related circuitry 1268, the battery connectors 1246 and 1264, as well as two batteries connected in series, which may be monitored by the signals BATMON, BATMONZ, BATT_TH, EXT_BAT_ES1 and EXT_BAT_MES2.

Figure 13:
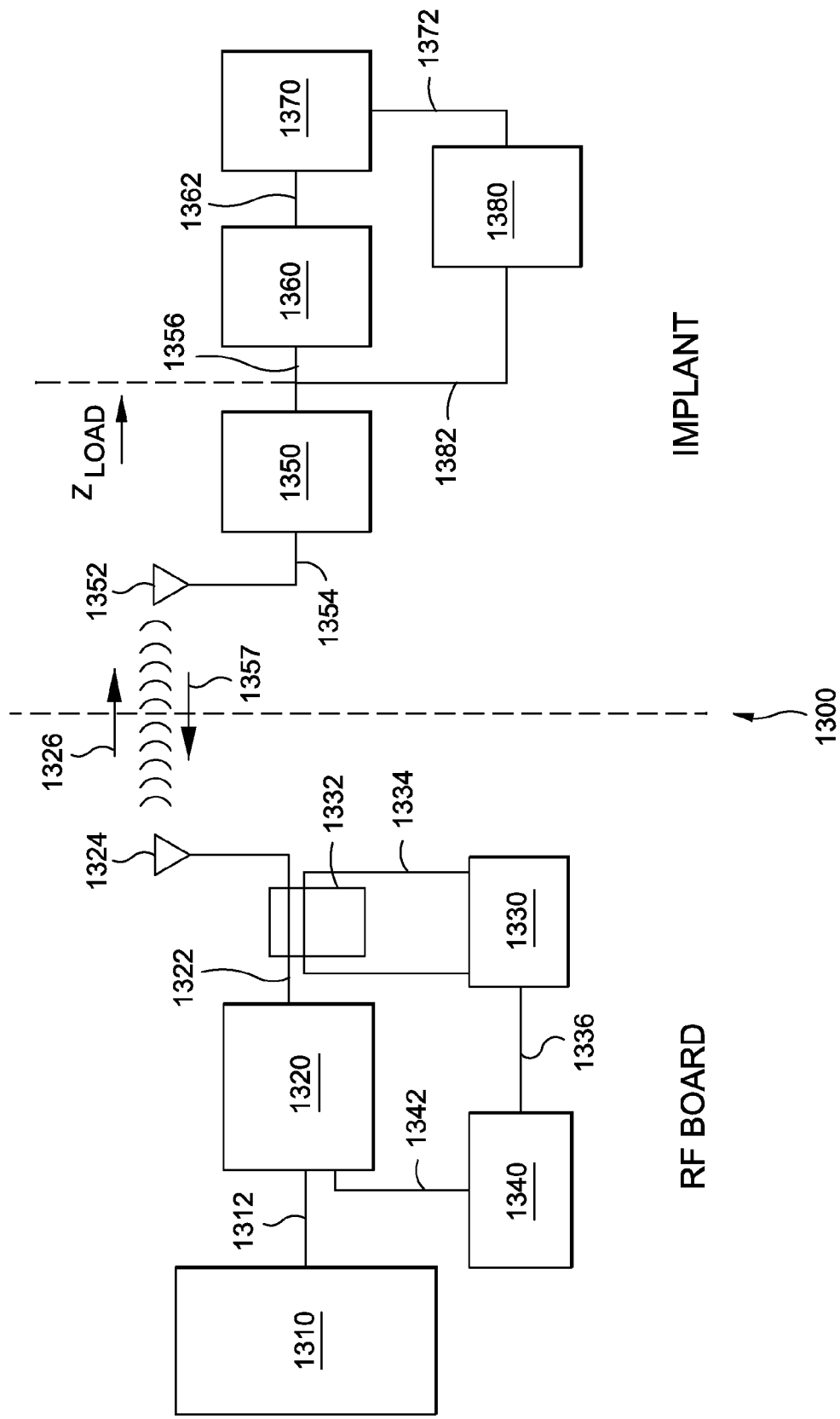
FIG. 13 shows a schematic view of a power regulation subsystem of the RARP gastric band system according to an embodiment of the present invention.

The discussion now turns to the power regulation subsystem of the remotely adjustable remotely power (RARP) gastric band system. Referring to FIG. 13, a schematic view of a power regulation subsystem 1300 is shown according to an embodiment of the present invention. Generally, the power regulation subsystem 1300 may be implemented by various devices (blocks) of the RF Board and of the Implant. The RF Board may include a modulation device (block) 1320, an external antenna 1324, a demodulation device (block) 1330, a power supply device (block) 1340, and a controller device (block) 1310. The Implant may include an implantable antenna 1352, a rectifying device (first device block) 1350, a maximum power sensing device (second device block) 1360, a regulation device (third device block) 1370, and an impedance switching device (fourth device block) 1380.

To initiate the power induction process, the controller device 1310 may send a transmission signal 1312 to enable the modulation device 1320. Depending on the operation mode of the RF Board, the transmission signal 1312 can be activation based or interrupt based. After being enabled, the modulation device 1320 may generate an amplitude modulation signal for driving the external antenna node 1322. The external antenna node 1322 may be a transmission line that couples between the external antenna 1324 and the modulation device 1320. As a result, the external antenna 1324 may transmit a telemetric signal 1326 according to the amplitude modulation signal.

The telemetric signal 1326 may travel across air and penetrate the body tissue of the patient, such that it may be received by the implantable antenna 1352. Based on the principles of electromagnetic induction, an alternate current (AC) may be induced at the implant antenna node 1354. The rectifying device 1350 may rectify the voltage associate with the alternate current, so as to deliver a DC input voltage ($V_{IN}$) on the DC input voltage ($V_{IN}$) node 1356. The maximum power sensing device 1360 may monitor the level of the DC input voltage $V_{IN}$. When the DC input voltage $V_{IN}$ exceeds a certain predetermined threshold voltage value, the maximum power sensing device 1360 may generate a regulation signal 1362 to activate the regulation device 1370.

After being activated, the regulation device 1370 may generate a regulation voltage 1372. The magnitude of which may depend on a voltage difference (potential difference) between the DC input voltage $V_{IN}$ and the predetermined threshold voltage value. Thus, the magnitude of the regulation voltage 1372 may represent or indicate the amount of regulation that may be needed. Generally, the DC input voltage $V_{IN}$ may be a function of a transmission distance between the external antenna 1324 and the implantable antenna 1352. When the transmission distance decreases, the signal strength of the telemetric signal 1326 may increase, thereby causing the DC input voltage $V_{IN}$ to rise. Thus, as the external antenna 1324 approaches the implantable antenna 1352, the regulation voltage 1372 may increase. In order to communicate the need to regulate with the RF Board, the regulation voltage 1362 may be used for generating one or more feedback signals and/or messages.

The impedance switching device (switching device) 1380 may receive and process the regulation voltage 1362. After processing the regulation voltage 1362 along with other signals, the impedance switching device 1380 may couple and decouple the DC input voltage $V_{IN}$ node 1356 to and from an additional impedance component at a feedback frequency. Generally, the feedback frequency may be determined based on the regulation voltage 1362 and some other factors. In one embodiment, for example, the feedback frequency may be inversely proportional to the regulation voltage 1362. In another embodiment, for example, the feedback frequency may be directly proportional to the regulation voltage 1362.

By switching on and off the additional impedance component, the impedance switching device 1380 may generate a feedback signal 1382, which may superimpose the regular DC input voltage $V_{IN}$. That is, the overall load impedance ($Z_{LOAD}$) may be adjusted by the feedback frequency of feedback signal 1382.

According to the principle of mutual inductance, the fluctuation of the overall load impedance and/or the feedback signal 1382 may manifest as a passive telemetric signal 1356, which may be received by the external antenna 1324. Consequently, the feedback frequency of the feedback signal may be seen as a message (envelop) frequency of the passive telemetric signal 1357.

In order to separate the passive telemetric signal 1357 from the outbound amplitude modulation signal, the RF Board may use a sensing device (block) 1332 to sense or extract a feedback profile 1334 of the passive telemetric signal 1357 from the external antenna node 1322. The feedback profile 1334 may have a frequency tracking the feedback frequency of the feedback signal. In one embodiment, for example, the sensing device 1332 may be a directional coupler. The demodulation device 1330 may receive the feedback profile 1334 and determine and/or extract the message frequency embedded in the feedback profile 1334.

Consequentially, the demodulation device 1330 may generate a voltage supply control signal 1336 based on the feedback frequency. The power supply device 1340 may process the voltage supply control signal 1336 and regulate the RF supply voltage 1342 accordingly. Because the modulation device 1320 may be powered by the RF supply voltage 1342, the amplitude modulation signal may be indirectly regulated by the power supply device 1340. As a result, the power induced by the amplitude modulation signal may be increased or decreased depending on the feedback signal 1382.

More specifically, the amplitude modulation signal may have a carrier frequency and a magnitude (modulation amplitude). Depending on the load impedance, the carrier frequency may be selected from a range of radio frequencies (about 30 kHz to about 300 GHz) for maximum power transfer. For example, the carrier frequency may be about 27 MHz when the load impedance is about 50Ω.

The modulation amplitude may be controlled by the RF supply voltage 1342, and it may determine the amount of power being transferred from the RF Board to the implant. Thus, power transfer may be regulated by adjusting the modulation amplitude, which may depend on the RF supply voltage 1342. For example, when the implant receives excessive power, which may cause overheating in the implant, the RF supply voltage 1342 may be lowered to reduce the modulation amplitude of the amplitude modulation signal. For another example, when the implant receives insufficient power, which may cause the implant to be turned off, the RF supply voltage 1342 may be augmented to increase the modulation amplitude of the amplitude modulation signal.

Figure 14:
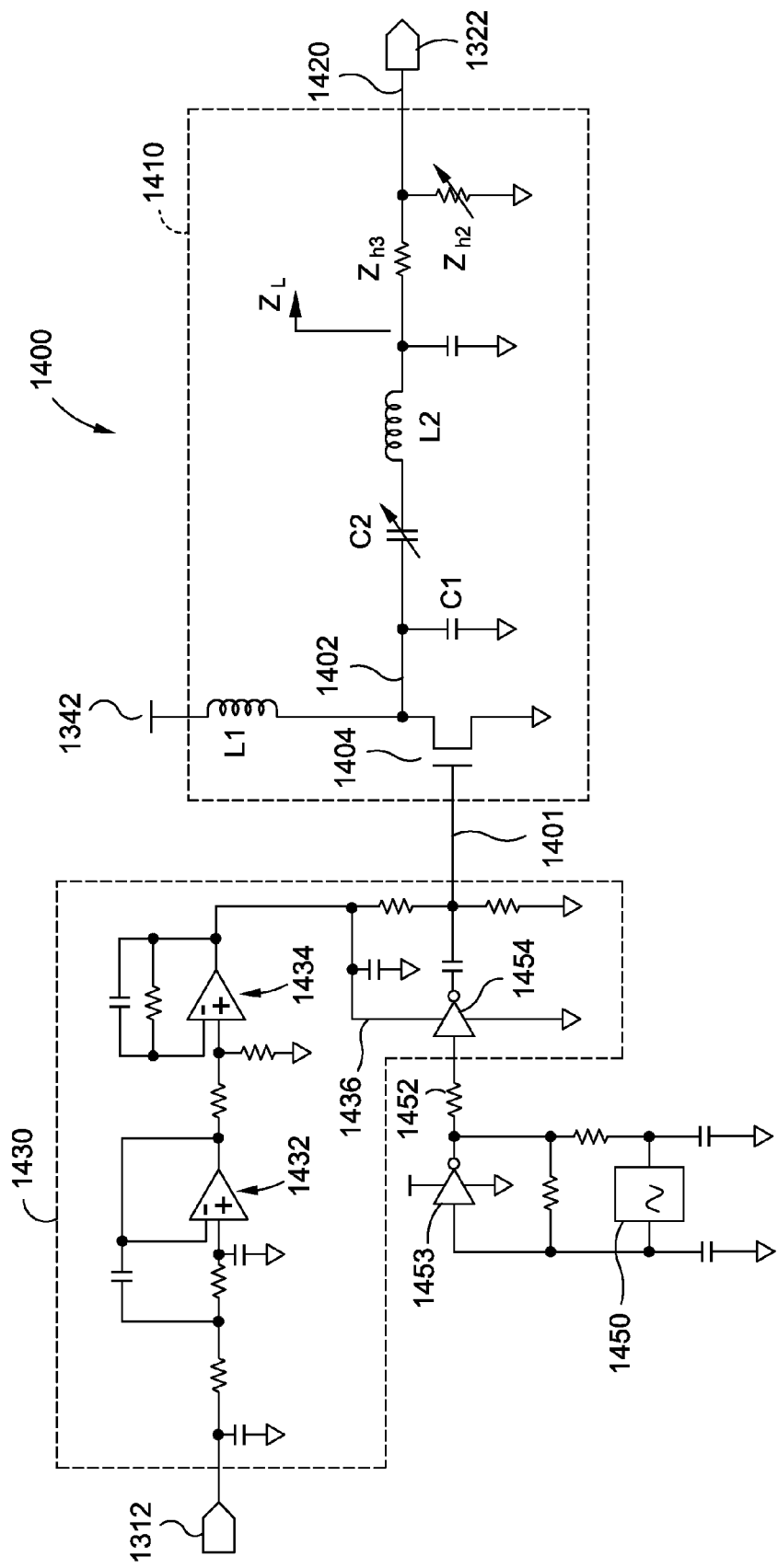
FIG. 14 shows a schematic view of a modulation device according to an embodiment of the present invention.

In FIG. 14, a schematic view of a modulation device 1400 is shown according to an embodiment of the present invention. Generally, the modulation device 1400 may be used for implementing the functional features of the modulation device 1320. Particularly, the modulation device 1400 may include an activation block (activation device path) 1430 for enabling or disabling the generation of the amplitude modulation signal, an oscillating device 1450 for generating a carrier frequency signal 1452, and a class E amplifier block (amplifier device path) 1410 for generating the amplitude modulation signal 1420. The oscillating device 1450 may be a crystal oscillator, and it may be used for controlling the carrier frequency of the amplitude modulated signal 1420.

The activation block 1430 may include a first stage amplifier 1432 for amplifying the transmission signal 1312, and a second stage amplifier 1434 for generating a data override signal 1436. Generally, the carrier frequency signal 1452 may be buffered by a first stage inverter 1453 and a second stage inverter 1454. Although the first stage inverter 1453 may be powered on by a separate power source, the second stage inverter 1454 may be enabled or disabled by the data override signal 1436.

When the RF Board is powering the implant, the data override signal 1436 may be low, such that the carrier frequency signal 1452 may drive a switching node 1401. Alternatively, when the RF Board is transmitting data, the data override signal 1436 may be high, such that the second inverter stage 1454 may be turned off momentarily during data transmission. As a result, the carrier frequency signal 1452 may be blocked from driving the switching node 1401.

The class E amplifier block 1410 may have a common source stage 1404 for driving a first intermediate node 1402. The output of the common source stage 1404 may have a frequency component, which may be controlled by the carrier frequency signal 1452 of the oscillating device 1450, and an amplitude component, which may be controlled by the RF supply voltage 1342. Depending on the regulation level, the amplitude component may change as the transmission distance varies. In one embodiment, for example, the amplitude component may range from about 3 V to about 16 V. In another embodiment, for example, the amplitude component may range from about 5V to about 14 V. As discussed earlier, the power induced in the Implant may be regulated by adjusting the amplitude component of the amplitude modulation signal 1420, which may be dictated by the RF supply voltage 1342.

Figure 15:
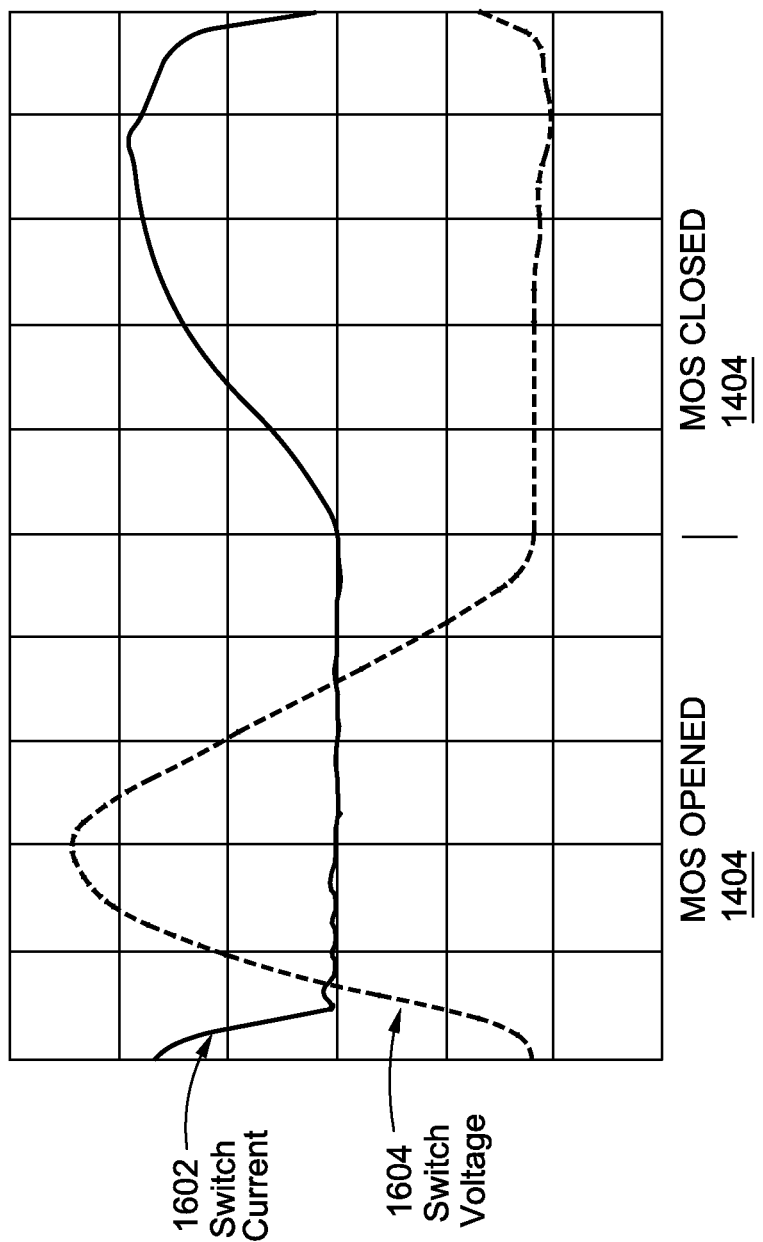
FIG. 15 shows a diagram with an ideal voltage curve and an ideal current curve of a Class E amplifier according to an embodiment of the present invention.
Figure 16:
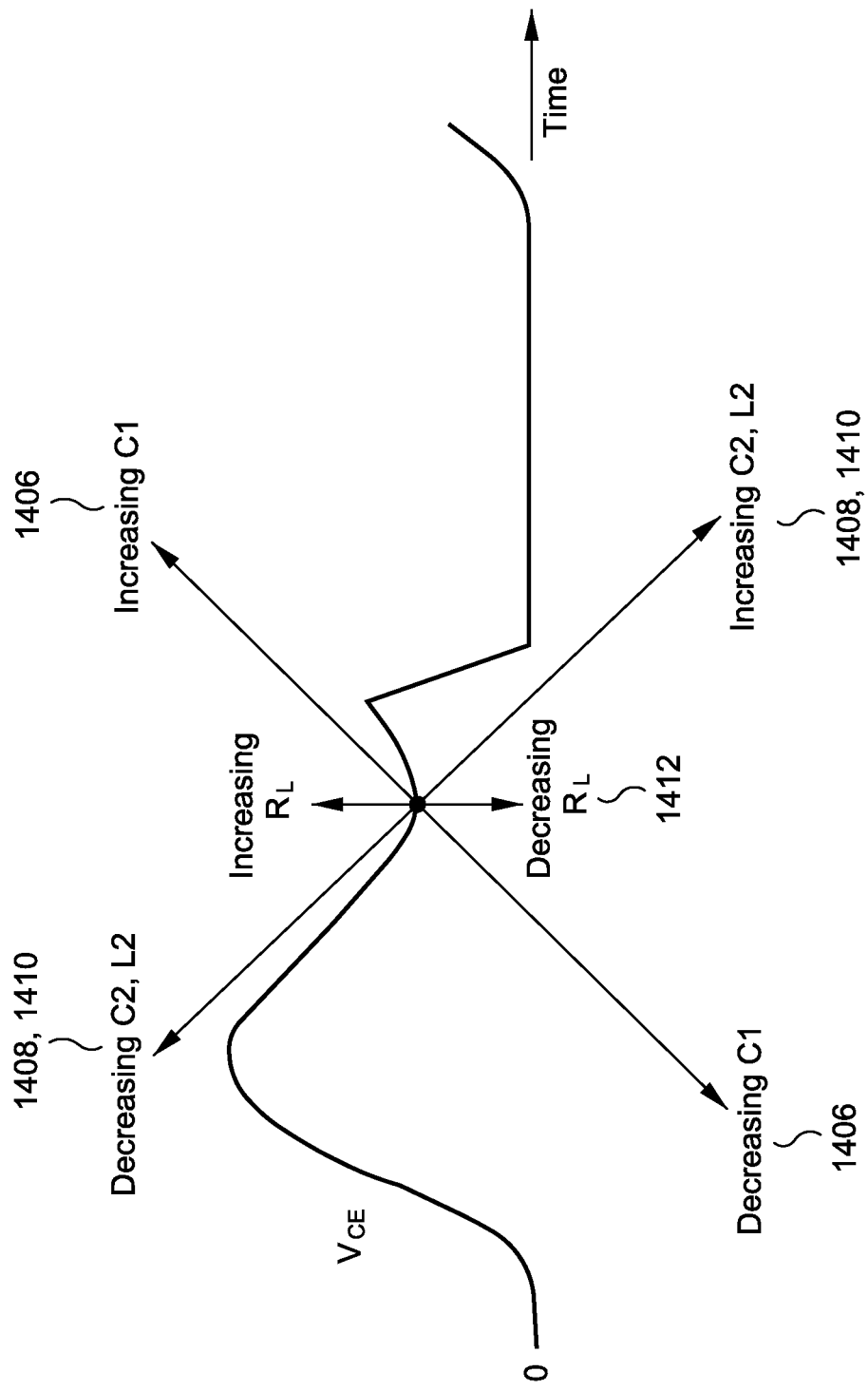
FIG. 16 shows the adjustability of tail end of the voltage curve in the Class E amplifier according to an embodiment of the present invention.

Referring to FIG. 15, the class E amplifier block 1410 may have a relatively low sensitivity to any variation in the load $Z_L$, and it may have a high efficiency as long as the transitions at the (common source state) MOS switch 1404 occur while the current or the voltage is null. Referring to FIG. 16, the capacitor C2 and the impedance Zh2 may be the adjustable components in the amplifier block 1410, such that the transition point may be moved left and/or right by adjusting the value of the capacitor C2, and it may be moved up and/or down by adjusting the value of the impedance Zh2.

Figure 17:
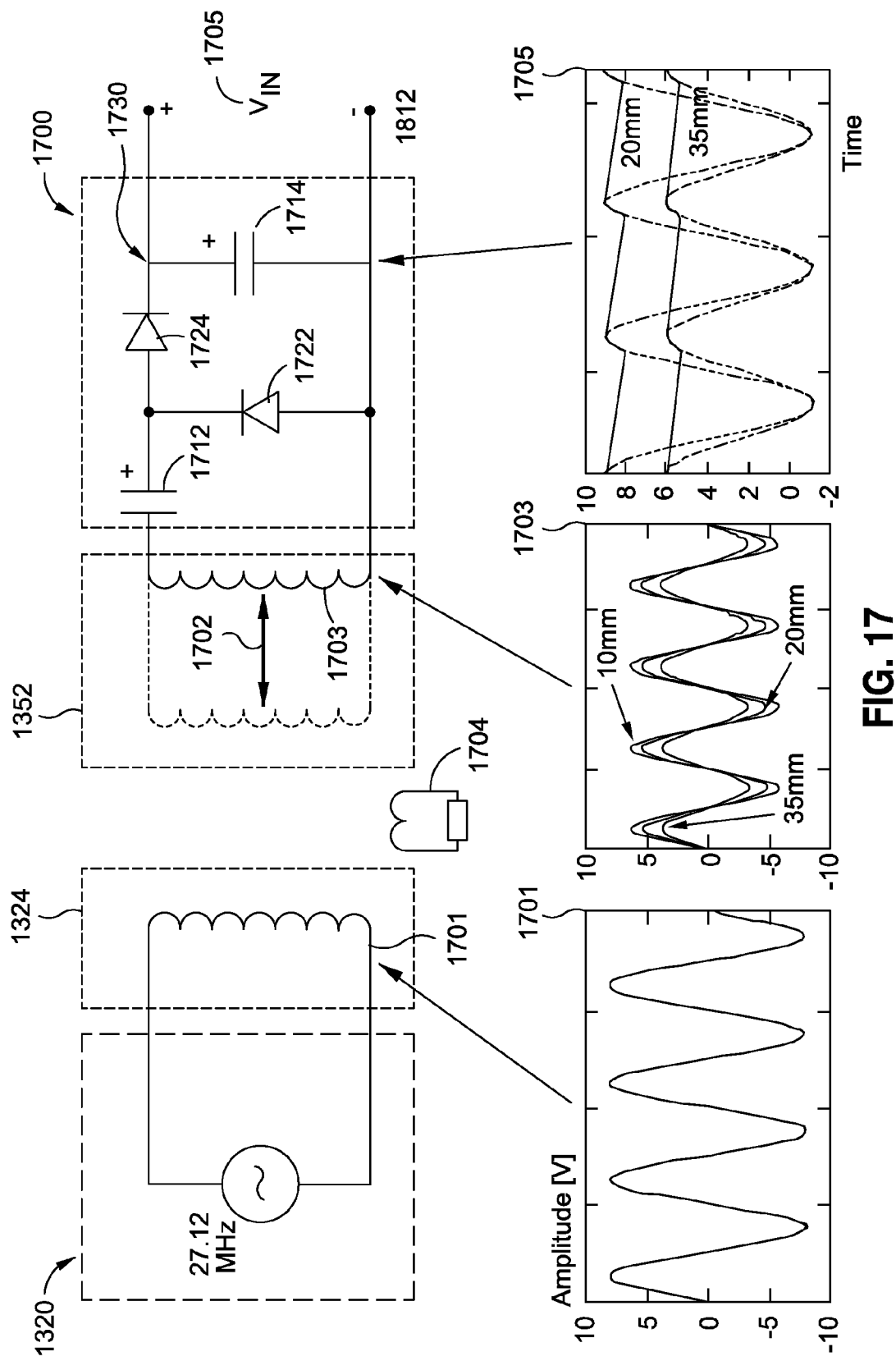
FIG. 17 shows a schematic view of a rectifying device according to an embodiment of the present invention.

In FIG. 17, a schematic view of a rectifying device 1700 is shown according to an embodiment of the present invention. Generally, the rectifying device 1700 may implement the functional features of the rectifying device 1350 as discussed in FIG. 13. Particularly, the rectifying device 1700 may include a first capacitor 1712, a second capacitor 1714, a first diode 1722, and a second diode 1724. More specifically, the first and second capacitors 1712 and 1714 may function as a pair of charge storage (or bootstrap) devices, while the first and second diodes 1722 and 1724 may function as a pair of voltage directing devices.

The modulation device 1320 may drive the external antenna 1324 with an amplitude modulation signal 1701, which may generate an alternate current in the external antenna 1324. As a result, electromagnetic waves may be emitted from the external antenna 1324, and they may propagate through air and penetrate the body tissue of the patient. A small portion of the electromagnetic waves may be absorbed by a secondary parasite 1704, while a large portion of the electromagnetic waves may induce alternate voltage 1703 in the implantable antenna 1352.

The amplitude of the induced voltage 1703 may be affected by a transmission distance 1720 separating the external antenna 1324 and the implantable antenna 1352. For example, the amplitude of the induced voltage 1703 may decrease when the transmission distance 1720 increases from 10 mm to 20 mm. For another example, the amplitude of the induced voltage 1703 may increase when the transmission distance 1720 decreases from 35 mm to 20 mm.

The induced voltage 1703 may be rectified by the first and second diodes 1722 and 1724. As a result, the output nodes 1730 of the rectifying device 1700 may deliver the DC input voltage ($V_{IN}$) 1705. The two-diode configuration may allow the $V_{IN}$ to have a relatively high magnitude, which may be slightly less than two times of the induced voltage 1703. When the transmission distance 1702 is large (e.g. greater than 35 mm), it is advantageous to have the relative high magnitude $V_{IN}$ to compensate the energy loss to the secondary parasite 1704. However, when the transmission distance 1702 is small (e.g. less than 10 mm), the relative high magnitude $V_{IN}$ may be problematic because it may produce excessive energy, which may lead to overheating within the implant.

Figure 18:
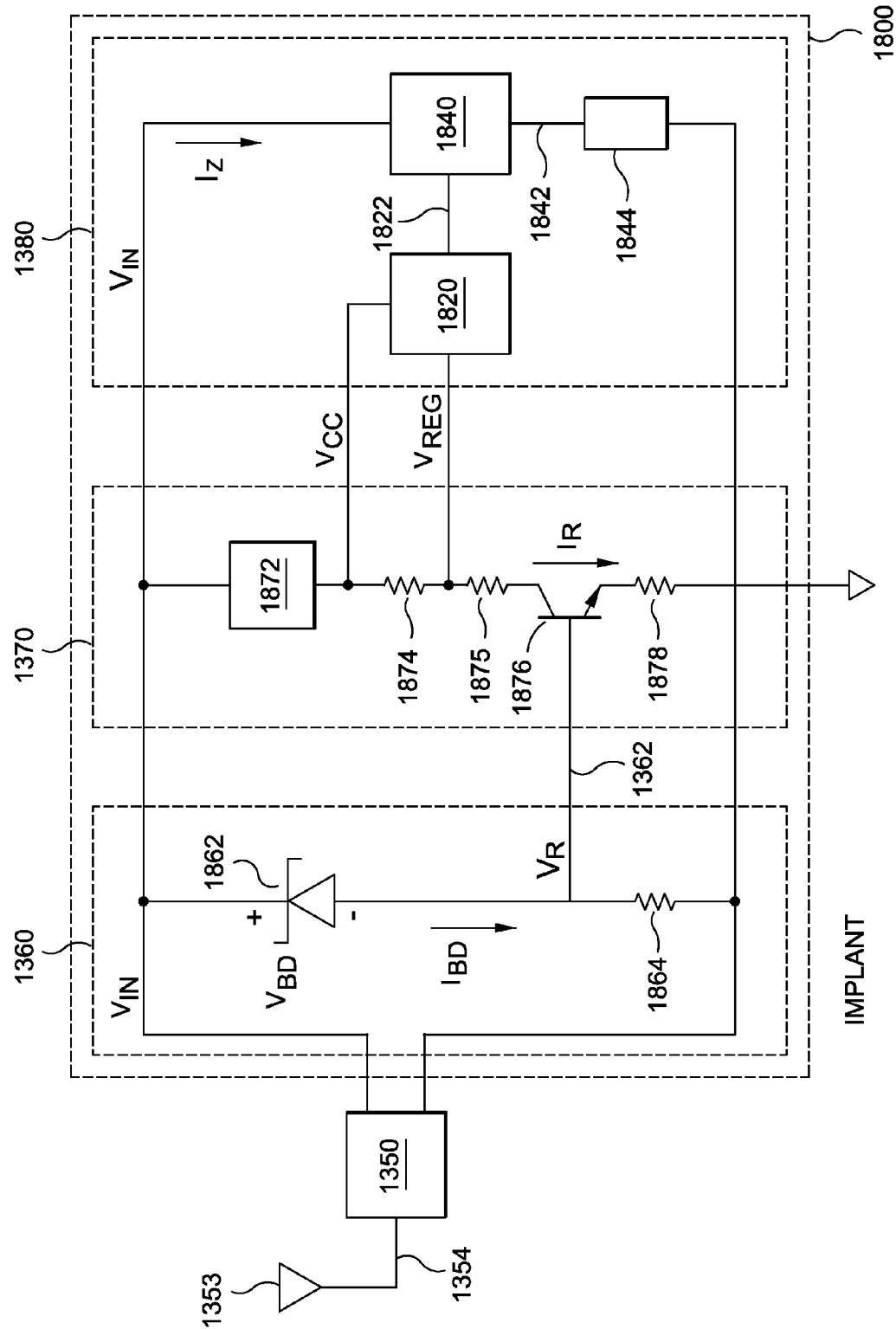
FIG. 18 shows an implant power regulation subsystem according to an embodiment of the present invention.

To prevent overheating, the Implant may include a power regulation subsystem to provide feedback information to adjust the output energy of the modulation device. In FIG. 18, an implant power regulation subsystem (a.k.a. the power system) 1800 is shown according to an embodiment of the present invention. Generally, the implant power regulation subsystem 1800 may include the maximum power sensing device (second device block) 1360, the regulation device (third device block) 1370, and the impedance switching device (fourth device block) 1380.

The maximum power sensing device 1360 may include a Zener diode 1862 and a first pull down resistor 1844. In one configuration, the positive terminal of the Zener diode 1862 may be coupled to the DC input voltage ($V_{IN}$) node and the negative terminal of the Zener diode 1862 may be coupled to the first pull down resistor 1844, which may be coupled to an internal ground node. The Zener diode 1862 may have a breakdown voltage $V_{BD}$ across its positive and negative terminals. When the DC input voltage ($V_{IN}$) is less than the breakdown voltage $V_{BD}$, the Zener diode 1862 may be under forward bias, such that the Zener diode 1862 is unlikely to sink any current from the DC input voltage ($V_{IN}$) node. As a result, the first pull down resistor 1864 may pull the regulation signal to ground.

However, when the DC input voltage ($V_{IN}$) reaches and/or exceeds the breakdown voltage $V_{BD}$, the Zener diode 1862 may be under reverse bias, such that the Zener diode 1862 may begin to draw a breakdown current $I_{BD}$ from the DC input voltage ($V_{IN}$) node. As a result, the regulation signal 1362 may maintain a voltage level $V_R$ across the first pull down resistor 1864. Depending on the design goal, the breakdown voltage $V_{BD}$ may be predetermined to accommodate the power consumption of the implant. That is, the breakdown voltage $V_{BD}$ may be chosen at a range that is substantially equal to or close by the predetermined threshold voltage. In one embodiment, for example, the breakdown voltage $V_{BD}$ may be about 3 V. In another embodiment, for example, the breakdown voltage $V_{BD}$ may be about 7 V. In yet another embodiment, for example, the breakdown voltage $V_{BD}$ may be about 5.6 V.

Although the sinking of the breakdown current $I_{BD}$ may have little effect on the $V_{IN}$ value, it may help generate the regulation signal 1362. The voltage level $V_R$ of the regulation signal 1362 may indicate or represent a desirable level of regulation. Mainly, the breakdown current $I_{BD}$ may be highly sensitive to the change of $V_{IN}$ value, so that the regulation signal voltage level $V_R$ may track closely to the amount of the excessive DC input voltage $V_{IN}$.

The regulating device 1370 may include a voltage regulator 1872, a first pull up resistor 1874, a second pull up resistor 1875, a transistor 1876, and a second pull down resistor 1878. The voltage regulator 1872 may be used for generating a relatively constant local voltage $V_{CC}$ at a first node (e.g., the $V_{CC}$ node). The constant local voltage $V_{CC}$ may supply power to various electronic components of the implant. For example, the local voltage $V_{CC}$ may supply power to the current path formed partially by the first and second pull up resistors 1874 and 1875. Generally, the local voltage $V_{CC}$ may be less than the DC input voltage $V_{IN}$ and the predefined threshold voltage, which may be approximated by the breakdown voltage $V_{BD}$ of the Zener diode 1862.

When the regulation signal voltage level $V_R$ is less than the threshold voltage of the transistor 1876, there may be little or no regulation current $I_R$ because the transistor 1876 is not conducting. As such, the regulation voltage $V_{REG}$ may be substantially equal to the local voltage $V_{CC}$.

However, when the DC input voltage $V_{IN}$ exceeds the breakdown voltage $V_{BD}$ of the Zener diode 1862, the regulation signal voltage level $V_R$ may begin to rise, and eventually, it may overcome the threshold voltage of the transistor 1876. As a result, the transistor 1876 may be turned on and draw the regulation current $I_R$. The regulation current $I_R$ may cause a potential drop across the first pull up resistor 1874, which is connected between the first node and a second node (e.g., the $V_{REG}$ node). Consequently, the regulation voltage $V_{REG}$ may decline as the regulation signal voltage level $V_R$ increase. With the help of the pull up resistor 1874, the regulation current $I_R$ creates a regulation margin (i.e., potential difference) between the $V_{CC}$ node and the $V_{REG}$ node.

From the point where the transistor 1876 begins to conduct to the point where the transistor 1876 becomes saturated, the regulation voltage $V_{REG}$ may achieve substantial linearity with the regulation signal voltage $V_R$, which may be driven primarily by the breakdown current $I_{BR}$. As such, the regulation device 1370 may perform the power regulation task when the DC input voltage $V_{IN}$ exceeds the breakdown voltage $V_{BD}$ by a regulation margin. The regulation margin may be represented by the voltage level $V_R$ of the regulation signal 1362. In one embodiment, for example, the regulation margin may range from about 0.05 V to about 10V. In another embodiment, for example, the regulation margin may range from about 0.1 V to about 5V. In yet another embodiment, for example, the regulation margin may range from about 1 V to about 3 V.

The transistor 1876 may amplify the regulation margin between the DC input voltage and the predefined threshold. As such, the potential difference between the local voltage $V_{CC}$ and the regulation voltage $V_{REG}$ may be highly responsive and sensitive to any slight change in the regulation margin.

After the regulation voltage $V_{REG}$ begins to decline, the impedance switching device 1380 may be activated. Generally, the impedance switching device 1380 may include a frequency modulation device (block) 1820, a switch 1840, and an impedance component 1844. The frequency modulation device 1880 may generate a frequency modulation signal 1822. The frequency modulation signal 1822 may have a modulated frequency that is based on and/or represent the value of the regulation voltage $V_{REG}$. In one embodiment, for example, the modulated frequency of the frequency modulation signal 1822 may be directly proportional to the potential difference between the local voltage $V_{CC}$ and the regulation voltage $V_{REG}$. In another embodiment, for example, the modulated frequency of the frequency modulation signal 1822 may be inversely proportional to the potential difference between the local voltage $V_{CC}$ and the regulation voltage $V_{REG}$. In any event, the feedback signal as discussed in FIG. 13 may include the frequency modulation signal 1822.

The frequency modulation signal 1822 may be used for turning on and off the switch 1840. According to the modulated frequency of the frequency modulation signal 1822, the impedance component 1844 may be periodically connected to and disconnected from the DC input voltage ($V_{IN}$) node. The impedance component 1844 may act as an additional load and in the form of a pull down device. Because additional switching current $I_Z$ is sunk by the impedance component 1844, the DC input voltage $V_{IN}$ may drop and rise at the modulated frequency of the frequency modulation signal 1822.

As a result, the profile of the DC input voltage $V_{IN}$ may be superimposed by the profile of the frequency modulation signal 1822. The superimposed $V_{IN}$ profile may become a modulated amplitude (e.g., the message envelop) of the passive telemetric signal 1357. As a result, the switch 1840 may transform the frequency modulation signal 1822 to a frequency modulated amplitude modulated signal, such as the passive telemetric signal 1357. The passive telemetric signal 1357 may be received and demodulated by the RF Board as part of the power regulation process.

Figure 19:
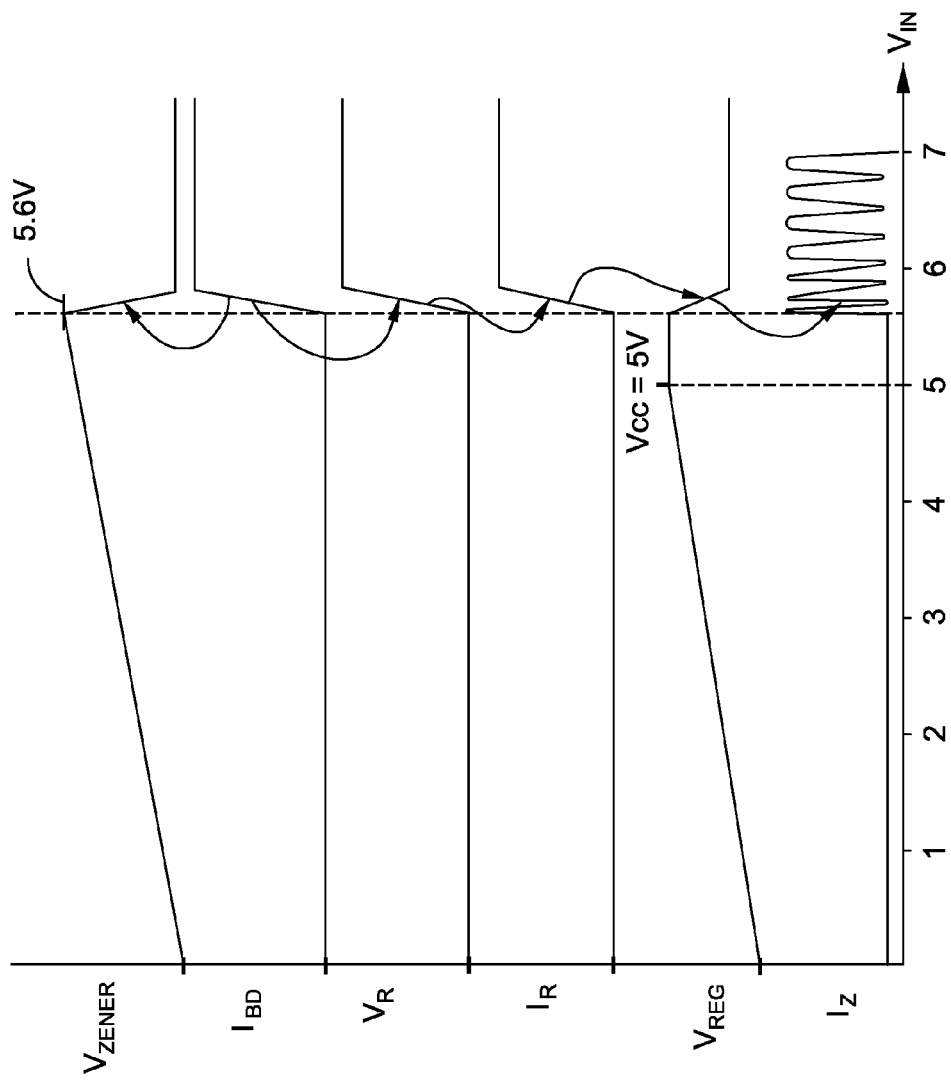
FIG. 19 shows various waveforms of various signals of the implant power regulation subsystem according to an embodiment of the present invention.

Referring to FIG. 19, various waveforms of the implant power regulation subsystem 1800 are shown according to an embodiment of the present invention. Initially, the voltage across the Zener diode 1862 ($V_{ZENER}$) may increase linearly and track the DC input voltage $V_{IN}$ when the DC input voltage $V_{IN}$ is less than the breakdown voltage $V_{BD}$. As such, the breakdown current $I_{BD}$ may be kept at minimum and the regulation signal voltage level $V_R$ may be close to ground.

Because the regulation signal voltage level $V_R$ does not overcome the threshold voltage of the transistor 1876, there may be minimum or no regulation current $I_R$ flowing through the first and second pull down resistors 1874 and 1875. As a result, the regulation voltage $V_{REG}$ may track closely to the local voltage $V_{CC}$. Since $V_{CC}$ may be set a voltage level (e.g. 5 V) lower than the breakdown voltage $V_{BD}$ (e.g. 5.6 V), the regulation voltage VREG may be saturated before the regulation mechanism is triggered. At this stage, the impedance component 1844 may be decoupled from the $V_{IN}$ node, such that only minimum or no switching current $I_Z$ may be sunk from the $V_{IN}$ node.

When the DC input voltage $V_{IN}$ begins to exceed the breakdown voltage $V_{BD}$, the Zener diode 1862 may begin to conduct the breakdown current $I_{BD}$. As a result, the regulation signal voltage level $V_R$ may begin to rise and it may eventually overcome the threshold voltage of the transistor 1876. From the point when the transistor 1876 begins to conduct the regulation current $I_R$ to the point when the transistor 1876 becomes saturated (i.e. maximum $I_R$), the power regulation subsystem 1800 may be under rapid regulation. That is, the regulation voltage $V_{REG}$ may be highly sensitive to the slightest increase in the DC input voltage $V_{IN}$.

As the regulation current $I_R$ increases, the regulation voltage $V_{REG}$ may begin to decline, which may cause the frequency modulation device 1820 to generate the frequency modulation signal 1822. Driven by the frequency modulation signal 1822, the switch 1840 may cause the impedance component 1844 to be coupled to or decoupled from the $V_{IN}$ node. Accordingly, the switching current $I_Z$ may share the frequency of the frequency modulation signal 1840. As discussed earlier, the frequency of the frequency modulation signal 1840 may be inversely proportional to the difference between the local voltage $V_{CC}$ and the regulation voltage $V_{REG}$. Hence, the frequency of the frequency modulation signal 1840, which may be represented by the profile of the switching current $I_Z$, may decrease as regulation voltage VREG drops further away from local voltage $V_{CC}$.

The discussion now turns to a double modulation scheme adopted by the Implant in providing feedback information to the RF Board. The feedback information may include the value of the regulation voltage $V_{REG}$ and/or the patient's biometrics data. Generally, the Implant may include a memory device for storing the patient's biometrics data, such as the patient's identity and event records pertinent to the patient's gastric band adjustment history. Among other information, each of the event records may record the current gastric band position and the adjustment date. It is desirable that the Implant may telemetrically transmit various pieces of feedback information in a compact and efficient manner.

Figure 20:
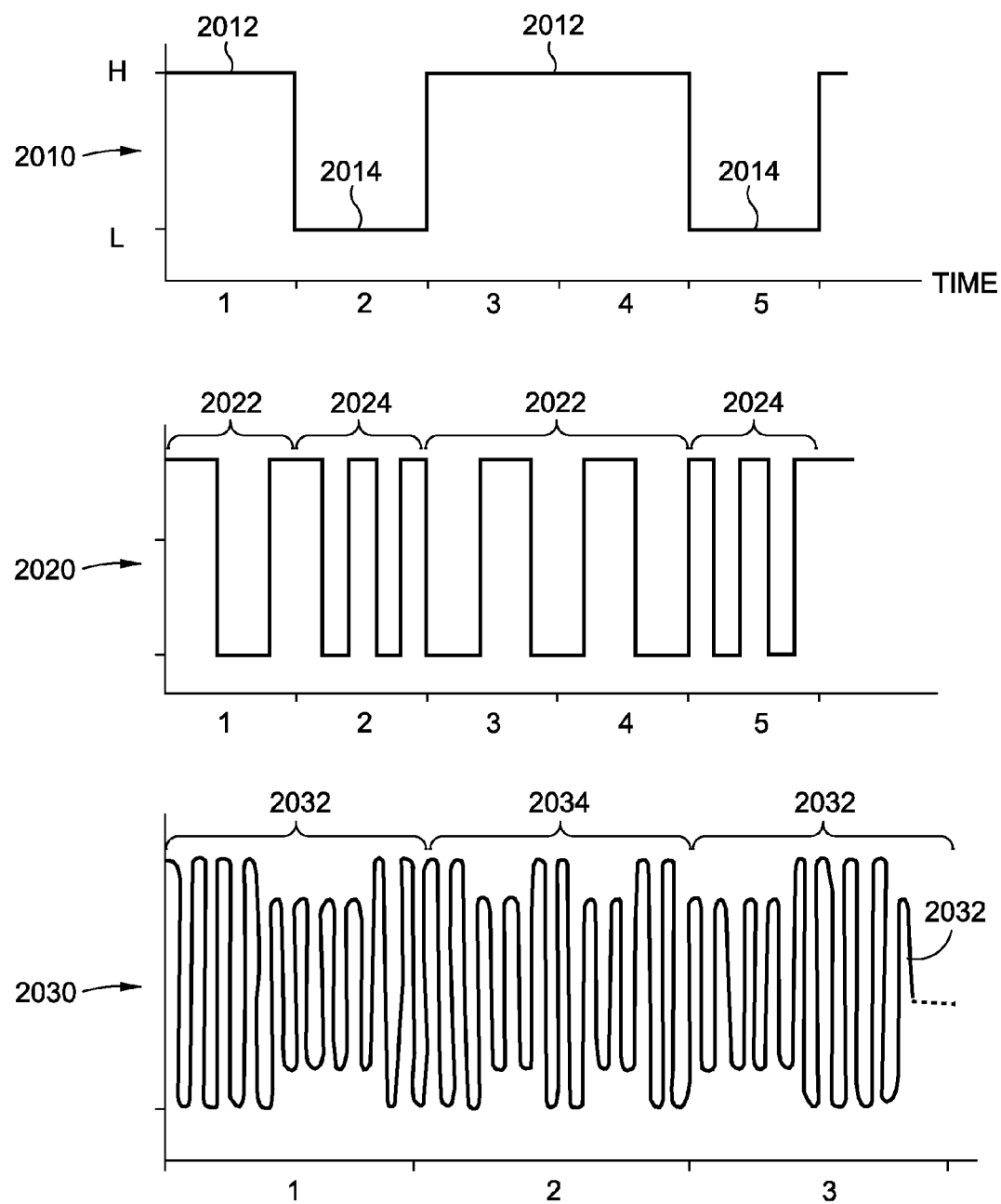
FIG. 20 shows various waveforms of a double modulation (frequency modulated amplitude modulation) scheme according to an embodiment of the present invention.

In FIG. 20, waveforms of a double modulation (frequency modulated amplitude modulation) scheme are shown according to an embodiment of the present invention. Initially, there may be a data signal 2010 to be transmitted from the Implant to the RF Board. The data signal 2010 may have a high state 2012 and a low state 2014, each of which may represent one of the binary states. For example, the data signal 2010 may have the high state 2012 during time period (TP) 1, the low state 2014 during TP 2, the high state 2012 during both TP 3 and TP 4, and the low state 2014 during TP 5.

Next, a frequency modulation may be applied to the digital signal 2010 to form a frequency modulation signal 2020. Generally, the frequency modulation may be performed by the frequency modulation device 1820 or any other similar devices, such as a LTC6900 chip. The frequency modulation signal 2020 may have one or more modulated frequencies, such as a first (low) frequency 2022 and a second (high) frequency 2024. Depending on the assignment scheme, the first and second frequencies 2022 and 2024 may be assigned to one of the low state 2012 or the high state 2024 of the data signal 2010.

In the present case, for example, the first frequency 2022 may be assigned to the high state 2012, and the second frequency 2024 may be assigned to the low state 2024. Accordingly, the frequency modulation signal 2020 may have the first frequency 2022 during TP 1, the second frequency 2024 during TP 2, the first frequency 2022 during TP 3 and TP 4, and the second frequency 2022 during TP 5.

The frequency modulation signal 2020 may be used for encoding two or more signals simultaneously. In one embodiment, for example, the frequency modulation signal 2020 may be used for encoding two digital signals with four logic states. As such, the frequency modulation signal 2020 may have four frequency levels assigned to the four logic states. In another embodiment, for example, the frequency modulation signal 2020 may be used for encoding three digital signals with eight logic states. Accordingly, the frequency modulation signal 2020 may have eight frequency levels assigned to the eight logic states.

In yet another embodiment, for example, the frequency modulation signal 2020 may be used for encoding one digital signal and one analog signal. The digital signal may carry feedback information regarding the patient's biometrics. The analog signal may carry feedback information regarding the value of the regulation voltage $V_{REG}$. Accordingly, the frequency modulation signal 2020 may have a first frequency band and a second frequency band. Particularly, the high state of the digital signal and the spectrum of the analog signal may be jointly represented by the first frequency band, while the low state of the digital signal and the spectrum of the analog signal may be jointly represented by the second frequency band.

After the frequency modulation signal 2020 is generated, it may be combined, mixed, or superimposed with the original amplitude modulated carrier to form a frequency modulated amplitude modulation signal 2030. The original amplitude modulated carrier may be originated from the RF Board, and it may retain its carrier frequency at the implant antenna. As such, the frequency modulated amplitude modulation signal 2030 may have a common carrier frequency and a message frequency. The common carrier frequency may be constant throughout the entire transmission period, while the message (envelop) frequency may track closely to the first and second frequencies 2022 and 2024 of the frequency modulation signal 2020. Accordingly, the frequency modulated amplitude modulation signal 2030 may have a first message (envelop) frequency 2032 during TP 1, a second message (envelop) frequency 2034 during TP 2, and the first message frequency 2032 during TP 3.

Using the frequency modulated amplitude modulation signal 2030 to provide feedback information may provide several advantages. For example, the transmission of the frequency modulated amplitude modulation signal 2030 may consume very little energy from the Implant because it may take advantage of the original amplitude modulation signal and it may be passively transmitted. For another example, the intermediate frequency modulation scheme may allow multiple pieces of information to be transmitted simultaneously, thereby increasing the transmission efficiency and shortening the total transmission time. For another example, the frequency modulated amplitude modulation signal 2030 may only require one communication channel. As such, the external antenna and the implant antenna may be transferring power and communicating at the same time. For yet another example, the frequency modulated amplitude modulation signal 2030 may have a high tolerance to parasitic noise. Mainly, the underlying information may be encoded in different frequency levels and/or frequency bands, which may be highly resistive to distortion caused by parasitic noise.

Figure 21:
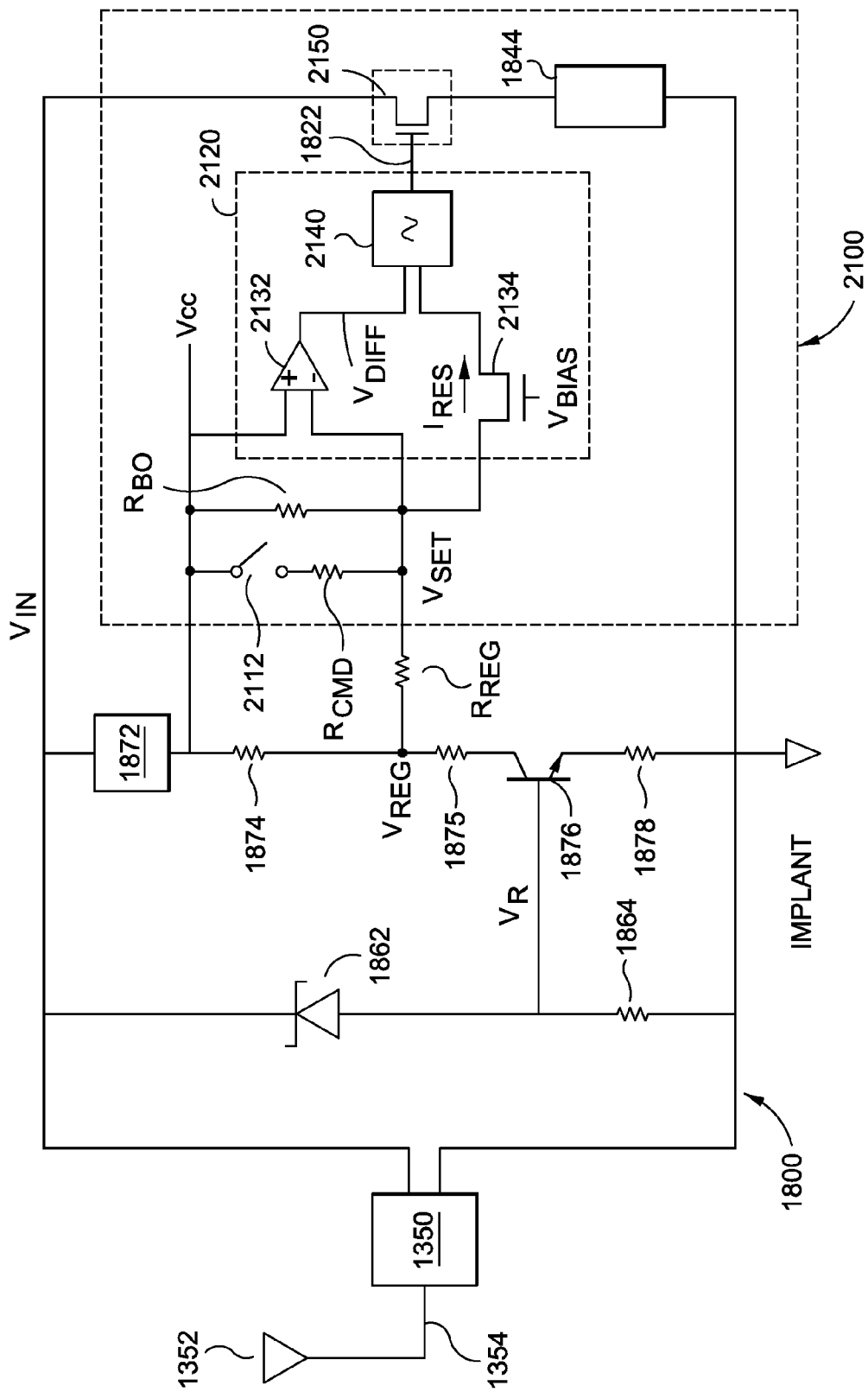
FIG. 21 shows a schematic view of a double modulation subsystem according to an embodiment of the present invention.

FIG. 21 shows a schematic view of a double modulation subsystem 2100 according to an embodiment of the present invention. Generally, the double modulation subsystem 2100 may help generate the feedback signal for communicating the value of the regulation voltage $V_{REG}$ to the RF Board. As such, the double modulation subsystem 2100 may be used as a communication system and in conjunction with the power regulation subsystem 1800.

The double modulation subsystem 2100 may include a frequency modulation device 2120, an output transistor 2150, a data switch 2112, a voltage regulation resistor $R_{REG}$, a data resistor $R_{CMD}$, and a bias resistor $R_{BO}$. The frequency modulation device 2120 may have similar functional features as the frequency modulation device 1820. Moreover, the frequency modulation device 2120 may adjust a switching frequency ($f_{SW}$) of the frequency modulated signal 1822 according to the regulation voltage and the status of the data switch 2112.

The data switch 2112 may be used for generating serial data signals similar to the data signal 2010 as shown in FIG. 20. More specifically, the data switch 2112 may be controlled by the implant microcontroller 476 (previously shown in FIG. 4), which may encode various information to the data signal.

In one embodiment, for example, the implant microcontroller may encode the patient's identification information to the data signal. In another embodiment, for example, the implant microcontroller may encode the patient's gastric band adjustment record to the data signal. In yet another embodiment, for example, the implant microcontroller may encode a handshake confirmation message to the data signal.

The frequency modulation device 2120 may be implemented by a LTC 6900 chip or other equivalent devices. From a functional standpoint, the frequency modulation device 2120 may determine the switching frequency according to the local voltage $V_{CC}$, a set voltage $V_{SET}$ and an input current $I_{RES}$. Similar to the power system as shown in FIG. 18, the regulation voltage $V_{REG}$ may be generated by the regulation device 1370 at a first node (e.g., the $V_{REG}$ node). The set voltage $V_{SET}$ at a second node (e.g., the $V_{SET}$ node) may be controlled by a data path, which may include the data switch 2112 and the command resistor $R_{CMD}$. Moreover, the voltage regulator 1872 may generate the local voltage $V_{CC}$ at a third node (e.g., the $V_{CC}$ node). The local voltage $V_{CC}$ may perform as a current source for the pull up resistor 1874 and the data path.

In one embodiment, the frequency modulation device 2120 may include a differential amplifier 2132, a pass transistor 2134, and an oscillator 2140. The differential amplifier 2132 may generate an input differential voltage $V_{DIFF}$ by amplifying the potential difference between the local voltage $V_{CC}$ and a set voltage $V_{SET}$ (i.e. $V_{CC} - V_{SET}$). The pass transistor 2134 may be biased by a bias voltage $V_{BIAS}$ to pass the input current $I_{RES}$ from the $V_{SET}$ node to the oscillator 2140. After receiving the input differential voltage $V_{DIFF}$ and the input current $I_{RES}$, the oscillator 2140 may generate the frequency modulation signal 1822 with the switching frequency $f_{SW}$, which may be modeled by Equation 1:

$$f_{SW} = 1 \text{ MHz} \times 20 \text{ k}\Omega \times \frac{I_{RES}}{(V_{CC} - V_{SET})}.$$

Generally, the input current $I_{RES}$ may be a summation of several currents joining at the $V_{SET}$ node. For example, when the data switch 2112 is closed, it may conduct a data current ($I_{CMD}$) from the $V_{CC}$ node to the $V_{SET}$ node. The data current $I_{CMD}$ may be characterized as $(V_{CC} - V_{SET})/R_{CMD}$. For another example, a regulation current $I_{REG}$ may be conducted across the regulation resistor $R_{REG}$. The magnitude of the regulation current $I_{REG}$ may depend on the level of regulation, such that it may range from $(V_{CC} - V_{SET})/R_{REG}$ to about $0.5^*(V_{CC} - V_{SET})/R_{REG}$. For yet another example, a bias current $I_{BO}$ may be conducted across the bias resistor $R_{BO}$, and it may be characterized as $(V_{CC} - V_{SET})/R_{BO}$.

When the data signal is at a low state (i.e. data switch 2112 closed) and when there is no power regulation, the switching frequency may be modeled by Equation 2, which recites:

$$f_{SW,LL,NR} = 1 \text{ MHz} \times 20 \text{ k}\Omega \times \left(\frac{1}{R_{BO}} + \frac{1}{R_{REG}} + \frac{1}{R_{CMD}}\right).$$

When the data signal is at a high state (i.e. data switch 2112 open) and when there is no power regulation, the switching frequency may be modeled by Equation 3, which recites:

$$f_{SW,HL,NR} = 1 \text{ MHz} \times 20 \text{ k}\Omega \times \left(\frac{1}{R_{BO}} + \frac{1}{R_{REG}}\right).$$

When the data signal is at a low state and when there is maximum power regulation, the switching frequency may be modeled by Equation 4, which recites:

$$f_{SW,LL,MR} = f_{SW,LL,NR} - 1 \text{ MHz} \times 10 \text{ k}\Omega \times \left(\frac{V_{CC}}{R_{REG} \times (V_{CC} - V_{SET})}\right).$$

When the data signal is at a high state and when there is maximum power regulation, the switching frequency may be modeled by Equation 5, which recites:

$$f_{SW,LL,MR} = f_{SW,HL,NR} - 1 \text{ MHz} \times 10 \text{ k}\Omega \times \left(\frac{V_{CC}}{R_{REG} \times (V_{CC} - V_{SET})}\right).$$

When the data signal is at a low state and when the regulation voltage is at $V_{REG}$, the switching frequency may be modeled by Equation 6, which recites:

$$f_{SW,LL,VR} = f_{SW,LL,NR} - 1 \text{ MHz} \times 20 \text{ k}\Omega \times \left(\frac{V_{CC} - V_{REG}}{R_{REG} \times (V_{CC} - V_{SET})}\right).$$

For low output level and regulation voltage at $V_{REG}$, the switching frequency may be modeled by Equation 7, which recites:

$$f_{SW,HL,VR} = f_{SW,HL,NR} - 1 \text{ MHz} \times 20 \text{ k}\Omega \times \left(\frac{V_{CC} - V_{REG}}{R_{REG} \times (V_{CC} - V_{SET})}\right).$$

As persons skilled in the art may readily appreciate, the value of the swing frequency $f_{SW}$ may depend on the resistances of the various resistors, which may be adjusted to meet various design goals. In one embodiment, for example, the resistance of the bias resistor $R_{BO}$ may be about 29.43 k$\Omega$. In another embodiment, for example, the resistance of the regulation resistor $R_{REG}$ may be about 1 M$\Omega$. In yet another embodiment, for example, the resist $R_{CMD}$ may be about 430 k$\Omega$. Moreover, $V_{CC}$ may be set at about 5V, such that $V_{SET}$ may be at about 3.9V.

Accordingly, the swing frequency $f_{SW,LL,NR}$ may be about 746 kHz, the swing frequency $f_{SW,HL,NR}$ may be about 699.5 kHz, the swing frequency $f_{SW,LL,MR}$ may be about 700.5 kHz, and the swing frequency $f_{SW,HL,MR}$ may be about 654 kHz. Furthermore, the swing frequency $f_{SW,LL,VR}$ may range from about 746 kHz to about 700.5 kHz, while the swing frequency $f_{SW,HL,VR}$ may range from about 699.5 kHz to about 654 kHz.

Figure 22:
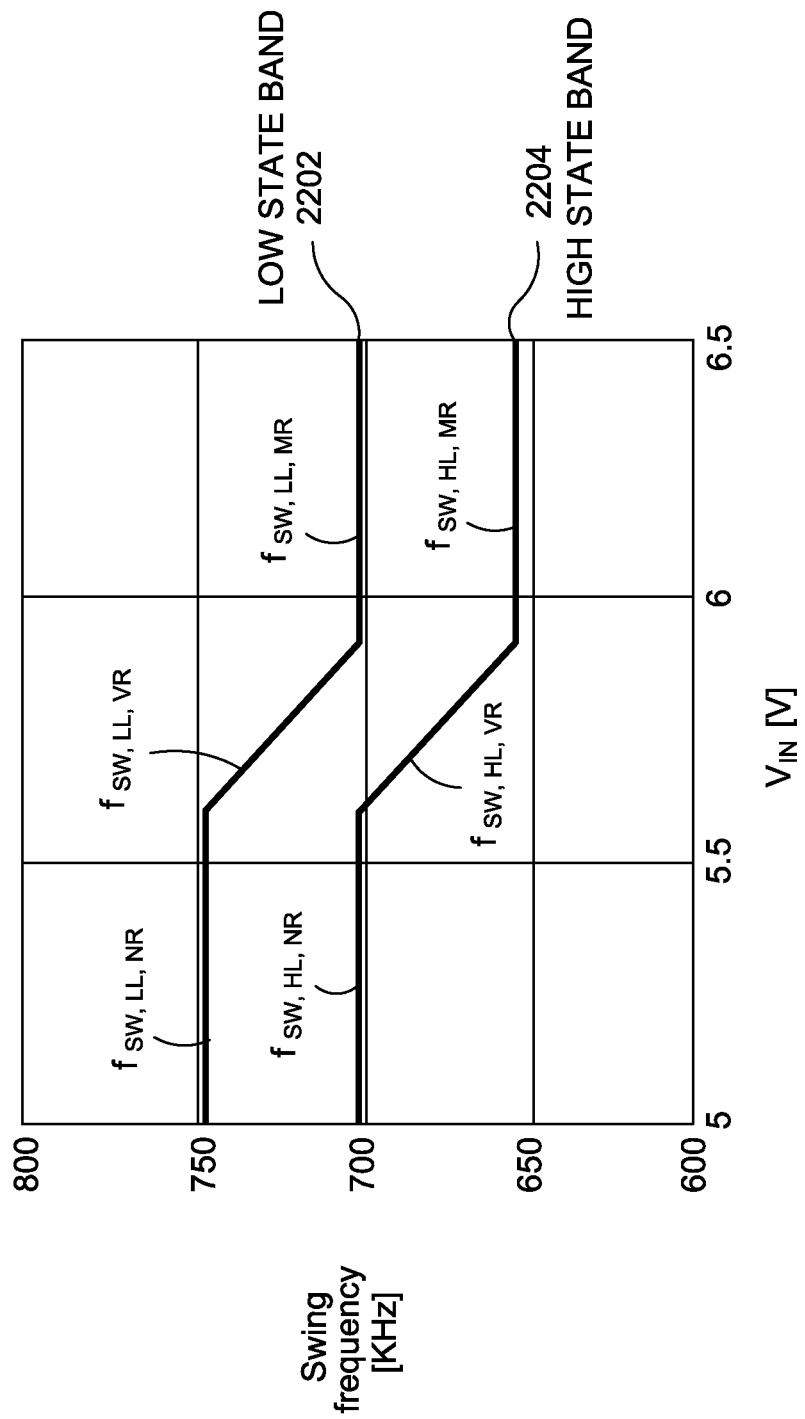
FIG. 22 shows a frequency chart of the double modulation scheme according to an embodiment of the present invention.

Referring to FIG. 22, a frequency chart of the double modulation scheme is shown according to the above parameters. With a binary data signal, the double modulation scheme may include a low state band 2202 and a high state band 2204. The low state band 2202 may represent the range of swing frequencies that may be assigned to the low state value of the data signal. Similarly, the high state band 2204 may represent the range of swing frequencies that may be assigned to the high state value of the data signal. Because the swing frequency may incorporate or embedded with power regulation information, each of the low and high state bands 2202 and 2204 may have a maximum swing frequency (i.e. $f_{SW,LL,NR}$ and $f_{SW,HL,NR}$) for representing a no-regulation scenario, a transient swing frequency (i.e. $f_{SW,LL,VR}$ and $f_{SW,HL,VR}$) for representing a rapid regulation scenario, and a minimum swing frequency (i.e. $f_{SW,LL,MR}$ and $f_{SW,HL,NR}$) for representing a maximum-regulation scenario.

Although FIG. 22 shows only two swing frequency bands, the frequency modulation device 2100 may provide two or more swing frequency bands. In one embodiment, for example, the frequency modulation device 2100 may provide four swing frequency bands for encoding two binary data signals. In another embodiment, for example, the frequency modulation device 2100 may provide eight swing frequency bands for encoding three binary data signals. In yet another embodiment, for example, the frequency modulation device 2100 may provide sixteen swing frequency bands for encoding four binary data signals.

Figure 23:
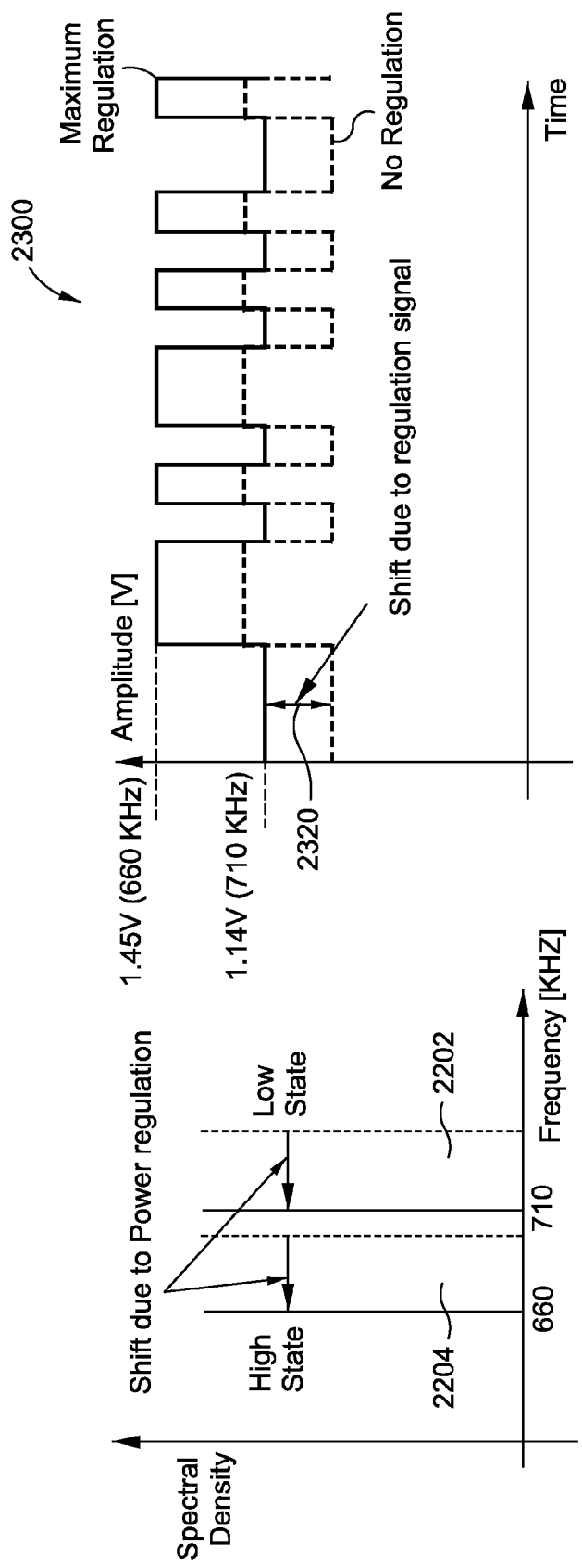
FIG. 23A shows a frequency spectrum of the frequency modulation feedback signal according to an embodiment of the present invention.
FIG. 23B shows a demodulation of the frequency modulated amplitude modulation signal according to an embodiment of the present invention.

The discussion now turns to the demodulation scheme and the demodulation device used for decoding the feedback signals from the Implant. FIG. 23A shows a frequency spectrum of the frequency modulation feedback signal according to an embodiment of the present invention. Generally, the frequency modulation feedback signal may occupy one of the low state band 2202 or the high state band 2204 to transmit a single binary bit of data. However, the frequency modulation feedback signal may shift from a higher end of the band to a lower end of the band as the regulation voltage $V_{REG}$ of the implant increases. Such intra-band frequency shift may occur during the transmission of the single binary bit of data. Advantageously, the RF Board may be able to regulate the power within the Implant in real time, so that the regulation process may be independent of the data transmission process.

FIG. 23B shows a demodulation 2300 of the frequency modulated amplitude modulation signal according to an embodiment of the present invention. Generally, the demodulation signal may map a low frequency band to a high voltage state, and it may map a high frequency band to a low voltage state. Moreover, the demodulation signal may have a first DC level 2310 when the implant requests no regulation, and it may have a second DC level 2330 when the Implant requests power reduction (or power regulation). Accordingly, a potential difference 2320 between the first and second DC levels 2310 and 2320 may correspond to the level of power reduction requested by the Implant.

FIG. 23B shows that the maximum regulation demodulation signal may overlap with the no regulation demodulation signal. However, in an alternative embodiment, the maximum regulation demodulation signal and the no regulation demodulation signal may occupy non-overlapping voltage ranges.

Figure 24:
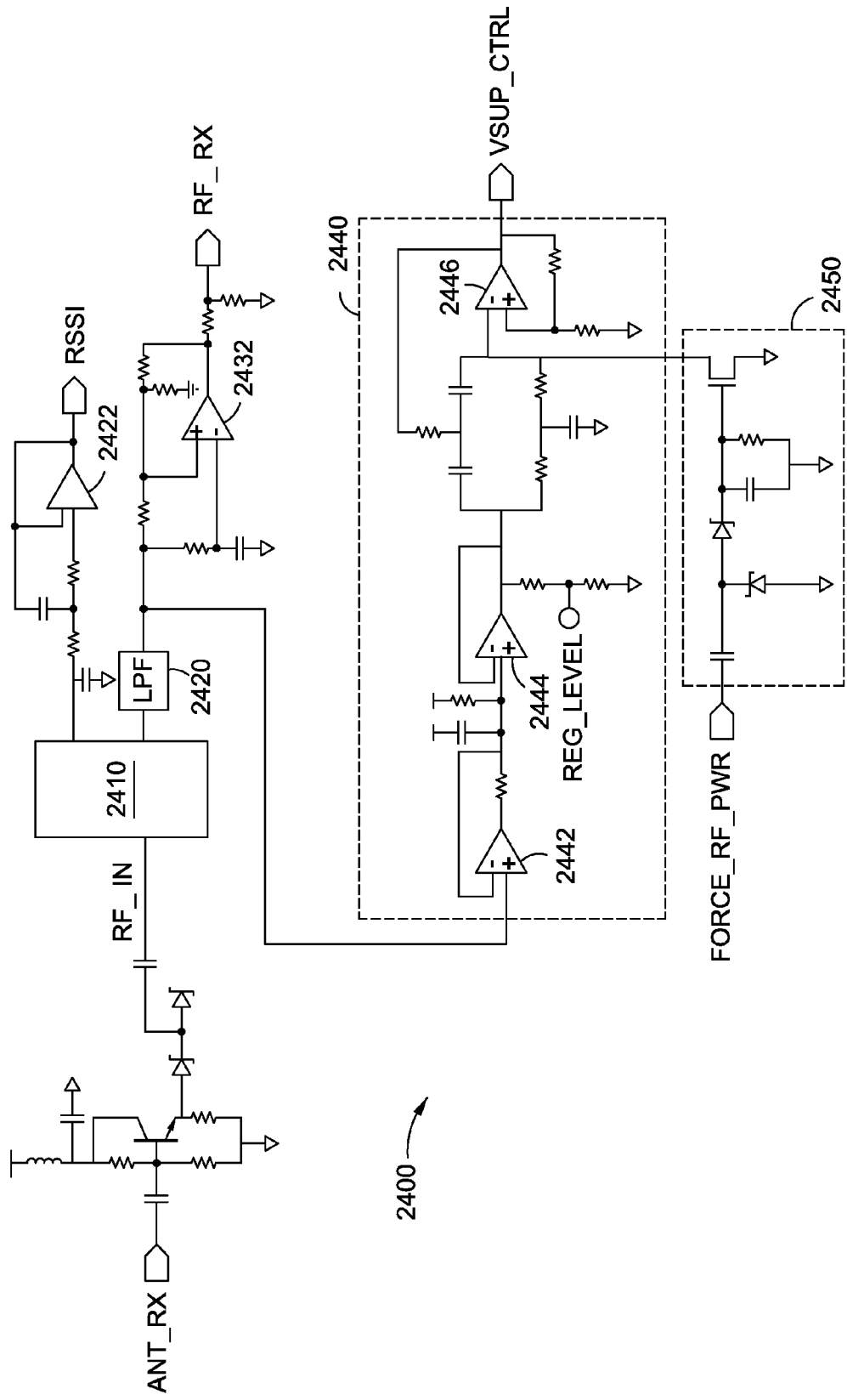
FIG. 24 shows a schematic view of a demodulation device according to an embodiment of the present invention.

Referring to FIG. 24, a schematic view of a demodulation device 2400 is shown according to an embodiment of the present invention. Generally, the demodulation device 2400 may implement the functional features of the demodulation device 1330 as discussed in FIG. 13. Particularly, the demodulation device 2400 may include a demodulation processor 2410, a low pass filter 2420, a signal strength amplifying stage 2422, a data amplifying stage 2432, a three-stage power control amplifying stage 2440, and a power override device 2450.

The demodulation processor 2410 may be used for processing the signal ANT_RX, which may be received and extracted from the external antenna. The signal strength amplifying stage 2422 may receive the processed signal and generate a signal strength indicator signal RSSI. Generally, the signal strength indicator signal RSSI may indicate the strength of the telemetric coupling between the external antenna and the implant antenna.

The low pass filter 2420 may be used for filtering out the high frequency component of the processed signal. As such, the carrier frequency may be eliminated, and the frequency modulated feedback signal may be further processed. Next, the data amplifying stage 2432 may receive the filtered signal and generate a data signal RF_RX according to the state band of the filtered signal. Simultaneously, the three-stage power control amplifying stage 2440 may receive the filtered signal and generate a voltage supply control signal VSUP_CTRL according to the frequency shift caused by the regulation voltage VREG.

Accordingly, the power supply device 1340 (previously shown in FIG. 13) may use the voltage supply control signal VSUP_CTRL to adjust the RF supply voltage 1342. Because the modulation device 1320 may be powered by the RF supply voltage 1342, the amplitude component of the amplitude modulation signal may be controlled indirectly by the RF supply voltage 1342. As a result, the power transmission may be regulated by reducing the amplitude component of the amplitude modulation signal.

Additionally, the three-stage power control amplifying stage may include a second stage 2444 for generating a regulation level signal REG_LEVEL, which may indicate the level of regulation requested by the Implant. Generally, the level of regulation may be higher when the Implant's DC input voltage VIN is much higher than the breakdown voltage VBD. Alternatively, the level of regulation may be lower when the Implant's DC input voltage VIN is below or slightly above the breakdown voltage VBD.

Figure 25:
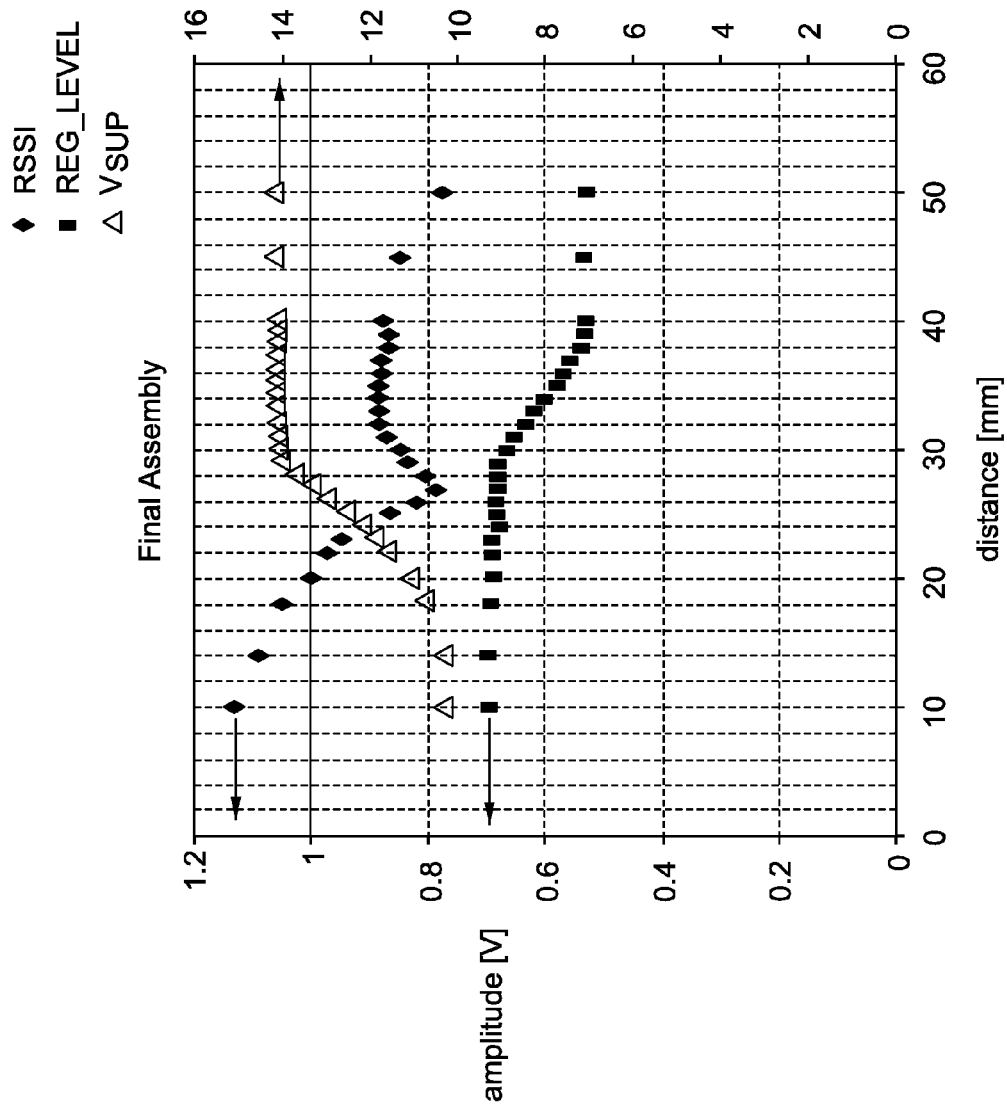
FIG. 25 shows the relationship among various signals of the demodulation device and a distance between the external antenna and the implant antenna according to an embodiment of the present invention.

FIG. 25 shows the relationship among various output signals of the demodulation device and a transmission distance separating the external antenna and the implant antenna. Generally, as the transmission distance increases, the signal strength indicator signal RSSI and the regulation level signal REG_LEVEL may increase. As such, the RF voltage supply VSUP may decrease to reduce the power transmission to the Implant. As shown in FIG. 25, the RF Board and the Implant may undergo rapid power regulation when the transmission distance ranges from 30 mm to about 40 mm. Moreover, the RF Board and the Implant may undergo maximum power regulation when the transmission distance is below 20 mm.

According to an embodiment of the present invention and referring again to FIG. 11, the FM demodulator in the RF demodulator block 1108 may generate a received signal strength indicator (RSSI), a REG_LEVEL signal and a VSUP_CTRL signal. Ultimately the VSUP_CTRL signal controls the output voltage VSUP. FIG. 25 shows some exemplary results of the RSSI signal, the REG_LEVEL signal, and the output voltage VSUP at various transmission distances.

Figure 26:
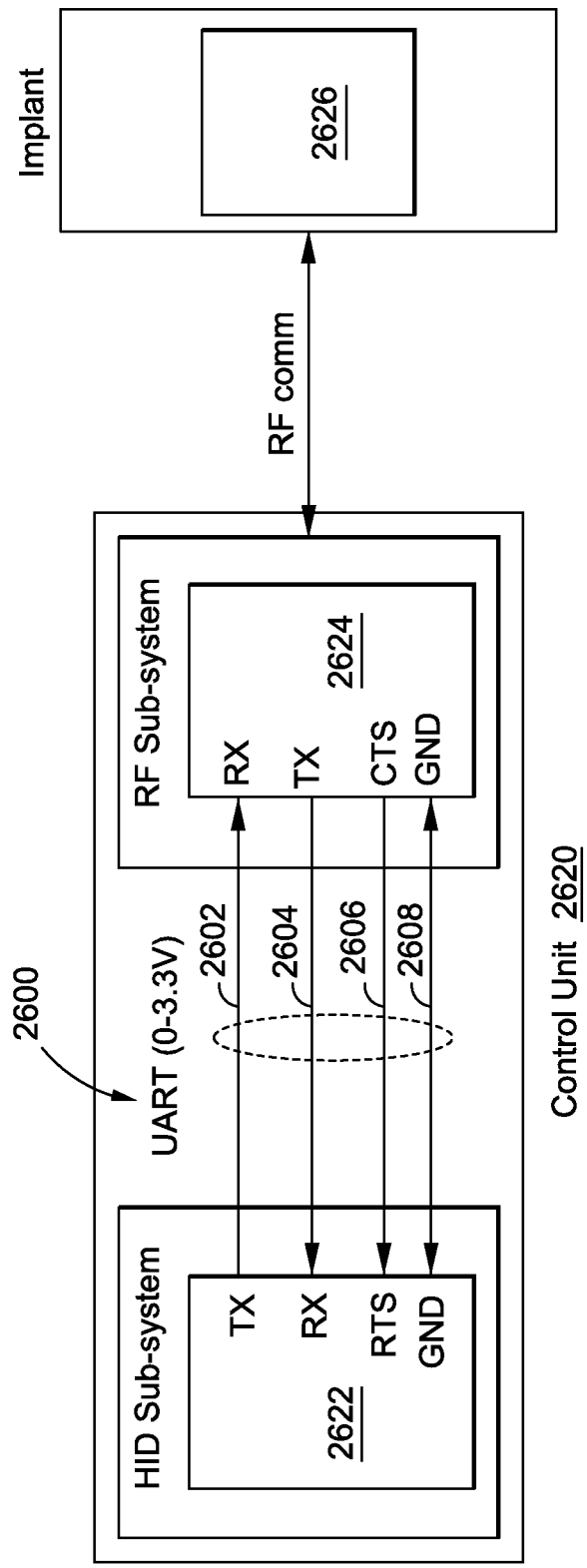
FIG. 26 shows the communication protocol among the HID subsystem, RF subsystem and the implant according to an embodiment of the present invention.

The discussion now turns to the software algorithms implemented in the HID subsystem and the RF subsystem. FIG. 26 shows the communication protocol UART 2600 among the HID subsystem, RF subsystem, and the implant according to an embodiment of the present invention. Generally, the HID microcontroller 2622 may function as the master device within the control device (control unit) 2620 and it may control most user interfaces, such as the display device, the buttons, the audio output device (e.g., speaker), and the memory devices. The HID microcontroller 2622 may send command message 2602 to the RF microcontroller 2624, and request the RF microcontroller 2624 to perform several functions.

The RF microcontroller 2624 may perform as a slave to the HID microcontroller 2622. Nevertheless, the RF microcontroller 2624 may send notification messages 2604 to the HID microcontroller 2622 even without being requested. The RF microcontroller 2626 may control the power induction process in the implant, the charging circuit in the docking station, the communication to and from the implant, and the communication with the HID microcontroller 2622. The GND-GND link 2608 may provide the "0 Volt" reference for all other signals. The RTS-CTS link 2606 may be a flux control line, which may be used for stopping the incoming flux of data from the HID sub-system when the RF sub-system is not ready to accept them.

Figure 27:
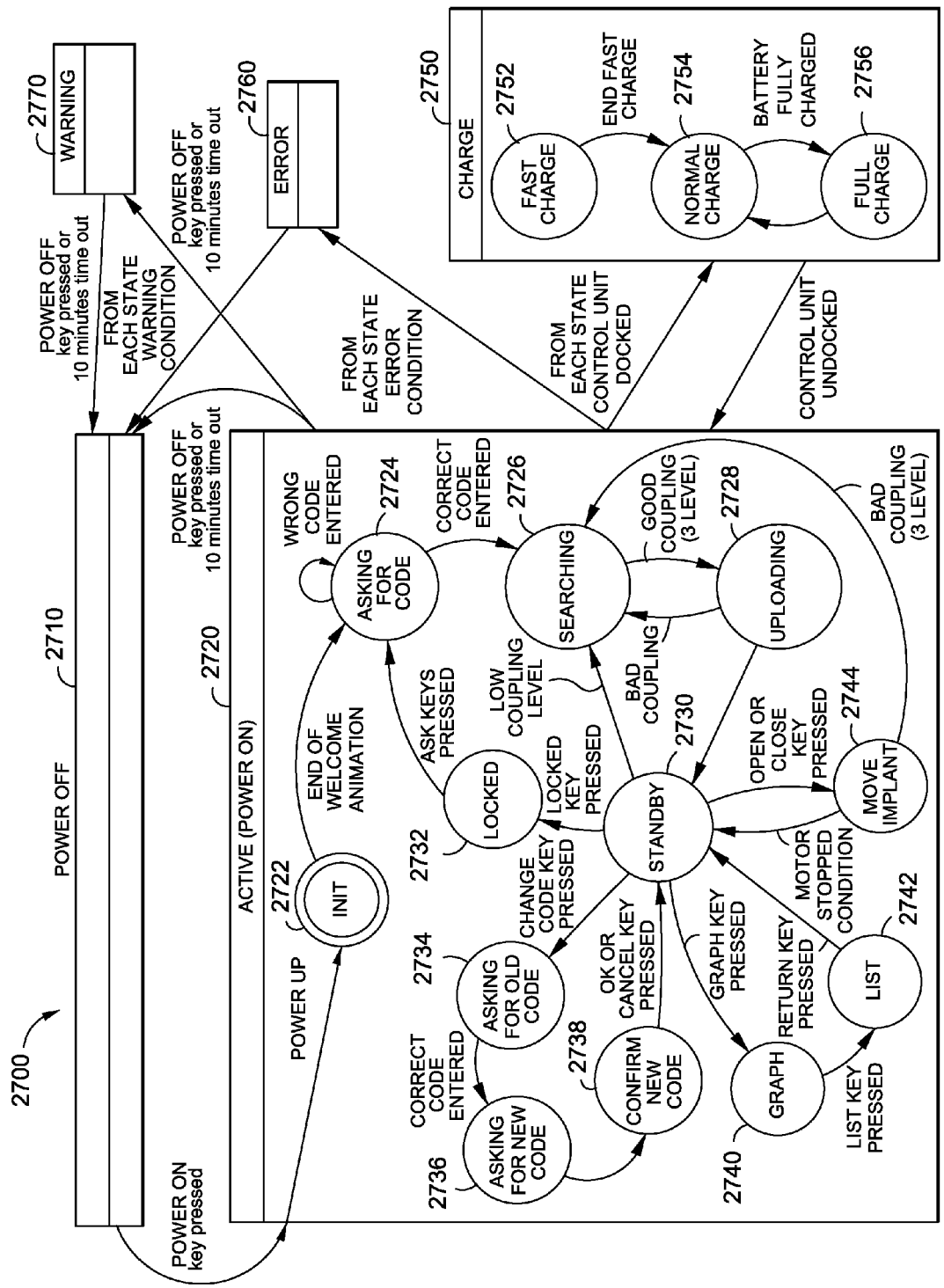
FIG. 27 shows the state diagram of an HID subsystem algorithm according to an embodiment of the present invention.

FIG. 27 shows the state diagram of the HID subsystem algorithm 2700 according to an embodiment of the present invention. Each state and transition will be discussed in detail in conjunction with FIGS. 8A-8R, which shows various screen shots of the control device. Generally, there may be five major blocks of states, including the power off block 2710, the active or power on block 2720, the charge block 2750, the error block 2760, and the warning block 2770.

The transition from the power off block 2710 to the power on block 2720 may be triggered by pressing the power on button on the control device 110 as shown in FIGS. 5A and 5B. Similarly, the transition from the power on block 2720 to the power off block 2710 may be triggered by pressing the power off button or after a 10-minute time out delay since a user has not interacted with the HID subsystem.

Generally, any state within the power on block 2720 may transit to the warning block 2770 and/or the error block 2760. To exit the warning block 2770 and/or the error block 2760, the user may enter the power off block 2710 by pressing the power off button or waiting for the 10-minute time out delay.

The charge block 2750 may be entered when the control device is connected to the docking station during the active mode. Once the control device is disconnected from the docking station, the charge block 2750 may return to a previous state of the power on block 2720. Normally, the returned state may be a state from which the charge block 2750 is transited initially.

As the power on block 2720 is initiated, the INIT state 2722 may initialize the HID subsystem, display the welcome screen, and load the code entry screen. After that, the ASKING FOR CODE state 2724 may be entered. The ASKING FOR CODE state 2724 may repeat itself until a correct 4-digit pass code is received, upon which the SEARCHING state 2726 may be entered. Once the external antenna is positioned close enough to the implant to establish a sufficient good telemetric (or electromagnetic) coupling, which may be represented by three out of five search bars in the searching screen, the UPLOADING state 2728 may be initiated.

In the UPLOADING state 2728, the loading start screen may be displayed, followed by the loading end screen. Moreover, the implant is powered up and the communication with the implant is initiated. If, at any point of the UPLOADING state 2728, the telemetric coupling deteriorates and becomes insufficient, the HID subsystem may return to the SEARCHING state 2726. Otherwise, the patient information is uploaded from the implant such that the STANDBY state 2730 may be initiated.

The STANDBY state 2730 may lead to several states depending on the triggering conditions. For example, if the magnetic coupling deteriorates and becomes insufficient, the HID subsystem may return to the SEARCHING state 2726. For another example, if the Locked key is pressed, the HID subsystem may enter the LOCKED state 2732 in which the locked screen may be displayed, and from which any key may be pressed to return to the ASKING FOR CODE state 2724.

For yet another example, if the code-change auxiliary key is pressed, the HID subsystem may enter the ASKING FOR OLD CODE state 2734 in which the enter-old-code screen may be displayed. Once the correct 4-digit code is received and the Next auxiliary key is pressed, the ASKING FOR NEW CODE state 2736 may be entered, in which the enter-new-code screen may be displayed. After receiving the new 4-digit code, the HID subsystem may enter the CONFIRM NEW CODE state 2738, in which the confirm-or-cancel-code screen may be displayed and the user may elect to either confirm or cancel the entered code. If the user presses the OK auxiliary key to confirm the entered code, the code changed screen may be displayed and the HID subsystem may return to the STANDBY state 2730; otherwise, if the user presses the Cancel auxiliary key to cancel the entered new code, the HID subsystem may simply return to the STANDBY state 2730.

While in the STANDBY state 2730, the user may request a graph of the patient's gastric band adjustment history by pressing the Chart auxiliary key. Accordingly, the GRAPH state 2740 may be entered, and the history plot screen may be displayed. From the GRAPH state 2740, the HID subsystem may enter the LIST state 2742 if the user presses the List auxiliary key, thereby loading the history list screen. After reviewing the history plot screen and/or the history list screen, the user may press the Return key to return to the STANDBY state 2730.

Moreover, the user may adjust the width of the gastric band from the STANDBY state 2730. For example, when the Open button is pressed, the HID subsystem may enter the MOVE IMPLANT state 2744, in which the opening screen may be displayed. Accordingly, the implant motor may drive the gastric band to expand its diameter. For another example, when the Close button is pressed, the HID subsystem may initiate the MOVE IMPLANT state 2744, in which the closing screen may be displayed. Accordingly, the implant motor may drive the gastric band to constrict its diameter.

In order to achieve a desirable gastric band diameter, the user may repeat the above process either by pressing the Open button or Close button repeatedly, or by pressing the Open button and the Close button alternately. During the MOVE IMPLANT state 2744, if the implant motor is blocked and such blockage is detected, the HID subsystem may return to the STANDBY state 2730. Moreover, during the MOVE IMPLANT state 2744, if the magnetic coupling deteriorates and becomes insufficient, the HID subsystem may return to the SEARCHING state 2726.

When the control device is connected to the docking station, the CHARGE block 2750 may be entered, during which the battery recharging may be performed and the battery recharging screen may be displayed. In the CHARGE block 2750, the initial state is the FAST CHARGE state 2752, during which the recharging process is controlled by current. Once the fast charging is complete, the NORMAL CHARGE state 2754 may be entered, and the battery recharging process may be controlled by voltage. Once the battery is fully charged, the HID subsystem may enter the FULL CHARGE state 2756. The HID subsystem may alternate between the NORMAL CHARGE state 2754 and the FULL CHARGE state 2756 if the control device remained connected to the docking station long enough for the battery to dissipate some of the charges.

Figure 28:
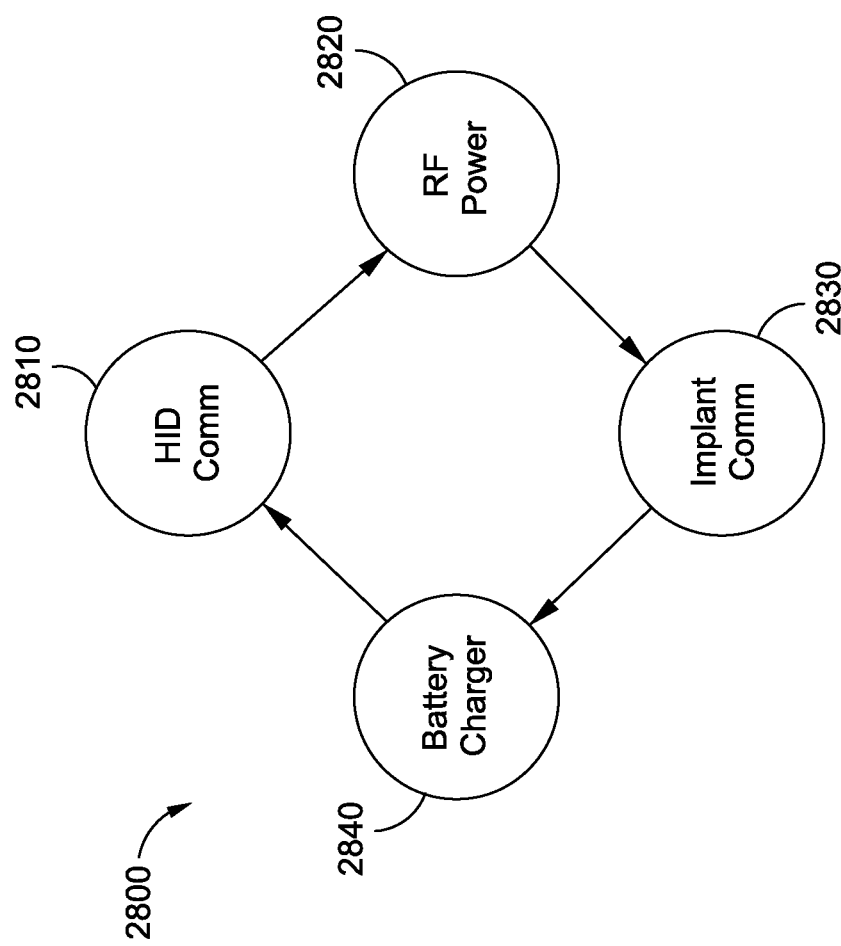
FIG. 28 shows the state diagram of an RF subsystem algorithm according to an embodiment of the present invention.

The discussion now turns to the RF subsystem algorithm. FIG. 28 shows the state diagram of an RF subsystem algorithm 2800 according to an embodiment of the present invention. The RF subsystem powers and communicates with the implant, such that it may manage the implant's telemetric (electromagnetic) coupling, control the implant's power consumption, count the motor steps, and receive feedback information from the implant. The RF subsystem may also communicate with the HID subsystem, monitor battery recharging, respond errors and interrupts, and perform cyclic redundant check (CRC), delay, filtering and driving.

As shown in FIG. 28, the RF module cycles among four different states, each of them may last about 500 μs. The first state may be the HID Communication state 2810, in which the RF subsystem may receive up to two commands from the HID subsystem. In response, the RF subsystem may respond to these commands by sending up to eight notification messages. The second state may be the RF Power state 2820, in which the power level to the implant may be monitored and controlled. The third state may be the Implant Communication state 2830, in which data may be sent to and/or received from the implant. The received data may be further analyzed in this state. The fourth state may be the Battery Charger state 2840, in which battery power may be monitored and controlled if the control device (control device) is properly connected to the docking station. Generally, the RF subsystem may cycle or return back to the HID Communication state 2810 after completing the Battery Charger state 2840.

Referring again to FIG. 26, the HID microcontroller 2622 may interact with the RF microcontroller 2624 through a UART interface 2600. Generally, the HID microcontroller 2622 (master) may send up to two commands consecutively. The HID microcontroller 2622 (master) may demand answer messages from the RF microcontroller 2624 (slave). In response, the slave may send up to eight notifications consecutively to the master. According to an embodiment of the present invention, Table 2 below shows the data structures for the command, the answer message and the notification message.

TABLE 2

Data structures of the command message, the answer message, and the notification message.

| HEADER | | | DATA | | CRC |
|---|---|---|---|---|---|
| CODE | SEQ | LENGTH | DATA[0] | ... [Length − 1] | CRC |
| COMMAND FROM MASTER (HID) | | | | | |
| 16-bit | 16-bit | 16-bit | 16-bit | ... 16-bit | 16-bit |
| ANSWER MESSAGE FROM SLAVE (RF) | | | | | |
| 0x0000 | 16-bit | 16-bit | 16-bit | ... 16-bit | 16-bit |
| NOTIFICATION MESSAGE FROM SLAVE (RF) | | | | | |
| 0x4154 | 16-bit | 16-bit | 16-bit | ... 16-bit | 16-bit |

These command and messages may share a similar data structure, which may includes a six-byte header followed by a 2*LENGTH-byte long data field and a two-byte CRC code. As discussed herein, LENGTH may be a predefined parameter specifying the length of the data. Within the six-byte header, the first two bytes contain the command code, the next two bytes contain a sequence number, and the last two bytes describe the LENGTH of the following data field. The data field may be empty if LENGTH equals 0.

Generally, the HID master does not transmit all the header bytes at one time. In one embodiment, for example, FIG. 29A shows a command only communication protocol between the HID and RF subsystems. More particularly, the HID master may send a two-byte command code to the RF slave, which may respond by sending back an ACK message. Upon receiving the ACK message, the HID master may begin transmitting the Sequence bytes, the LENGTH bytes, and the CRC bytes according to the shown order.

Figure 29B:
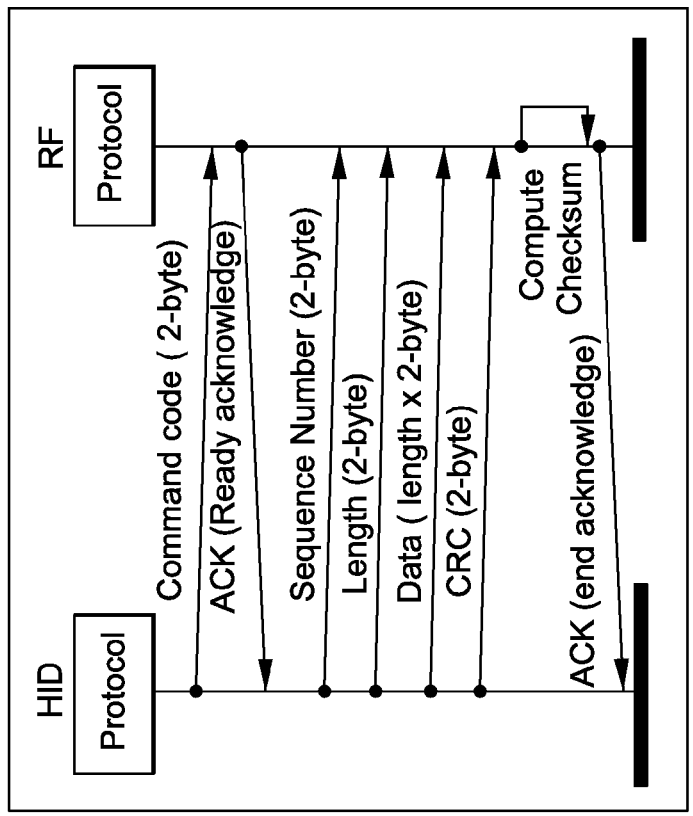
FIG. 29B shows a command-data communication protocol between the HID and RF subsystems according to an embodiment of the present invention.
Figure 29A:
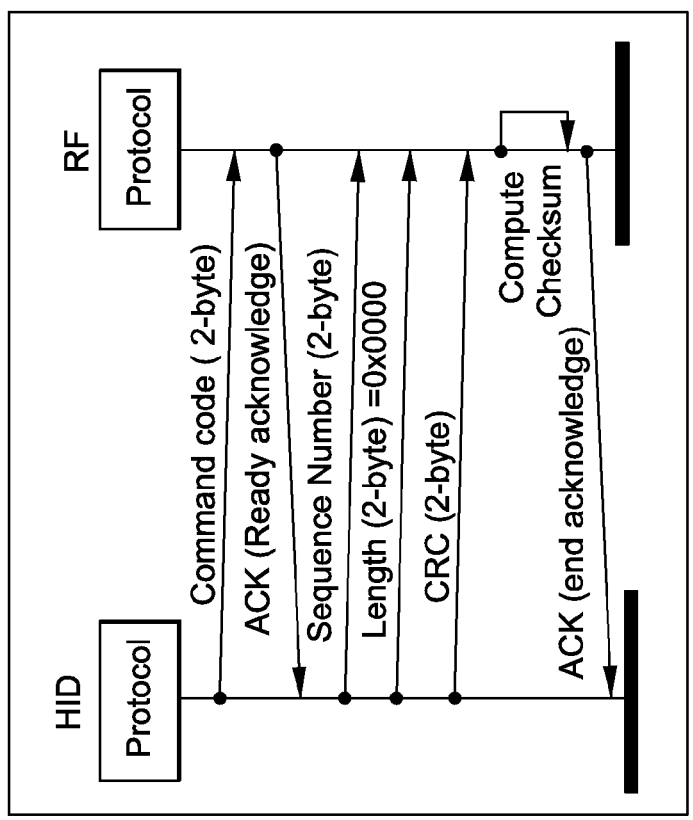
FIG. 29A shows a command only communication protocol between the HID and RF subsystems according to an embodiment of the present invention.

In another embodiment, for example, FIG. 29B shows a command-data communication protocol between the HID and RF subsystems. The protocol illustrated in FIG. 29B may be similar to the protocol illustrated in FIG. 29A except that the Data bytes may be sent after the LENGTH bytes.

Figure 30:
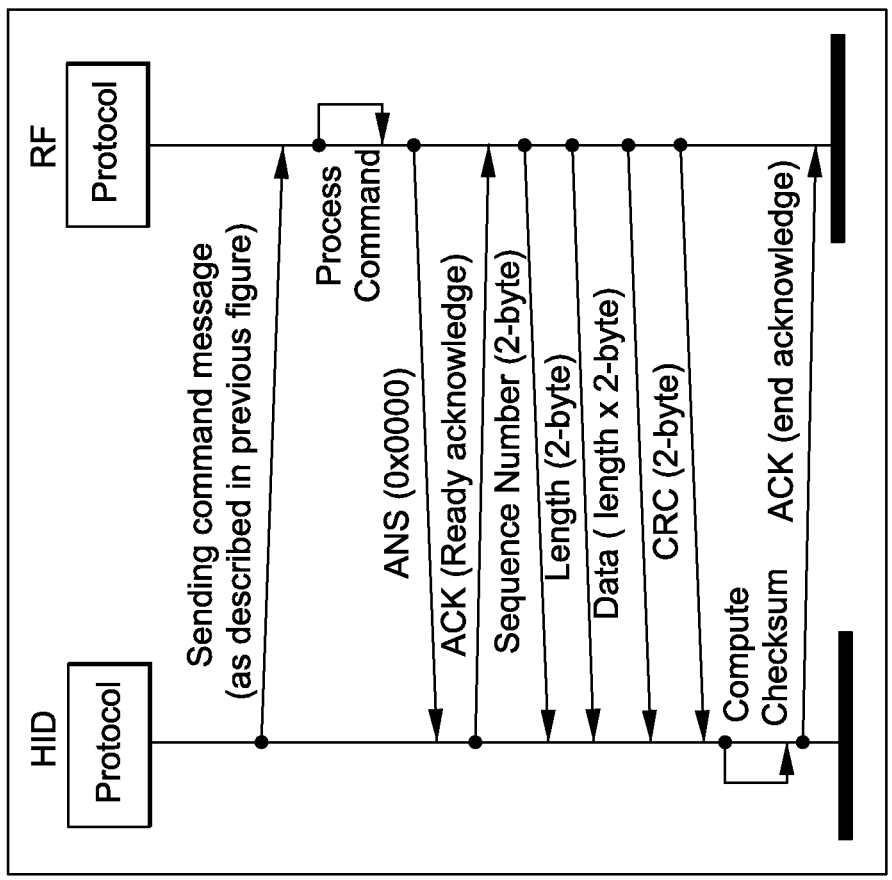
FIG. 30 shows an answer message communication protocol from the RF subsystem according to an embodiment of the present invention.
Figure 31:
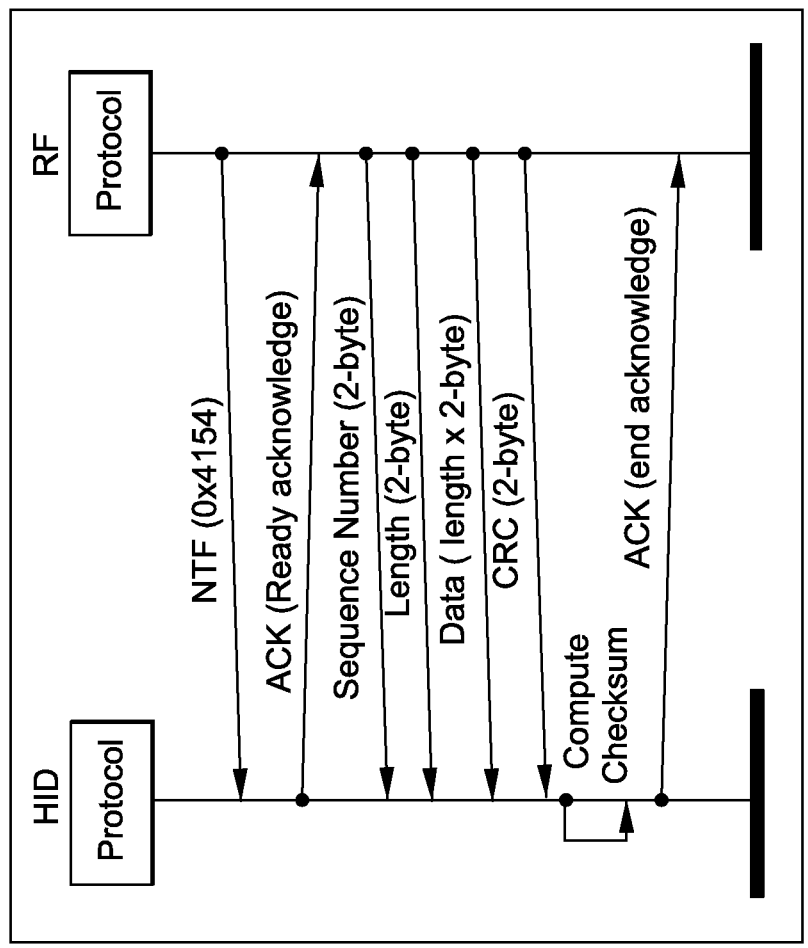
FIG. 31 shows a notification message communication protocol from the RF subsystem according to an embodiment of the present invention.

Next, FIG. 30 shows an answer message communication protocol from the RF subsystem according to an embodiment of the present invention. After receiving and processing the command message from the HID master, the RF slave may send back an answer message with data structure as shown in Table 2. Similarly, FIG. 31 shows that the RF slave may initiate notification message without receiving prior command from the HID master.

Figure 32:
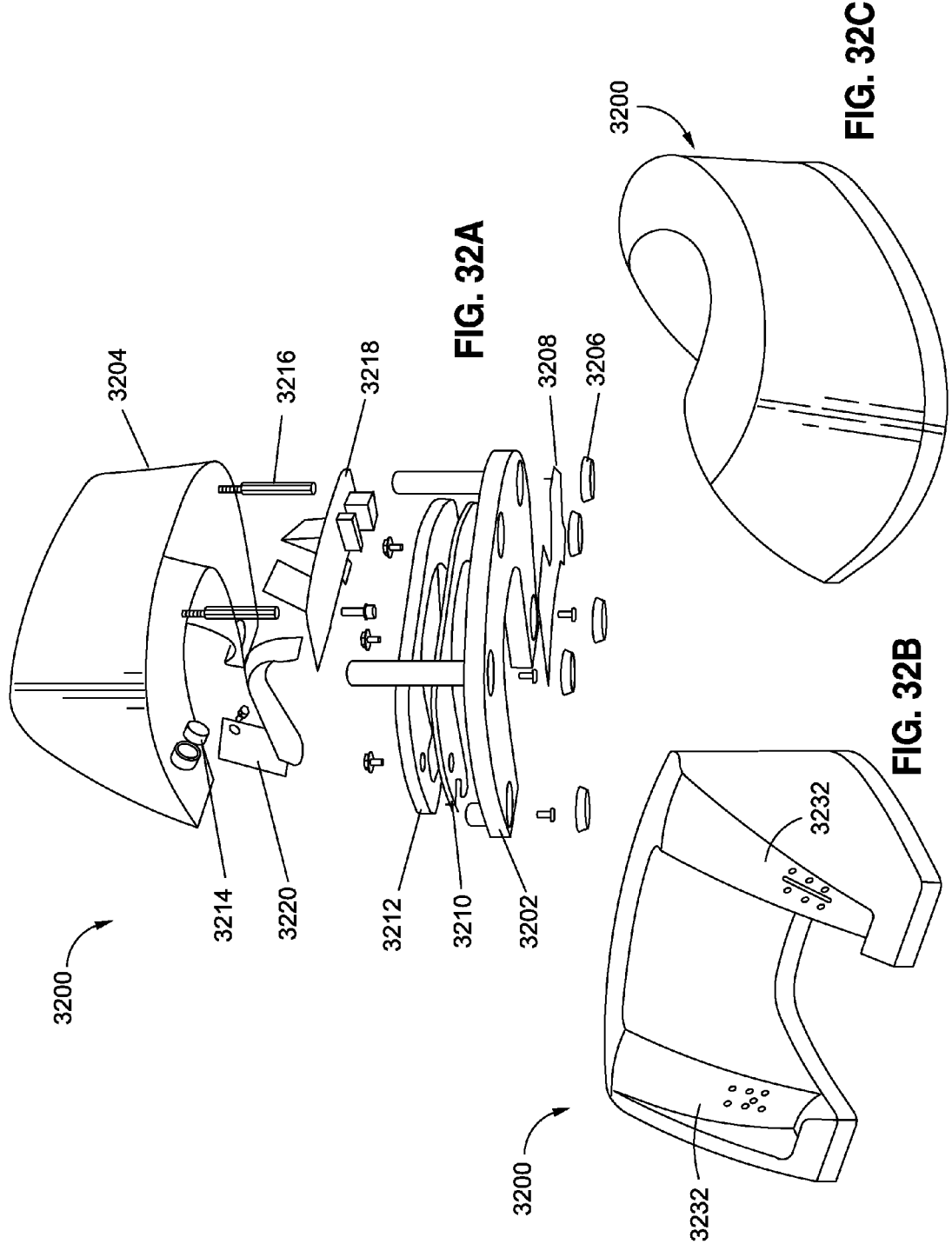
FIGS. 32A-32C show an exploded view, a front view and a back view of a docking station according to an embodiment of the present invention.

The discussion now turns to the features of the docking station. FIGS. 32A-32C show an exploded view, a front view and a back view of a docking station 3200 according to an embodiment of the present invention. Generally, the docking station 3200 may include a bottom shell 3202, a top shell 3204, four rubber foot 3206, a regulatory sticker 3208, a ballast 2 bottom 3210, a ballast 1 top 3212, a magnet 3214, two alignment pins 3216, a main PCB 3218, and a supplementary PCB 3220.

The docking station 3200 may have a saddle structure 3232, which may provide one or more contact point for coupling with the control device. The main PCB 3218 may be used for performing power protection to protect the docking station 3200 and the control device from the power surge of the power adapter. Moreover, the main PCB 3218 may assist the RF subsystem in monitoring the charging status and the charging temperature.

Figure 33:
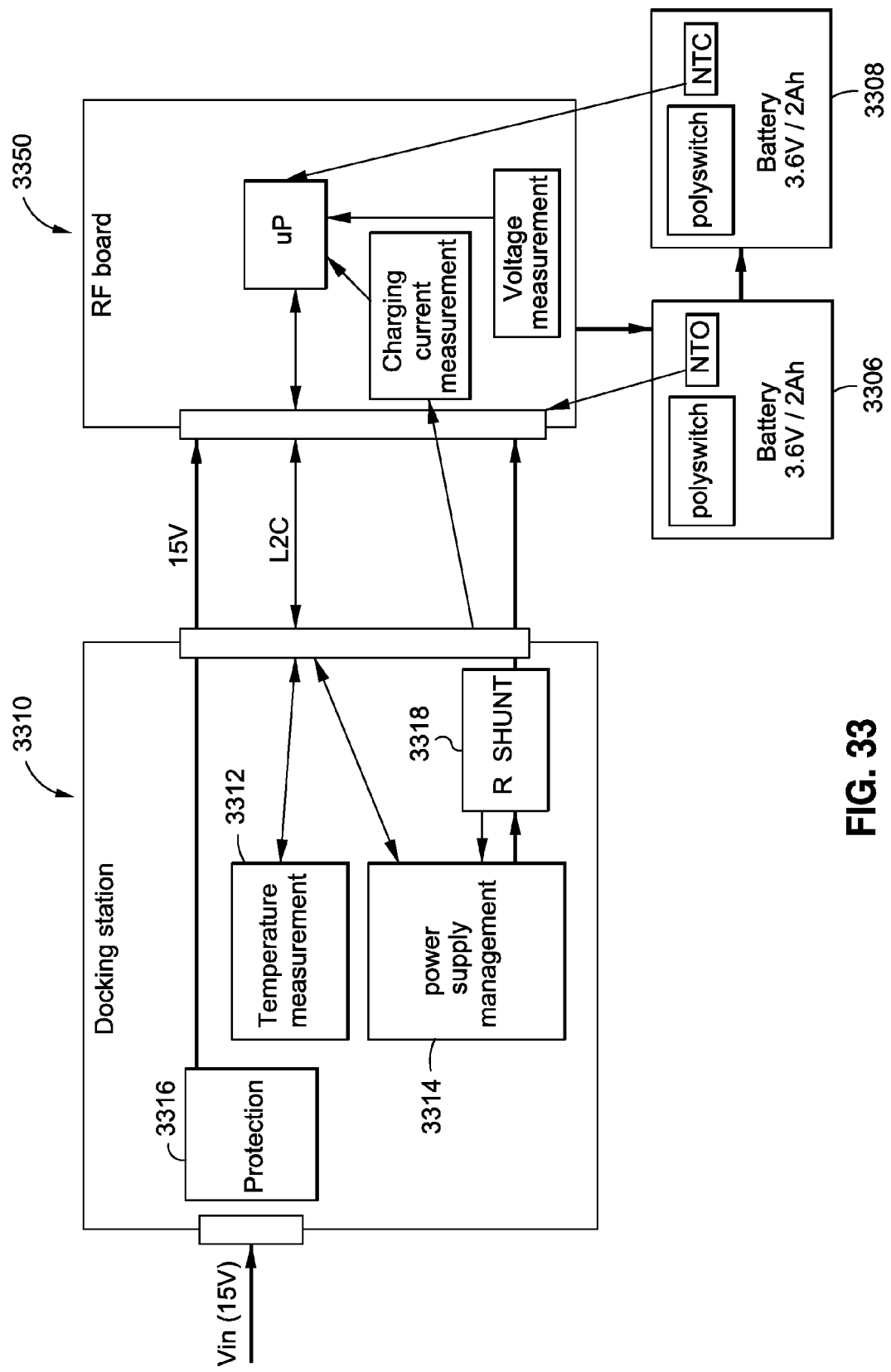
FIG. 33 shows a schematic view of the docking station interacting with the RF Board according to an embodiment of the present invention.

FIG. 33 shows a schematic view of the docking station subsystem 3310 interacting with the RF Board 3350 according to an embodiment of the present invention. The docking station system 3310 may be implemented by the main PCB 3218 (see FIG. 32), and it may include a temperature measurement block 3312, a power supply management block 3314, a protection block 3316, and a shunt resistance device 3318. The power supply management block 3314 may interact with the RF board 3350 to perform battery charging (charging status) management and charging temperature (overheat prevention) management.

Charging current may be estimated by measuring voltage across the shunt resistance device 3318. In one embodiment, for example, the shunt resistance device 3318 may have a resistance of about 0.015Ω. Moreover, there may be NTC thermistors inside the batteries for proper temperature measurement, as well as several polyswitches for resetting the circuit in case of power surges at the battery level.

Figure 34:
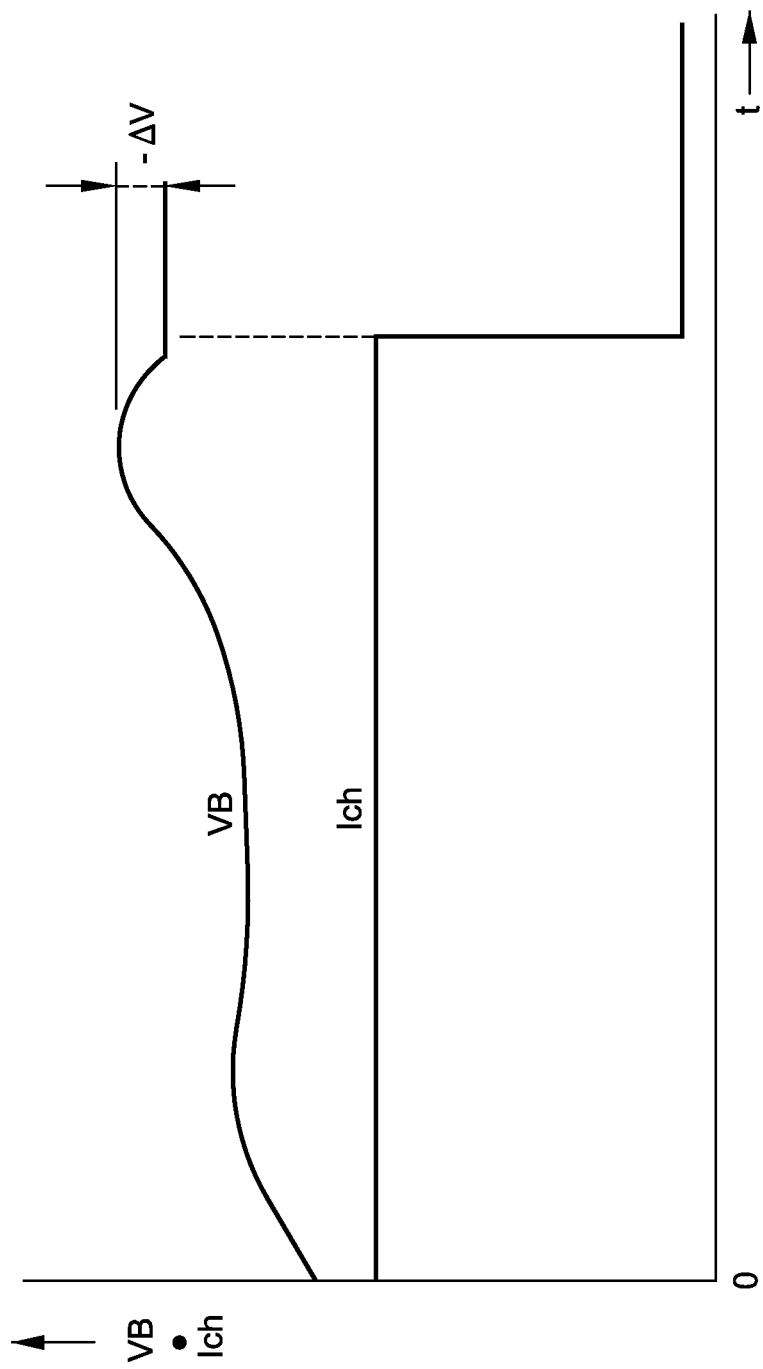
FIG. 34 shows a fast charge mode voltage-current chart according to an embodiment of the present invention.

FIG. 34 shows a fast charge mode voltage-current chart according to an embodiment of the present invention. At the beginning of the fast charge mode, the charging process is controlled through a constant current $I_{ch}$. According to an embodiment of the current invention, $I_{ch}$ may be about 5 A. After the battery charge $V_B$ reaches a certain voltage, it will decrease by $\Delta V$ and the charging circuit then switches to the normal charge mode.

The RF board may perform the charge monitoring. A dedicated NiMh charger chip (e.g., the LTC1759 chip) may be used for controlling the charging process. The LTC1759 chip may use temperature measurement of the battery pack to adjust its charging algorithm. The LTC1759 chip may be a high current DC-to-DC power supply controlled by a NiMH charger controller, both of which may be included in a single chip. Thus, the LTC1759 chip may control the power given to the battery pack and ensure that it complies with the charging profile as shown in FIG. 34.

The discussion now turns to the retractable external antenna (external antenna with retractable cable). FIGS. 35A-35B show a perspective view and an exploded view of an external antenna with retractable cable according to an embodiment of the present invention. Generally, the retractable external antenna 3500 may include an antenna bottom 3502, an antenna top 3504, a winding drum 3506, a gear wheel 3508, a button 3510, a button ring 3512, a metal plate 3514, a PCB 3516, a tap 3518, a compression spring 3522, a drive spring 3524, an antenna cable 3526, a gear wheel pin 3528, a center axis 3530, a winding drum lid 3532, a sound barrier 3534, a glide plate 3536, and a ball bearing 3538.

To achieve smooth retraction, the retractor components are placed inside of the winding drum 3506 while the antenna cable 3526 retracts on the circumferential surface of the winding drum 3506. In order to enable proper power induction, the cable of the antenna may be fully deployed until a green marker can be seen. Otherwise, the coiled antenna cable may absorb excessive power induction energy. The retractable external antenna can be attached to the control device by pushing the connector against the control device until a "click" is heard, which signifies that the antenna cable 3626 is locked. Once locked, the antenna cable 3626 is in a suitable configuration. The locking mechanism ensures a good electromagnetic coupling by establishing a unique and stable resting position for the cable.

The gear wheel 3508 may include a small spring loaded pin (gear wheel pin) 3528. The antenna top 3504 may have a small hole (not shown). The "click" sound may be produced when the spring loaded pin 3528 enters into the small hole. This may occur when the spring loaded pin 3528 is in front of the hole after the antenna cable 3526 is fully unwound. When the bottom ring 3512 is pressed, the spring loaded pin 3528 may be disengaged, thereby releasing the antenna cable 3526.

Figure 36B:
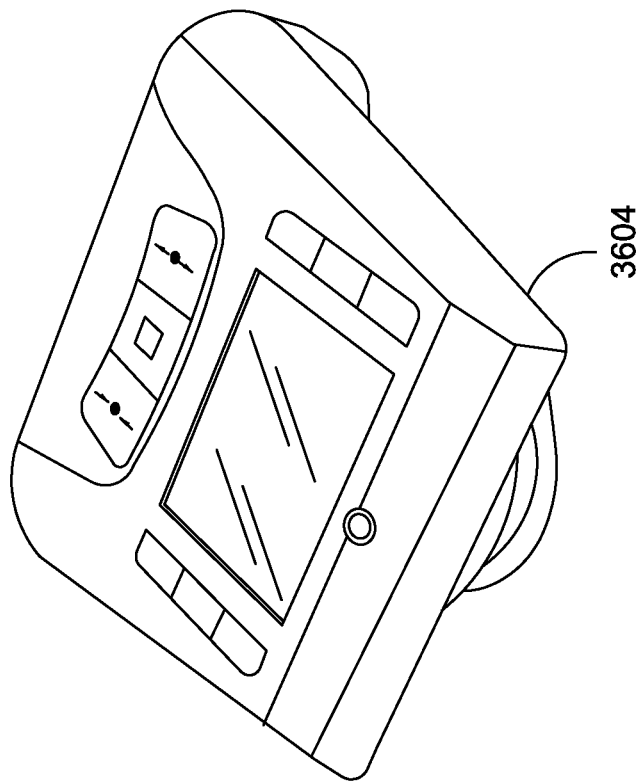
FIGS. 36A-36B show a perspective front view and a perspective back view of the retractable external antenna being stored at the back of the control device according to an embodiment of the present invention.
Figure 36A:
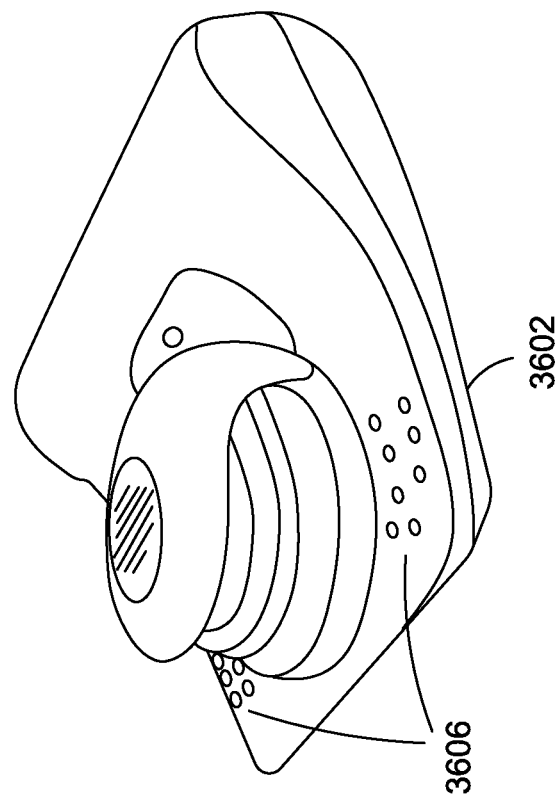

As shown in FIGS. 36A and 36B, the retractable external antenna 3500 may be stored at the back of the control device according to an embodiment of the present invention. The magnetic pins 3606 of the control device provide easy connection points for connecting to the docking station.

The discussion now turns to various structural and functional features of the implant. Referring to FIGS. 37A-37B, a perspective view and an exploded view of the implant 3700 (e.g., a gastric band system) are shown according to an embodiment of the present invention. Generally, the implant 3700 may include a membrane shell 3702, a dorsal element 3704, a motor sleeve 3706, an implant electronic device enclosure (protection case) base and cable sleeve 3708, a manipulation handle 3710, a cable sleeve 3712, a skeleton 3714, an implant electronic device enclosure (protection case) cover 3716, a motor and cable assembly 3718, a flexible screw assembly 3720, an implant electronic device PCB 3722, and a stabilizing tube 3724.

The dorsal element 3704 may have a first end, a second end, and a curvy semi-tubular body connecting the first and second ends. The first end of the dorsal element 3704 may have a flange lock and a first opening, while the second end of the dorsal element 3704 may have an open compartment.

Similarly, the skeleton 3714 may have a distal end, a proximal end, and a ladder body connecting the distal end and the proximal end. The proximal end of the skeleton 3714 may have an open compartment for receiving the motor assembly 3718. Initially, the distal end of the skeleton 3714 may slide into the second end of the dorsal element 3704, along its semi-tubular body, and stop at the first end of the dorsal element 3704. The distal end of the skeleton 3714 may be secured to the first end of the dorsal element 3704, while the open compartment of the skeleton 3714 may fit into the open compartment of the dorsal element 3704. In such manner, the ladder body of the skeleton 3714 may push against the inner surface of the semi-tubular body of the dorsal element 3704.

Accordingly, the skeleton 3714 may provide support to the semi-tubular body of the dorsal element.

The stabilizing tube 3724 may be inserted into the ladder body of the skeleton 3714, such that it may be used for filling in the space defined by the ladder body and for stabilizing the ladder structure.

The motor assembly 3718 may have a motor coupled to a motor cable. The motor may be arranged to receive and maneuver the flexible screw assembly 3720. For example, the motor may have one or more set of rotors and/or gears for engaging a threaded section of the flexible screw assembly 3720. The motor may move a crimped end of the flexible screw assembly 3720 towards or away from the motor.

The flexible screw assembly 3720 may have a hooked end, which may be guided through a center conduit (space) of the stabilizing tube 3724. Because the stabilizing tube 3724 is adapted to the curvy shape of the dorsal element 3704, the flexible screw assembly 3720 may be bended with the stabilizing tube 3724. After leaving the stabilizing tube 3724, the hook end of the flexible screw assembly 3720 may be secured to the distal end of the skeleton, which may be secured to the first end of the dorsal element.

Next, the motor of the motor assembly 3718 may engage the flexible screw assembly 3720. The flexible screw assembly may have an inner section that is inserted into the stabilizing tube 3724. Also, the flexible screw assembly 3720 may have an outer section that stays outside of the stabilizing tube 3724 and extends beyond the open compartments of the skeleton 3714 and of the dorsal element 3704. The motor of the motor assembly 3718 may then engage the threaded section of the flexible screw assembly 3720, and move the crimped end of the flexible screw assembly 3720 away from the motor.

The membrane shell 3102 may have a tubular body, which may be used for covering the semi-tubular body of the dorsal element 3704. The cable sleeve 3712 may be used for covering and protecting the motor cable, and the motor sleeve 3706 may be used for covering and protecting the motor.

The open end of the motor cable may be soldered onto the implant electronic device PCB 3722, which may be protected by the enclosure cover 3716 and the enclosure base 3708. The flange of the manipulation handle 3710 may be inserted through the hole of the implant electronic device enclosure, folded over, and secured to the implant electronic device enclosure by applying an appropriate amount of MED2-4213 silicon glue or the equivalent thereof on the flange and the cavity of the manipulation handle 3710. The tapered end of the manipulation handle may be inserted and guided through the opening located at the first end of the dorsal element 3704, thereby leading the second end of the dorsal element 3704 to be inserted into the first end of the dorsal element 3704.

Consequently, the dorsal element 3704, and the membrane shell 3702, may form a ring structure. Particularly, the ring structure may have an adjustable ventral (inner) ring surface and a rigid dorsal (outer) ring surface. The adjustable ventral ring surface may be equipped with several cushion members for applying pressure against the stomach of a patient.

As persons skilled in the art may readily appreciate, an appropriate amount of MED2-4213 silicon glue, or the equivalence thereof, may be applied to various components, and the various junctions of thereof, of the implant 3700 for strengthening the overall structure of the implant 3700.

The discussion now turns to the implant electronic device protection case (enclosure) components. Generally, the implant electronic device PCB 3722 may be coupled to the motor cable, such that the implant electronic device PCB 3722 may send control signals to the motor and sense a motor coil current of the motor. The implant electronic device PCB 3722, and the junction at which the implant electronic device is coupled to the motor cable, may be protected by the implant electronic device enclosure, which may include the enclosure cover 3716, the enclosure base 3708, and the strain relieving sheath 3850.

Figure 38A:
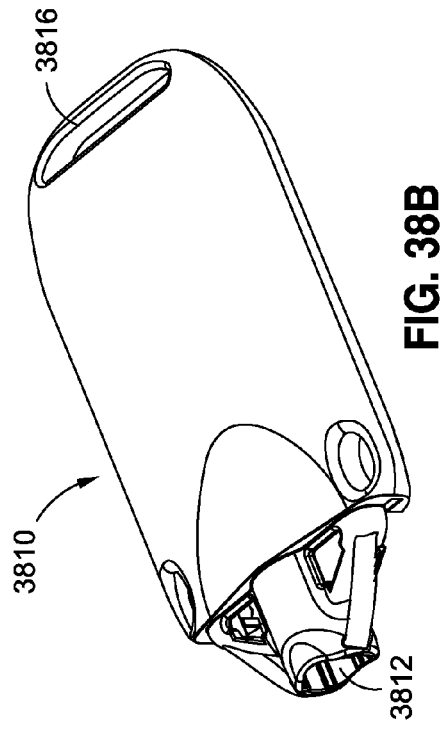
Figure 38B:
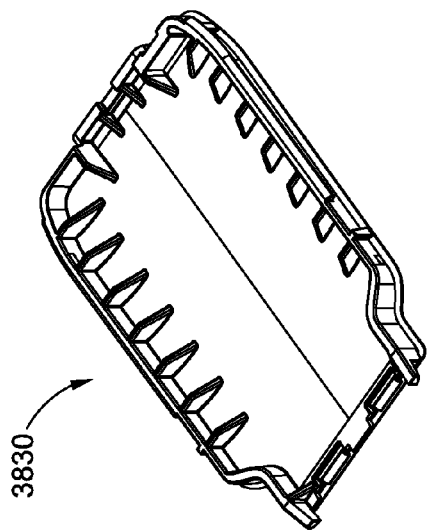

FIGS. 38A and 38B shows a top perspective view and a bottom perspective view of an enclosure base shell 3810 according to an embodiment of the present invention. Generally, the enclosure base shell 3810 may be part of the enclosure base 3708. Particularly, the enclosure base shell 3810 may include a compartment 3814 for fitting the electronic device PCB 3722, a cable port 3812 for receiving and guiding the motor cable, and a handle hinge 3816 for receiving the flange of the manipulation handle 3710.

Figure 38C:
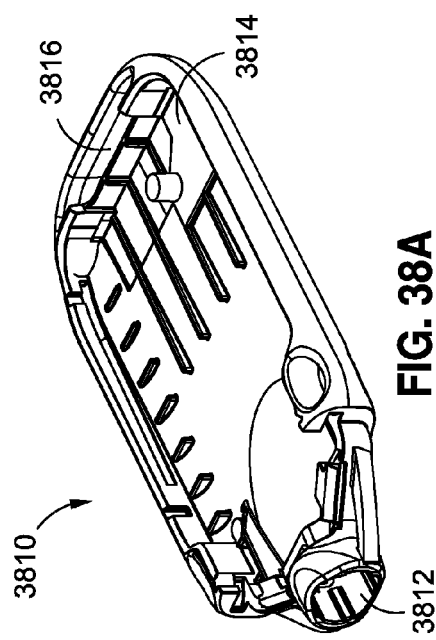

Referring to FIG. 38C, a perspective view of a cladding 3820 is shown according to an embodiment of the present invention. Generally, the cladding 3820 may be part of the enclosure cover 3716. Particularly, the cladding 3820 may be coupled to and cooperate with the enclosure base shell 3810 for guiding and protecting the motor cable. The cladding 3820 may include a plurality of openings to allow silicon material to be overmolded therein.

Figure 38D:
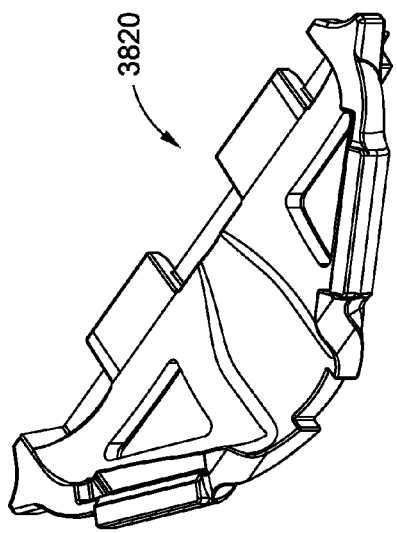

Referring to FIG. 38D, a perspective view of an enclosure cover shell 3830 is shown according to an embodiment of the present invention. Generally, the enclosure cover shell 3830 may be part of the enclosure cover 3716. The enclosure cover shell 3830 may be detachably coupled to the enclosure base shell 3810 and the cladding 3820 to form the enclosure case. The enclosure case may provide stability and protection for the implant electronic device PCB 3722 and for the connection established between the implant electronic device PCB 3722 and the motor cable.

Referring to FIG. 38E, the strain relieving sheath 3850 may be used for providing flexible support for the motor cable around the cable port 3812 area. The strain relieving sheath 3850 may help prevent breakage of the motor cable by restraining the motion of the motor cable around the cable port 3812 area. Referring to FIG. 38F, the extremity of the strain relieving sheath 3850 may have a silicone-PEEK overmolding and a plurality of internal bumps 3852 for keeping the cladding 3820 centered and for distributing the glue evenly.

The discussion now turns to the implant electronic device PCB 3722. FIGS. 39A-39B show a top view and a bottom view of an implant electronic system board (PCB) 3900, which may be used for implementing the functional features of the implant electronic device PCB 3722. Referring to FIG. 39A, the PCB 3900 may include a power regulation subsystem circuitry 3901, a microprocessor 3902, and an implant antenna 3904. The implant (internal) antenna 3904 may loop around the periphery of the PCB 3900, and it may be responsible for receiving the RF signals transmitted from the external antenna of the control device.

The power regulation subsystem circuitry 3904 may be coupled to the implant antenna 3904 via the L2 connection port 3906. The power regulation subsystem circuitry 3901 may include a power regulator 3908 for maintaining the local voltage $V_{CC}$. Moreover, the power regulation subsystem circuitry 3904 may receive the induced power and generate the power regulation signals when the DC input voltage $V_{IN}$ is above certain predetermined threshold (e.g. 5.6 V).

The microprocessor 3902 may be coupled to the power regulation subsystem circuitry 3901. The microprocessor 3902 may be coupled with the implant antenna 3904. Generally, the microprocessor 3902 may be used for generating frequency modulation signals, which may be embedded with power regulation information and gastric band adjustment history information.

Particularly, the microprocessor 3902 may be used for receiving and processing commands send from the control device 110 as shown in FIG. 1. For example, the microprocessor 3902 may receive a gastric band adjustment command from the control device 110. In response, the microprocessor 3902 may send motor step signal to the motor for adjusting the width of the gastric band.

Moreover, the microprocessor 3902 may receive a gastric band adjustment history request command from the control device 110. In response, the microprocessor 3902 may retrieve the requested data from a memory device (not shown) and send the retrieved data back to the control device. In one embodiment, the microprocessor 3902 may have about 8 kB of programmable memory, 512 Bytes of data memory, 512 Bytes of SRAM, two timers, several input and out pins, one comparator, an A/D converter and several interrupt sources.

Referring to FIG. 39B, the bottom surface of the implant electronic system board 3900 may have nine oval connection pads 3912, each of which may be soldered to one of nine motor wires of the motor cable. Among the nine ovals connection pads 3912, eight of them may be grouped in four parallel pairs to provide redundancy protection. The remaining one oval connection pad 3912 may be soldered to an FC wire. The large metallic surface 3914 may be soldered to a motor cable center ground wire (GND).

The discussion now turns to the structural and functional features of the manipulation handle 3710. FIGS. 40A-40C show various views of a manipulation hand 4000, which may be used for implementing the functional features of the manipulation handle 3710. Generally, the manipulation hand 4000 may have a tapered end 4042, a base end 4044, an elongated body 4043 connecting the tapered end 4042 and the base end 4044, and a flange 4052 coupled to the base end 4044.

The flange 4052 may engage the handle hinge 3816 of the implant electronic device enclosure 3810. The profiled of the elongated body 4043 may allow easier insertion into the opening of the dorsal element. Specifically, the elongated body 4043 may have an increase thickness from the tapered end 4042 to the base end 4044. Moreover, the elongated body 4043 may have helicoidal arrows 4046, which may be used for indicating the direction for insertion. In one embodiment, the helicoidal arrows 4046 may form on one side of the elongated body 4043. In another embodiment, the helicoidal arrows 4046 may form on both sides of the elongated body 4043 as shown in FIG. 40C. Accordingly, the helicoidal arrows 4046 may be viewed at most angles during the implant procedure.

Referring to FIG. 40B, the manipulation handle 4000 may have first, second, third and fourth widths. In one embodiment, for example, the first width 4002 may be about 10.34 mm, the second width 4004 may be about 17 mm, the third width 4006 may be about 3.33 mm, and the fourth width 4008 may be about 4.2 mm.

Referring to FIG. 40C, the manipulation handle 4000 may have a flange length 4010 and a body length 4038. In one embodiment, for example, the flange length 4010 may be about 13.5 mm, and the body length 4038 may be about 100.3 mm. The flange 4052 may have a flange thickness 4012, which may be about 1.4 mm. The elongated body 4043 may have twelve thicknesses. In one embodiment, for example, the first thickness 4014 may be about 4.96 mm, the second thickness 4016 may be about 4.5 mm, the third thickness 4018 may be about 3.9 mm, the fourth thickness 4020 may be about 3.6 mm, the fifth thickness 4022 may be about 3.45 mm, the sixth thickness 4024 may be about 3.42 mm, the seven thickness 4026 may be about 3.4 mm, the eighth thickness 4028 may be about 3.2 mm, the ninth thickness 4030 may be about 3.03 mm, the tenth thickness 4032 may be about 2.9 mm, the eleventh thickness 4034 may be about 2.8 mm, and the twelfth thickness 4036 may be about 1.7 mm.

Figure 41:
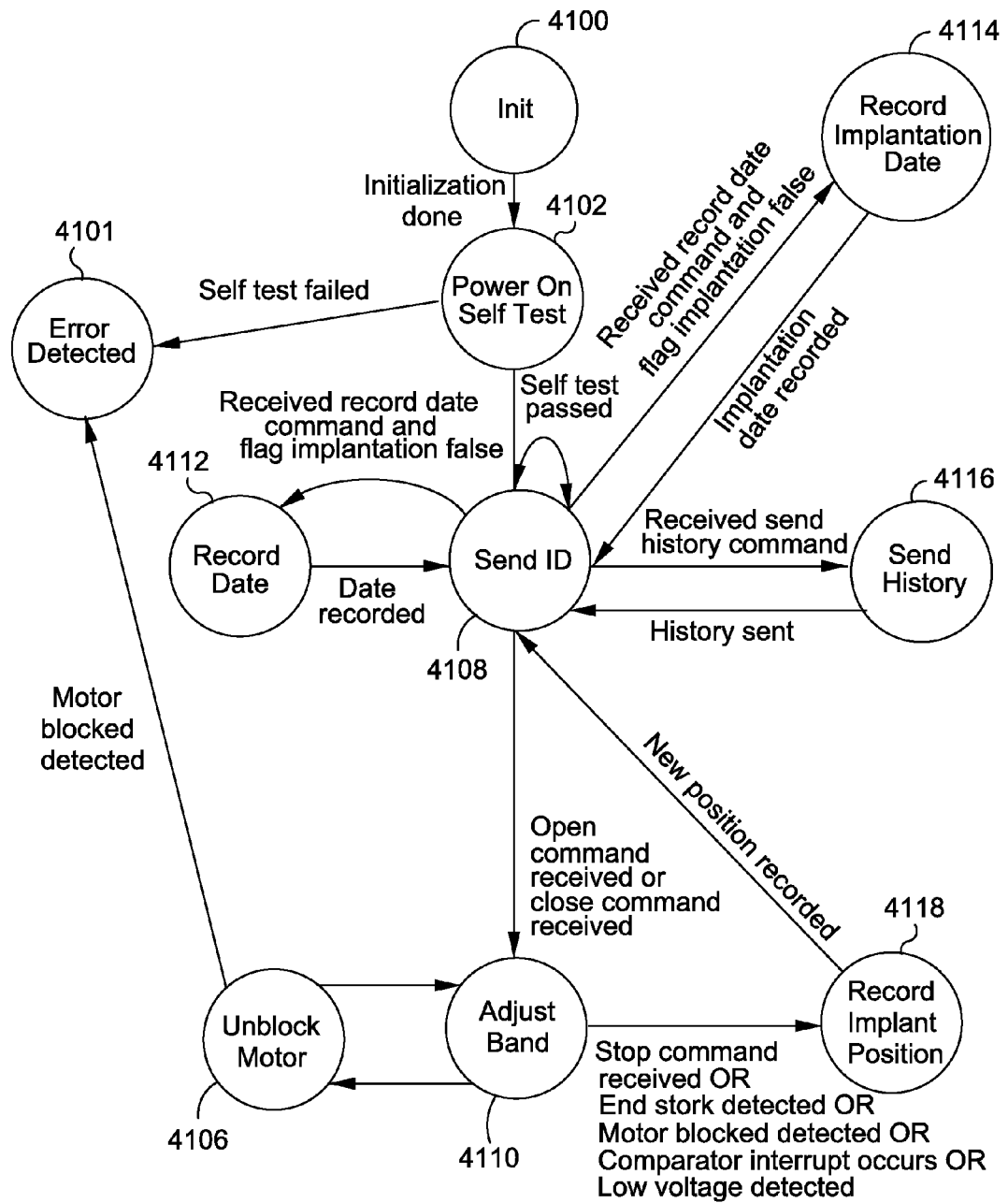
FIG. 41 shows a state diagram of implant electronic device software algorithm according to an embodiment of the present invention.

The discussion now turns to the software algorithm of the implant electronic system. In FIG. 41, a state diagram of implant electronic device software algorithm is shown according to an embodiment of the present invention. Generally, the implant electronic device software algorithm may be executed by the microprocessor 3902 to perform various functions, such as driving the motor, counting the motor steps, detecting and eliminating motor blockage, storing and sending the patient's identification number and record information, such as the implantation date and the history of the last ten adjustments, and performing a self test on motor coils and other electronic components.

Upon receiving inductive power from the RF Board, the implant electronic system may enter the "Init" state 4100, in which the microprocessors, the A/D converters, the input/output devices, interrupt devices, comparator, and watchdog devices may be initialized. Once the initialization is completed, the implant electronic system may enter the "Power On Self Test" state 4102, in which the motor coils may be tested. If the self test is successful, the implant electronic system may enter the "Send ID" state 4108. Otherwise, the implant electronic system may enter the "Error Detected" state 4104, in which the RF transponder may notify the control device 110 with the appropriate message.

The "Send ID" state 4102 may be the default state, such that it may loop itself and continuously send ID messages back to the control device 110 until additional command is sent form the control device.

Figures 42A, 42B:
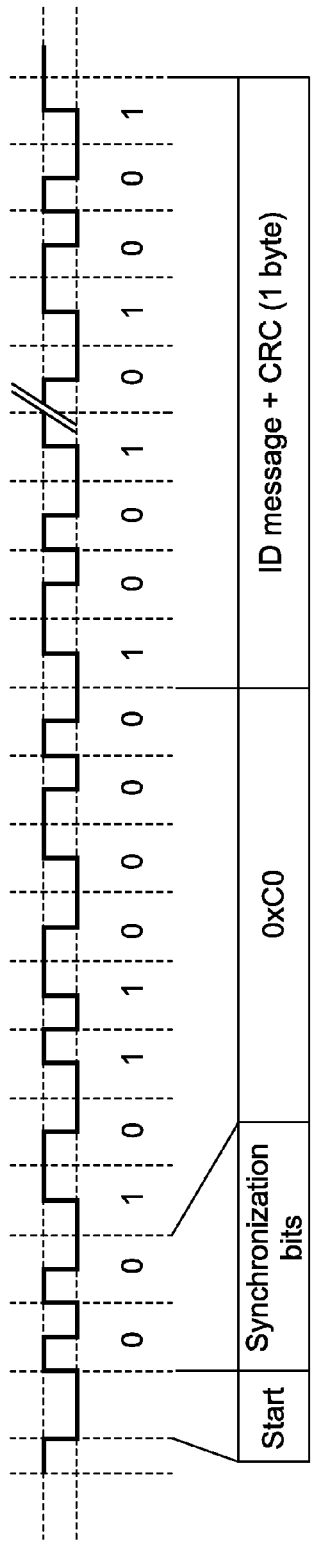
FIGS. 42A-42B show a transmission sequence and a data structure of an identification message to the control device according to an embodiment of the present invention.

Referring to FIGS. 42A and 42B, the data structure of the ID messages may include three ID bytes, two status bytes, three motor position bytes, and one CRC code check byte.

Referring again to FIG. 41, the implant electronic system may transit out of the "Send ID" state 4102 once it receives a command from the control device. For example, the implantation date will be recorded in the EEPROM in the "Record Date" state 4112 if a "record date" command is received and the implantation flag is False. For another example, the last 10 implant's positions will be sent back to the control device during the "Send History" state 4116 if a "send history" command is received.

Moreover, the implant electronic system may enter the "Adjust Band" state 4110 if an "Open" or "Close" command is received. During the "Adjust Band" state, the motor sequence may be activated, such that the motor may be directed to rotate clockwise or counter-clockwise.

A complete list of commands and the associating transmission protocol can be found on FIGS. 43B and 44B. Particularly, FIG. 43B illustrates the data structure of commands that do not require additional parameters being sent to the implant, whereas FIG. 44B illustrates the data structure of commands that require additional parameter.

Among the no-parameter commands, the "ImplantRequestStopPower" command may instruct the implant to stop powering the motor; the "ImplantRequestSelfTest" command may request the implant to perform a self test procedure; the "ImplantGetCurrentDate" command may request the implant to get the current date; the "ImplantGetSerialNumber" may instruct the implant to get the serial number; the "ImplantGetFirmwareVersion" may instruct the implant to get the firmware version; the "ImplantGetStepCounter" command may instruct the implant to gets the current motor step counter; the "ImplantEepromRecovery" command may instruct the implant to recover all stored EEPROM memory; and the "ImplantGetExtendedStatusRegister" command may instruct the implant to get value of an extended status register.

Among the with-parameter commands, the "ImplantOpenNStep" command may ask the implant to turn the stepper motor clockwise by a number of steps in order to open the band; the "ImplantCloseNStep" command may ask the implant to turn the stepper motor counter-clockwise by N number of steps in order to close the band; the "ImplantWriteByteEeprom" command may instruct the implant to write a byte of data into the EEPROM; the "ImplantSetCurrentDate" command may instruct the implant to set and store the current date; the "ImplantReadHistory" command may instruct the implant to read the adjustment history; the "ImplantGetParameters" command may instruct the implant to get some specific parameters; and the "ImplantReadEepromRecovery" may instruct the implant to recover a specific record stored in EEPROM.

Referring again to FIG. 41, motor coil currents may be monitored during the motor sequence initialization and throughout the motor rotation phase for detecting and eliminating motor blockage. If a motor blockage is detected, the implant electronic system may enter the "Unblock Motor" state 4106 to resolve the motor blockage issue. In one embodiment, the motor may be directed to reduce its rotation speed, so that it may generate more torque to overcome the motor blockage. In another embodiment, the motor may be directed to change the rotation direction if the motor speed reduction scheme fails to remove the motor blockage.

If these two schemes do not resolve the motor blockage issue, the implant electronic system may enter the "Error Detected" state 4104, in which an error message will be sent to the control device 110.

Otherwise, the implant electronic system may return to the "Adjust Band" state 4110 to continue adjusting the gastric band. When the adjustment is completed, the implant electronic system may enter the "Record Implant Position" state 4118, in which the last adjustment and the received date will be recorded in the EEPROM.

Figure 49:
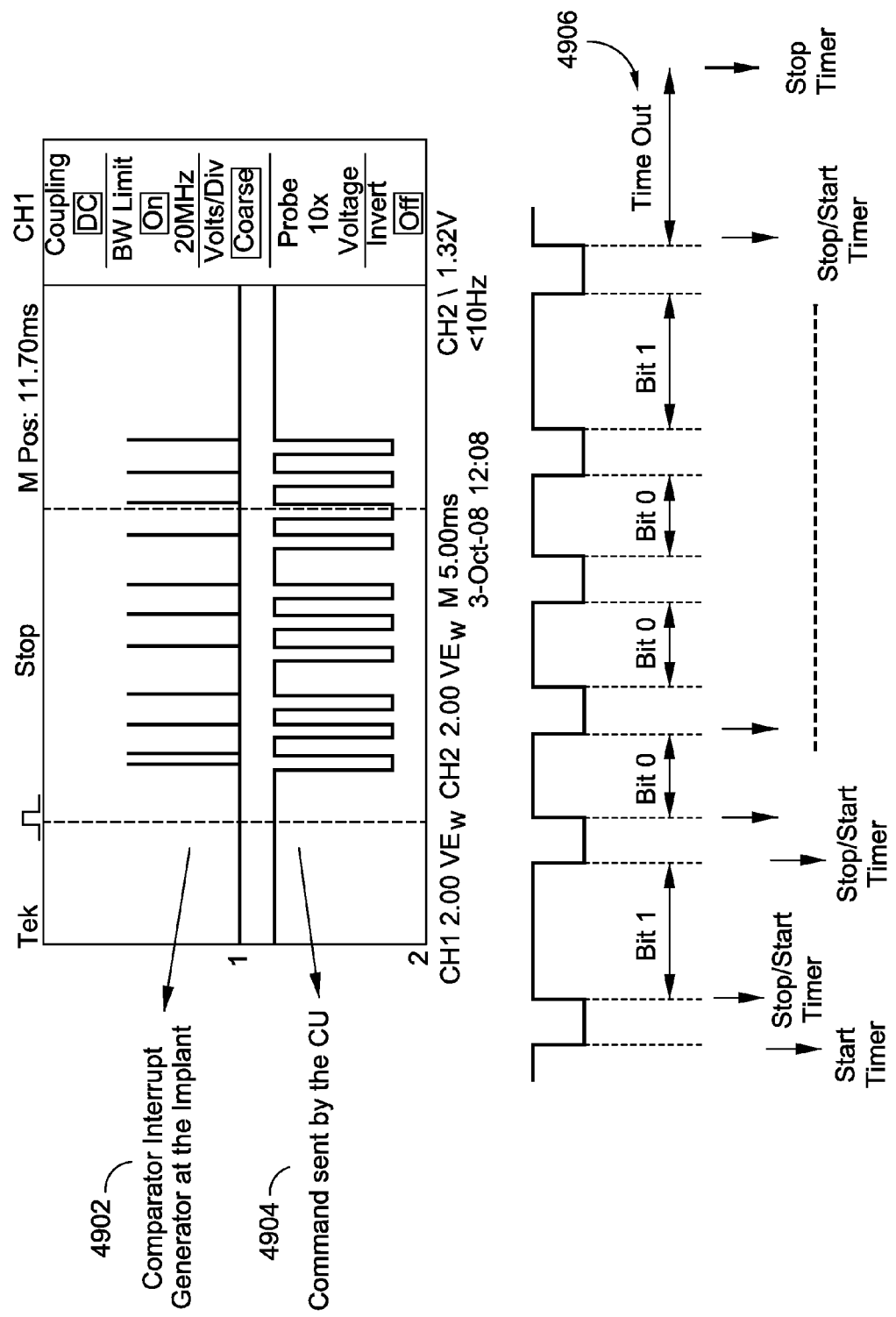
FIG. 49 shows a timing diagram of a computer interrupt upon a detection of a control device command at the implant according to an embodiment of the present invention.

The discussion now turns to the communication protocol between the control device and the implant electronic system. FIG. 49 shows a timing diagram of a computer interrupt sequence upon a detection of a control device command at the implant. The command 4904 may be sent by the control device, and it may be carried by an amplitude modulation signal at a carrier frequency of about 27 MHz. Once the command 4904 is separated from the carrier, it may be fed to a comparator to generate the interrupt sequence 4902. Referring to the digital sequence 4906, the interrupts may be used for starting and/or stopping a timer. For example, a low state values (bit 0) and a high state values (bit 1) may be characterized as a short period and a long period, respectively.

Referring to FIG. 43A, the implant may acknowledge the reception of a command by responding with an ACK message if the command does not contain any parameter. Referring to the FIG. 44A, the control device may send a command with parameters. In one embodiment, the parameters and the Cyclic Redundant Check (CRC) code may be sent at about 2 ms intervals. If the CRC code verification is successful, the implant may then respond with an ACK message, which may confirm that the command is properly received. Otherwise, the implant may send a NACK message to prompt the control device to resend the command. As shown in FIGS. 45A and 45B, the data structures of the ACK message and the NACK message may be similar except for the last four bits.

Figure 46A:
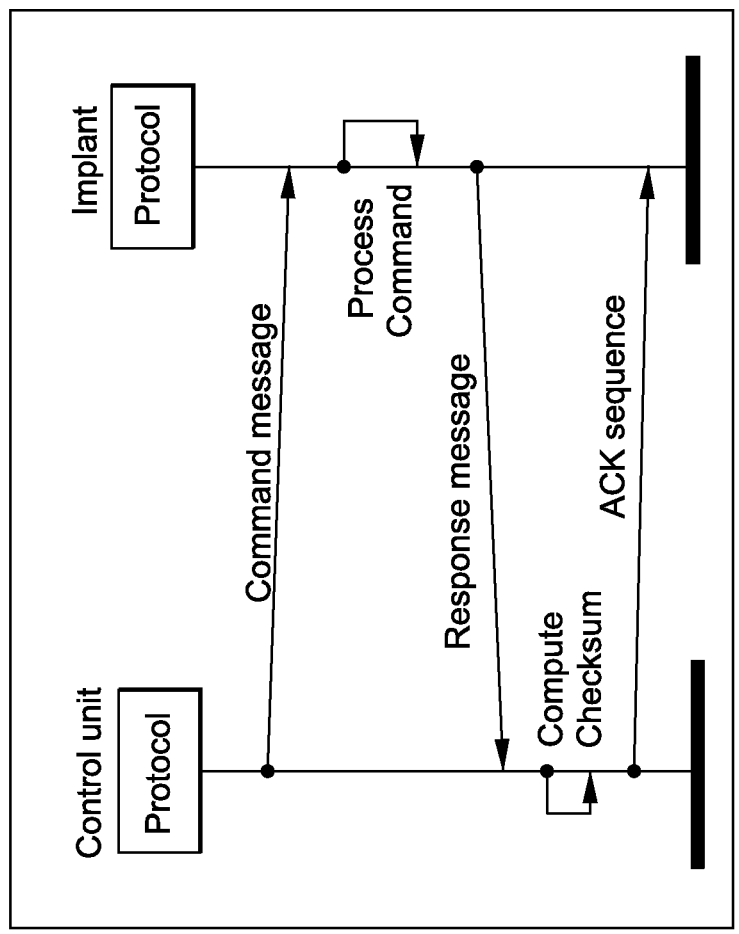
FIG. 46A shows a command-response protocol according to an embodiment of the present invention.

Referring to FIG. 46A, several commands may request information from the implant. In response, the implant may embed the requested information in a response message. Upon receiving the response message and the embedded information, the control device may respond with an ACK message.

Figure 46B:
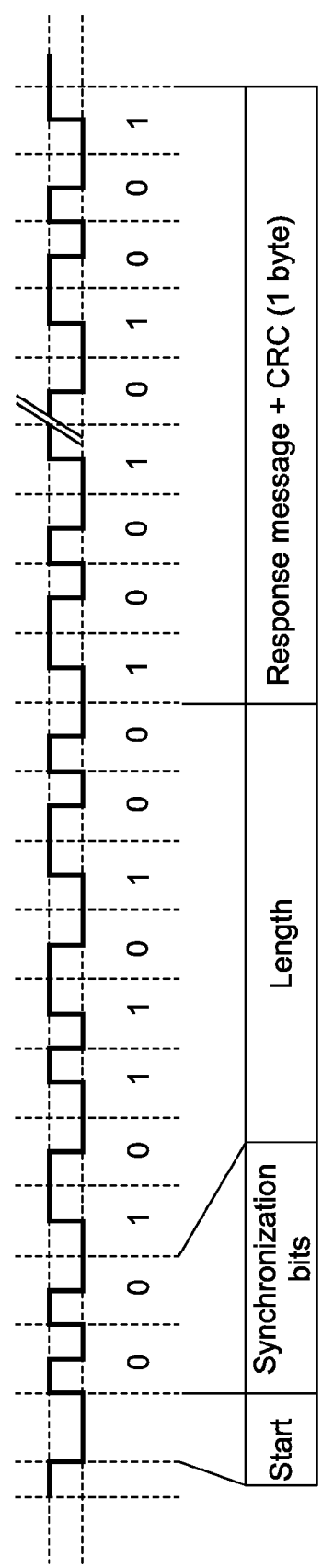
FIG. 46B shows a data structure of a response message according to an embodiment of the present invention.

In FIG. 46B, a data structure of a response message is shown according to an embodiment of the present invention. Generally, the response message may include a start bit, two synchronization bits, eight "length" bits, several response message bits the size of which is defined by the value contains in the "length" bits, and eight CRC bits.

Figures 47A, 47B:
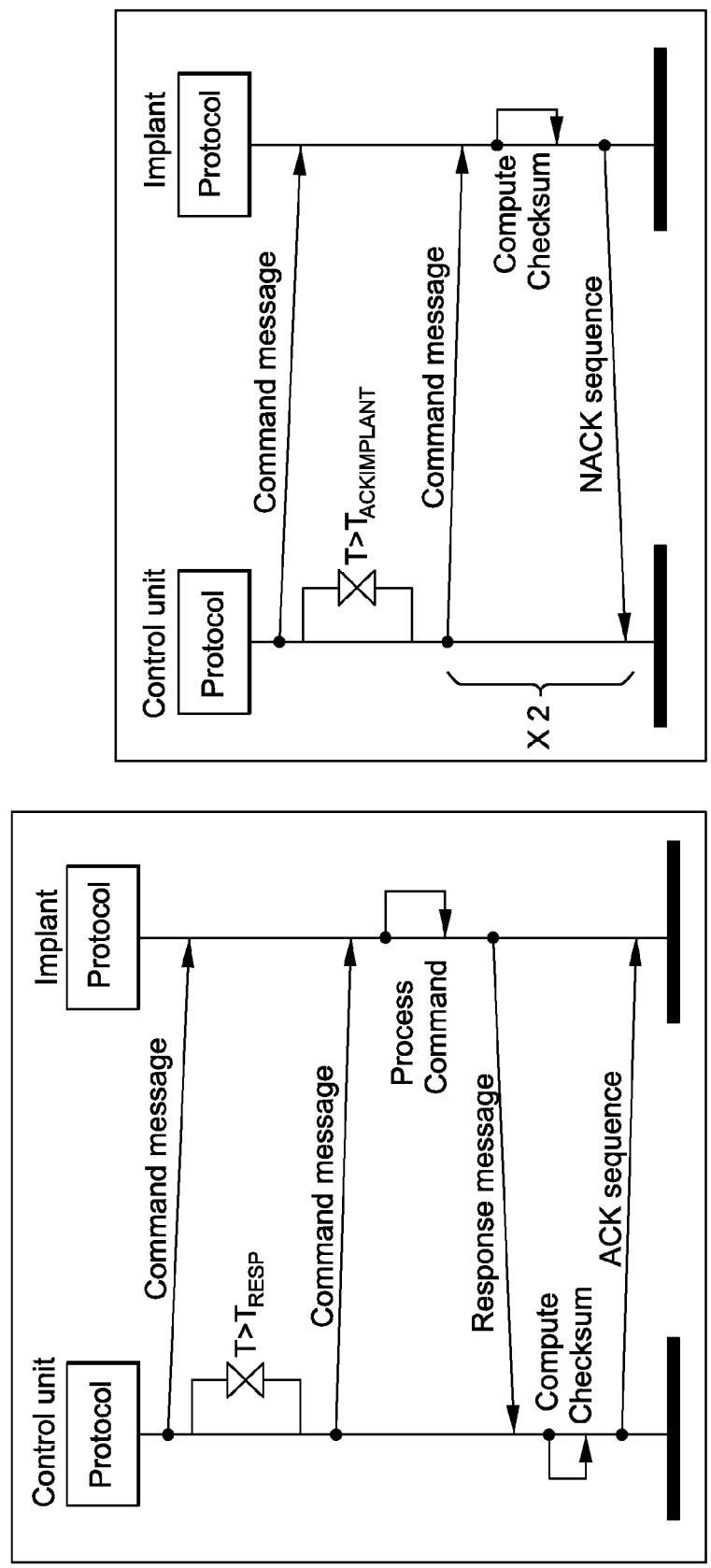
FIG. 47A shows a time out protocol with control device checksum according to an embodiment of the present invention.
FIG. 47B shows a time out protocol with implant checksum according to an embodiment of the present invention.

Referring to FIGS. 47A and 47B, several timeout conditions may be met when the implant takes more than 200 ms to send back either an ACK message or a response message. Generally, timeout conditions and/or a NACK message from the implant may trigger the resending of commands from the control device. According to an embodiment of the present invention, this resending mechanism may repeat up to about five times.

Figure 50:
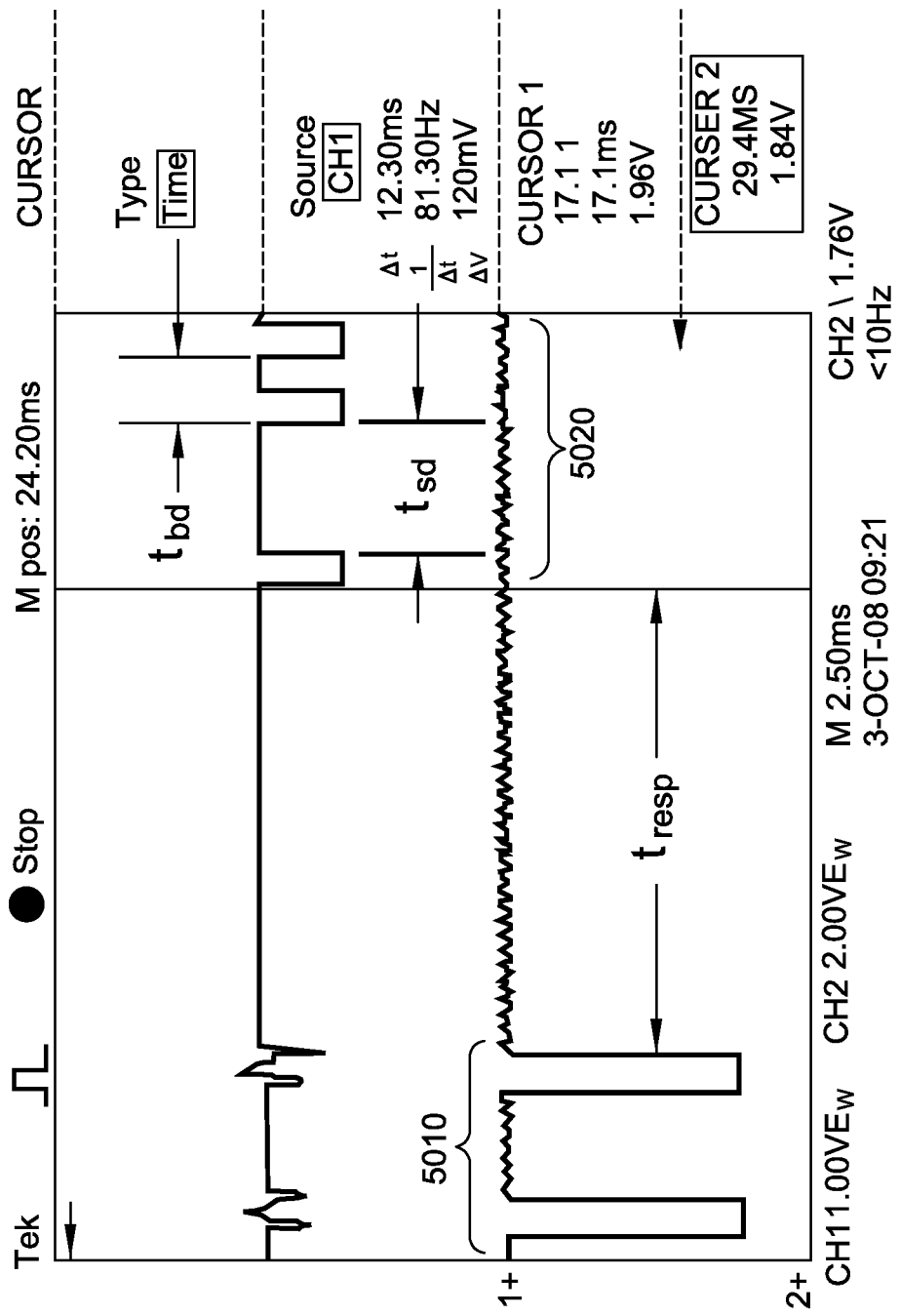
FIG. 50 shows a timing diagram of the control device's command and the implant's response according to an embodiment of the present invention.

FIG. 50 shows a screen shot of the timing diagrams of the control device's command and the implant's response. The response time $t_{resp}$ may be measured from the sending of the command 5010 (from the control device 110) to the sending of the response 5020 (from the implant). The start pulse duration $t_{sd}$ may be the duration for transmitting the first response pulse, and the data bit duration $t_{db}$ may be the duration for transmitting one message data bit. In one embodiment, the start pulse duration $t_{sd}$ may be set at 400 µs and the data bit duration $t_{db}$ may be set at 200 µs. In order to instruct the microcontroller to stop its current task and get ready to receive the message, the start bit duration may be set to low.

Figure 48:
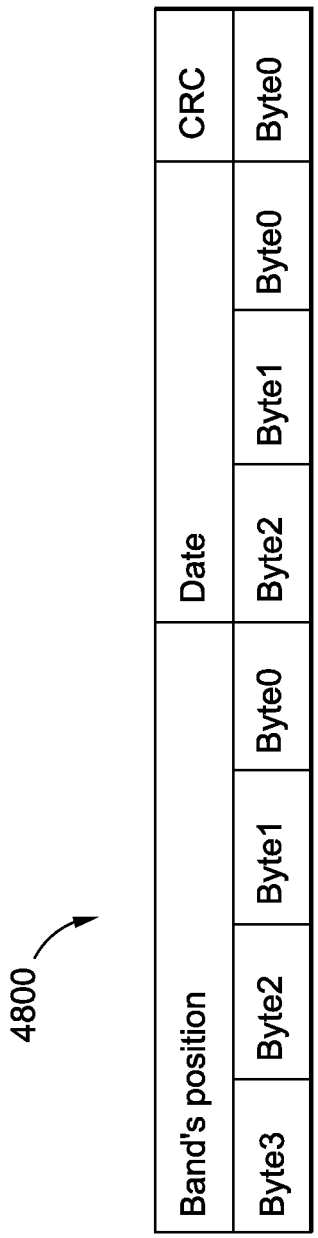
FIG. 48 shows a data structure of implant adjustment history record according to an embodiment of the present invention.

The discussion now turns to the gastric band adjustment history storage function of the implant electronic system. In FIG. 48, a data structure of implant adjustment history record 4800 (hereafter "history data record") may be shown according to an embodiment of the present invention. Generally, the history data record 4800 may reserve four bytes for storing gastric band position information, three bytes for storing date information, and one byte for storing CRC code.

Particularly, the gastric band position may be represented by about 71,000 motor steps, which may be stored in the four-byte data field. Because the EEPROM in the CAD has a size of about 512 bytes, information may be stored in duplicates of 256-byte size in a first record location and a second record location. Advantageously, the implant electronic device may be able to use the second set of records for data if the first set of records is corrupted.

The motor used in the implant may be a step motor. One step of the motor may correspond to one binary value stored in the counter. The stored value of "0" may represent a substantially (or fully) open band, while a stored value of "71, 000" may represent a substantially (or fully) closed band. Moreover, more than one control devices may access and retrieve information from the implant, such that multiple care-takers and/or physicians may monitor and adjust the gastric band for the patient.

Figure 55B:
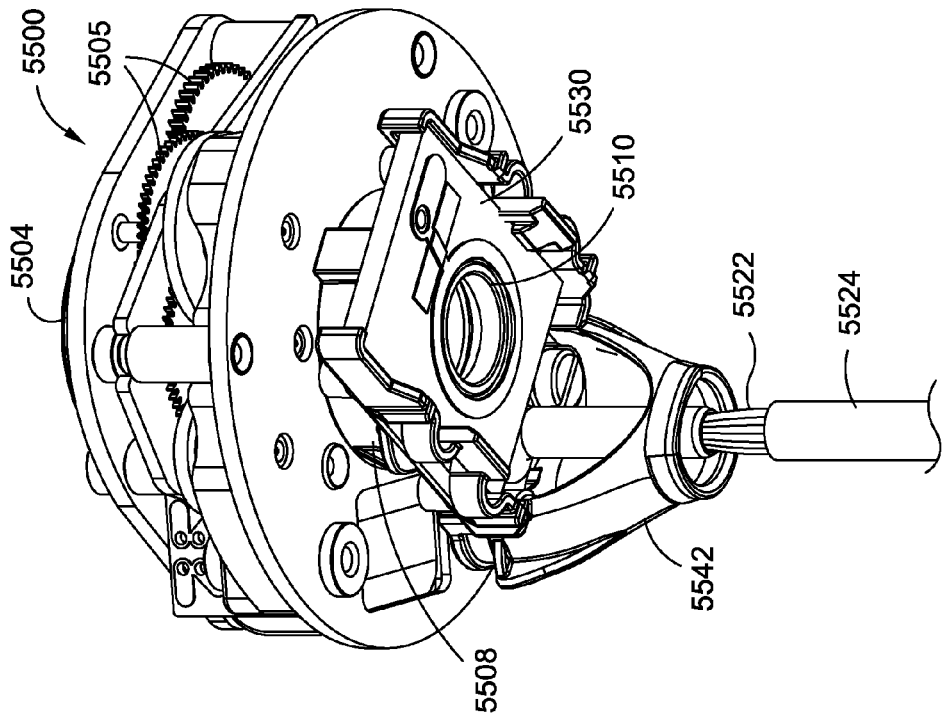
FIGS. 55A-55B show a perspective top view and a perspective bottom view of a motor according to an embodiment of the present invention.
Figure 55A:
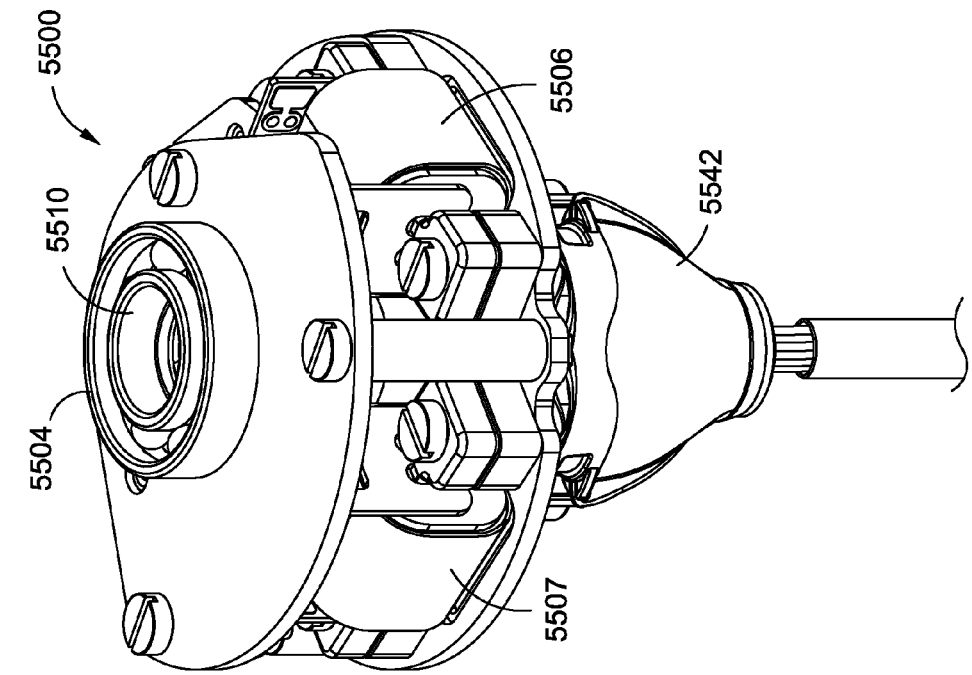

The discussion now turns to the operation of the motor. Referring to FIGS. 55A-55B a perspective top view and a perspective bottom view of a motor 5500 according to an embodiment of the present invention. Generally, the motor 5500 may be used for implementing the functional features of the motor assembly 3718 as shown in FIG. 37B. The motor 5500 may include the upper bearings 5504, lower bearings 5508, a set of motor gears 5505, a first motor coil 5506, a second motor coil 5507, a maneuver channel 5510, and a motor switch PCB 5530.

The motor switch PCB 5530 may have a layer of gold plate over the copper layer and large pads for cleaner thermo soldering, and the set of motor gears 5505 may be covered by dry lubrication with a diamond like coating (DLC) to achieve better surface tension for avoiding water drop formation.

The maneuver channel 5510 may be used for receiving the threaded section of the flexible screw. When the set of gears 5505 are turned, the flexible screw may be maneuvered along the maneuver channel 5510. In a band widening step, for example, the flexible screw may be maneuvered from the upper bearing 5504 side of the maneuver channel 5510 to the lower bearing 5508 side of the maneuver channel 5510. In a band tightening step, for example, the flexible screw may be maneuvered from the lower bearing 5508 side of the maneuver channel 5510 to the upper bearing 5504 side of the maneuver channel 5510.

The motor 5500, the motor wires 5522, and the flexible screw may be protected by several devices. Before entering the motor 5500, for example, the motor wires 5522 may be protected by the motor cable 5524. At or near the lower bearings 5508, for example, the motor wires 5522 may be protected by a cable cone 5542 of a motor traveling PCB protection cap 5540.

Figure 55D:
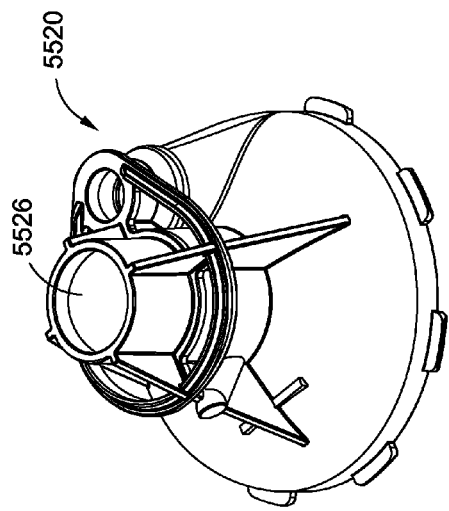
FIGS. 55C-55D show a perspective bottom view and a perspective top view of a motor cap according to an embodiment of the present invention.
Figure 55F:
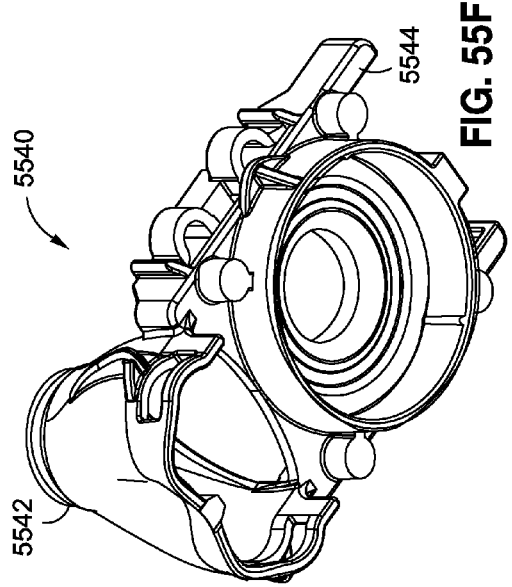
FIGS. 55E-55F show a perspective bottom view and a perspective top view of a motor traveling PCB protection cap according to an embodiment of the present invention.
Figure 55C:
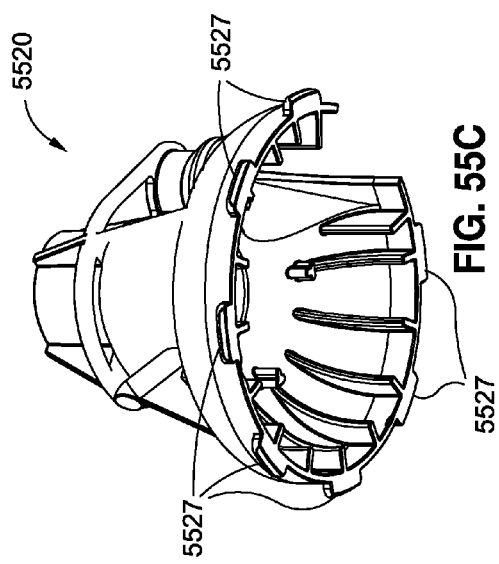
Figure 55E:
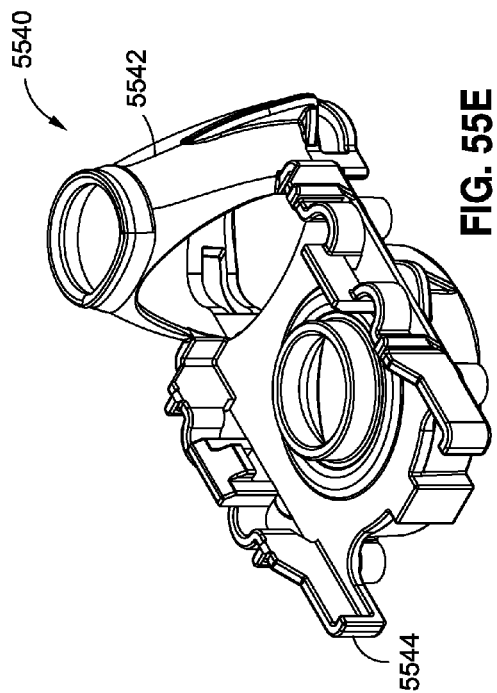

Referring to FIGS. 55E-55F, a perspective bottom view and a perspective top view of a motor traveling PCB protection cap 5540 are shown according to an embodiment of the present invention. The motor traveling PCB protection cap 5540 may include the cable cone and a PCB brace 5544. The cable cone 5542 may be used for protecting the motor wires 5522. The PCB brace 5544 may be used for protecting the lower bearings 5508 and holding the motor switch PCB 5530. The motor traveling PCB protection cap 5540 may be made of a PEEK material, and it may be mounted to the lower bearing 5508 of the motor 5500.

FIGS. 55C-55D show a perspective bottom view and a perspective top view of motor cap 5520 according to an embodiment of the present invention. The motor cap 5520 may cover the motor traveling PCB protection cap 5540 and thereby providing further protection for the lower bearing 5508 of the motor 5500. The motor cap 5520 may define a maneuver aperture 5526, which may help guide the longitudinal movement of the flexible screw 5560. The motor cap 5520 may include a set of flanges 5527, which may be used for anchoring to the skeleton 5800. The motor 5500 may be partially secured by the motor cap 5520 and the motor traveling PCB protection cap 5540. After receiving and securing the motor 5500, the motor cap 5520 may anchor the motor 5500 to the skeleton 5800. The motor cap 5520 may have several rails to allow silicone to form overmolding thereon.

Figure 55G:
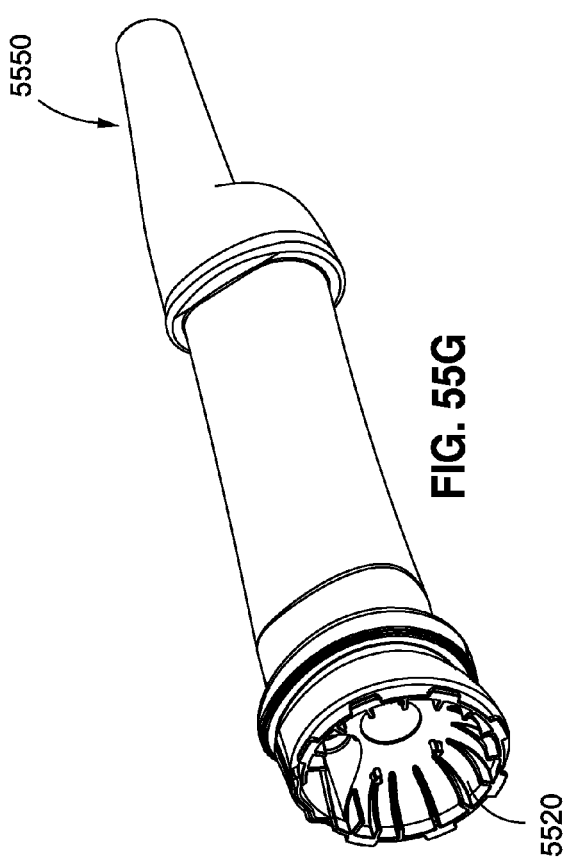
FIGS. 55G-55H show a perspective side view and a side view of a motor sleeve according to an embodiment of the present invention.
Figure 55H:
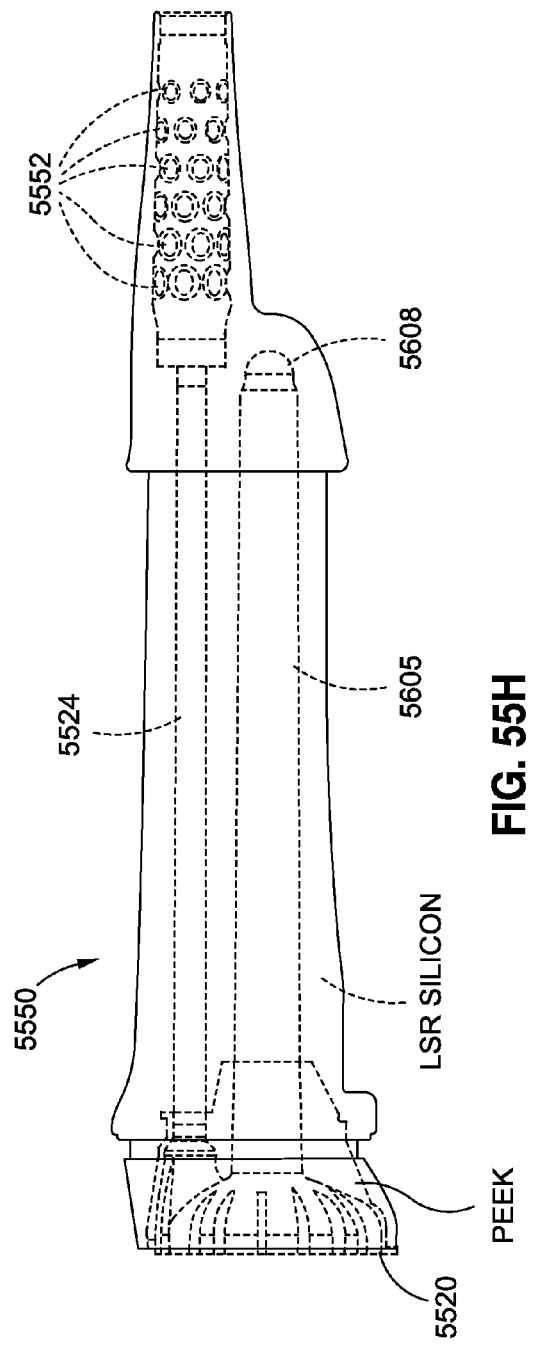

The motor cable 5524 and part of the flexible screw may be further protected by an overmold motor sleeve. Referring to FIGS. 55G-55H, a perspective side view and a perspective front view of a motor sleeve 5550 are shown according to an embodiment of the present invention. The motor sleeve 5550 may be made of an LSR silicon material overmolded on a PEEK material. The LSR silicon overmolded PEEK may provide a sealing surface to protect fluid from entering the motor 5500. Moreover, the motor sleeve 5550 a plurality of internal bumps 5552 to facilitate even gluing between the interior of the motor sleeve 5550 and the motor cable 5524.

Figure 55I:
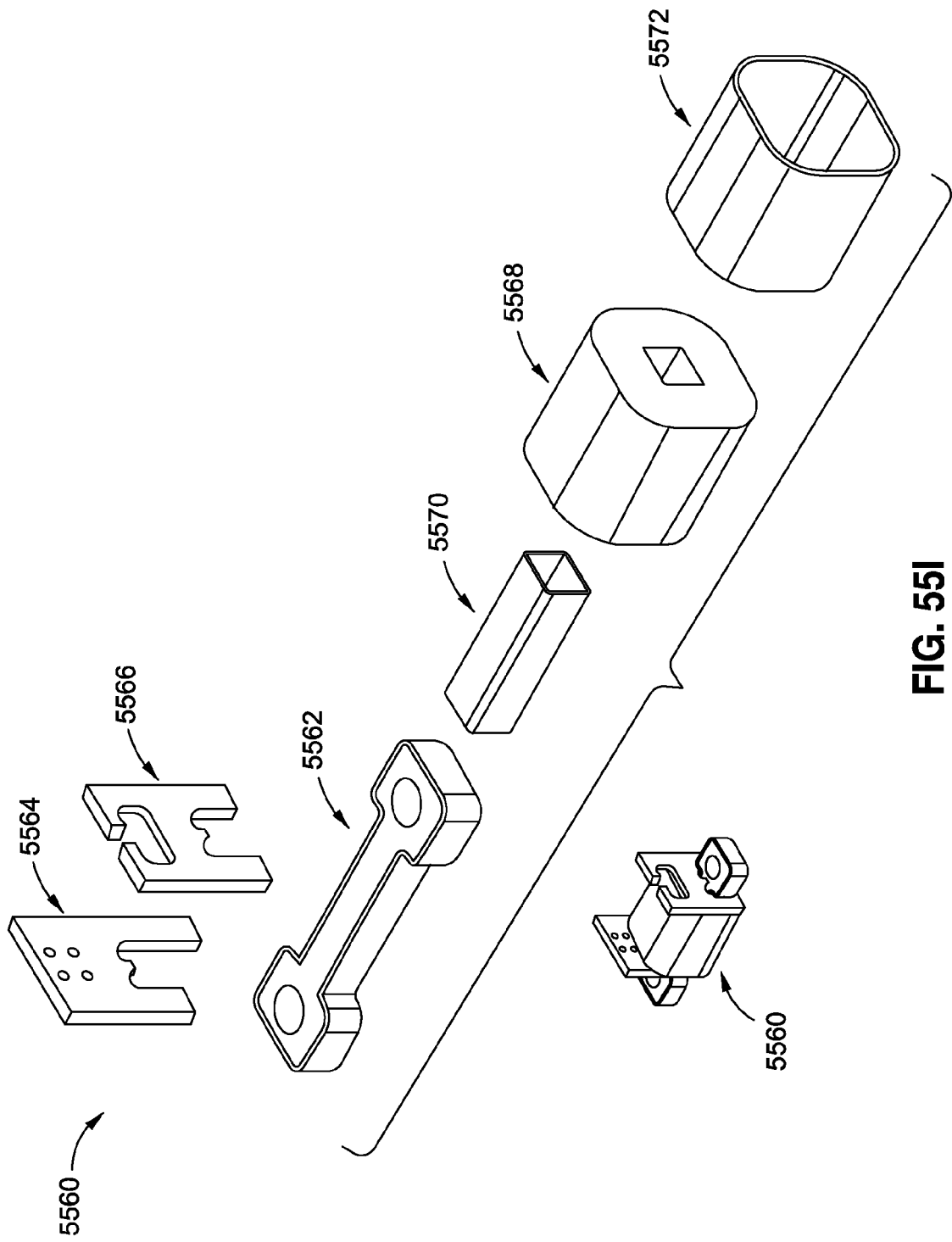
FIG. 55I shows an exploded view of a motor coil according to an embodiment of the present invention.

FIG. 55I shows an exploded view of a motor coil 5560 according to an embodiment of the present invention. Generally, the motor coil 5560 may be used for implementing the first and/or second motor coils 5506 and 5507. Particularly, the motor coil 5560 may include a first connection board 5564, a second connection board 5566, a core 5562, an inner shield 5570, a coil body 5568, and an outer shield 5572.

The first and second connection boards 5564 and 5566 may provide a connection interface between the motor wires and the coil body 5568. Moreover, the first and second connection boards 5564 and 5568 may help secure the coil body 5568 around the center of the core 5562. The first and second connection boards 5564 and 5568 may engage the core 5562 and sandwich the coil body 5568 between both ends of the core 5562. The coil body 5568 may have several coils that are made of silver wire. When current passes through the coils, the coil body 5568 may induce a magnetic flux along the core 5562. The inner and outer shield 5570 and 5572 may shield the coil body 5568 from electromagnetic interference, such that the magnetic flux generated by one motor coil (e.g., the motor coil 5506 or 5507) will not interfere with the magnetic flux generated by another motor coil (e.g., the motor coil 5507 or 5506).

Figure 55K:
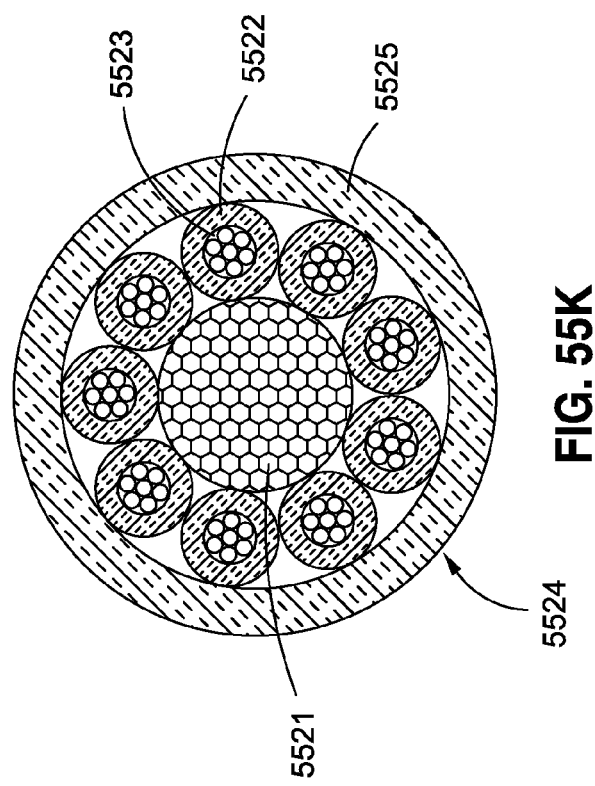
FIGS. 55J-55K show various views of the motor cable according to an embodiment of the present invention.
Figure 55J:
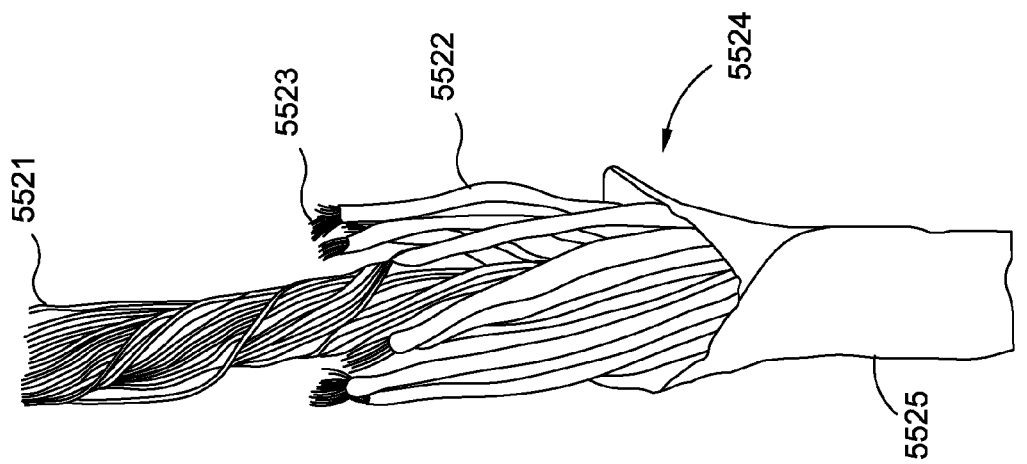

FIGS. 55J-55K show various views of the motor cable 5524 according to an embodiment of the present invention. Generally, the motor cable 5524 may include a central conductor 5521, nine twisted wires 5522, and a PTFE tape 5525. The central conductor 5521 may be crimped and attached to the motor 5500 on one end, and it may be crimped and soldered to the implant electronic system PCB 3722 on the other end. The central conductor 5521 may be a ground wire or a skeleton wire depending on the particular circuit configuration being used.

Specifically, the central conductor 5521 may include ninety-one MP35NLT alloy wires each with diameter of 0.04 mm. The nine twisted wires 5522 may be connected to the first and second motor coils or the end of a travel switch. Each of the nine twisted wires 5522 may include seven AISI316L silver plated stainless steel wires 5523, each of which may have a diameter of 0.12 mm.

Figure 56:
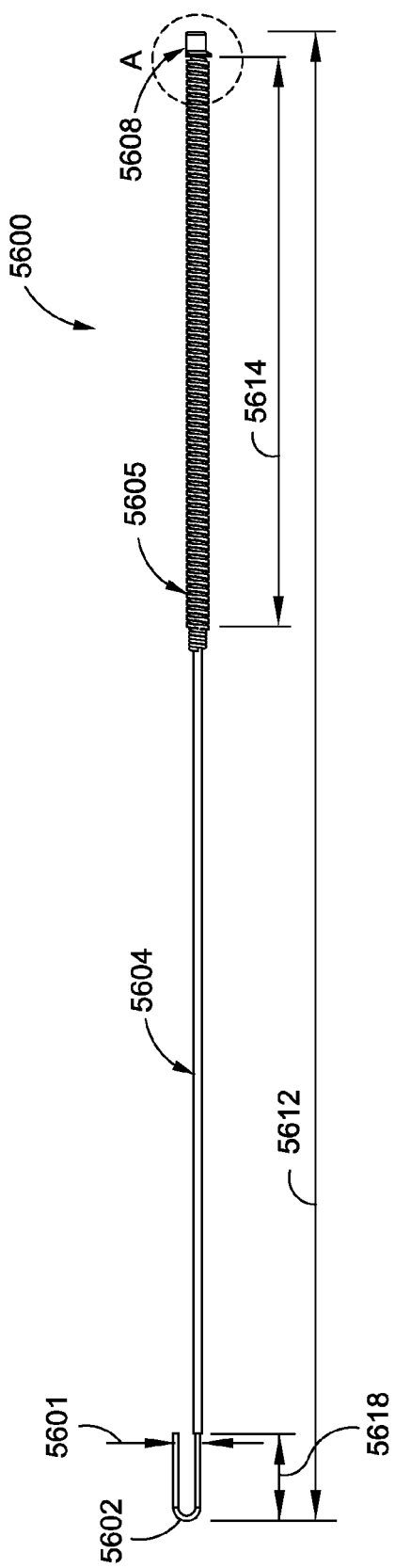
FIG. 56 shows a side view of a flexible screw according to an embodiment of the present invention.
Figure 57E:
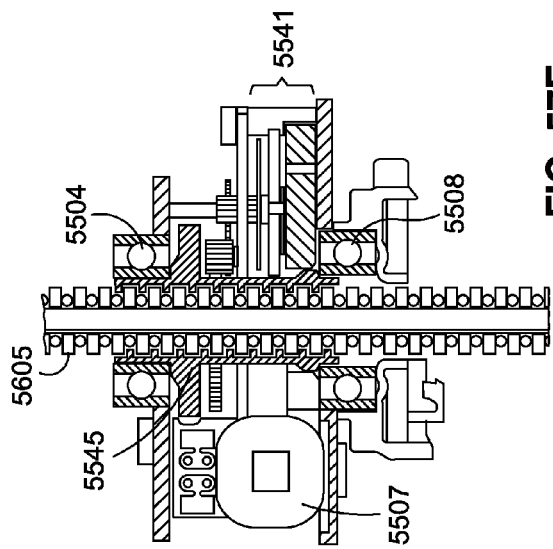
Figure 57G:
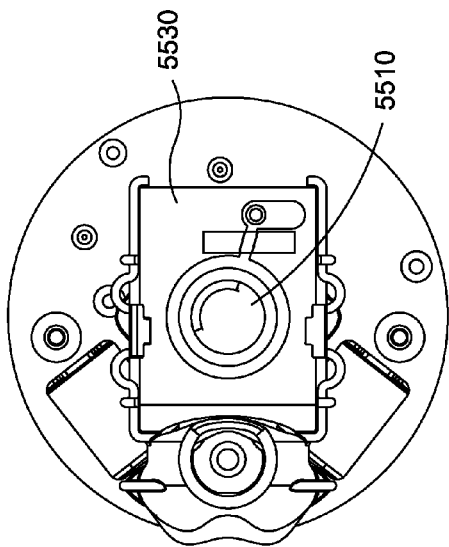
Figure 57D:
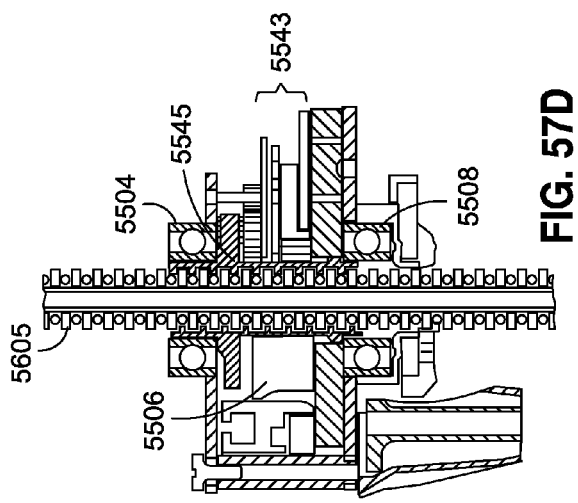
Figure 57F:
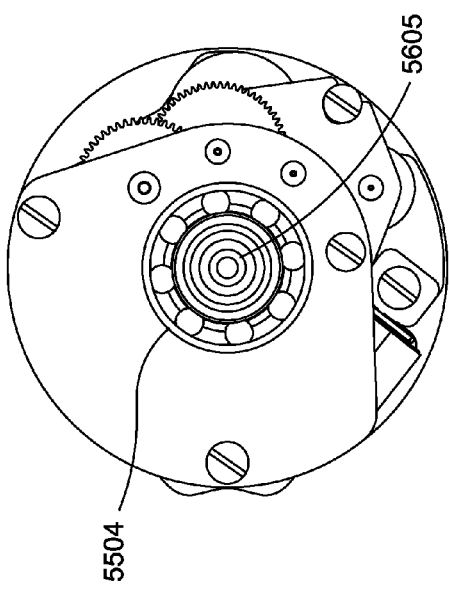
Figure 57H:
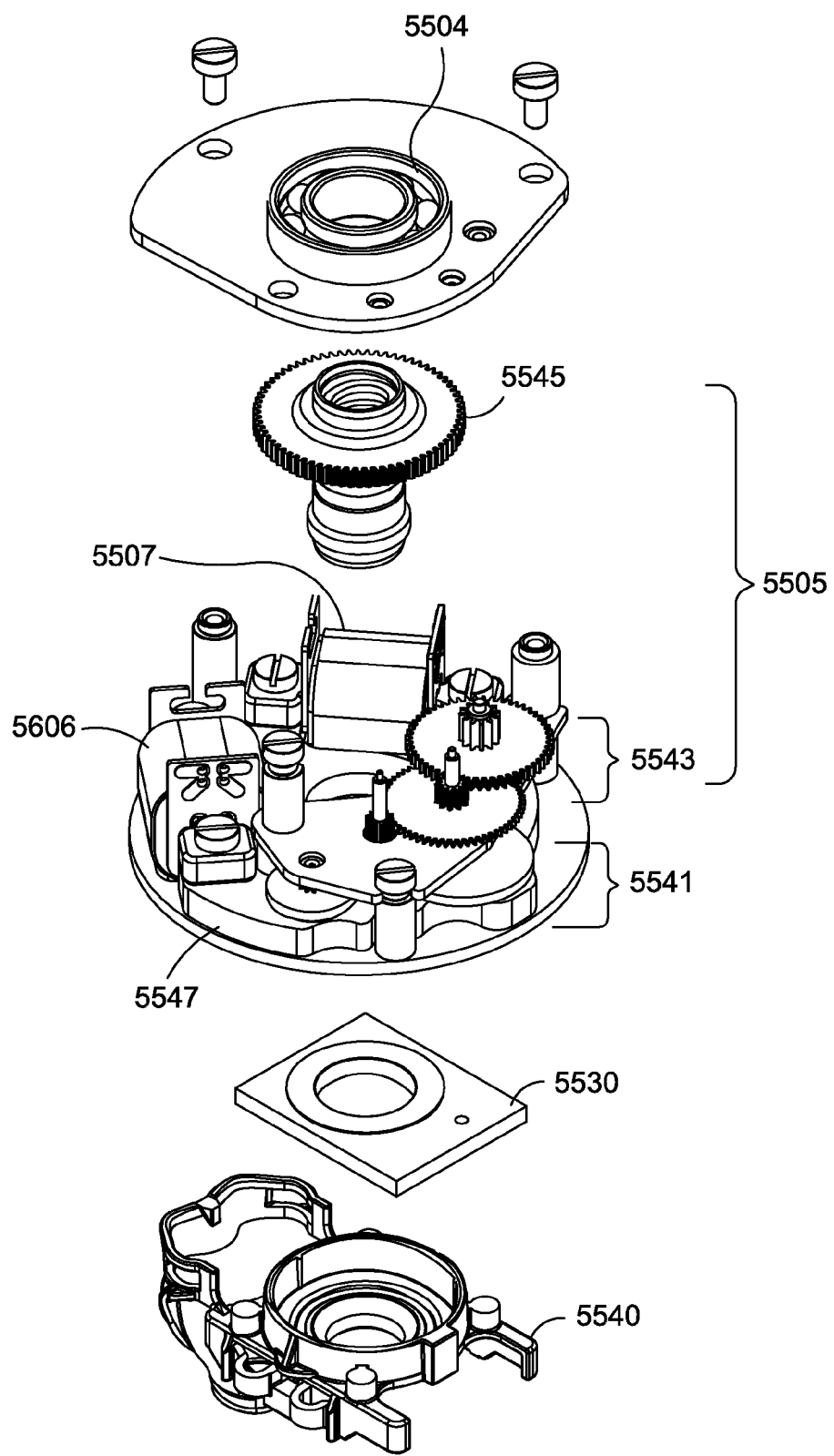

FIG. 56 shows a side view of a flexible screw assembly 5600 according to an embodiment of the present invention. Generally, the flexible screw assembly 5600 may be used for implementing the functional features of the flexible screw assembly 3720. The flexible screw assembly 5600 may have a hook end 5602, a central wire 5604, an intercalary wire (threaded section) 5605, and a crimped end 5608. The central wire 5604 may be surrounded by the stabilizing tube as discussed in FIG. 37B, and it may be attached to the end of the intercalary wire 5605 opposite to a crimped end 5608. Moreover, the central wire 5604 may be used for controlling the size of the gastric band when the intercalary wire 5605 is being moved back and forth the maneuver channel 5510 of the motor 5500 (see FIGS. 55A and 55B).

The flexible screw assembly 5600 may have an overall length 5612 of about 136.20 mm and with a tolerant range of about 0.1 mm. The intercalary wire 5605 may have an overall length 5614 of about 52 mm and with a tolerant range of about 0.1 mm. The hook member 5602 may have a width 5601 and a length 5618. The width 5601 may be about 2.5 mm and with a tolerant range of about 0.1 mm, whereas the length 5618 may be about 8 mm and with a tolerant range of about 0.1 mm.

FIGS. 57A-57H provide various views of the motor 5500 engaging the flexible screw 5600 to illustrate the structural and functional relationships between the motor 5500 and the flexible screw assembly 5600. Initially, each of the first and second motor coils 5506 and 5507 may receive a motor current from the implant electronic device PCB 3722 and via the motor wires 5522. The first and second motor coils 5506 may each generate a magnetic flux in response to the received motor current. The generated magnetic flux may be collected by the stator 5547, which may convert the magnetic flux to mechanical force for driving a set of rotors 5541.

The set of rotors 5541 may be engaged to and for driving the set of gears 5505. The set of gears 5505 may include a set of auxiliary gears 5543 and a primary gear 5545. The set of auxiliary gears 5543 may be engaged between the rotor 5541 and the primary gear 5545, such that the set of auxiliary gears 5543 may redirect the mechanical force from the rotor 5543 to the primary gear 5545.

The primary gear 5545 may be positioned within the maneuver channel 5510. The upper bearings 5504 and the lower bearings 5508 may help position, stabilize, and secure the primary gear 5545 within the maneuver channel 5510. The primary gear 5545 may have an internal threaded section for engaging the external thread of the intercalary wire 5606 of the flexible screw 5600. When the primary gear 5545 is set to rotate, it may move the intercalary wire 5606 along the maneuver channel 5510. As such, upon receiving the mechanical force, the primary gear 5545 may actual a relative longitudinal movement between the motor 5500 and the flexible screw 5600.

Because of the relative longitudinal movement actuated by the primary gear 5545, the motor 5500 may slide along the intercalary wire 5606. When the gastric band is formed, the hook end 5602 of the flexible screw 5600 may be positioned in the proximity of the motor 5500. As such, the size of the gastric band, which can be defined in diameter and/or circumference, may be adjusted by varying a relative distance between the hook end 5602 and an engagement position on the intercalary wire 5606. More specifically, the engagement position is a position at which the motor 5500 may engage the intercalary wire 5606. The size of the gastric band may be increased by sliding the motor 5500 toward the crimped end 5608 of the flexible screw 5600. Similarly, the size of the gastric band may be reduced by sliding the motor 5500 toward the hook end 5602 of the flexible screw 5600.

Figure 51:
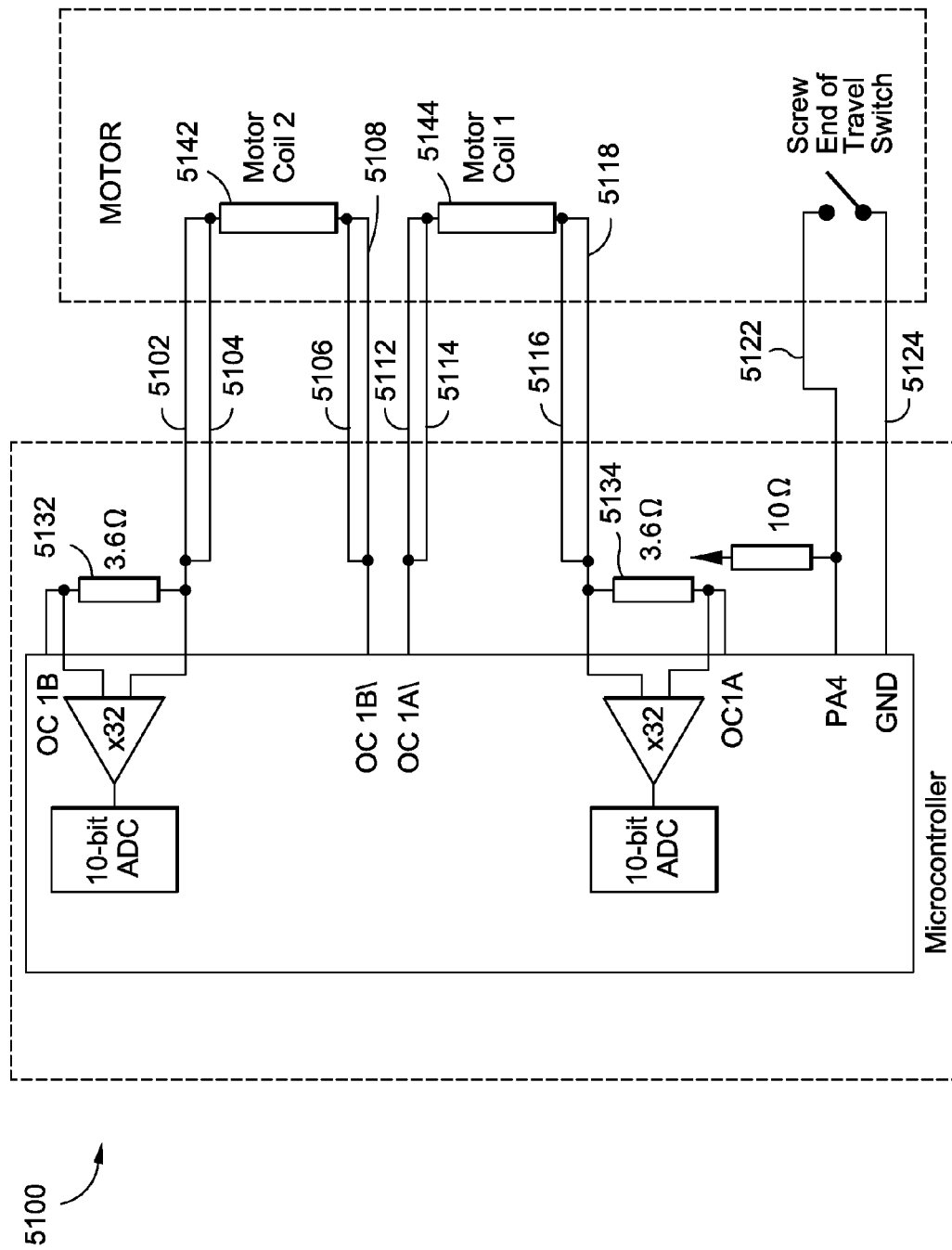
FIG. 51 shows a schematic view of a motor coil current measurement system according to an embodiment of the present invention.

The discussion now turns to the motor and the motor blockage detection mechanism. Referring to FIG. 51, a schematic view of a motor coil current measurement system 5100 is shown according to an embodiment of the present invention. The connection between the motor and the implant electronic device may be established via ten conductor cable wires. The cable wires 5122 and 5124 may be connected to the screw end of a travel switch. In one embodiment, the cable wire 5122 may be one of the motor wires 5522, and the cable wire 5124 may be the center conductor 5521 as shown in FIG. 55K.

Generally, the eight cable wires connecting to the motor coils may be duplicated and connected in parallel. In one embodiment, for example, the cable wire 5102 may duplicate the cable wire 5104, the cable wire 5106 may duplicate the cable wire 5108, the cable wire 5112 may duplicate the cable wire 5114, and the cable wire 5116 may duplicate the cable wire 5118. Each of the cable wires 5102, 5104, 5106, 5108, 5112, 5114, 5116, and 5118 may be implemented by one of the nine motor wires 5522 as shown in FIG. 55K.

The cable wires 5102 and 5104 may be connected to a first end of the motor coil 2, while the cable wires 5106 and 5108 may be connected to a second end of the motor coil 2. Similarly, the cable wires 5112 and 5114 may be connected to a first end of the motor coil 1, while the cable wires 5116 and 5118 may be connected to a second end of the motor coil 1.

As previously discussed, the control device may request the patient's identification number and history data from the implant electronic system before the gastric band adjustment process. In response, the implant electronic system may retrieve and send back the requested information. After receiving the requested information, the control device may be ready for adjustment. At this point, the user may elect to tighten or loosen the gastric band.

When the electronic device receives band adjustment commands from the control device, it may initiate a motor-on sequence which may include a motor positioning phase, a motor startup phase, and a motor drive phase. During the motor position phase, the motor is moved to a known position prior to the actual rotation start. Table 3 may illustrate the motor positioning phase:

TABLE 3

Sequences during motor positioning.

| Direction | Duration [ms] | Coil 1 | Coil 2 |
|---|---|---|---|
| Band Closing | 5 | NEG | POS |
|  | 60 | NEG | NEG |
| Band Opening | 5 | POS | POS |
|  | 60 | POS | NEG |

A positive pulse POS and a negative pulse NEG may be used for driving the motor coils. During a band closing sequence, for example, the first motor coil may receive a negative pulse for 5 ms and then another negative pulse for 60 ms, whereas the second motor coil may receive a positive pulse for 5 ms and a negative pulse for 60 ms. Table 4 may provide four pulse pair steps for rotating the motor:

TABLE 4

Sequences for motor rotation.

| Pulse Pair Label | Band Closing | | Band Opening | |
|---|---|---|---|---|
|  | Coil 1 | Coil 2 | Coil 1 | Coil 2 |
| PPL0 | POS | NEG | NEG | NEG |
| PPL1 | POS | POS | NEG | POS |
| PPL2 | NEG | POS | POS | POS |
| PPL3 | NEG | NEG | POS | NEG |

The pulse pair (PP) combination parameters may be stored in the implant electronic device's EEPROM. Generally, two pairs of pulses may drive a full turn of the motor, thereby completing a single motor step. Accordingly, two motor steps may be completed after executing pulse pairs PPL0 to PPL3. The completion of each motor step may be reported back to the control device for monitoring purposes. During the motor startup phase, the duration of the pulses may be gradually decreased from about 5.12 ms down to about 2.6 ms with a delta of about 0.15 ms after each pulse.

During the motor drive phase, a motor blockage may be detected. The motor drive phase may be used for refining a minimal pulse duration, which may range from about 2.6 ms to about 1.2 ms. The minimal pulse duration may allow the motor coils to turn smoothly without any motor blockage.

Referring again to FIG. 51, the minimal pulse duration may be refined by detecting the motor coil currents across the resistors 5132 and/or 5134. The motor coil currents may be amplified by an analog amplifier and then digitized by an analog-to-digital converter (ADC). In one embodiment, the analog amplifier may be configured to have an amplifying power of 32, and the ADC may be configured to generate a 10-bit digital number for representing the value of the motor coil current.

Generally, the resistance of the resistors 5132 and 5134 may be much smaller than the resistance of the motor coils 5142 and 5144. In one embodiment, for example, the resistance of the motor coil 5142 or 5144 may be 167 times of the resistance of the resistor 5132 or 5134. In another embodiment, for example, the resistance of the resistors 5132 and 5134 may each be about 3.6Ω, whereas the resistance of the motor coils 5142 and 5144 may each be about 600Ω. As such, the voltage drop across the resistors 5132 and 5134 may be minimal when compared to the voltage drop across the motor coil resistors 5142 and 5144. Therefore, the resistance of the resistors 5132 and 5134 may have little effect on the overall current flowing of the first and second motor coils.

Sources of motor blockage may include increased force required to close the band as its materials get more compressed. As the radius of the band reduces, it would also become more difficult to pull on the flexible screw 5600 regardless of the presence of other materials. Biological tissue also gets more compressed as radius decreases, leading to more required force from the motor. The motor may be rated at a pulling force of 20 N but with typical pulling force of 27 N, such that it would get stalled as the required force would be higher than the typical pulling force.

Figure 52:
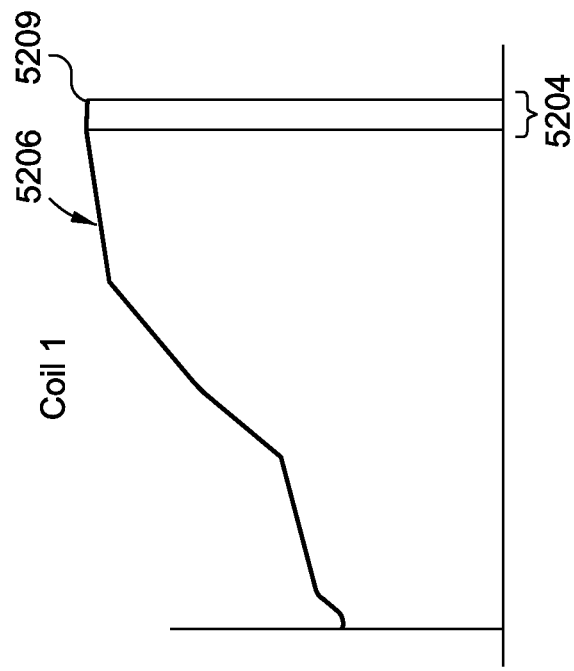
FIG. 52 shows a graph for measuring an integral motor coil current according to an embodiment of the present invention.
Figure 53:
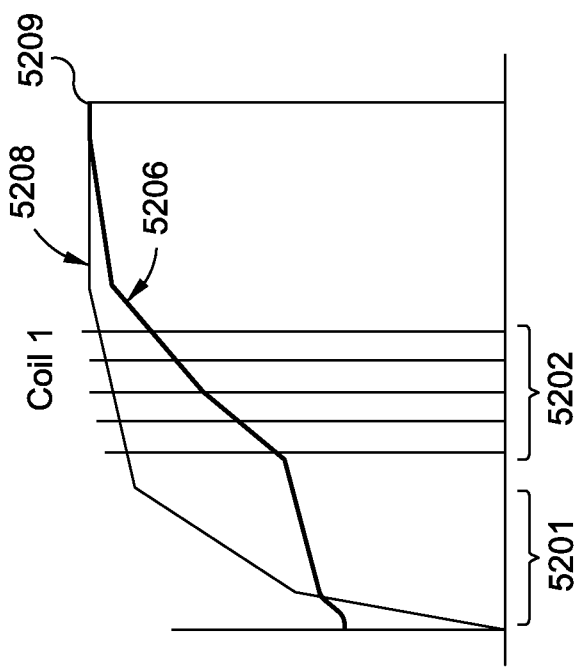
FIG. 53 shows a graph for measuring a maximum motor coil current according to an embodiment of the present invention.

The trend of motor coil current may indicate motor blockage or the lack thereof. As shown in FIG. 52, for example, a first current profile 5206 may represent a motor coil current of an unblocked motor, and a second current profile 5208 may represent a motor coil current of a blocked motor. In general, the resistance of a blocked motor may be higher than an unblocked motor. To maintain a relatively constant voltage across the motor, the motor coil current of a blocked motor (e.g., the second current profile 5208) may increase rapidly during an initial period 5201 of a motor step but slowly during a middle period 5202 of the motor step.

On the other hand, the resistance of an unblocked motor is typically lower than that of a blocked motor. As such, the motor coil current of an unblocked motor (e.g., the first current profile 5206) may increase slowly during the initial period 5201 but rapidly during the middle period 5202. Both motor coil currents (e.g., the first and second current profiles 5206 and 5208) may reach a maximum motor coil current 5209 at an ending period 5204 of the motor step. However, during the middle period 5202, the integral sum of the blocked motor coil current (e.g., the second current profile 5208) may be much greater than the integral sum of the unblocked motor coil current (e.g., the first current profile 5206). This phenomenon may be attributed by the early ramping of the blocked motor coil current and the late ramping of the unblocked motor coiled current.

Based on several measurements, the integral sum of the blocked motor current during the middle period 5202 is typically greater than the maximum motor coil current 5209. To the contrary, the integral sum of the unblocked motor current during the middle period 5202 is typically less than the maximum motor coil current 5209. As such, the integral sum of a particular motor coil current during the middle period 5202 may be compared to the maximum motor coil current 5209 in determining whether the motor is blocked.

Figure 54:
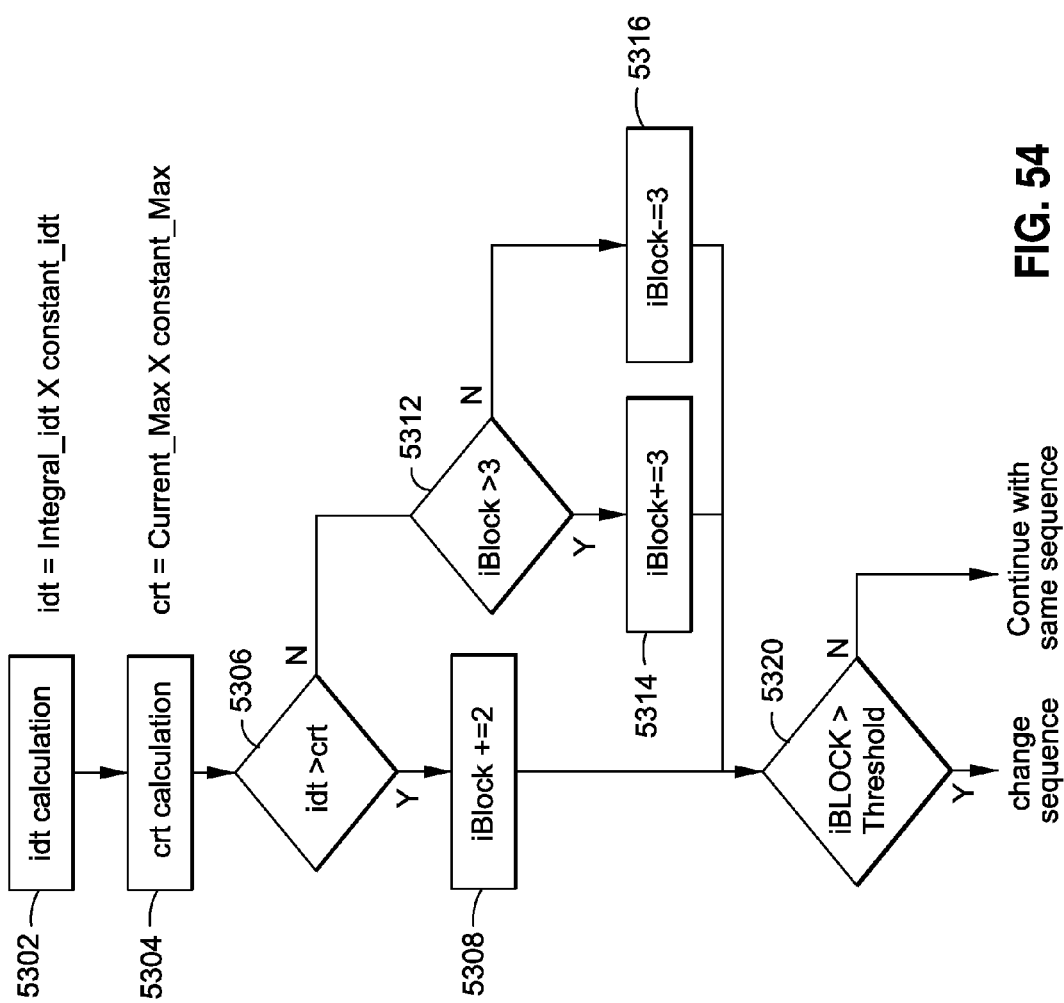
FIG. 54 shows a software algorithm for detecting motor blockage according to an embodiment of the present invention.

According to an embodiment of the present invention and as shown in FIG. 54, the implant electronic device (e.g., a processing device) may execute a software algorithm for detecting motor blockage. The software algorithm may take advantage of the aforementioned principle, and it may be stored in a tangible computer readable medium. In one embodiment, for example, the tangible computer readable medium may include a flash memory in the implant electronic device. In another embodiment, for example, the tangible computer readable medium may include, but not limited to, random access memory (RAM), flash memory, read-only memory (ROM), EPROM, EEPROM, registers, hard disk, removable disk, CD-ROM, DVD, Blu-ray disk, wireless channels, and various other media capable of storing, containing or carrying instruction(s) and/or data. In yet another embodiment, the motor coil current may be measured by the implant electronic device, while the motor blockage detection software algorithm may be stored in and executed by the control unit.

In step 5302, an integral sum value (idt) may be calculated by measuring the integral sum of motor coil current (Integral_idt) and normalizing the measurement. In one embodiment, the measurement may be performed during the PPL2 pulse pair, and the normalization may be performed by multiplying the measured integral sum of motor coil current (Integral_idt) by a predetermined parameter (constant idt).

In step 5304, the maximum current (crt) may be calculated by measuring the maximum motor coil current (Current_Max) and normalizing the measurement. In one embodiment, the measurement may be performed during the PPL3 pulse pair, and the normalization may be performed by multiplying the measured maximum motor coil current (Current_Max) by a predetermined parameter (constant_Max).

In step 5308, a determination can be made regarding whether the integral sum value (idt) is greater than the maximum current (crt). If a positive determination is made, the algorithm may proceed to step 5308, in which the value of a block register (iBlock) may be augmented. The block register value augmentation may be representative of the possibility that the motor is blocked. Hence, the higher the value of block register is, the more likely that the motor blockage has occurred.

On the other hand, if a negative determination is made in step 5308, the algorithm may proceed to step 5312, in which the value of the block register (iBlock) may be compared with a predefined value. If the value of the block register is less than the predefined value, a reduction step 5316 may be executed for reducing the value of the block register. In one embodiment, the value of the block register may be a negative number. If the value of the block register is greater than the predefined value, an increment step 5314 may be executed for augmenting the value of the block register.

In step 5320, a determination is made regarding whether a motor blockage has occurred. The value of the block register may be compared with a predefined threshold. The predefined threshold may represent a threshold probability that a motor blockage has occurred. If the value of the block register does not reach the predefined threshold, the algorithm may assume no motor blockage has happened yet, and it may return to step 5302 for the next motor sequence. However, if the value of the block register exceeds the predefined threshold, the algorithm may determine that the motor is blocked, and it may enter a different sequence.

Once a motor blockage is detected, the implant electronic device may direct the motor to decrease its speed and to enhance the motor torque. In one embodiment, for example, the implant electronic device may decrease the pulse duration to about 1.2 ms to produce more motor torque. If the motor load decreases, thereby requiring less motor torque, the implant electronic device may direct the motor to increase its speed again.

The discussion now turns to several gastric band components. Referring to FIGS. 58A-58C, various views of a bendable skeleton 5800 may be shown according to an embodiment of the present invention. Generally, the bendable skeleton 5800 may be used for implementing the functional features of the skeleton 3814. The bendable skeleton may be made of a PEEK material, which may be corrosion resistive and durable against stress.

The bendable skeleton 5800 may have an open compartment 5802 for receiving and securing the motor, a ladder body 5804 for supporting the dorsal ring surface of the gastric band, and a distal end member 5806 for providing an anchor point for the hook end (element) 5602 of the flexible screw 5600 to the first end of the dorsal element. The ladder body 5804 may also embrace the stabilizing tube 5820. In return, the stabilizing tube 5802 may guide the center wire of the flexible screw assembly to travel from the open compartment 5802 to the distal end member 5806 of the bendable skeleton 5800.

The open compartment 5802 may have a diameter 5808, a vertical distance 5810 separating the open compartment 5802 and the distal end member 5806, and an overall length 5812. In one embodiment, the diameter 5805 may be about 13.6 mm, the vertical distance 5810 may be about 67.6 mm, and the overall length 5812 may be about 111.23 mm.

Figure 59A:
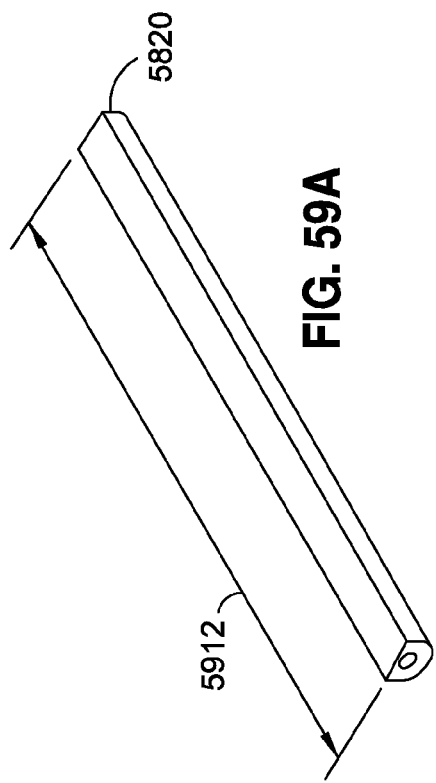
FIGS. 59A-59B show a perspective view and a cross-sectional view of the stabilizing tube according to an embodiment of the present invention.
Figure 59B:
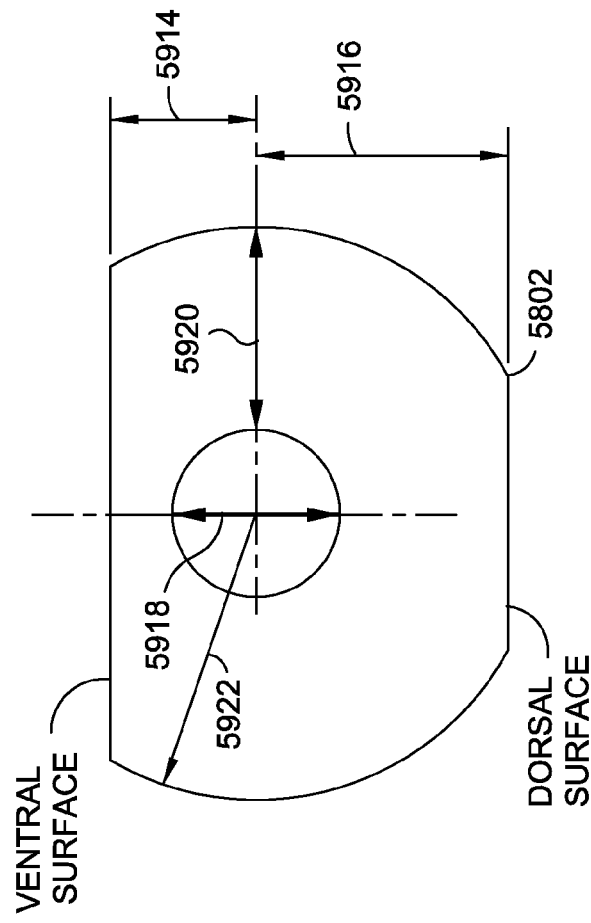

FIGS. 59A-59B show a perspective view and a cross-sectional view of the stabilizing tube 5820 according to an embodiment of the present invention. Generally, the stabilizing tube 5820 may be made of an ePTFE material. The stabilizing tube 5820 may have an overall length 5912, a first height 5914, a second height 5916, a radius 5922, a thickness 5920, and a channel radius 5918. In one embodiment, the overall length 5912 may be about 130 mm, the first height 5914 may be about 2.55 mm, the second height 5916 may be about 4.4 mm, the radius 5922 may be about 5 mm, the thickness 5920 may be about 3.5 mm, and the channel diameter 5918 may be about 3 mm.

FIGS. 60A-60D show various views of a dorsal element 6000 according to an embodiment of the present invention. Generally, the dorsal element 6000 may be used for implementing the functional features of the dorsal element 3704 as shown in FIG. 37B. The dorsal element 6000 may include an open compartment 6001, an opening 6002, and a semi-tubular ring (body) 6022 connecting the open compartment 6001 and the opening 6002. The side wall of the open compartment 6001 may have a locking protrusion and a ring-locked indicator 6030 formed on the locking protrusion. During the band formation, the open compartment 6001 may be inserted into the opening 6002, which may have a clip ring with a locking flange 6006. The locking flange may have a port for securing the locking protrusion. Once the locking protrusion is secured by the flange port, the ring-lock indicator 6030 may become visible.

Figure 61B:
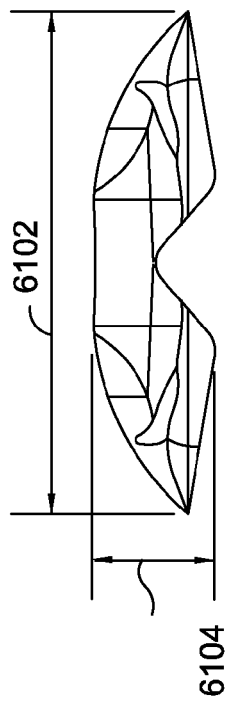
FIGS. 61A-61C show various views of an anti-slip cushion according to an embodiment of the present invention.
Figure 61C:
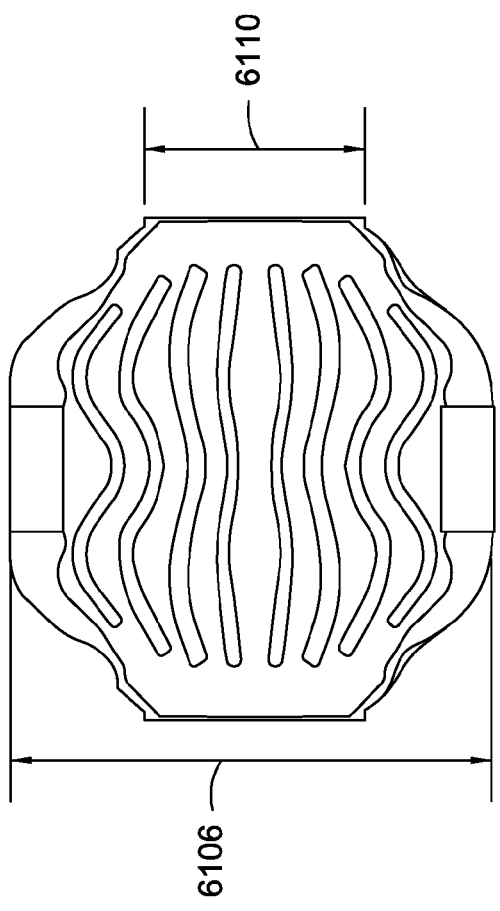
Figure 61A:
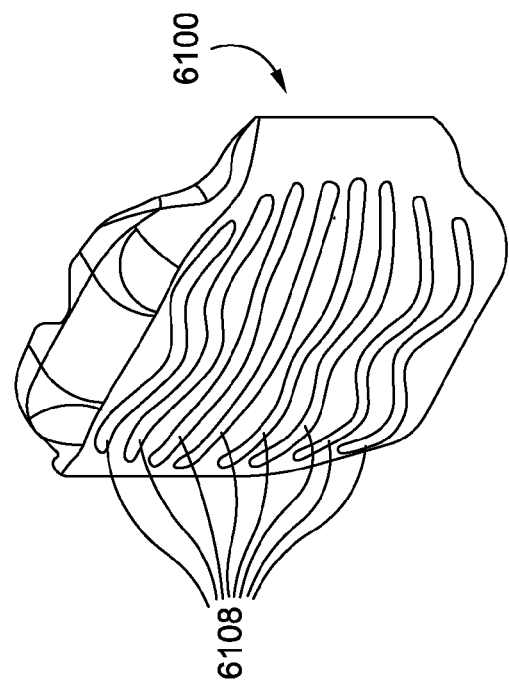

FIGS. 61A-61C show various views of an anti-slip cushion 6100 according to an embodiment of the present invention. The cushion 6100 may have a width 6102, a thickness 6104, a first length 6106, and a second length 6110. In one embodiment, the width 6102 may be about 17.92 mm, the thickness 6104 may be about 4.42 mm, the first length 6106 may be about 17.3 mm, and the second length 6110 may be slightly shorter than the first length 6106.

The front surface of the cushion 6100 may be symmetrical along a vertical axis, and it may have a convex shield-like surface with an array of curvy groove lines 6108 to provide more friction. Advantageously, the curvy groove lines 6108 may help the gastric band to remain in contact with the patient stomach and reduce the likelihood of band slippage. Moreover, the shield-like convex surface of the cushion 6100 may efficiently stimulate the vagus nerve of the patient.

FIGS. 62A-62C show various views of a membrane shell 6200 according to an embodiment of the present invention. In general, the membrane shell 6200 may include a tubular structure made of several segments 6208. The tubular structure 6202 may have a circular contour, and it may be used for encapsulating the dorsal element 6000, the skeleton 5800, and part of the flexible screw 5600. The segments 6208 may be used for receiving the cushions 6100. The membrane shell 6200 may be made of several NuSil LSR silicones, depending on the level of hardness it is designed to achieve. In one embodiment, for example, the membrane shell 6200 may be made of MED-4870, which is a silicone with a hardness of about 70 Shore A.

FIGS. 63A-63C show various views of a cushioned membrane shell 6300 according to an embodiment of the present invention. The cushioned membrane shell 6300 may include several cushions 6308, which may be made of MED-4801. When compared to MED-4870, MED-4801 may have a hardness of about 1 Shore A. Accordingly, the cushioned membrane shell 6300 may have a soft inner circumferential surface and a hard outer circumferential surface.

In an alternative embodiment, the cushions 6308 may be made of a silicone elastomer external shell filled with saline solution or made of a silicone elastomer external shell filled with silicone gel. Specifically, the silicone elastomer for the cushions may have a hardness ranges from about 1 Shore A to about 10 Shore A, whereas the silicone elastomer for the membrane shell may have a hardness ranges from about 20 Shore A to about 45 Shore A.

Unless otherwise indicated, all numerical parameters used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the present invention are approximations, the numerical values set forth in the specific examples are reported as precisely as possible. Any numerical value, however, inherently contains certain errors necessarily resulting from the standard deviation found in their respective testing measurements.

The terms "a," "an," "the," and similar referents used in the context of describing the present invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the present invention otherwise claimed. No language in the specification should be construed as indicating any non-claimed element essential to the practice of the present invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, certain references have been made to patents and printed publications throughout this specification. Each of the above-cited references and printed publications are individually incorporated herein by reference in their entirety.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the present invention disclosed herein are illustrative of the principles of the present invention. Other modifications that may be employed are within the scope of the present invention. Thus, by way of example, but not of limitation, alternative configurations of the present invention may be utilized in accordance with the teachings herein. Accordingly, the present invention is not limited to that precisely as shown and described.

What is claimed is:

1. A remotely powered and remotely adjustable gastric band system, comprising:
 a remote control device configured to transmit a telemetric signal having an amplitude and a carrier frequency, wherein a magnitude of the amplitude of the telemetric signal varies to adjust a transmitted power of the telemetric signal in response to a telemetric feedback signal received by the remote control device;
 an implantable power device telemetrically coupled to the remote control device, and configured to convert the transmitted power of the telemetric signal and to generate the telemetric feedback signal in response to the implantable power device sensing that the converted power exceeds a predetermined threshold, the telemetric feedback signal having a message frequency based on a difference between the converted power and the threshold; and
 a gastric band for forming a ventral ring surface around a stomach of a patient, the gastric band coupled to the implantable power device, and configured to receive at least a portion of the converted power from the implantable power device and adjust the ventral ring surface in response to the telemetric signal transmitted from the remote control device.

2. The gastric band system of claim 1, wherein the implantable power device includes:
   an implantable antenna for receiving the telemetric signal from the remote control device,
   a rectifying device coupled to the implantable antenna, and configured to rectify the received telemetric signal to form a DC input voltage at a DC input node,
   a power sensing device configured to receive a DC input voltage and generate a regulation signal when the DC input voltage exceeds a predetermined threshold,
   a regulation device coupled to the power sensing device, and configured to generate a regulation voltage in response to the regulation signal, and
   a frequency modulation device coupled to the regulation device, and configured to generate a frequency modulation signal with a modulated frequency representing the regulation voltage,
   wherein the message frequency of the feedback signal tracks the modulated frequency of the frequency modulation signal.

3. The gastric band system of claim 2, wherein the implantable power device includes:
   a switch coupled to the frequency modulation device, and configured to perform an amplitude modulation at the implantable antenna, the amplitude modulation adjusting the amplitude of the telemetric signal based on the frequency modulation signal.

4. The gastric band system of claim 1, wherein the remote control device includes:
   an external antenna configured to transmit the telemetric signal and receive the feedback signal,
   a sensing device coupled to the external antenna, and configured to sense the feedback signal,
   a demodulation device coupled to the sensing device, and configured to extract the message frequency from the sensed feedback signal and generate a voltage control signal based on the message frequency, and
   a modulation device coupled to the demodulation device and the external antenna, and configured to adjust the amplitude of the telemetric signal based on the voltage control signal and transmit the adjusted telemetric signal to the external antenna.

5. The gastric band system of claim 4, wherein the sensing device includes a directional coupler configured to separate the feedback signal from the telemetric signal.

6. The gastric band system of claim 1, wherein the threshold power is associated with a physical condition of the implantable power device when the implantable device is subject to a power level at or above the threshold power.

7. The gastric band system of claim 1, wherein the threshold power is associated with an overheating condition of the implantable power device when the implantable device is subject to a power level at above the threshold power.

* * * * *